US012653883B2

(12) United States Patent
Jooss et al.

(10) Patent No.: US 12,653,883 B2
(45) Date of Patent: Jun. 16, 2026

(54) ALPHAVIRUS NEOANTIGEN VECTORS AND INTERFERON INHIBITORS

(71) Applicant: Gritstone bio, Inc., Emeryville, CA (US)

(72) Inventors: Karin Jooss, Emeryville, CA (US); Amy Rachel Rappaport, San Francisco, CA (US); Leonid Gitlin, Foster City, CA (US)

(73) Assignee: Seattle Project Corp., Dover, DE (US)

( * ) Notice: Subject to any disclaimer, the term of this patent is extended or adjusted under 35 U.S.C. 154(b) by 244 days.

(21) Appl. No.: 17/291,984

(22) PCT Filed: Nov. 7, 2019

(86) PCT No.: PCT/US2019/060355

§ 371 (c)(1),
(2) Date: May 6, 2021

(87) PCT Pub. No.: WO2020/097393

PCT Pub. Date: May 14, 2020

(65) Prior Publication Data

US 2022/0125919 A1 Apr. 28, 2022

Related U.S. Application Data

(60) Provisional application No. 62/756,980, filed on Nov. 7, 2018.

(51) Int. Cl.

| | |
|---|---|
| ***A61K 39/395*** | (2006.01) |
| ***A61K 31/519*** | (2006.01) |
| ***A61K 31/7105*** | (2006.01) |
| ***A61K 35/761*** | (2015.01) |
| ***A61K 39/00*** | (2006.01) |
| ***A61K 39/21*** | (2006.01) |
| ***A61P 35/00*** | (2006.01) |
| ***A61P 37/04*** | (2006.01) |
| ***C12N 15/86*** | (2006.01) |

(52) U.S. Cl.

CPC ........ *A61K 39/3955* (2013.01); *A61K 31/519* (2013.01); *A61K 31/7105* (2013.01); *A61K 35/761* (2013.01); *A61K 39/0011* (2013.01); *A61K 39/21* (2013.01); *A61P 35/00* (2018.01); *A61P 37/04* (2018.01); *C12N 15/86* (2013.01); *A61K 2039/53* (2013.01); *A61K 2039/6037* (2013.01); *A61K 2039/627* (2013.01); *C12N 2710/10343* (2013.01); *C12N 2770/36134* (2013.01); *C12N 2770/36143* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,656,127 | A | 4/1987 | Mundy |
| 4,722,848 | A | 2/1988 | Paoletti et al. |
| 4,837,028 | A | 6/1989 | Allen |
| 5,019,369 | A | 5/1991 | Presant et al. |
| 5,204,253 | A | 4/1993 | Sanford et al. |
| 5,217,879 | A | 6/1993 | Huang et al. |
| 5,240,846 | A | 8/1993 | Collins et al. |
| 5,279,833 | A | 1/1994 | Rose |
| 5,505,947 | A | 4/1996 | Johnston et al. |
| 5,580,859 | A | 12/1996 | Felgner et al. |
| 5,589,466 | A | 12/1996 | Felgner et al. |
| 5,622,931 | A | 4/1997 | Edgington et al. |
| 5,643,576 | A | 7/1997 | Johnston et al. |
| 5,662,907 | A | 9/1997 | Kubo et al. |
| 5,814,482 | A | 9/1998 | Dubensky, Jr. et al. |
| 5,843,723 | A | 12/1998 | Dubensky, Jr. et al. |
| 5,849,561 | A | 12/1998 | Falck-Pedersen |
| 5,849,589 | A | 12/1998 | Tedder et al. |
| 5,851,796 | A | 12/1998 | Schatz |
| 5,891,994 | A | 4/1999 | Goldstein |
| 5,972,596 | A | 10/1999 | Pavlakis et al. |
| 6,015,686 | A | 1/2000 | Dubensky, Jr. et al. |
| 6,037,135 | A | 3/2000 | Kubo et al. |
| 6,083,716 | A | 7/2000 | Wilson et al. |
| 6,090,406 | A | 7/2000 | Popescu et al. |
| 6,193,981 | B1 | 2/2001 | Goldstein |
| 6,296,854 | B1 | 10/2001 | Pushko et al. |
| 6,312,946 | B1 | 11/2001 | Yeh et al. |
| 6,365,394 | B1 | 4/2002 | Gao et al. |
| 6,376,236 | B1 | 4/2002 | Dubensky, Jr. et al. |
| 6,413,935 | B1 | 7/2002 | Sette et al. |

(Continued)

FOREIGN PATENT DOCUMENTS

| | | | |
|---|---|---|---|
| CA | 2705787 | A1 | 6/2009 |
| CN | 101198620 | A | 6/2008 |

(Continued)

OTHER PUBLICATIONS

PCT/US2019/060355—International Serch Report and Written Opinion, Feb. 10, 2020, 20 pages.

(Continued)

*Primary Examiner* — Stacy B Chen

(74) *Attorney, Agent, or Firm* — Goodwin Procter LLP

(57) ABSTRACT

Disclosed herein are vectors that include alphavirus-based expression platforms. Also disclosed are methods associated with the alphavirus-based expression platforms and co-administration of an inhibitor of Type I interferon signaling.

18 Claims, 56 Drawing Sheets

Specification includes a Sequence Listing.

(56) References Cited

U.S. PATENT DOCUMENTS 6,514,731 B1 2/2003 Valenzuela et al.
6,531,135 B1 3/2003 Johnston et al.
6,610,321 B2 8/2003 Huang et al.
6,770,283 B1 8/2004 Garoff et al.
6,783,939 B2 8/2004 Olmsted et al.
7,078,218 B2 7/2006 Smith et al.
7,202,351 B1 4/2007 Sette et al.
7,283,337 B2 10/2007 Sakai et al.
7,285,265 B2 10/2007 Vogels et al.
7,291,498 B2 11/2007 Roy et al.
7,344,872 B2 3/2008 Gao et al.
7,468,181 B2 12/2008 Vogels et al.
7,531,180 B2 5/2009 Polo et al.
7,541,038 B2 6/2009 Kovacs et al.
7,557,200 B2 7/2009 Wu et al.
7,572,453 B2 8/2009 Polo et al.
7,572,628 B2 8/2009 Dubensky, Jr. et al.
7,605,235 B2 10/2009 Anderson et al.
7,732,129 B1 6/2010 Zhang et al.
7,744,900 B2 6/2010 Dubensky, Jr. et al.
7,771,979 B2 8/2010 Polo et al.
7,820,440 B2 10/2010 Vogels et al.
7,820,441 B2 10/2010 Chamberlain et al.
7,838,277 B2 11/2010 Gao et al.
7,850,977 B2 12/2010 Kamrud et al.
7,888,472 B2 2/2011 Sette et al.
8,052,967 B2 11/2011 Vogels et al.
8,093,021 B2 1/2012 Hurtado et al.
8,119,336 B2 2/2012 Sampath et al.
8,158,418 B2 4/2012 Polo et al.
8,216,834 B2 7/2012 Colloca et al.
8,252,574 B2 8/2012 Mason et al.
8,318,677 B2 11/2012 Weinschenk et al.
8,426,188 B2 4/2013 Weaver et al.
8,460,913 B2 6/2013 Kamrud et al.
8,614,082 B2 12/2013 Frolov et al.
8,617,533 B2 12/2013 Smith et al.
8,637,313 B2 1/2014 Chamberlain et al.
8,647,864 B2 2/2014 Polo et al.
8,673,319 B2 3/2014 Colloca et al.
8,680,258 B2 3/2014 Coffield et al.
8,691,563 B2 4/2014 Pushko et al.
8,722,044 B2 5/2014 Almagro et al.
8,951,525 B2 2/2015 Almagro et al.
8,961,995 B2 2/2015 Frolov et al.
8,999,333 B2 4/2015 Almagro et al.
9,017,696 B2 4/2015 Draper et al.
9,024,001 B2 5/2015 Tang et al.
9,101,572 B2 8/2015 Pushko et al.
9,115,402 B2 8/2015 Hacohen et al.
9,192,661 B2 11/2015 Jain et al.
9,217,159 B2 12/2015 Roy et al.
9,234,181 B2 1/2016 Tang et al.
9,249,191 B2 2/2016 Ueno et al.
9,254,265 B2 2/2016 Geall et al.
9,255,126 B2 2/2016 Polo et al.
9,273,288 B2 3/2016 Mason et al.
9,295,646 B2 3/2016 Brito et al.
9,340,830 B2 5/2016 Lipson et al.
9,353,353 B2 5/2016 Nabel et al.
9,402,888 B2 8/2016 Ertl et al.
9,416,370 B2 8/2016 Smith et al.
9,453,240 B2 9/2016 Chamberlain et al.
9,486,519 B2 11/2016 Sahin et al.
9,487,563 B2 11/2016 Nabel et al.
9,512,190 B2 12/2016 Ueno et al.
9,580,690 B2 2/2017 Weaver et al.
9,714,435 B2 7/2017 Dicks et al.
9,770,463 B2 9/2017 Geall et al.
9,795,668 B2 10/2017 Jain et al.
9,801,897 B2 10/2017 Geall et al.
10,055,540 B2 8/2018 Yelensky et al.
10,092,636 B2 10/2018 Binder
10,238,733 B2 3/2019 Brito et al.
10,240,128 B2 3/2019 Thirion et al.
10,487,332 B2 11/2019 Geall
10,532,067 B2 1/2020 Geall et al.
11,085,084 B2 8/2021 Diehn et al.
11,504,421 B2 11/2022 Blair et al.
11,510,973 B2 11/2022 Blair et al.
12,109,257 B2 10/2024 Blair et al.
2002/0065241 A1 5/2002 Shankara
2002/0119127 A1 8/2002 Sette et al.
2002/0137081 A1 9/2002 Bandman
2003/0044774 A1 3/2003 Valenzuela et al.
2003/0072767 A1 4/2003 Gaiger et al.
2003/0148262 A1 8/2003 Polo et al.
2003/0232324 A1 12/2003 Polo et al.
2004/0037843 A1 2/2004 Fikes et al.
2004/0115625 A1 6/2004 Ebner
2004/0248113 A1 12/2004 Sette et al.
2005/0003505 A1 1/2005 Marasco et al.
2005/0123555 A1 6/2005 Olmsted et al.
2005/0196754 A1 9/2005 Drmanac et al.
2005/0271676 A1 12/2005 Sette et al.
2006/0051405 A1 3/2006 MacLachlan et al.
2006/0083716 A1 4/2006 Kaufman et al.
2006/0093623 A1 5/2006 Andrieu et al.
2006/0198854 A1 9/2006 Pushko
2006/0252077 A1 11/2006 Buzby
2006/0292175 A1 12/2006 Polo et al.
2007/0031442 A1 2/2007 Sewell
2007/0055049 A1 3/2007 Grey et al.
2007/0224201 A1 9/2007 Wu et al.
2007/0231347 A1 10/2007 Wilson et al.
2008/0050393 A1 2/2008 Tang et al.
2008/0206837 A1 8/2008 Vogels et al.
2008/0241189 A1 10/2008 Wilson
2009/0075384 A1 3/2009 Kamrud et al.
2009/0081200 A1 3/2009 Wang
2009/0093050 A1 4/2009 Wu et al.
2009/0118181 A1 5/2009 Walker et al.
2009/0253184 A1 10/2009 Clarke et al.
2009/0305344 A1 12/2009 Polo et al.
2010/0041737 A1 2/2010 Naldini et al.
2010/0068218 A1 3/2010 Sette et al.
2010/0120897 A1 5/2010 Hurtado et al.
2010/0183665 A1 7/2010 Kamrud et al.
2010/0286070 A1 11/2010 Verheyden et al.
2010/0330121 A1 12/2010 Dubensky, Jr. et al.
2011/0052634 A1 3/2011 Weaver et al.
2011/0091496 A1 4/2011 Graham et al.
2011/0117124 A1* 5/2011 Sadoff ..................... A61P 37/04
435/456
2011/0129498 A1 6/2011 Cortese et al.
2011/0142880 A1 6/2011 Lemiale et al.
2011/0217332 A1 9/2011 Colloca et al.
2011/0293637 A1 12/2011 Hacohen et al.
2012/0258126 A1 10/2012 Scholler et al.
2012/0282290 A1 11/2012 Spencer et al.
2012/0328651 A1 12/2012 Colloca et al.
2013/0011426 A1 1/2013 Tureci et al.
2013/0123199 A1 5/2013 Lee
2013/0149375 A1 6/2013 Geall
2013/0171241 A1 7/2013 Geall
2013/0177639 A1 7/2013 Geall et al.
2013/0177640 A1 7/2013 Geall et al.
2013/0189351 A1 7/2013 Geall
2013/0195968 A1 8/2013 Geall et al.
2013/0195969 A1 8/2013 Geall et al.
2013/0202684 A1 8/2013 Geall et al.
2014/0010841 A1 1/2014 Weaver et al.
2014/0141070 A1 5/2014 Geall et al.
2014/0178438 A1 6/2014 Sahin et al.
2014/0227306 A1 8/2014 Ben-Yedidia et al.
2014/0227346 A1 8/2014 Geall et al.
2014/0234304 A1 8/2014 Almagro et al.
2014/0242152 A1 8/2014 Geall et al.
2014/0248314 A1 9/2014 Swanson et al.
2014/0255472 A1 9/2014 Geall et al.
2014/0271829 A1 9/2014 Lilja et al.
2014/0328793 A1 11/2014 Gavegnano et al.
2015/0001108 A1 1/2015 Lee et al.
2015/0110831 A1 4/2015 Gilbert et al.

(56) References Cited

U.S. PATENT DOCUMENTS

| | | | |
|---|---|---|---|
| 2015/0125465 | A1 | 5/2015 | Binder et al. |
| 2015/0125477 | A1 | 5/2015 | Kuttruff-Coqui et al. |
| 2015/0140068 | A1 | 5/2015 | Barnett et al. |
| 2015/0167003 | A1 | 6/2015 | Naldini et al. |
| 2015/0307897 | A1 | 10/2015 | Soden et al. |
| 2016/0008447 | A1 | 1/2016 | Hacohen et al. |
| 2016/0074506 | A1 | 3/2016 | Jain et al. |
| 2016/0101170 | A1 | 4/2016 | Hacohen et al. |
| 2016/0199513 | A1 | 7/2016 | Bancel et al. |
| 2016/0289674 | A1 | 10/2016 | Bancel et al. |
| 2016/0331822 | A1 | 11/2016 | Hacohen et al. |
| 2016/0339090 | A1 | 11/2016 | Hacohen et al. |
| 2016/0354409 | A1 | 12/2016 | Wang et al. |
| 2017/0028044 | A1 | 2/2017 | Soon-Shiong et al. |
| 2017/0199961 | A1 | 7/2017 | Yelensky et al. |
| 2017/0212984 | A1 | 7/2017 | Yelensky et al. |
| 2017/0340721 | A1 | 11/2017 | Volkmann et al. |
| 2018/0000913 | A1 | 1/2018 | Hacohen et al. |
| 2018/0008690 | A1 | 1/2018 | Ng et al. |
| 2018/0050059 | A1 | 2/2018 | Geall et al. |
| 2018/0055922 | A1 | 3/2018 | Hacohen et al. |
| 2018/0153975 | A1 | 6/2018 | Fritsch et al. |
| 2018/0363066 | A1 | 12/2018 | Chalmers et al. |
| 2019/0025308 | A1 | 1/2019 | Cummings et al. |
| 2019/0060432 | A1 | 2/2019 | Hacohen et al. |
| 2019/0134184 | A1 | 5/2019 | Yu et al. |
| 2019/0256924 | A1 | 8/2019 | Vogelstein et al. |
| 2019/0270766 | A1 | 9/2019 | Hogrefe et al. |
| 2020/0010849 | A1 | 1/2020 | Blair et al. |
| 2020/0197500 | A1 | 6/2020 | Blair et al. |
| 2021/0113673 | A1 | 4/2021 | Boucher et al. |
| 2021/0213122 | A1 | 7/2021 | Blair et al. |
| 2022/0090138 | A1 | 3/2022 | Jooss et al. |
| 2022/0226453 | A1 | 7/2022 | Blair et al. |
| 2023/0040907 | A1 | 2/2023 | Levin et al. |
| 2024/0067985 | A1 | 2/2024 | Blair et al. |
| 2024/0100139 | A1 | 3/2024 | Juneja |
| 2025/0121052 | A1 | 4/2025 | Gitlin et al. |
| 2025/0249084 | A1 | 8/2025 | Blair et al. |
| 2025/0270589 | A1 | 8/2025 | Blair et al. |

FOREIGN PATENT DOCUMENTS

| | | | |
|---|---|---|---|
| CN | 101579528 | A | 11/2009 |
| CN | 101721698 | A | 6/2010 |
| CN | 102170900 | A | 8/2011 |
| CN | 110003314 | A | 7/2019 |
| EP | 1585812 | A2 | 10/2005 |
| EP | 2044947 | A1 | 4/2009 |
| EP | 2370584 | A1 | 10/2011 |
| EP | 2590670 | B1 | 5/2013 |
| EP | 2590676 | B1 | 5/2013 |
| EP | 2917353 | A1 | 9/2015 |
| EP | 2947149 | A1 | 11/2015 |
| FR | 2650840 | A1 | 2/1991 |
| JP | 2007-534295 | A | 11/2007 |
| JP | 2011-504724 | A | 2/2011 |
| JP | 2014-209917 | A | 11/2014 |
| KR | 20060017635 | A | 2/2006 |
| RU | 2206329 | C2 | 6/2003 |
| WO | 1991/02087 | A1 | 2/1991 |
| WO | 1991/06309 | A1 | 5/1991 |
| WO | 1992/15712 | A1 | 9/1992 |
| WO | 1993/24640 | A2 | 12/1993 |
| WO | 1995/07994 | A2 | 3/1995 |
| WO | 1995/13392 | A1 | 5/1995 |
| WO | 1996/13597 | A2 | 5/1996 |
| WO | 1996/18373 | A1 | 6/1996 |
| WO | 9618372 | A2 | 6/1996 |
| WO | 1997/41241 | A1 | 11/1997 |
| WO | 1999016884 | A1 | 4/1999 |
| WO | 2000/018433 | A2 | 4/2000 |
| WO | 2001/055177 | A2 | 8/2001 |
| WO | 2001054719 | A2 | 8/2001 |
| WO | 2001/073027 | A2 | 10/2001 |
| WO | 2003/083065 | A2 | 10/2003 |
| WO | 2004/023973 | A2 | 3/2004 |
| WO | 2004/055166 | A2 | 7/2004 |
| WO | 2005/016961 | A1 | 2/2005 |
| WO | 2005/033265 | A2 | 4/2005 |
| WO | 2005/071093 | A2 | 8/2005 |
| WO | 2006/078294 | A2 | 7/2006 |
| WO | 2006/090090 | A2 | 8/2006 |
| WO | 2007/024708 | A2 | 3/2007 |
| WO | 2007/047749 | A1 | 4/2007 |
| WO | 2008/122811 | A2 | 10/2008 |
| WO | 2008/145685 | A1 | 12/2008 |
| WO | 2009/079185 | A2 | 6/2009 |
| WO | 2011/128704 | A1 | 10/2011 |
| WO | 2011/143656 | A2 | 11/2011 |
| WO | 2012/006359 | A1 | 1/2012 |
| WO | 2012/006377 | A2 | 1/2012 |
| WO | 2012/006376 | A3 | 4/2012 |
| WO | 2012/172058 | A1 | 12/2012 |
| WO | 2012/172277 | A1 | 12/2012 |
| WO | 2014/072929 | A1 | 5/2014 |
| WO | 2014/168874 | A2 | 10/2014 |
| WO | 2015/085233 | A1 | 6/2015 |
| WO | 2015/095811 | A2 | 6/2015 |
| WO | 2016044530 | A1 | 3/2016 |
| WO | 2016/085904 | A1 | 6/2016 |
| WO | 2016/100975 | A1 | 6/2016 |
| WO | 2016/100977 | A1 | 6/2016 |
| WO | 2016/122414 | A1 | 8/2016 |
| WO | 2016/124670 | A1 | 8/2016 |
| WO | 2016/154047 | A2 | 9/2016 |
| WO | 2016/154246 | A1 | 9/2016 |
| WO | 2016/187508 | A3 | 1/2017 |
| WO | 2017/106638 | A1 | 6/2017 |
| WO | 2017/151940 | A2 | 9/2017 |
| WO | 2017/173321 | A1 | 10/2017 |
| WO | 2017/184590 | A1 | 10/2017 |
| WO | 2017/192924 | A1 | 11/2017 |
| WO | 2017/220463 | A1 | 12/2017 |
| WO | 2018/028438 | A1 | 2/2018 |
| WO | 2018/039131 | A1 | 3/2018 |
| WO | 2018/098362 | A1 | 5/2018 |
| WO | 2018/102585 | A1 | 6/2018 |
| WO | 2018/104911 | A1 | 6/2018 |
| WO | 2018/116193 | A1 | 6/2018 |
| WO | 2018/119115 | A1 | 6/2018 |
| WO | 2018/187356 | A2 | 10/2018 |
| WO | 2018195357 | A1 | 10/2018 |
| WO | 2018208856 | A1 | 11/2018 |
| WO | 2018/227030 | A1 | 12/2018 |
| WO | 2018/232330 | A1 | 12/2018 |
| WO | 2019/090156 | A1 | 5/2019 |
| WO | 2019/170773 | A1 | 9/2019 |
| WO | 2019/226939 | A1 | 11/2019 |
| WO | 2019/226941 | A1 | 11/2019 |
| WO | 2020181240 | A1 | 9/2020 |
| WO | 2020/243719 | A1 | 12/2020 |
| WO | 2021/003348 | A1 | 1/2021 |
| WO | 2021/092095 | A1 | 5/2021 |
| WO | 2021/119545 | A1 | 6/2021 |
| WO | 2021/142437 | A1 | 7/2021 |
| WO | 2021203104 | A1 | 10/2021 |
| WO | 2021216775 | A2 | 10/2021 |
| WO | 2021236854 | A1 | 11/2021 |
| WO | 2022/032196 | A2 | 2/2022 |
| WO | 2021118226 | A1 | 6/2022 |
| WO | 2024238412 | A1 | 11/2024 |

OTHER PUBLICATIONS

Ngo et al., "CNTO 859, a humanized anti-tissue factor monoclonal antibody, is a potent inhibitor of breast cancer metastasis and tumor growth in xenograft models," International Journal of Cancer, vol. 120, No. 6, pp. 1261-1267, 2007.

Hong et al, Immuno-PET of Tissue Factor in Pancreatic Cancer, J Nucl Med, vol. 53, No. 11, pp. 1748-1754, 2012.

(56) References Cited

OTHER PUBLICATIONS

Trail et al., "Antibody drug conjugates for treatment of breast cancer. Novel targets and diverse approaches in ADC design," Pharmacol. Ther., vol. 181, pp. 126-142, 2018.
De Graaf et al., Beta-Glucuronidase-Mediated Drug Release, Curr Pharm Des., vol. 8, pp. 1391-1403, 2002.
Chari et al., Immunoconjugates Containing Novel Maytansinoids: Promising Anticancer Drugs, Cancer Research, vol. 52, pp. 127-131, 1992.
Kovtun et al., "Antibody-Mytansinoid Conjugates Designed to Bypass Multidrug Resistance," Cancer Research vol. 70, No. 6, pp. 2528-2537, 2010.
Vitetta et al., "Redesigning Nature's Poisons to Create Anti-Tumor Reagents," Science vol. 238, No. 4830, pp. 1098-1104, 1987.
Junutula et al., "Rapid identification of reactive cysteine residues for site-specific labeling of antibody-Fabs," Journal of Immunological Methods 332, No. 1-2 (2008): 41-52.
Junutula et al., "Site-specific conjugation of a cytotoxic drug to an antibody improves the therapeutic index." Nature Biotechnology 26, No. 8 (2008): 925.
Hofer et al., "An engineered selenocysteine defines a unique class of antibody derivatives," Proc. Natl. Acad. Sci. USA, 2008, 105:12451-12456.
Hofer et al., Molecularly defined antibody conjugation through a selenocysteine interface, Biochemistry, vol. 48, No. 50, p. 12047-12057, 2009.
Hjortoe et al., Tissue factor-factor VIIa-specific up-regulation of IL-8 expression in MDA-MB-231 cells is mediated by PAR-2 and results in increased cell migration, Blood, 2004, vol. 103, No. 8, pp. 3029-3037.
Sakurai et al., "Expression of Tissue Factor in Epithelial Ovarian Carcinoma is Involved in the Development of Venous Thromboembolism," International Journal of Gynecologic Cancer, vol. 27, No. 1, pp. 37-43, 2017.
Cocco et al., "Expression of Tissue factor in Adenocarcinoma and Squamous Cell Carcinoma of the Uterine Cervix: Implications for immunotherapy with hI-con1, a factor VII-IgGFc chimeric protein targeting tissue factor," BMC Cancer, vol. 11 p. 263, 2011.
Christensen et al., Urokinase-type plasminogen activator receptor (uPAR), tissue factor (TF) and epidermal growth factor receptor (EGFR): tumor expression patterns and prognostic value in oral cancer, BMC Cancer, vol. 17, p. 572, 2017.
Yao et al., Tissue Factor and VEGF Expression in Prostate Carcinoma A Tissue Microarray Study, Cancer Invest., vol. 27, pp. 430-434, 2009.
Abdulkadir et al., "Tissue factor expression and angiogenesisin human prostate carcinoma," Human Pathology 31, No. 4 (2000): 443-447.
Zhang et al., "Pathological expression of tissue factor confers promising antitumor response to a novel therapeutic antibody SC1 in triple negative breast cancer and pancreatic adenocarcinoma," Oncotarget vol. 8, No. 35, pp. 59086-59102, 2017.
Guan et al., "Tissue factor expression and angiogenesis in human glioma." Clinical Biochemistry 35, No. 4 (2002): 321-325.
Carneiro-Lobo et al., Ixolaris, a tissue factor inhibitor, blocks primary tumor growth and angiogenesis in a glioblastoma model, J Thromb Haemost, 2009, 7:1855-1864.
Yeh et al., "Upregulation of Tissue Factor by Activated Stat3 Contributes to Malignant Pleural Effusion Generation via Enhancing Tumor Metastasis and Vascular Permeability in Lung Adenocarcinoma," PLoS One, vol. 8, No. 9, p. e75287, 2013.
Regina et al., "Increased tissue factor expression is associated with reduced survival in non-small cell lung cancer and with mutations of TP53 and PTEN," Clinical Chemistry, vol. 55, No. 10, pp. 1834-1842, 2009.
Lo et al., "Tissue factor expression in the metaplasia-adenoma-carcinoma sequence of gastric cancer in a European population," British Journal of Cancer vol. 107, No. 7, pp. 1125-1130, 2012.
Chen et al., "Immunolocalisation of tissue factor in esophageal cancer is correlated with intratumoral angiogenesis and prognosis of the patient." Acta Histochemica 112, No. 3 (2010): 233-239.
Patry et al., "Tissue factor expression correlates with disease-specific survival in patients with node-negative muscle-invasive bladder cancer," International Journal of Cancer, vol. 122, No. 7, pp. 1592-1597, 2008.
Bromberg et al., Tissue factor promotes melanoma metastasis by a pathway independent of blood coagulation, Proc Natl Acad Sci U S A., 1995, 92:8205-8209.
Silva et al., "Increased Tissue Factor Expression is an Independent Predictor of Mortality in Clear Cell Carcinoma of the Kidney," Int Braz J Urol., 2014, 40:499-506.
Van Den Berg et al., "The relationship between tissue factor and cancer progression: insights from bench and bedside," Blood vol. 119, No. 4, pp. 924-932, 2012.
Tripisciano et al., "Different Potential of Extracellular Vesicles to Support Thrombin Generation: Contributions of Phosphatidylserine, Tissue Factor, and Cellular Origin," Scientific Reports vol. 7, No. 1, pp. 1-11, 2017.
Teplyakov et al., "Crystal structure of tissue factor in complex with antibody 10H10 reveals the signaling epitope," Cellular Signalling vol. 36, pp. 139-144, 2017.
Liepe et al., "A large fraction of HLA class I ligands are proteasome-generated spliced peptides," Science vol. 354, No. 6310, Oct. 21, 2016.
Smith et al., "Comparison of biosequences," Advances in Applied Mathematics vol. 2, No. 4, pp. 482-489, 1981.
Needleman et al., "A General Method Applicable to the Search for Similarities in the Amino Acid Sequence of Two Proteins," Journal of Molecular Biology, vol. 48, No. 3, pp. 443-453, 1970.
Pearson et al., "Improved tools for biological sequence comparison," Proceedings of the National Academy of Sciences, vol. 85, No. 8, pp. 2444-2448, 1988.
Altschul et al., "Basic Local Alignment Search Tool." Journal of Molecular Biology vol. 215, Issue 3 (1990): 403-410.
Kornher et al., "Mutation detection using nucleotide analogs that alter electrophoretic mobility," Nucleic Acids Research vol. 17, No. 19, pp. 7779-7784, 1989.
Sokolov, "Primer extension technique for the detection of single nucleotide in genomic DNA," Nucleic Acids Research, vol. 18, No. 12, p. 3671, 1990.
Syvänen et al., "A Primer-Guided Nucleotide Incorporation Assay in the Genotyping of Apolipoprotein E," Genomics 8, No. 4 (1990): 684-692.
Kuppuswamy et al., "Single nucleotide primer extension to detect genetic diseases: experimental application to hemophilia B (factor IX) and cystic fibrosis genes," Proceedings of the National Academy of Sciences vol. 88, No. 4, pp. 1143-1147, 1991.
Prezant et al., "Trapped-Oligonucleotide Nucleotide Incorporation (TONI) Assay, a Simple Method for Screening Point Mutations," Human Mutation 1, No. 2 (1992): 159-164.
Ugozzoli et al., "Detection of specific alleles by using allele-specific primer extension followed by capture on solid support," Genetic Analysis: Biomolecular Engineering 9, No. 4 (1992): 107-112.
Nyrén et al., "Solid phase DNA minisequencing by an enzymatic luminometric inorganic pyrophosphate detection assay." Analytical Biochemistry 208, No. 1 (1993): 171-175.
Syvänen et al., "Identification of Individuals by Analysis of Biallelic DNA Markers, Using PCR and Solid-Phase Minisequencing," American Journal of Human Genetics vol. 52, No. 1, p. 46 1993.
Merrifield, "Solid phase synthesis." Science 232 (1986): 341-348.
Dupuis et al., "Dendritic cells internalize vaccine adjuvant after intramuscular injection," Cellular Immunology 186, No. 1 (1998), 18-27.
Allison, "The mode of action of immunological adjuvants," Developments in Biological Standardization 92 (1998): 3-11.
Gabrilovich et al., "IL-12 and Mutant P53 Peptide-Pulsed Dendritic Cells for the Specific Immunotherapy of Cancer," Journal of Immunotherapy, vol. 19, No. 6 (1996): 414-418.
Tatsis et al., "Adenoviruses as vaccine vectors," Molecular Therapy vol. 10, No. 4, pp. 616-629, 2004.

(56) References Cited

OTHER PUBLICATIONS

Hu et al., "Immunization Delivered by Lentiviral Vectors for Cancer and Infectious Diseases, " Immunological Reviews, vol. 239, Issue 1, pp. 45-61, 2011.
Lundstrom, Kenneth. "Alphavirus-based vaccines." Current opinion in molecular therapeutics 4, No. 1 (2002): 28-34.
Alexander et al., "Linear PADRE T helper epitope and carbohydrate B cell epitope conjugates induce specific high titer IgG antibody responses." The Journal of Immunology 164, No. 3 (2000): 1625-1633.
Kim et al., "Neopepsee: accurate genome-level prediction of neoantigens by harnessing sequence and amino acid immunogenicity information." Annals of Oncology 29, No. 4 (2018): 1030-1036.
Ott et al., "An immunogenic personal neoantigen vaccine for patients with melanoma." Nature 547, No. 7662 (2017): 217-221.
Avogadri F, et al., Alphavirus replicon particles expressing TRP-2 provide potent therapeutic effect on melanoma through activation of humoral and cellular immunity. PLoS One. Sep. 10, 2010;5(9)1-8.
Carroll et al., "Alphavirus replicon-based adjuvants enhance the immunogenicity and effectiveness of Fluzone in rhesus macaques." Vaccine 29, No. 5 (2011): 931-940.
Fluet et al., "Effects of rapid antigen degradation and VEE glycoprotein specificity on immune responses induced by a VEE replicon vaccine." Virology 370, No. 1 (Jan. 2008): 22-32.
Ljungberg et al,. "Increased immunogenicity of a DNA-launched Venezuelan equine encephalitis virus-based replicon DNA vaccine." Journal of virology 81, No. 24 (2007): 13412-13423.
Ogawa et al., "An Attempt of Cytokine Gene Therapy Using Adenovirus Vectors," Partial Translation of: Biotherapy, 1998, vol. 12 No. 5, p. 785-787.
Thompson et al., "The contribution of type I interferon signaling to immunity induced by alphavirus replicon vaccines." Vaccine 26, No. 39 (2008): 4998-5003.
Carter et al., "Absolute quantification of somatic DNA alterations in human cancer," Nature Biotechnology vol. 30, No. 5, 413-421, 2012.
Qiu et al., "Reviving virus based cancer vaccines by using cytomegalovirus vectors expressing modified tumor antigens," Oncolmmunology vol. 5, No. 1, p. e1056974, Jan. 2, 2016.
Farina et al., "Replication-Defective Vector Based on a Chimpanzee Adenovirus," Journal of Virology vol. 75, No. 23, pp. 11603-11613, 2001.
Ljungberg et al., "Self-replicating alphavirus RNA vaccines," Expert Review of Vaccines vol. 14, No. 2, pp. 177-194, Feb. 1, 2015.
Lundstrom, "Alphavirus-Based Vaccines, " Viruses vol. 6, No. 6, pp. 2392-2415, 2014.
Geall et al., "Nonviral delivery of self-amplifying RNA vaccines," Proceedings of the National Academy of Sciences, vol. 109, Issue 36, pp. 14604-14609, 2012.
Rodriguez et al., "DNA Immunization with Minigenes: Low Frequency of Memory Cytotoxic T Lymphocytes and Inefficient Antiviral Protection Are Rectified by Ubiquitination," Journal of Virology vol. 72, No. 6, pp. 5174-5181, 1998.
Velders et al., "Defined Flanking Spacers and Enhanced Proteolysis Is Essential for Eradication of Established Tumors by an Epitope String DNA Vaccine," The Journal of Immunology, vol. 166, No. 9, pp. 5366-5373, 2001.
Kreiter et al., "Increased Antigen Presentation Efficiency by Coupling Antigens to MHC Class I Trafficking Signals," The Journal of Immunology, vol. 180, No. 1, pp. 309-318, 2008.
Rodriguez et al., "DNA Immunization: Ubiquitination of a Viral Protein Enhances Cytotoxic T-Lymphocyte Induction and Antiviral Protection but Abrogates Antibody Induction," Journal of Virology vol. 71, No. 11, pp. 8497-8503, 1997.
James et al., "Tetramer-guided epitope mapping reveals broad, individualized repertoires of tetanus toxin-specific CD4+ T cells and suggests HLA-based differences in epitope recognition," International Immunology vol. 19, No. 11, pp. 1291-1301, 2007.
Jayaraman et al., "Maximizing the Potency of siRNA Lipid Nanoparticles for Hepatic Gene Silencing In Vivo," Angewandte Chemie vol. 51, pp. 8529-8533, 2012.
Démoulins et al., "Polyethylenimine-based polyplex delivery of self-replicating RNA vaccines," Nanomedicine: Nanotechnology, Biology and Medicine vol. 12, No. 3, pp. 711-722, Apr. 1, 2016.
Chahal et al., "Dendrimer-RNA nanoparticles generate protective immunity against lethal Ebola, H1N1 influenza, and Toxoplasma gondii challenges with a single dose," Proceedings of the National Academy of Sciences vol. 113, No. 29 E4133-E4142, Jul. 19, 2016.
Vajdy et al., "Mucosal adjuvants and delivery systems for protein-, DNA- and RNA-based vaccines," Immunology and Cell Biology, vol. 82, No. 6, pp. 617-627, 2004.
Fleeton et al., "Self-Replicative RNA Vaccines Elicit Protection against Influenza A Virus, Respiratory Syncytial Virus, and a Tickborne Encephalitis Virus," The Journal of Infectious Diseases vol. 183, No. 9, pp. 1395-1398, 2001.
Strejan et al., "Suppression of chronic-relapsing experimental allergic encephalomyelitis in strain-13 guinea pigs by administration of liposome-associated myelin basic protein." Journal of Neuroimmunology 7 (1984): 27-41.
Johanning et al., "A Sindbis virus mRNA polynucleotide vector achieves prolonged and high level heterologous gene expression in vivo," Nucleic Aids Research vol. 23, Issue 9, pp. 1495-1501, 1995.
Martinon et al., "Induction of virus-specific cytotoxic T lymphocytes in vivo by liposome-entrapped mRNA," European Journal of Immunology 23, No. 7 (1993): 1719-1722.
Leitner et al., "DNA and RNA-based vaccines: principles, progress and prospects," Vaccine vol. 18, No. 9-10, pp. 765-777, 1999.
Del Val et al., "Efficient Processing of an Antigenic Sequence for Presentation by MHC Class I Molecules Depends on Its Neighboring Residues in the Protein," Cell vol. 66, No. 6, pp. 1145-1153, 1991.
Holzhütter et al., "A Theoretical Approach Towards the Identification of Cleavage-Determining Amino Acid Motifs of the 20S Proteasome," Journal of Molecular Biology, vol. 286, Issue 4, pp. 1251-1265, 1999.
Nussbaum et al., "Cleavage motifs of the yeast 20S proteasome β subunits deduced from digests of enolase 1," Proceedings of the National Academy of Sciences, vol. 95, No. 21, pp. 12504-12509, 1998.
Eggers et al., "The Cleavage Preference of the Proteasome Governs the Yield of Antigenic Peptides," The Journal of Experimental Medicine vol. 182, No. 6, pp. 1865-1870, 1995.
Borthwick et al., "Vaccine-elicited human T cells recognizing conserved protein regions inhibit HIV-1." Molecular therapy 22, No. 2 (2014): 464-475.
Ager et al., "31st Annual Meeting and Associated Programs of the Society for Immunotherapy of Cancer (SITC 2016): part two," in Journal for Immuno Therapy of Cancer, vol. 4, Supplement 1, p. 73, 2016.
Warimwe et al. "Immunogenicity and efficacy of a chimpanzee adenovirus-vectored Rift Valley fever vaccine in mice," Virology Journal vol. 10, No. 1, pp. 1-9, 2013.
Cappuccini et al. "Immunogenicity and efficacy of the novel cancer vaccine based on simian adenovirus and MVA vectors alone and in combination with PD-1 mAb in a mouse model of prostate cancer," Cancer Immunol. Immunother. vol. 65, No. 6, pp. 701-713, Apr. 6, 2016.
Aurisicchio et al., "Immunogenicity and Therapeutic Efficacy of a Dual-Component Genetic Cancer Vaccine Cotargeting Carcinoembryonic Antigen and HER2/neu in Preclinical Models," Human Gene Therapy, vol. 25, Issue 2, pp. 121-131, Feb. 2014.
Morris et al. "Simian adenoviruses as vaccine vectors." Future Virology, vol. 11, No. 9 pp. 649-659, Sep. 15, 2016.
Letourneau et al. "Design and Pre-Clinical Evaluation of a Universal HIV-1 Vaccine," PloS ONE, vol. 2, No. 10, p. e984, 2007.
Colloca et al., "Vaccine Vectors Derived from a Large Collection of Simian Adenoviruses Induce Potent Cellular Immunity Across Multiple Species," Science Translational Medicine, vol. 4, No. 115, 115ra2, 2012.

(56) References Cited

OTHER PUBLICATIONS

Levy et al. "A melanoma multiepitope polypeptide induces specific CD8+ T-cell response," Cellular Immunology, vol. 250, No. 1-2, pp. 24-30, 2007.
Tatsis et al. "Chimpanzee-origin adenovirus vectors as vaccine carriers," Gene Therapy vol. 13, No. 5, pp. 421-429, 2006.
Zappasodi et al., "Alphavirus-based vaccines in melanoma: rationale and potential improvements in Immunotherapeutic combinations." Immunotherapy 7, No. 9 (Sep. 2015): 981-997.
Riabov et al., "Anti-tumor effect of the alphavirus-based virus-like particlevector expressing prostate-specific antigen in a HLA-DR transgenic mouse model of prostate cancer." Vaccine 33, No. 41 (Oct. 5, 2015): 5386-5395.
Fang et al., "Stable antibody expression at therapeutic levels using the 2A peptide." Nature biotechnology 23, No. 5 (2005): 584-590.
Wu et al., "Targeting genes: delivery and persistent expression of a foreign gene driven by mammalian regulatory elements in vivo." Journal of Biological Chemistry 264, No. 29 (1989): 16985-16987.
Fisher et al., "The transmembrane domain of diphtheria toxin improves molecular conjugate gene transfer." Biochemical Journal 321, No. 1 (1997): 49-58.
Szoka et al., "Comparative properties and methods of preparation of lipid vesicles (liposomes)." Annual review of biophysics and bioengineering 9, No. 1 (1980): 467-508.
Wolff et al., "Direct gene transfer into mouse muscle in vivo." Science 247, No. 4949 (1990): 1465-1468.
Felgner et al., "Lipofection: a highly efficient, lipid-mediated DNA-transfection procedure." Proceedings of the National Academy of Sciences 84, No. 21 (1987): 7413-7417.
Mannino et al., "Liposome mediated gene transfer." Biotechniques 6, No. 7 (1988): 682-690.
Konarska et al., "Recognition of cap structure in splicing in vitro of mRNA precursors." Cell 38, No. 3 (1984): 731-736.
Huang, "Sindbis virus vectors for expression in animal cells." Current Opinion in Biotechnology 7, No. 5 (1996): 531-535.
Wan et al., "High-sensitivity monitoring of ctDNA by patient-specific sequencing panels and integration of variant reads." bioRxiv (2019): 759399, pp. 1-37.
Wang et al., "Identification of T Cell Receptors Targeting KRAS-Mutated Human Tumors", Cancer Immunology Research 4(3) Mar. 2016, pp. 204-214.
PCT/US2019/060355—International Preliminary Report on Patentability, May 11, 2021, 15 pages.
Hacohen et al., "Getting personal with neoantigen-based therapeutic cancer vaccines." Cancer immunology research 1, No. 1 (2013): 11-15.
Karasaki et al., "Identification of individual cancer-specific somatic mutations for neoantigen-based immunotherapy of lung cancer." Journal of Thoracic Oncology 11, No. 3 (Mar. 2016): 324-333.
Andreatta et al., "Gapped sequence alignment using artificial neural networks: application to the MHC class I system," Bioinformatics 1 (Feb. 15, 2015): 7 pages.
Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.
Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.
Nielsen et al., "The role of the proteasome in generating cytotoxic T-cell epitopes: insights obtained from improved predictions of proteasomal cleavage," Immunogenetics vol. 57, No. 1-2, pp. 33-41, 2005.
Boisvert et al., "A Quantitative Spatial Proteomics Analysis of Proteome Turnover in Human Cells, " Molecular & Cellular Proteomics, vol. 11, Issue. 3, Mar. 1, 2012.
Duan et al., "Genomic and bioinformatic profiling of mutational neoepitopes reveals new rules to predict anticancer Immunogenicity," Journal of Experimental Medicine vol. 211, No. 11, Oct. 20, 2014.
Calis et al., "Properties of MHC Class I Presented Peptides That enhance immunogenicity." PLoS Comput Biol. vol. 9, Issue 10 (Oct. 24, 2013): e1003266, 13 pages.
Zhang et al., "Intra-tumor Heterogeneity in Localized Lung Adenocarcinomas Delineated by Multi-region Sequencing," Science vol. 346, No. 6206, pp. 256-259, 2014.
Walter et al., "Clonal Architecture of Secondary Acute Myeloid Leukemia," New England Journal of Medicine, vol. 366, Issue 12, pp. 1090-1098, 2012.
Hunt et al., "Characterization of Peptides Bound to the Class I MHC Molecule HLA-A2. 1 by Mass Spectrometry," Science vol. 255, pp. 1261-1263, 1992.
Zarling et al., "Identification of class I MHC-associated phosphopeptides as targets for cancer immunotherapy," Proceedings of the National Academy of Sciences, vol. 103, No. 40, pp. 14889-14894, 2006.
Abelin et al., "Complementary IMAC enrichment methods for HLA-associated phosphopeptide identification by mass spectrometry," Nature Protocols 10(9) (2015): 1308-1318.
Barnstable et al., "Production of Monoclonal Antibodies to Group A Erythrocytes, HLA and Other Human Cell Surface Antigens—New Tools for Genetic Analysis," Cell vol. 14, 9-20, 1978.
Goldman et al., "HLA-DA monoclonal antibodies inhibit the proliferation of normal and chronic granulocytic leukaemia myeloid progenitor cell," British Journal of Haematology 52, No. 3 (1982): 411-420.
Eng et al., "Comet: An open-source MS/MS sequence database search tool," Proteomics vol. 13, No. 1, pp. 22-24, 2013.
Eng et al., "A Deeper Look into Comet—Implementation and Features," Journal of the American Society for Mass Spectrometry vol. 26, No. 11, pp. 1865-1874, 2015.
Käll et al., "Semi-supervised learning for peptide identification from shotgun proteomics datasets," Nature Methods vol. 4, No. 11, pp. 923-925, 2007.
Käll et al., "Assigning Significance to Peptides Identified by Tandem Mass Spectrometry Using Decoy Databases," Journal of Proteome Research vol. 7, No. 01, pp. 29-34, 2008.
Käll et al., "Non-parametric estimation of posterior error probabilities associated with peptides identified by tandem mass spectrometry," Bioinformatics vol. 24, No. 16, pp. i42-i48, 2008.
Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.
Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.
Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.
Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.
Aarnoudse et al., "Tcr Reconstitution in Jurkat Reporter Cells Facilitates the Identification of Novel Tumor Antigens by CDNA Expression Cloning," International Journal of Vancer 99, 7013 (2002).
Alexander et al., "Development of High Potency Universal DR-Restricted Helper Epitopes by Modification of High Affinity DR-Blocking Peptides." Immunity vol. 1, Issue 9 (1994): 751-761.
Banu et al., "Building and Optimizing a Virus-specific T Cell Receptor Library for Targeted Immunotherapy in Viral Infections." Scientific Reports vol. 4, pp. 4166, 2014.
Cornet et al., "Optimal organization of a polypeptide-based candidate cancer vaccine composed of cryptic tumor peptides with enhanced immunogenicity," Vaccine vol. 24, No. 12, pp. 2102-2109, 2006.
Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.

(56) References Cited

OTHER PUBLICATIONS

Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.
Janetzki et al., "Guidelines for the automated evaluation of Elispot assays," Nature Protocols vol. 10, No. 7, pp. 1098-1115, Jul. 2015.
Lyons et al., "Influence of Human CD8 on Antigen Recognition by T-Cell Receptor-Transduced Cells," Cancer Research vol. 66, No. 23, pp. 11455-11461, 2006.
Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.
Panina-Bordignon et al., "Universally immunogenic T cell epitopes: promiscuous binding to human MHC class II and promiscuous recognition by T cells," European Journal of Immunology 19, No. 12 (1989): 2237-2242.
Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.
Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.
Pushko et al., "Replicon-Helper Systems from Attenuated Venezuelan Equine Encephalitis Virus: Expression of Heterologous Genes in Vitro and Immunization against Heterologous Pathogens in Vivo," Virology vol. 239, No. 2, pp. 389-401, 1997.
Strauss et al., "The Alphaviruses: Gene Expression, Replication, and Evolution," Microbiological Reviews, vol. 58, No. 3, pp. 491-562, 1994.
Rhême et al., "Alphaviral cytotoxicity and its implication in vector development," Experimental Physiology vol. 90, No. 1, pp. 45-52, 2005.
Riley et al., "Recent advances in nanomaterials for gene delivery—a review," Nanomaterials, vol. 7, No. 5, p. 94, 2017.
Frolov et al., "Cis-acting RNA elements at the 5' end of Sindbis virus genome RNA regulate minus- and plus-strand RNA synthesis," RNA vol. 7, No. 11, pp. 1638-1651, 2001.
Jose et al., "A structural and functional perspective of alphavirus replication and assembly," Future Microbiology, vol. 4, No. 7, pp. 837-856, 2009.
Li et al., "RSEM: accurate transcript quantification from RNA-Seq data with or without a reference genome." BMC bioinformatics 12, No. 1 (2011): 323, 16 pages.
Pearson et al., "MHC class I-associated peptides derive from selective regions of the human genome," The Journal of Clinical Investigation, vol. 126, No. 12, pp. 4690-4701, Dec. 1, 2016.
Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.
Kreiter et al., "Mutant MHC class II epitopes drive therapeutic immune responses to cancer," Nature, vol. 520, No. 7549, pp. 692-696, Apr. 2015.
Andreatta et al., "Accurate pan-specific prediction of peptide-MHC class II binding affinity with improved binding core identification." Immunogenetics 67, No. 11-12 (Nov. 2015): 641-650.
Nielsen et al., "NN-align. An artificial neural network-based alignment algorithm for MHC class II peptide binding prediction," BMC Bioinformatics, vol. 10, No. 1, p. 296, 2009.
Nielsen et al., "Prediction of MHC class II binding affinity using SMM-align, a novel stabilization matrix alignment method," BMC Bioinformatics, vol. 8, No. 1, pp. 238, 2007.
Zhang, et al., "PEAKS DB: De Novo Sequencing Assisted Database Search for Sensitive and Accurate Peptide Identification," Molecular & Cellular Proteomics vol. 11, No. 4, 2012.
Jensen et al., "Improved methods for predicting peptide binding affinity to MHC class II molecules," Immunology vol. 154, Issue 3, pp. 394-406, 2018.
Abbas et al., "Structure of human IFIT1 with capped RNA reveals adaptable mRNA binding and mechanisms for sensing N1 and N2 ribose 2?-O methylations." Proceedings of the National Academy of Sciences 114, No. 11 (2017): E2106-E2115.
Nezafat et al., "A novel multi-epitope peptide vaccine against cancer: an in silico approach." Journal of theoretical biology 349 (2014): 121-134.
Mohammed et al., "Phosphorylation-dependent interaction between antigenic peptides and MHC class I: a molecular basis for the presentation of transformed self." Nature immunology 9, No. 11 (2008): 1236-1243.
Toes et al., "Protective anti-tumor immunity induced by vaccination with recombinant adenoviruses encoding multiple tumor-associated cytotoxic T lymphocyte epitopes in a string-of-beads fashion." Proceedings of the National Academy of Sciences 94, No. 26 (1997): 14660-14665.
Wei et al., "Dendritic cells expressing a combined PADRE/MUC4-derived polyepitope DNA vaccine induce multiple cytotoxic T-cell responses." Cancer biotherapy & radiopharmaceuticals 23, No. 1 (2008): 121-128.
Meko'o et al., "Immunopreventive effects against murine H22 hepatocellular carcinoma in vivo by a DNA vaccine targeting a gastrin-releasing peptide." Asian Pacific Journal of Cancer Prevention 15, No. 20 (2014): 9039-9043.
Huang et al., "DNA vaccines for cervical cancer." American journal of translational research 2, No. 1 (2010): 75, 13 pages.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs, " Molecular Pharmaceutics 12 (11) ( ): 3986-3998, Nov. 2, 2015.
Koizume et al., "Tissue Factor - Factor VII Complex as a Key Regulator of Ovarian Cancer Phenotypes," Biomarkers in Cancer vol. 7, pp. 1-13, Aug. 5, 2015.
Schumacher et al., "Neoantigens in cancer immunotherapy," Science vol. 348, Issue 6230, pp. 69-74, Apr. 3, 2015.
Rivas et al., "Effect of predicted protein-truncating genetic variants on the human transcriptome," Science vol. 348, No. 6235, pp. 666-669, May 8, 2015.
Sakuma et al., "Lentiviral vectors: basic to translational," Biochemical Journal 443, No. 3 (2012): 603-618.
Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.
Zufferey et al., "Self-Inactivating Lentivirus Vector for Safe and Efficient In Vivo Gene Delivery," Journal of Virology vol. 72, No. 12, pp. 9873-9880, 1998.
Gros et al., "Prospective identification of neoantigen-specific lymphocytes in the peripheral blood of melanoma patients," Nature Medicine vol. 22, Issue 4, pp. 433-438, Feb. 22, 2016.
Strønen et al., "Targeting of cancer neoantigens with donor-derived T cell receptor repertoires," Science 352, No. 6291 (May 19, 2016): 1337-1341.
Lu et al., "Efficient identification of mutated cancer antigens recognized by T cells associated with durable tumor regressions," Clinical Cancer Research vol. 20, No. 13, pp. 3401-3410, 2014.
Stover et al., "New use of BCG for recombinant vaccines," Nature vol. 351, No. 6326, pp. 456-460, 1991.
Boshart et al., "A Very Strong Enhancer is Located Upstream of an Immediate Early Gene of Human Cytomegalovirus," Cell vol. 41, No. 2, 521-530, 1985.
Kost et al., "The nucleotide sequence of the chick cytoplasmic b-actin gene," Nucleic Acids Research vol. 11, No. 23, pp. 8287-8301, 1983.
Shukla et al., "Comprehensive analysis of cancer-associated somatic mutations in class I HLA genes," Nature Biotechnology vol. 33, No. 11. pp. 1152-1158, Nov. 2015.
Mcgranahan et al., "Allele-specific HLA loss and immune escape in lung cancer evolution," Cell vol. 171, No. 6, pp. 1259-1271, 2017.

(56) References Cited

OTHER PUBLICATIONS

Van Loo et al., "Allele-specific copy number analysis of tumors," Proceedings of the National Academy of Sciences, vol. 107, No. 39, pp. 16910-16915, 2010.
Desrichard et al., "Cancer neoantigens and applications for immunotherapy," Clinical Cancer Research vol. 22, No. 4, pp. 807-812, Feb. 15, 2016.
Gubin et al., "Tumor neoantigens: Building a framework for personalized cancer immunotherapy," The Journal of Clinical Investigation, vol. 125, No. 9, pp. 3413-3421, Sep. 2015.
Rizvi et al., "Mutational landscape determines sensitivity to PD-1 blockade in non-small cell lung cancer," Science vol. 348, No. p. 6230, Apr. 3, 2015.
Snyder et al., "Genetic Basis for Clinical Response to CTLA-4 Blockade in Melanoma," New England Journal of Medicine, vol. 371, No. 23, pp. 2189-2199, 2014.
Carreno et al., "A dendritic cell vaccine increases the breadth and diversity of melanoma neoantigen-specific T cells." Science 348, No. 6236 (Apr. 2, 2015): 9 pages.
Tran et al., "Cancer Immunotherapy Based on Mutation-Specific CD4+ T Cells in a Patient with Epithelial Cancer," Science vol. 344, No. 6184, pp. 641-645, 2014.
Lundegaard et al., "State of the art and challenges in sequence based T-cell epitope prediction," Immunome Research vol. 6, No. 2, pp. 1-14, 2010.
Yadav et al., "Predicting immunogenic tumour mutations by combining mass spectrometry and exome sequencing," Nature, vol. 515, No. 7528, pp. 572-576, 2014.
Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.
Van Allen et al., "Genomic correlates of response to CTLA-4 blockade in metastatic melanoma," Science vol. 350, No. 6257, pp. 207-211, Nov. 11, 2015.
Yoshida et al., "Splicing factor mutations and cancer," Wiley Interdisciplinary Reviews: RNA 5, No. 4 (2014): 445-459.
Cancer Genome Atlas Research Network, "Comprehensive molecular profiling of lung adenocarcinoma," Nature, vol. 511, pp. 543-550, 2014.
Rajasagi et al., "Systematic identification of personal tumor-specific neoantigens in chronic lymphocytic leukemia," Blood, vol. 124, No. 3, pp. 453-462, 2014.
Cieslik et al., "The use of exome capture RNA-seq for highly degraded RNA with application to clinical cancer sequencing," Genome Research vol. 25, No. 9, 1372-1381, Sep. 1, 2015.
Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.
Saunders et al., Strelka: accurate somatic small-variant calling from sequenced tumor-normal sample pairs, Bioinformatics vol. 28, No. 14, pp. 1811-1817, 2012.
Cibulskis et al., "Sensitive detection of somatic point mutations in impure and heterogeneous cancer samples," Nature Biotechnology vol. 31, No. 3, pp. 213-219, 2013.
Wilkerson et al., "Integrated RNA and DNA sequencing improves mutation detection in low purity tumors," Nucleic Acids Research, vol. 42, p. e107, 2014.
Mose et al., "ABRA: improved coding indel detection via assembly-based realignment," Bioinformatics, vol. 30, No. 19, pp. 2813-2815, 2014.
Ye et al., "Pindel: a pattern growth approach to detect break points of large deletions and medium sized insertions from paired-end short reads," Bioinformatics vol. 25, No. 21, pp. 2865-2871, 2009.
Lam et al., "Nucleotide-resolution analysis of structural variants using BreakSeq and a breakpoint library," Nature Biotechnology vol. 28, No. 1, pp. 47-55 2010.
Frampton et al., "Development and validation of a clinical cancer genomic profiling test based on massively parallel DNA sequencing," Nature Biotechnology vol. 31, No. 11, 2013.
Boegel et al., "HLA typing from RNA-Seq sequence reads," Genome Medicine vol. 4, Issue 12, 2013.
Liu et al., "ATHLATES: accurate typing of human leukocyte antigen through exome sequencing," Nucleic Acids Research vol. 41, No. 14, 2013.
Mayor et al., "HLA typing for the next generation," PLoS One vol. 10, No. 5, May 27, 2015.
Roy et al., "Assessing long-distance RNA sequence connectivity via RNA-templated DNA-DNA ligation," Elife vol. 4, p. e03700, Apr. 13, 2015.
Song et al., "CLASS: constrained transcript assembly of RNA-seq reads," BMC Bioinformatics, vol. 14, Supp. 5, S14, BioMed Central, 2013.
Maretty et al. "Bayesian transcriptome assembly," Genome Biology vol. 15, No. 10, Oct. 2014.
Pertea et al., "StringTie enables improved reconstruction of a transcriptome from RNA-seq reads," Nature Biotechnology vol. 33, No. 3, pp. 290-295, Mar. 2015.
Roberts et al., "Identification of novel transcripts in annotated genomes using RNA-Seq," Bioinformatics vol. 27, No. 17, pp. 2325-2329, 2011.
Vitting-Seerup et al., "spliceR: an R package for classification of alternative splicing and prediction of coding potential from RNA-seq data," BMC Bioinformatics, vol. 15, Issue 1, pp. 1-7, 2014.
Skelly et al., "A powerful and flexible statistical framework for testing hypotheses of allele-specific gene expression from RNA-seq data," Genome Research vol. 21, No. 10, pp. 1728-1737, 2011.
Anders et al., "HTSeq-a Python framework to work with high-throughput sequencing data." Bioinformatics vol. 31, No. 2 (Jan. 15, 2015): 166-169.
Furney et al., "SF3B1 Mutations Are Associated with Alternative Splicing in Uveal Melanoma," Cancer Discovery vol. 3, Issue 10, pp. 1122-1129, 2013.
Zhou et al., "A Chemical Genetics Approach for the Functional Assessment of Novel Cancer Genes," Cancer Research vol. 75, No. 10, pp. 1949-1958, May 15, 2015.
Maguire et al., "SF3B1 mutations constitute a novel therapeutic target in breast cancer," The Journal of Pathology vol. 235, No. 4 pp. 571-580, Mar. 2015.
Carithers et al., "A Novel Approach to High-Quality Postmortem Tissue Procurement: The GTEx Project," Biopreservation and Biobanking, vol. 13, No. 5, 311-319, Oct. 1, 2015.
Xu et al., "RNA Compass: A Dual Approach for Pathogen and Host Transcriptome Analysis of RNA-Seq Datasets," PloS ONE, vol. 9, Issue 2, p. e89445, 2014.
Y. Kawakami, (2002) "Isoloation of melanoma antigons recognized by T-Cells and development of antigen specific immunotherapy," vol. 15 p. 208-216.
Hung CF, et al. (2007), "DNA vaccines encoding Ii-PADRE generates potent PADRE-specific CD4+ T-cell immune responses and enhances vaccine potency," Mol. Ther., 15(6):1211-9.
Cross et al., (2015) Therapeutic DNA vaccination against colorectal cancer by targeting the MYB oncoprotein., Clin Transl Immunology., 4(1):1-9.
Huang et al, "Adenovirus Early Region 4 Encodes Two Gene Products with Redundant Effects in Lytic Infection", Journal of Virology, vol. 63, No. 6, pp. 2605-2615, Jun. 1989.
Thomas et al, "Effects of the Deletion of Early Region 4 (E4) Open Reading Frame 1 (orf1), orf1-2, orf1-3 and orf1-4 on Virus-Host Cell Interaction, Transgene Expression, and Immunogenicity of Replicating Adenovirus HIV Vaccine Vectors", PLOS One, vol. 8, No. 10, Article e76344, Oct. 15, 2013.
Barouch et al., "Elicitation of high-frequency cytotoxic T-lymphocyte responses against both dominant and subdominant simian-human immunodeficiency virus epitopes by DNA vaccination of rhesus monkeys." Journal of Virology. Mar. 2001;75(5):2462-7. doi: 10.1128/JVI.75.5.2462-2467.2001.
Amara et al., "Control of a mucosal challenge and prevention of AIDS by a multiprotein DNA/MVA vaccine." Science. Apr. 6, 2001;292(5514):69-74. doi: 10.1126/science.1058915.

(56) References Cited

OTHER PUBLICATIONS

Verhoef et al., "Des-enkephalin-gamma-endorphin (DE gamma E): biotransformation in rat, dog and human plasma." Eur J Drug Metab Pharmacokinet. Oct.-Dec. 1986;11(4):291-302. doi: 10.1007/BF03189114.

Callendret et al., "Heterologous viral RNA export elements improve expression of severe acute respiratory syndrome (SARS) coronavirus spike protein and protective efficacy of DNA vaccines against SARS." Virology. Jul. 5, 2007;363(2):288-302. doi: 10.1016/j.virol.2007.01.012.

Stronen et al., Targeting of cancer neoantigens with donor-derived T cell receptor repertoires, Science. (2016) 352 (6291):1337-41.

Fisher and Wilson, "Biochemical and functional analysis of an adenovirus-based ligand complex for gene transfer." Biochem J. Apr. 1, 1994;299 ( Pt 1)(Pt 1): 49-58. doi: 10.1042/bj2990049.

Lundstrom, "Self-Replicating RNA Viruses for RNA Therapeutics." Molecules. Dec. 13, 2018;23(12):3310. doi: 10.3390/molecules23123310.

McKay, et al. "Self-amplifying RNA SARS-COV-2 lipid nanoparticle vaccine candidate induces high neutralizing antibody titers in mice," BIORXIV, Apr. 25, 2020, pp. 1-14.

Grifoni, A., et al., "A Sequence Homology and Bioinformatic Approach Can Predict Candidate Targets for Immune Responses to SARS-COV-2," Cell Host Microbe. Apr. 8, 2020;27(4):671-680.

E. Fast, et al., "Potential T-cell and B-cell epitopes of 2019-nCOV." BioRxiv, (2020): 2020-02, Abstract.

Agnihothram, S., et al. "Development of a Broadly Accessible Venezuelan Equine Encephalitis Virus Replicon Particle Vaccine Platform," J Virol. May 14, 2018;92(11):e00027-18.

Tarke, A., et al., Comprehensive analysis of TÂ cell immunodominance and immunoprevalence of SARS-CoV-2 epitopes in COVID-19 cases. Cell Rep Med. Feb. 16, 2021;2(2):1-20.

Grifoni Alba et al: "Targets of T Cell Responses to SARS-CoV-2 Coronavirus in Humans with COVID-19 Disease and Unexposed Individuals", Cell, Elsevier, Amsterdam Nl, vol. 181, No. 7, May 14, 2020, p. 1489.

Megede, I. et al. Evaluation of human Immunodeficiency virus type 1 subtype C gag, pol, and gagpol DNA and alphavirus replicon vaccines, Vaccine 24:2755-2763 (2006).

* cited by examiner

| # | HLA | Sequence | Origin |
|---|---|---|---|
| 1 | A*0201 | NLVPMVATV | HCMV pp65 (495- 503) |
| 2 | A*0201 | CLGGLLTMV | EBV LMP2A(426-434) |
| 3 | A*0201 | GLCTLVAML | EBV BMLF1 (280-288) |
| 4 | A*0201 | LLFGYPVYV | HTLV-1 Tax (11-19) |
| 5 | A*0201 | GILGFVFTL | Influenza A Matrix 1 (58- 66) |
| | MHC-II | AKFVAAWTLKAAA | PADRE (artificial seq) |
| | MHC-II | QYIKANSKFIGITE | Tetanus toxoid (830-844) |

| # | HLA | Sequence | Origin |
|---|---|---|---|
| 1 | A*02:01 | NLVPMVATV | HCMV pp65 495-504 |
| 2 | A*02:01 | CLGGLLTMV | EBV LMP-2 426-434 |
| 3 | A*02:01 | GLCTLVAML | EBV BMLF-1 259-267 |
| 4 | A*02:01 | LLFGYPVYV | HTLV1 Tax 11-19 |
| 5 | A*02:01 | GILGFVFTL | Influenza A MP 58-66 |
| 6 | A*02:01 | DLMGYIPAV | HCV core 132-140 |
| 7 | A*02:01 | FLPSDFFPSV | HBV core antigen 18-27 |
| 8 | A*02:01 | FLLTRILTI | HBV envelope 183-191 |
| 9 | A*02:01 | WLSLLVPFV | HBV surface antigen 172-181 |
| 10 | A*02:01 | FLLSLGIHL | HBV polymerase 573-581 |
| 11 | A*02:01 | ILKEPVHGV | HIV-1 RT 476-484 |
| 12 | A*02:01 | YMLDLQPETT | HPV 16 E7 11-20 |
| 13 | A*02:01 | CINGVCWTV | HCV NS3 1073-1081 |
| 14 | A*02:01 | YLLPRRGPRL | HCV core 35-44 |
| 15 | A*02:01 | FLYALALLL | EBV LMP-2 356-364 |
| 16 | A*02:01 | AAGIGILTV | MELAN-A/MART-1 (27-35) |
| 17 | A*02:01 | SLLMWITQV | NY-ESO-1(157-165) C9V |
| 18 | A*03:01 | KLGGALQAK | CVM-IE1 |
| 19 | A*03:01 | RLRAEAQVK | EBV-EBNA-3a |
| 20 | B*44:05 | EENLLDFVRF | EBV EBNASC (281-290) |
| 21 | B*44:05 | EEYLQAFTY | Self ABCD3 protein |

FIG 5B

NHP Epitopes

| | MHC | Sequence |
|---|---|---|
| 1 | Mamu*01 | CTPYDINQM |
| 4 | Mamu*01 | TTPESANL |
| 7 | Mamu*01 | CAPPGYALL |
| 10 | Mamu*01 | SGPKTNIIV |
| 14 | Mamu*01 | LSPRTLNAW |
| 18 | Mamu*01 | TVPWPNASL |

Human Epitopes

| | HLA | Sequence |
|---|---|---|
| 3 | A*02:01 | GILGFVFTL |
| 6 | A*02:01 | LLFGYPVYV |
| 9 | A*02:01 | GLCTLVAML |
| 12 | A*02:01 | NLVPMVATV |
| 16 | A*02:01 | CLGGLLTMV |

Murine MHC-I Epitopes

| | MHC | Sequence |
|---|---|---|
| 2 | H-2Kb | SIINFEKL |
| 5 | H-2Ld | SPSYAYHQF |
| 8 | H-2Db | EGPRNQDWL |
| 11 | H-2Kb | DWENVSPEL |
| 13 | H-2Kb | SIIVFNLL |
| 15 | H-2Db | ASMTNMELM |
| 17 | H-2Db | AQLANDVVL |
| 19 | H-2Kb | SVYDFFVWL |
| 20 | H-2Ld | MNKYAYHML |

Universal MHC-II Epitopes

| | HLA | Sequence |
|---|---|---|
| 1 | MHC-II | AKFVAAWTLKAAA |
| 2 | MHC-II | QYIKANSKFIGITEL |

FIG 6B

VEE-MAG25mer srRNA-LNP1(100 μg)

SEQUENCE LISTING

```
<160> NUMBER OF SEQ ID NOS: 196

<210> SEQ ID NO 1
<211> LENGTH: 36519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagatga ggcacctgag agacctgccc    600

gatgagaaaa tcatcatcgc ttccgggaac gagattctgg aactggtggt aaatgccatg    660

atgggcgacg accctccgga gcccccccacc ccatttgaga caccttcgct gcacgatttg    720

tatgatctgg aggtggatgt gcccgaggac gatcccaatg aggaggcggt aaatgatttt    780

tttagcgatg ccgcgctgct agctgccgag gaggcttcga gctctagctc agacagcgac    840

tcttcactgc atacccctag acccggcaga ggtgagaaaa agatccccga gcttaaaggg    900

gaagagatgg acttgcgctg ctatgaggaa tgcttgcccc cgagcgatga tgaggacgag    960

caggcgatcc agaacgcagc gagccaggga gtgcaagccg ccagcgagag ctttgcgctg   1020

gactgcccgc ctctgcccgg acacggctgt aagtcttgtg aatttcatcg catgaatact   1080

ggagataaag ctgtgttgtg tgcactttgc tatatgagag cttacaacca ttgtgtttac   1140

agtaagtgtg attaagttga actttagagg gaggcagaga gcagggtgac tgggcgatga   1200

ctggtttatt tatgtatata tgttctttat ataggtcccg tctctgacgc agatgatgag   1260

acccccacta caaagtccac ttcgtcaccc ccagaaattg gcacatctcc acctgagaat   1320
```

```
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gccttttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggaggggta ttcagccctt atctgacggg   3540
gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg gaatggccat   3720
```

```
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata aataaacgga gacggttgtt gattttaaca   3960
cagagtctga atctttattt gatttttcgc gcgcggtagg ccctggacca ccggtctcga   4020
tcattgagca cccggtggat cttttccagg acccggtaga ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
tctttgagga ggagactgat ggccacgggc agccctttgg tgtaggtgtt tacaaatctg   4260
ttgagctggg agggatgcat gcggggggag atgaggtgca tcttggcctg gatcttgaga   4320
ttggcgatgt taccgcccag atcccgcctg ggggttcatgt tgtgcaggac caccagcacg   4380
gtgtatccgg tgcacttggg gaatttatca tgcaacttgg aagggaaggc gtgaaagaat   4440
ttggcgacgc ctttgtgccc gcccaggttt tccatgcact catccatgat gatggcgatg   4500
ggcccgtggg cggcggcctg ggcaaagacg tttcgggggt cggacacatc atagttgtgg   4560
tcctgggtga ggtcatcata ggccatttta atgaatttgg ggcggagggt gccggactgg   4620
gggacaaagg taccctcgat cccgggggcg tagttcccct cacagatctg catctcccag   4680
gctttgagct cggagggggg gatcatgtcc acctgcgggg cgataaagaa cacggtttcc   4740
ggggcggggg agatgagctg ggccgaaagc aagttccgga gcagctggga cttgccgcag   4800
ccggtggggc cgtagatgac cccgatgacc ggctgcaggt ggtagttgag ggagagacag   4860
ctgccgtcct cccggaggag gggggccacc tcgttcatca tctcgcgcac gtgcatgttc   4920
tcgcgcacca gttccgccag gaggcgctct ccccccaggg ataggagctc ctggagcgag   4980
gcgaagtttt tcagcggctt gagtccgtcg gccatgggca ttttggagag ggtttgttgc   5040
aagagttcca ggcggtccca gagctcggtg atgtgctcta cggcatctcg atccagcaga   5100
cctcctcgtt tcgcgggttg ggacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcgggggc gtaggcgtcc gcgccgcagt gggcgcagac ggtctcgcac tccacgagcc   5520
aggtgaggtc gggctggtcg gggtcaaaaa ccagtttccc gccgttcttt ttgatgcgtt   5580
tcttaccttt ggtctccatg agctcgtgtc cccgctgggt gacaaagagg ctgtccgtgt   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtccccctc gtccacatcc aggaaggtga ttggcttgta agtgtaggcc acgtgaccgg   5880
gggtcccggc cggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
```

-continued

```
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg ggcagggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg ggcacctcg gcccggttgt   7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtcccccg tttcttcttg ggcggctggg gcgacggggg cggtgcctct tccatggtta   8460
```

```
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggagggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccgggggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcgggcgat   9660
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
```

-continued ttgttttgtt tgtttttgcc agatgcatcc cgtactgcgg cagatgcgcc cccaccaccc 10860
tccaccgcaa caacagcccc ctccacagcc ggcgcttctg cccccgcccc agcagcaact 10920
tccagccacg accgccgcgg ccgccgtgag cggggctgga cagagttatg atcaccagct 10980
ggccttggaa gagggcgagg ggctggcgcg cctgggggcg tcgtcgccgg agcggcaccc 11040
gcgcgtgcag atgaaaaggg acgctcgcga ggcctacgtg cccaagcaga acctgttcag 11100
agacaggagc ggcgaggagc ccgaggagat gcgcgcggcc cggttccacg cggggcggga 11160
gctgcggcgc ggcctggacc gaaagagggt gctgagggac gaggatttcg aggcggacga 11220
gctgacgggg atcagccccg cgcgcgcgca cgtggccgcg gccaacctgg tcacggcgta 11280
cgagcagacc gtgaaggagg agagcaactt ccaaaaatcc ttcaacaacc acgtgcgcac 11340
cctgatcgcg cgcgaggagg tgaccctggg cctgatgcac ctgtgggacc tgctggaggc 11400
catcgtgcag aaccccacca gcaagccgct gacggcgcag ctgttcctgg tggtgcagca 11460
tagtcgggac aacgaagcgt tcagggaggc gctgctgaat atcaccgagc ccgagggccg 11520
ctggctcctg gacctggtga acattctgca gagcatcgtg gtgcaggagc gcgggctgcc 11580
gctgtccgag aagctggcgg ccatcaactt ctcggtgctg agtttgggca agtactacgc 11640
taggaagatc tacaagaccc cgtacgtgcc catagacaag gaggtgaaga tcgacgggtt 11700
ttacatgcgc atgaccctga aagtgctgac cctgagcgac gatctggggg tgtaccgcaa 11760
cgacaggatg caccgtgcgg tgagcgccag caggcggcgc gagctgagcg accaggagct 11820
gatgcatagt ctgcagcggg ccctgaccgg ggccgggacc gagggggaga gctactttga 11880
catgggcgcg gacctgcact ggcagcccag ccgccgggcc ttggaggcgg cggcaggacc 11940
ctacgtagaa gaggtggacg atgaggtgga cgaggagggc gagtacctgg aagactgatg 12000
gcgcgaccgt atttttgcta gatgcaacaa caacagccac ctcctgatcc cgcgatgcgg 12060
gcggcgctgc agagccagcc gtccggcatt aactcctcgg acgattggac ccaggccatg 12120
caacgcatca tggcgctgac gacccgcaac cccgaagcct ttagacagca gccccaggcc 12180
aaccggctct cggccatcct ggaggccgtg gtgccctcgc gctccaaccc cacgcacgag 12240
aaggtcctgg ccatcgtgaa cgcgctggtg gagaacaagg ccatccgcgg cgacgaggcc 12300
ggcctggtgt acaacgcgct gctggagcgc gtggcccgct acaacagcac caacgtgcag 12360
accaacctgg accgcatggt gaccgacgtg cgcgaggccg tggcccagcg cgagcggttc 12420
caccgcgagt ccaacctggg atccatggtg gcgctgaacg ccttcctcag cacccagccc 12480
gccaacgtgc ccggggcca ggaggactac accaacttca tcagcgccct gcgcctgatg 12540
gtgaccgagg tgccccagag cgaggtgtac cagtccgggc cggactactt cttccagacc 12600
agtcgccagg gcttgcagac cgtgaacctg agccaggctt tcaagaactt gcagggcctg 12660
tggggcgtgc aggccccggt cggggaccgc gcgacggtgt cgagcctgct gacgccgaac 12720
tcgcgcctgc tgctgctgct ggtggccccc ttcacggaca gcggcagcat caaccgcaac 12780
tcgtacctgg gctacctgat taacctgtac cgcgaggcca tcggccaggc gcacgtggac 12840
gagcagacct accaggagat cacccacgtg agccgcgccc tgggccagga cgacccgggc 12900
aacctggaag ccaccctgaa ctttttgctg accaaccggt cgcagaagat cccgccccag 12960
tacgcgctca gcaccgagga ggagcgcatc ctgcgttacg tgcagcagag cgtgggcctg 13020
ttcctgatgc aggagggggc cacccccagc gccgcgctcg acatgaccgc gcgcaacatg 13080
gagcccagca tgtacgccag caaccgcccg ttcatcaata aactgatgga ctacttgcat 13140
cgggcggccg ccatgaactc tgactatttc accaacgcca tcctgaatcc ccactggctc 13200

-continued

```
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggaccccgt gaccgagctg gtcatgcccg  14580
gggtgtacac caacgaggct ttccatcccg atattgtctt gctgcccggc tgcggggtgg  14640
acttcaccga gagccgcctc agcaacctgc tgggcattcg caagaggcag cccttccagg  14700
aaggcttcca gatcatgtac gaggatctgg aggggggcaa catccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
```

```
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt gggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgcccccgta  17940
```

cgaggaggcg gtgaaactgg gtctgcccac cacgcggccc atcgcgcccc tggccaccgg 18000
ggtgctgaaa cccgaaaagc ccgcgaccct ggacttgcct cctccccagc cttcccgccc 18060
ctctacagtg gctaagcccc tgccgccggt ggccgtggcc cgcgcgcgac ccgggggcac 18120
cgcccgccct catgcgaact ggcagagcac tctgaacagc atcgtgggtc tgggagtgca 18180
gagtgtgaag cgccgccgct gctattaaac ctaccgtagc gcttaacttg cttgtctgtg 18240
tgtgtatgta ttatgtcgcc gccgccgctg tccaccagaa ggaggagtga agaggcgcgt 18300
cgccgagttg caagatggcc accccatcga tgctgcccca gtgggcgtac atgcacatcg 18360
ccggacagga cgcttcggag tacctgagtc cgggtctggt gcagtttgcc cgcgccacag 18420
acacctactt cagtctgggg aacaagttta ggaaccccac ggtggcgccc acgcacgatg 18480
tgaccaccga ccgcagccag cggctgacgc tgcgcttcgt gcccgtggac cgcgaggaca 18540
acacctactc gtacaaagtg cgctacacgc tggccgtggg cgacaaccgc gtgctggaca 18600
tggccagcac ctactttgac atccgcggcg tgctggatcg ggccctagc ttcaaaccct 18660
actccggcac cgcctacaac agtctggccc ccaagggagc acccaacact tgtcagtgga 18720
catataaagc cgatggtgaa actgccacag aaaaaaccta tacatatgga aatgcacccg 18780
tgcagggcat taacatcaca aaagatggta ttcaacttgg aactgacacc gatgatcagc 18840
caatctacgc agataaaacc tatcagcctg aacctcaagt gggtgatgct gaatggcatg 18900
acatcactgg tactgatgaa aagtatggag gcagagctct taagcctgat accaaaatga 18960
agccttgtta tggttctttt gccaagccta ctaataaaga aggaggtcag gcaaatgtga 19020
aaacaggaac aggcactact aaagaatatg acatagacat ggctttcttt gacaacagaa 19080
gtgcggctgc tgctggccta gctccagaaa ttgttttgta tactgaaaat gtggatttgg 19140
aaactccaga tacccatatt gtatacaaag caggcacaga tgacagcagc tcttctatta 19200
atttgggtca gcaagccatg cccaacagac ctaactacat tggtttcaga gacaacttta 19260
tcgggctcat gtactacaac agcactggca atatgggggt gctggccggt caggcttctc 19320
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100
tctacgccac cttcttcccc atggcgcaca acacggcctc cacgctcgag gccatgctgc 20160
gcaacgacac caacgaccag tccttcaacg actacctctc ggcggccaac atgctctacc 20220
ccatcccggc caacgccacc aacgtgccca tctccatccc ctcgcgcaac tgggccgcct 20280

-continued tccgcggctg gtccttcacg cgtctcaaga ccaaggagac gccctcgctg ggctccgggt 20340
tcgaccccta cttcgtctac tcgggctcca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctacaa ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760
ccatgcgcca gggccagccc taccccgcca actaccccta cccgctcatc ggcaagagcg 20820
ccgtcaccag cgtcacccag aaaaagttcc tctgcgacag ggtcatgtgg cgcatcccct 20880
tctccagcaa cttcatgtcc atgggcgcgc tcaccgacct cggccagaac atgctctatg 20940
ccaactccgc ccacgcgcta gacatgaatt tcgaagtcga ccccatggat gagtccaccc 21000
ttctctatgt tgtcttcgaa gtcttcgacg tcgtccgagt gcaccagccc caccgcggcg 21060
tcatcgaggc cgtctacctg cgcacccccct tctcggccgg taacgccacc acctaagctc 21120
ttgcttcttg caagccatgg ccgcgggctc cggcgagcag gagctcaggg ccatcatccg 21180
cgacctgggc tgcgggccct acttcctggg caccttcgat aagcgcttcc cgggattcat 21240
ggccccgcac aagctggcct gcgccatcgt caacacggcc ggccgcgaga ccgggggcga 21300
gcactggctg gccttcgcct ggaacccgcg ctcgaacacc tgctacctct tcgacccctt 21360
cgggttctcg gacgagcgcc tcaagcagat ctaccagttc gagtacgagg gcctgctgcg 21420
ccgcagcgcc ctggccaccg aggaccgctg cgtcaccctg gaaaagtcca cccagaccgt 21480
gcagggtccg cgctcggccg cctgcgggct cttctgctgc atgttcctgc acgccttcgt 21540
gcactggccc gaccgcccca tggacaagaa ccccaccatg aacttgctga cgggggtgcc 21600
caacggcatg ctccagtcgc cccaggtgga acccaccctg cgccgcaacc aggaggcgct 21660
ctaccgcttc ctcaactccc actccgccta ctttcgctcc caccgcgcgc gcatcgagaa 21720
ggccaccgcc ttcgaccgca tgaatcaaga catgtaaacc gtgtgtgtat gttaaatgtc 21780
tttaataaac agcactttca tgttacacat gcatctgaga tgatttattt agaaatcgaa 21840
agggttctgc cgggtctcgg catggcccgc gggcagggac acgttgcgga actggtactt 21900
ggccagccac ttgaactcgg ggatcagcag tttgggcagc ggggtgtcgg ggaaggagtc 21960
ggtccacagc ttccgcgtca gttgcagggc gcccagcagg tcgggcgcgg agatcttgaa 22020
atcgcagttg ggacccgcgt tctgcgcgcg ggagttgcgg tacacggggt tgcagcactg 22080
gaacaccatc agggccgggt gcttcacgct cgccagcacc gtcgcgtcgg tgatgctctc 22140
cacgtcgagg tcctcggcgt tggccatccc gaagggggtc atcttgcagg tctgccttcc 22200
catggtgggc acgcacccgg gcttgtggtt gcaatcgcag tgcaggggga tcagcatcat 22260
ctgggcctgg tcggcgttca tccccgggta catggccttc atgaaagcct ccaattgcct 22320
gaacgcctgc tgggccttgg ctccctcggt gaagaagacc ccgcaggact tgctagagaa 22380
ctggttggtg gcgcacccgg cgtcgtgcac gcagcagcgc gcgtcgttgt tggccagctg 22440
caccacgctg cgcccccagc ggttctgggt gatcttggcc cggtcggggt tctccttcag 22500
cgcgcgctgc ccgttctcgc tcgccacatc catctcgatc atgtgctcct tctggatcat 22560
ggtggtcccg tgcaggcacc gcagcttgcc ctcggcctcg gtgcacccgt gcagccacag 22620
cgcgcacccg gtgcactccc agttcttgtg ggcgatctgg gaatgcgcgt gcacgaagcc 22680
ctgcaggaag cggcccatca tggtggtcag ggtcttgttg ctagtgaagg tcagcggaat 22740
gccgcggtgc tcctcgttga tgtacaggtg gcagatgcgg cggtacacct cgccctgctc 22800
gggcatcagc tggaagttgg ctttcaggtc ggtctccacg cggtagcggt ccatcagcat 22860
agtcatgatt tccataccct tctcccaggc cgagacgatg ggcaggctca tagggttctt 22920
caccatcatc ttagcgctag cagccgcggc caggggggtcg ctctcgtcca gggtctcaaa 22980
gctccgcttg ccgtccttct cggtgatccg caccgggggg tagctgaagc ccacggccgc 23040
cagctcctcc tcggcctgtc tttcgtcctc gctgtcctgg ctgacgtcct gcaggaccac 23100
atgcttggtc ttgcggggtt tcttcttggg cggcagcggc ggcggagatg ttggagatgg 23160
cgagggggag cgcgagttct cgctcaccac tactatctct tcctcttctt ggtccgaggc 23220
cacgcggcgg taggtatgtc tcttcggggg cagaggcgga ggcgacgggc tctcgccgcc 23280
gcgacttggc ggatggctgg cagagcccct tccgcgttcg ggggtgcgct cccggcggcg 23340
ctctgactga cttcctccgc ggccggccat tgtgttctcc tagggaggaa caacaagcat 23400
ggagactcag ccatcgccaa cctcgccatc tgccccccacc gccgacgaga agcagcagca 23460
gcagaatgaa agcttaaccg ccccgccgcc cagccccgcc acctccgacg cggccgtccc 23520
agacatgcaa gagatggagg aatccatcga gattgacctg ggctatgtga cgcccgcgga 23580
gcacgaggag gagctggcag tgcgcttttc acaagaagag atacaccaag aacagccaga 23640
gcaggaagca gagaatgagc agagtcaggc tgggctcgag catgacggcg actacctcca 23700
cctgagcggg ggggaggacg cgctcatcaa gcatctggcc cggcaggcca ccatcgtcaa 23760
ggatgcgctg ctcgaccgca ccgaggtgcc cctcagcgtg gaggagctca gccgcgccta 23820
cgagttgaac ctcttctcgc cgcgcgtgcc ccccaagcgc cagcccaatg gcacctgcga 23880
gcccaacccg cgcctcaact tctacccggt cttcgcggtg cccgaggccc tggccaccta 23940
ccacatcttt ttcaagaacc aaaagatccc cgtctcctgc cgcgccaacc gcacccgcgc 24000
cgacgccctt ttcaacctgg gtcccggcgc ccgcctacct gatatcgcct ccttggaaga 24060
ggttcccaag atcttcgagg gtctgggcag cgacgagact cgggccgcga acgctctgca 24120
aggagaagga ggagagcatg agcaccacag cgccctggtc gagttggaag gcgacaacgc 24180
gcggctggcg gtgctcaaac gcacggtcga gctgacccat ttcgcctacc cggctctgaa 24240
cctgcccccc aaagtcatga gcgcggtcat ggaccaggtg ctcatcaagc gcgcgtcgcc 24300
catctccgag gacgagggca tgcaagactc cgaggagggc aagcccgtgg tcagcgacga 24360
gcagctggcc cggtggctgg gtcctaatgc tagtccccag agtttggaag agcggcgcaa 24420
actcatgatg gccgtggtcc tggtgaccgt ggagctggag tgcctgcgcc gcttcttcgc 24480
cgacgcggag accctgcgca aggtcgagga gaacctgcac tacctcttca ggcacgggtt 24540
cgtgcgccag gcctgcaaga tctccaacgt ggagctgacc aacctggtct cctacatggg 24600
catcttgcac gagaaccgcc tggggcagaa cgtgctgcac accaccctgc gcggggaggc 24660
ccggcgcgac tacatccgcg actgcgtcta cctctacctc tgccacacct ggcagacggg 24720
catgggcgtg tggcagcagt gtctggagga gcagaacctg aaagagctct gcaagctcct 24780
gcagaagaac ctcaagggtc tgtggaccgg gttcgacgag cgcaccaccg cctcggacct 24840
ggccgacctc attttccccg agcgcctcag gctgacgctg cgcaacggcc tgcccgactt 24900
tatgagccaa agcatgttgc aaaactttcg ctctttcatc ctcgaacgct ccggaatcct 24960
gcccgccacc tgctccgcgc tgccctcgga cttcgtgccg ctgaccttcc gcgagtgccc 25020

-continued

```
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
```

-continued

```
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aatttttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
```

```
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgtgggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaag gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcacccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
```

gatgacttcg accccgtcta cccctacgat gcagacaacg caccgaccgt gcccttcatc 32220
aacccccccct tcgtctcttc agatggattc caagagaagc ccctgggggt gttgtccctg 32280
cgactggccg accccgtcac caccaagaac ggggaaatca ccctcaagct gggagagggg 32340
gtggacctcg attcctcggg aaaactcatc tccaacacgg ccaccaaggc cgccgcccct 32400
ctcagttttt ccaacaacac catttccctt aacatggatc accccttttta cactaaagat 32460
ggaaaattat ccttacaagt ttctccacca ttaaatatac tgagaacaag cattctaaac 32520
acactagctt taggttttgg atcaggttta ggactccgtg gctctgcctt ggcagtacag 32580
ttagtctctc cacttacatt tgatactgat ggaaacataa agcttacctt agacagaggt 32640
ttgcatgtta caacaggaga tgcaattgaa agcaacataa gctgggctaa aggtttaaaa 32700
tttgaagatg gagccatagc aaccaacatt ggaaatgggt tagagtttgg aagcagtagt 32760
acagaaacag gtgttgatga tgcttaccca atccaagtta aacttggatc tggccttagc 32820
tttgacagta caggagccat aatggctggt aacaaagaag acgataaact cactttgtgg 32880
acaacacctg atccatcacc aaactgtcaa atactcgcag aaaatgatgc aaaactaaca 32940
ctttgcttga ctaaatgtgg tagtcaaata ctggccactg tgtcagtctt agttgtagga 33000
agtggaaacc taaaccccat tactggcacc gtaagcagtg ctcaggtgtt tctacgtttt 33060
gatgcaaacg gtgttctttt aacagaacat tctacactaa aaaaatactg gggtataggg 33120
cagggagata gcatagatgg cactccatat accaatgctg taggattcat gcccaattta 33180
aaagcttatc caaagtcaca aagttctact actaaaaata atatagtagg gcaagtatac 33240
atgaatggag atgtttcaaa acctatgctt ctcactataa ccctcaatgg tactgatgac 33300
agcaacagta catattcaat gtcattttca tacacctgga ctaatggaag ctatgttgga 33360
gcaacatttg gggctaactc ttataccttc tcatacatcg cccaagaatg aacactgtat 33420
cccaccctgc atgccaaccc ttcccacccc actctgtgga acaaactctg aaacacaaaa 33480
taaaataaag ttcaagtgtt ttattgattc aacagtttta caggattcga gcagttattt 33540
ttcctccacc ctcccaggac atggaataca ccaccctctc cccccgcaca gccttgaaca 33600
tctgaatgcc attggtgatg gacatgcttt tggtctccac gttccacaca gtttcagagc 33660
gagccagtct cgggtcggtc agggagatga aaccctccgg gcactcccgc atctgcacct 33720
cacagctcaa cagctgagga ttgtcctcgg tggtcgggat cacggttatc tggaagaagc 33780
agaagagcgg cggtgggaat catagtccgc gaacgggatc ggccggtggt gtcgcatcag 33840
gccccgcagc agtcgctgcc gccgccgctc cgtcaagctg ctgctcaggg ggtccgggtc 33900
cagggactcc ctcagcatga tgcccacggc cctcagcatc agtcgtctgg tgcggcgggc 33960
gcagcagcgc atgcggatct cgctcaggtc gctgcagtac gtgcaacaca gaaccaccag 34020
gttgttcaac agtccatagt tcaacacgct ccagccgaaa ctcatcgcgg gaaggatgct 34080
acccacgtgg ccgtcgtacc agatcctcag gtaaatcaag tggtgccccc tccagaacac 34140
gctgcccacg tacatgatct ccttgggcat gtggcggttc accacctccc ggtaccacat 34200
caccctctgg ttgaacatgc agccccggat gatcctgcgg aaccacaggg ccagcaccgc 34260
cccgcccgcc atgcagcgaa gagaccccgg gtcccggcaa tggcaatgga ggacccaccg 34320
ctcgtacccg tggatcatct gggagctgaa caagtctatg ttggcacagc acaggcatat 34380
gctcatgcat ctcttcagca ctctcaactc ctcgggggtc aaaaccatat cccagggcac 34440
ggggaactct tgcaggacag cgaaccccgc agaacagggc aatcctcgca cagaacttac 34500

```
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcctg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
gtaaatcgtt ctctccagca ccaggcaggc cacggggtct ccggcgcgac cctcgtaaaa  35820
attgtcgcta tgattgaaaa ccatcacaga gagacgttcc cggtggccgg cgtgaatgat  35880
tcgacaagat gaatacaccc ccggaacatt ggcgtccgcg agtgaaaaaa agcgcccgag  35940
gaagcaataa ggcactacaa tgctcagtct caagtccagc aaagcgatgc catgcggatg  36000
aagcacaaaa ttctcaggtg cgtacaaaat gtaattactc cctcctgca caggcagcaa  36060
agcccccgat ccctccaggt acacatacaa agcctcagcg tccatagctt accgagcagc  36120
agcacacaac aggcgcaaga gtcagagaaa ggctgagctc taacctgtcc acccgctctc  36180
tgctcaatat atagcccaga tctacactga cgtaaaggcc aaagtctaaa aatacccgcc  36240
aaataatcac acacgcccag cacacgccca gaaaccggtg acacactcaa aaaaatacgc  36300
gcacttcctc aaacgcccaa aactgccgtc atttccgggt tcccacgcta cgtcatcaaa  36360
acacgacttt caaattccgt cgaccgttaa aaacgtcacc cgccccgccc ctaacggtcg  36420
cccgtctctc agccaatcag cgccccgcat ccccaaattc aaacacctca tttgcatatt  36480
aacgcgcaca aaaagtttga ggtatattat tgatgatgg                         36519
```

<210> SEQ ID NO 2
<211> LENGTH: 31588
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

-continued

```
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagtagg gataacaggg taatgacatt    600
gattattgac tagttgttaa tagtaatcaa ttacggggtc attagttcat agcccatata    660
tggagttccg cgttacataa cttacggtaa atggcccgcc tggctgaccg cccaacgacc    720
cccgcccatt gacgtcaata atgacgtatg ttcccatagt aacgccaata gggactttcc    780
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
ccgggatgtt ccaggcactg tccgaaggct gcacacccta tgatattaac cagatgctga   1320
atgtcctggg agaccaccag gtctctggcc tggagcagct ggagagcatc atcaacttcg   1380
agaagctgac cgagtggaca agctccaatg tgatgcctat cctgtcccca ctgaccaagg   1440
gcatcctggg cttcgtgttt accctgacag tgccttctga gcggggcctg tcttgcatca   1500
gcgaggcaga cgcaaccaca ccagagtccg ccaatctggg cgaggagatc ctgtctcagc   1560
tgtacctgtg gccccgggtg acatatcact ccccttctta cgcctatcac cagttcgagc   1620
ggagagccaa gtacaagaga cacttcccag gctttggcca gtctctgctg ttcggctacc   1680
ccgtgtacgt gttcggcgat tgcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gcctttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctggc aaggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac cccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
```

```
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
cggtaggccc tggaccaccg gtctcgatca ttgagcaccc ggtggatctt ttccaggacc   3840
cggtagaggt gggcttggat gttgaggtac atgggcatga gcccgtcccg ggggtggagg   3900
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg aggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
```

cccagggata ggagctcctg gagcgaggcg aagtttttca gcggcttgag tccgtcggcc 4800
atgggcattt tggagagggt ttgttgcaag agttccaggc ggtcccagag ctcggtgatg 4860
tgctctacgg catctcgatc cagcagacct cctcgtttcg cgggttggga cggctgcggg 4920
agtagggcac cagacgatgg gcgtccagcg cagccagggt ccggtccttc cagggtcgca 4980
gcgtccgcgt cagggtggtc tccgtcacgg tgaaggggtg cgcgccgggc tgggcgcttg 5040
cgagggtgcg cttcaggctc atccggctgg tcgaaaaccg ctcccgatcg gcgccctgcg 5100
cgtcggccag gtagcaattg accatgagtt cgtagttgag cgcctcggcc gcgtggcctt 5160
tggcgcggag cttacctttg gaagtctgcc cgcaggcggg acagaggagg gacttgaggg 5220
cgtagagctt gggggcgagg aagacggact cgggggcgta ggcgtccgcg ccgcagtggg 5280
cgcagacggt ctcgcactcc acgagccagg tgaggtcggg ctggtcgggg tcaaaaacca 5340
gtttcccgcc gttctttttg atgcgtttct tacctttggt ctccatgagc tcgtgtcccc 5400
gctgggtgac aaagaggctg tccgtgtccc cgtagaccga ctttatgggc cggtcctcga 5460
gcggtgtgcc gcggtcctcc tcgtagagga accccgccca ctccgagacg aaagcccggg 5520
tccaggccag cacgaaggag gccacgtggg acgggtagcg gtcgttgtcc accagcgggt 5580
ccaccttttc cagggtatgc aaacacatgt ccccctcgtc cacatccagg aaggtgattg 5640
gcttgtaagt gtaggccacg tgaccggggg tcccggccgg gggggtataa aagggtgcgg 5700
gtccctgctc gtcctcactg tcttccggat cgctgtccag gagcgccagc tgttggggta 5760
ggtattccct ctcgaaggcg ggcatgacct cggcactcag gttgtcagtt tctagaaacg 5820
aggaggattt gatattgacg gtgccggcgg agatgccttt caagagcccc tcgtccatct 5880
ggtcagaaaa gacgatcttt ttgttgtcga gcttggtggc gaaggagccg tagagggcgt 5940
tggagaggag cttggcgatg gagcgcatgg tctggttttt ttccttgtcg gcgcgctcct 6000
tggcggcgat gttgagctgc acgtactcgc gcgccacgca cttccattcg gggaagacgg 6060
tggtcagctc gtcgggcacg attctgacct gccagccccg attatgcagg gtgatgaggt 6120
ccacactggt ggccacctcg ccgcgcaggg gctcattagt ccagcagagg cgtccgccct 6180
tgcgcgagca gaaggggggc agggggtcca gcatgacctc gtcggggggg tcggcatcga 6240
tggtgaagat gccgggcagg aggtcggggt caaagtagct gatggaagtg gccagatcgt 6300
ccagggcagc ttgccattcg cgcacggcca gcgcgcgctc gtagggactg aggggcgtgc 6360
cccagggcat gggatgggta agcgcggagg cgtacatgcc gcagatgtcg tagacgtaga 6420
ggggctcctc gaggatgccg atgtaggtgg ggtagcagcg ccccccgcgg atgctggcgc 6480
gcacgtagtc atacagctcg tgcgaggggg cgaggagccc cgggcccagg ttggtgcgac 6540
tgggcttttc ggcgcggtag acgatctggc ggaaaatggc atgcgagttg gaggagatgg 6600
tgggcctttg gaagatgttg aagtgggcgt ggggcagtcc gaccgagtcg cggatgaagt 6660
gggcgtagga gtcttgcagc ttggcgacga gctcggcggt gactaggacg tccagagcgc 6720
agtagtcgag ggtctcctgg atgatgtcat acttgagctg tccctttttgt ttccacagct 6780
cgcggttgag aaggaactct tcgcggtcct tccagtactc ttcgaggggg aacccgtcct 6840
gatctgcacg gtaagagcct agcatgtaga actggttgac ggccttgtag gcgcagcagc 6900
ccttctccac ggggagggcg taggcctggg cggccttgcg cagggaggtg tgcgtgaggg 6960
cgaaagtgtc cctgaccatg accttgagga actggtgctt gaagtcgata tcgtcgcagc 7020
ccccctgctc ccagagctgg aagtccgtgc gcttcttgta ggcggggttg ggcaaagcga 7080
aagtaacatc gttgaagagg atcttgcccg cgcggggcat aaagttgcga gtgatgcgga 7140

```
aaggttgggg cacctcggcc cggttgttga tgacctgggc ggcgagcacg atctcgtcga   7200
agccgttgat gttgtggccc acgatgtaga gttccacgaa tcgcggacgg cccttgacgt   7260
ggggcagttt cttgagctcc tcgtaggtga gctcgtcggg gtcgctgagc ccgtgctgct   7320
cgagcgccca gtcggcgaga tgggggttgg cgcggaggaa ggaagtccag agatccacgg   7380
ccagggcggt ttgcagacgg tcccggtact gacggaactg ctgcccgacg gccatttttt   7440
cgggggtgac gcagtagaag gtgcgggggt ccccgtgcca gcgatcccat ttgagctgga   7500
gggcgagatc gagggcgagc tcgacgagcc ggtcgtcccc ggagagtttc atgaccagca   7560
tgaaggggac gagctgcttg ccgaaggacc ccatccaggt gtaggtttcc acatcgtagg   7620
tgaggaagag cctttcggtg cgaggatgcg agccgatggg gaagaactgg atctcctgcc   7680
accaattgga ggaatggctg ttgatgtgat ggaagtagaa atgccgacgg cgcgccgaac   7740
actcgtgctt gtgtttatac aagcggccac agtgctcgca acgctgcacg ggatgcacgt   7800
gctgcacgag ctgtacctga gttcctttga cgaggaattt cagtgggaag tggagtcgtg   7860
gcgcctgcat ctcgtgctgt actacgtcgt ggtggtcggc ctggccctct tctgcctcga   7920
tggtggtcat gctgacgagc ccgcgcggga ggcaggtcca gacctcggcg cgagcgggtc   7980
ggagagcgag gacgagggcg cgcaggccgg agctgtccag ggtcctgaga cgctgcggag   8040
tcaggtcagt gggcagcggc ggcgcgcggt tgacttgcag gagtttttcc agggcgcgcg   8100
ggaggtccag atggtacttg atctccaccg cgccattggt ggcgacgtcg atggcttgca   8160
gggtcccgtg cccctggggt gtgaccaccg tcccccgttt cttcttgggc ggctggggcg   8220
acgggggcgg tgcctcttcc atggttagaa gcggcggcga ggacgcgcgc cgggcggcag   8280
gggcggctcg gggcccggag gcaggggcgg caggggcacg tcggcgccgc gcgcgggtag   8340
gttctggtac tgcgcccgga gaagactggc gtgagcgacg acgcgacggt tgacgtcctg   8400
gatctgacgc ctctgggtga aggccacggg acccgtgagt ttgaacctga aagagagttc   8460
gacagaatca atctcggtat cgttgacggc ggcctgccgc aggatctctt gcacgtcgcc   8520
cgagttgtcc tggtaggcga tctcggtcat gaactgctcg atctcctcct cttgaaggtc   8580
tccgcggccg gcgcgctcca cggtggccgc gaggtcgttg gagatgcggc ccatgagctg   8640
cgagaaggcg ttcatgcccg cctcgttcca gacgcggctg tagaccacga cgccctcggg   8700
atcgcgggcg cgcatgacca cctgggcgag gttgagctcc acgtggcgcg tgaagaccgc   8760
gtagttgcag aggcgctggt agaggtagtt gagcgtggtg gcgatgtgct cggtgacgaa   8820
gaaatacatg atccagcggc ggagcggcat ctcgctgacg tcgcccagcg cctccaaacg   8880
ttccatggcc tcgtaaaagt ccacggcgaa gttgaaaaac tgggagttgc gcgccgagac   8940
ggtcaactcc tcctccagaa gacggatgag ctcggcgatg gtggcgcgca cctcgcgctc   9000
gaaggccccc gggagttcct ccacttcctc ttcttcctcc tccactaaca tctcttctac   9060
ttcctcctca ggcggcagtg gtggcggggg agggggcctg cgtcgccggc ggcgcacggg   9120
cagacggtcg atgaagcgct cgatggtctc gccgcgccgg cgtcgcatgg tctcggtgac   9180
ggcgcgcccg tcctcgcggg gccgcagcgt gaagacgccg ccgcgcatct ccaggtggcc   9240
gggggggtcc ccgttgggca gggagagggc gctgacgatg catcttatca attgccccgt   9300
agggactccg cgcaaggacc tgagcgtctc gagatccacg ggatctgaaa accgctgaac   9360
gaaggcttcg agccagtcgc agtcgcaagg taggctgagc acggtttctt ctggcgggtc   9420
atgttggttg ggagcggggc gggcgatgct gctggtgatg aagttgaaat aggcggttct   9480
```

```
gagacggcgg atggtggcga ggagcaccag gtctttgggc ccggcttgct ggatgcgcag   9540
acggtcggcc atgccccagg cgtggtcctg acacctggcc aggtccttgt agtagtcctg   9600
catgagccgc tccacgggca cctcctcctc gcccgcgcgg ccgtgcatgc gcgtgagccc   9660
gaagccgcgc tggggctgga cgagcgccag gtcggcgacg acgcgctcgg cgaggatggc   9720
ttgctggatc tgggtgaggg tggtctggaa gtcatcaaag tcgacgaagc ggtggtaggc   9780
tccggtgttg atggtgtagg agcagttggc catgacggac cagttgacgg tctggtggcc   9840
cggacgcacg agctcgtggt acttgaggcg cgagtaggcg cgcgtgtcga agatgtagtc   9900
gttgcaggtg cgcaccaggt actggtagcc gatgaggaag tgcggcggcg gctggcggta   9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca acttttttt  10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac ccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag gggagagct actttgacat gggcgcggac ctgcactggc agcccagccg  11700
ccgggccttg gaggcggcgg caggaccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
```

```
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggcccccttc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
cgcccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
```

-continued

```
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
gacgcagggc catgctcagg gcggccagac gcgcggcttc aggcgccagc gccggcagga  15720
cccggagacg cgcggccacg gcggcggcag cggccatcgc cagcatgtcc cgcccgcggc  15780
gagggaacgt gtactgggtg cgcgacgccg ccaccggtgt gcgcgtgccc gtgcgcaccc  15840
gcccccctcg cacttgaaga tgttcacttc gcgatgttga tgtgtcccag cggcgaggag  15900
gatgtccaag cgcaaattca aggaagagat gctccaggtc atcgcgcctg agatctacgg  15960
ccctgcggtg gtgaaggagg aaagaaagcc ccgcaaaatc aagcgggtca aaaaggacaa  16020
aaaggaagaa gaaagtgatg tggacggatt ggtggagttt gtgcgcgagt tcgccccccg  16080
gcggcgcgtg cagtggcgcg ggcggaaggt gcaaccggtg ctgagacccg gcaccaccgt  16140
ggtcttcacg cccggcgagc gctccggcac cgcttccaag cgctcctacg acgaggtgta  16200
cggggatgat gatattctgg agcaggcggc cgagcgcctg ggcgagtttg cttacggcaa  16260
gcgcagccgt tccgcaccga aggaagaggc ggtgtccatc ccgctggacc acggcaaccc  16320
cacgccgagc ctcaagcccg tgaccttgca gcaggtgctg ccgaccgcgg cgccgcgccg  16380
ggggttcaag cgcgagggcg aggatctgta ccccaccatg cagctgatgg tgcccaagcg  16440
ccagaagctg gaagacgtgc tggagaccat gaaggtggac ccggacgtgc agcccgaggt  16500
caaggtgcgg cccatcaagc aggtggcccc gggcctgggc gtgcagaccg tggacatcaa  16560
gattcccacg gagcccatgg aaacgcagac cgagcccatg atcaagccca gcaccagcac  16620
```

```
catggaggtg cagacggatc cctggatgcc atcggctcct agtcgaagac cccggcgcaa  16680
gtacggcgcg gccagcctgc tgatgcccaa ctacgcgctg catccttcca tcatccccac  16740
gccgggctac cgcggcacgc gcttctaccg cggtcatacc agcagccgcc gccgcaagac  16800
caccactcgc cgccgccgtc gccgcaccgc cgctgcaacc acccctgccg ccctggtgcg  16860
gagagtgtac cgccgcggcc gcgcacctct gaccctgccg cgcgcgcgct accacccgag  16920
catcgccatt taaactttcg cctgctttgc agatcaatgg ccctcacatg ccgccttcgc  16980
gttcccatta cgggctaccg aggaagaaaa ccgcgccgta gaaggctggc ggggaacggg  17040
atgcgtcgcc accaccaccg gcggcggcgc gccatcagca agcggttggg gggaggcttc  17100
ctgcccgcgc tgatccccat catcgccgcg gcgatcgggg cgatccccgg cattgcttcc  17160
gtggcggtgc aggcctctca gcgccactga gacacacttg gaaacatctt gtaataaacc  17220
aatggactct gacgctcctg gtcctgtgat gtgttttcgt agacagatgg aagacatcaa  17280
tttttcgtcc ctggctccgc gacacggcac gcggccgttc atgggcacct ggagcgacat  17340
cggcaccagc caactgaacg gggggcgcctt caattggagc agtctctgga gcgggcttaa  17400
gaatttcggg tccacgctta aaacctatgg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg gggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
```

-continued

```
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg accccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg gggggcgagca ctggctggcc ttcgcctgga acccgcgctc  21120
gaacacctgc tacctcttcg acccccttcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
```

```
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc atacccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
```

cgcggtgccc gaggccctgg ccacctacca catctttttc aagaaccaaa agatccccgt 23760
ctcctgccgc gccaaccgca cccgcgccga cgccctttc aacctgggtc ccggcgcccg 23820
cctacctgat atcgcctcct tggaagaggt tcccaagatc ttcgagggtc tgggcagcga 23880
cgagactcgg gccgcgaacg ctctgcaagg agaaggagga gagcatgagc accacagcgc 23940
cctggtcgag ttggaaggcg acaacgcgcg gctggcggtg ctcaaacgca cggtcgagct 24000
gacccatttc gcctacccgg ctctgaacct gccccccaaa gtcatgagcg cggtcatgga 24060
ccaggtgctc atcaagcgcg cgtcgcccat ctccgaggac gagggcatgc aagactccga 24120
ggagggcaag cccgtggtca gcgacgagca gctggcccgg tggctgggtc ctaatgctag 24180
tccccagagt ttggaagagc ggcgcaaact catgatggcc gtggtcctgg tgaccgtgga 24240
gctggagtgc ctgcgccgct tcttcgccga cgcggagacc ctgcgcaagg tcgaggagaa 24300
cctgcactac ctcttcaggc acgggttcgt gcgccaggcc tgcaagatct ccaacgtgga 24360
gctgaccaac ctggtctcct acatgggcat cttgcacgag aaccgcctgg ggcagaacgt 24420
gctgcacacc accctgcgcg gggaggcccg gcgcgactac atccgcgact gcgtctacct 24480
ctacctctgc cacacctggc agacgggcat gggcgtgtgg cagcagtgtc tggaggagca 24540
gaacctgaaa gagctctgca agctcctgca gaagaacctc aagggtctgt ggaccgggtt 24600
cgacgagcgc accaccgcct cggacctggc cgacctcatt ttccccgagc gcctcaggct 24660
gacgctgcgc aacggcctgc ccgactttat gagccaaagc atgttgcaaa actttcgctc 24720
tttcatcctc gaacgctccg gaatcctgcc cgccacctgc tccgcgctgc cctcggactt 24780
cgtgccgctg accttccgcg agtgcccccc gccgctgtgg agccactgct acctgctgcg 24840
cctggccaac tacctggcct accactcgga cgtgatcgag gacgtcagcg gcgagggcct 24900
gctcgagtgc cactgccgct gcaacctctg cacgccgcac cgctccctgg cctgcaaccc 24960
ccagctgctg agcgagaccc agatcatcgg caccttcgag ttgcaagggc ccagcgaagg 25020
cgagggttca gccgccaagg ggggtctgaa actcaccccg gggctgtgga cctcggccta 25080
cttgcgcaag ttcgtgcccg aggactacca tcccttcgag atcaggttct acgaggacca 25140
atcccatccg cccaaggccg agctgtcggc ctgcgtcatc acccaggggg cgatcctggc 25200
ccaattgcaa gccatccaga aatcccgcca agaattcttg ctgaaaaagg gccgcggggt 25260
ctacctcgac ccccagaccg gtgaggagct caaccccggc ttcccccagg atgccccgag 25320
gaaacaagaa gctgaaagtg gagctgccgc ccgtggagga tttggaggaa gactgggaga 25380
acagcagtca ggcagaggag gaggagatgg aggaagactg ggacagcact caggcagagg 25440
aggacagcct gcaagacagt ctggaggaag acgaggagga ggcagaggag gaggtggaag 25500
aagcagccgc cgccagaccg tcgtcctcgg cgggggagaa agcaagcagc acggatacca 25560
tctccgctcc gggtcggggt cccgctcgac cacacagtag atgggacgag accggacgat 25620
tcccgaaccc caccacccag accggtaaga aggagcggca gggatacaag tcctggcggg 25680
ggcacaaaaa cgccatcgtc tcctgcttgc aggcctgcgg gggcaacatc tccttcaccc 25740
ggcgctacct gctcttccac cgcggggtga actttccccg caacatcttg cattactacc 25800
gtcacctcca cagcccctac tacttccaag aagaggcagc agcagcagaa aaagaccagc 25860
agaaaaccag cagctagaaa atccacagcg gcggcagcag gtggactgag gatcgcggcg 25920
aacgagccgg cgcaaacccg ggagctgagg aaccggatct ttcccaccct ctatgccatc 25980
ttccagcaga gtcgggggca ggagcaggaa ctgaaagtca agaaccgttc tctgcgctcg 26040
ctcacccgca gttgtctgta tcacaagagc gaagaccaac ttcagcgcac tctcgaggac 26100

-continued

```
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caaccccttc tccggctccc ccggccacta cccggacgag ttcatcccga acttcgacgc  26880
catcagcgag tcggtggacg gctacgattg aaactaatca ccccccttatc cagtgaaata  26940
aagatcatat tgatgatgat tttacagaaa taaaaaataa tcatttgatt tgaaataaag  27000
atacaatcat attgatgatt tgagtttaac aaaaaaataa agaatcactt acttgaaatc  27060
tgataccagg tctctgtcca tgttttctgc caacaccact tcactcccct cttcccagct  27120
ctggtactgc aggccccggc gggctgcaaa cttcctccac acgctgaagg ggatgtcaaa  27180
ttcctcctgt ccctcaatct tcattttatc ttctatcaga tgtccaaaaa gcgcgtccgg  27240
gtggatgatg acttcgaccc cgtctacccc tacgatgcag acaacgcacc gaccgtgccc  27300
ttcatcaacc ccccccttcgt ctcttcagat ggattccaag agaagcccct gggggtgttg  27360
tccctgcgac tggccgaccc cgtcaccacc aagaacgggg aaatcaccct caagctggga  27420
gagggggtgg acctcgattc ctcgggaaaa ctcatctcca acacggccac caaggccgcc  27480
gcccctctca gtttttccaa caacaccatt tcccttaaca tggatcaccc cttttacact  27540
aaagatggaa aattatcctt acaagtttct ccaccattaa atatactgag aacaagcatt  27600
ctaaacacac tagctttagg ttttggatca ggtttaggac tccgtggctc tgccttggca  27660
gtacagttag tctctccact tacatttgat actgatggaa acataaagct taccttagac  27720
agaggtttgc atgttacaac aggagatgca attgaaagca acataagctg ggctaaaggt  27780
ttaaaatttg aagatggagc catagcaacc aacattggaa atgggttaga gtttggaagc  27840
agtagtacag aaacaggtgt tgatgatgct tacccaatcc aagttaaact tggatctggc  27900
cttagctttg acagtacagg agccataatg gctggtaaca aagaagacga taaactcact  27960
ttgtggacaa cacctgatcc atcaccaaac tgtcaaatac tcgcagaaaa tgatgcaaaa  28020
ctaacacttt gcttgactaa atgtggtagt caaatactgg ccactgtgtc agtcttagtt  28080
gtaggaagtg gaaacctaaa ccccattact ggcaccgtaa gcagtgctca ggtgtttcta  28140
cgttttgatg caaacggtgt tcttttaaca gaacattcta cactaaaaaa atactggggg  28200
tataggcagg gagatagcat agatggcact ccatatacca atgctgtagg attcatgccc  28260
aatttaaaag cttatccaaa gtcacaaagt tctactacta aaaataatat agtagggcaa  28320
gtatacatga atggagatgt ttcaaaacct atgcttctca ctataaccct caatggtact  28380
gatgacagca acagtacata ttcaatgtca ttttcataca cctggactaa tggaagctat  28440
```

-continued gttggagcaa catttggggc taactcttat accttctcat acatcgccca agaatgaaca 28500
ctgtatccca ccctgcatgc caacccttcc caccccactc tgtggaacaa actctgaaac 28560
acaaaataaa ataaagttca agtgttttat tgattcaaca gttttacagg attcgagcag 28620
ttatttttcc tccaccctcc caggacatgg aatacaccac cctctccccc cgcacagcct 28680
tgaacatctg aatgccattg gtgatggaca tgcttttggt ctccacgttc cacacagttt 28740
cagagcgagc cagtctcggg tcggtcaggg agatgaaacc ctccgggcac tcccgcatct 28800
gcacctcaca gctcaacagc tgaggattgt cctcggtggt cgggatcacg gttatctgga 28860
agaagcagaa gagcggcggt gggaatcata gtccgcgaac gggatcggcc ggtggtgtcg 28920
catcaggccc cgcagcagtc gctgccgccg ccgctccgtc aagctgctgc tcagggggtc 28980
cgggtccagg gactccctca gcatgatgcc cacggccctc agcatcagtc gtctggtgcg 29040
gcgggcgcag cagcgcatgc ggatctcgct caggtcgctg cagtacgtgc aacacagaac 29100
caccaggttg ttcaacagtc catagttcaa cacgctccag ccgaaactca tcgcgggaag 29160
gatgctaccc acgtggccgt cgtaccagat cctcaggtaa atcaagtggt gccccctcca 29220
gaacacgctg cccacgtaca tgatctcctt gggcatgtgg cggttcacca cctcccggta 29280
ccacatcacc ctctggttga acatgcagcc ccggatgatc ctgcggaacc acagggccag 29340
caccgccccg cccgccatgc agcgaagaga ccccgggtcc cggcaatggc aatggaggac 29400
ccaccgctcg tacccgtgga tcatctggga gctgaacaag tctatgttgg cacagcacag 29460
gcatatgctc atgcatctct tcagcactct caactcctcg gggtcaaaa ccatatccca 29520 gggcacgggg aactcttgca ggacagcgaa ccccgcagaa cagggcaatc ctcgcacaga 29580
acttacattg tgcatggaca gggtatcgca atcaggcagc accgggtgat cctccaccag 29640
agaagcgcgg gtctcggtct cctcacagcg tggtaagggg gccggccgat acgggtgatg 29700
gcgggacgcg gctgatcgtg ttcgcgaccg tgtcatgatg cagttgcttt cggacatttt 29760
cgtacttgct gtagcagaac ctggtccggg cgctgcacac cgatcgccgg cggcggtctc 29820
ggcgcttgga acgctcggtg ttgaaattgt aaaacagcca ctctctcaga ccgtgcagca 29880
gatctagggc ctcaggagtg atgaagatcc catcatgcct gatggctctg atcacatcga 29940
ccaccgtgga atgggccaga cccagccaga tgatgcaatt ttgttgggtt tcggtgacgg 30000
cgggggaggg aagaacagga agaaccatga ttaactttta atccaaacgg tctcggagta 30060
cttcaaaatg aagatcgcgg agatggcacc tctcgccccc gctgtgttgg tggaaaataa 30120
cagccaggtc aaaggtgata cggttctcga gatgttccac ggtggcttcc agcaaagcct 30180
ccacgcgcac atccagaaac aagacaatag cgaaagcggg agggttctct aattcctcaa 30240
tcatcatgtt acactcctgc accatcccca gataattttc atttttccag ccttgaatga 30300
ttcgaactag ttcctgaggt aaatccaagc cagccatgat aaagagctcg cgcagagcgc 30360
cctccaccgg cattcttaag cacaccctca taattccaag atattctgct cctggttcac 30420
ctgcagcaga ttgacaagcg gaatatcaaa atctctgccg cgatccctga gctcctccct 30480
cagcaataac tgtaagtact ctttcatatc ctctccgaaa tttttagcca taggaccacc 30540
aggaataaga ttagggcaag ccacagtaca gataaaccga agtcctcccc agtgagcatt 30600
gccaaatgca agactgctat aagcatgctg gctagacccg gtgatatctt ccagataact 30660
ggacagaaaa tcgcccaggc aatttttaag aaaatcaaca aaagaaaaat cctccaggtg 30720
gacgtttaga gcctcgggaa caacgatgaa gtaaatgcaa gcggtgcgtt ccagcatggt 30780
tagttagctg atctgtagaa aaaacaaaaa tgaacattaa accatgctag cctggcgaac 30840
aggtgggtaa atcgttctct ccagcaccag gcaggccacg gggtctccgg cgcgaccctc 30900
gtaaaaattg tcgctatgat tgaaaaccat cacagagaga cgttcccggt ggccggcgtg 30960
aatgattcga caagatgaat acaccccccgg aacattggcg tccgcgagtg aaaaaaagcg 31020
cccgaggaag caataaggca ctacaatgct cagtctcaag tccagcaaag cgatgccatg 31080
cggatgaagc acaaaattct caggtgcgta caaaatgtaa ttactcccct cctgcacagg 31140
cagcaaagcc cccgatccct ccaggtacac atacaaagcc tcagcgtcca tagcttaccg 31200
agcagcagca cacaacaggc gcaagagtca gagaaaggct gagctctaac ctgtccaccc 31260
gctctctgct caatatatag cccagatcta cactgacgta aaggccaaag tctaaaaata 31320
cccgccaaat aatcacacac gcccagcaca cgcccagaaa ccggtgacac actcaaaaaa 31380
atacgcgcac ttcctcaaac gcccaaaact gccgtcattt ccgggttccc acgctacgtc 31440
atcaaaacac gactttcaaa ttccgtcgac cgttaaaaac gtcacccgcc ccgcccctaa 31500
cggtcgcccg tctctcagcc aatcagcgcc ccgcatcccc aaattcaaac acctcatttg 31560
catattaacg cgcacaaaaa gtttgagg 31588

<210> SEQ ID NO 3
<211> LENGTH: 11447
<212> TYPE: DNA
<213> ORGANISM: Venezuelan equine encephalitis virus

<400> SEQUENCE: 3
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320

-continued

```
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
```

-continued

```
agcagtgtga agaccatgcc attaagctta gcatgttgac caagaaagct tgtctgcatc    3780

tgaatcccgg cggaacctgt gtcagcatag gttatggtta cgctgacagg gccagcgaaa    3840

gcatcattgg tgctatagcg cggcagttca agttttcccg ggtatgcaaa ccgaaatcct    3900

cacttgaaga gacggaagtt ctgtttgtat tcattgggta cgatcgcaag gcccgtacgc    3960

acaatcctta caagctttca tcaaccttga ccaacattta tacaggttcc agactccacg    4020

aagccggatg tgcaccctca tatcatgtgg tgcgagggga tattgccacg gccaccgaag    4080

gagtgattat aaatgctgct aacagcaaag gacaacctgg cggaggggtg tgcggagcgc    4140

tgtataagaa attcccggaa agcttcgatt tacagccgat cgaagtagga aaagcgcgac    4200

tggtcaaagg tgcagctaaa catatcattc atgccgtagg accaaacttc aacaaagttt    4260

cggaggttga aggtgacaaa cagttggcag aggcttatga gtccatcgct aagattgtca    4320

acgataacaa ttacaagtca gtagcgattc cactgttgtc caccggcatc ttttccggga    4380

acaaagatcg actaacccaa tcattgaacc atttgctgac agctttagac accactgatg    4440

cagatgtagc catatactgc agggacaaga aatgggaaat gactctcaag gaagcagtgg    4500

ctaggagaga agcagtggag gagatatgca tatccgacga ctcttcagtg acagaacctg    4560

atgcagagct ggtgagggtg catccgaaga gttctttggc tggaaggaag ggctacagca    4620

caagcgatgg caaaactttc tcatatttgg aagggaccaa gtttcaccag gcggccaagg    4680

atatagcaga aattaatgcc atgtggcccg ttgcaacgga ggccaatgag caggtatgca    4740

tgtatatcct cggagaaagc atgagcagta ttaggtcgaa atgccccgtc gaagagtcgg    4800

aagcctccac accacctagc acgctgcctt gcttgtgcat ccatgccatg actccagaaa    4860

gagtacagcg cctaaaagcc tcacgtccag aacaaattac tgtgtgctca tcctttccat    4920

tgccgaagta tagaatcact ggtgtgcaga agatccaatg ctcccagcct atattgttct    4980

caccgaaagt gcctgcgtat attcatccaa ggaagtatct cgtggaaaca ccaccggtag    5040

acgagactcc ggagccatcg gcagagaacc aatccacaga ggggacacct gaacaaccac    5100

cacttataac cgaggatgag accaggacta gaacgcctga gccgatcatc atcgaagagg    5160

aagaagagga tagcataagt ttgctgtcag atggcccgac ccaccaggtg ctgcaagtcg    5220

aggcagacat tcacgggccg ccctctgtat ctagctcatc ctggtccatt cctcatgcat    5280

ccgactttga tgtggacagt ttatccatac ttgacaccct ggagggagct agcgtgacca    5340

gcggggcaac gtcagccgag actaactctt acttcgcaaa gagtatggag tttctggcgc    5400

gaccggtgcc tgcgcctcga acagtattca ggaaccctcc acatcccgct ccgcgcacaa    5460

gaacaccgtc acttgcaccc agcagggcct gctcgagaac cagcctagtt tccaccccgc    5520

caggcgtgaa tagggtgatc actagagagg agctcgaggc gcttaccccg tcacgcactc    5580

ctagcaggtc ggtctcgaga accagcctgg tctccaaccc gccaggcgta aatagggtga    5640

ttacaagaga ggagtttgag gcgttcgtag cacaacaaca atgacggttt gatgcgggtg    5700

catacatctt ttcctccgac accggtcaag ggcatttaca acaaaaatca gtaaggcaaa    5760

cggtgctatc cgaagtggtg ttggagagga ccgaattgga gatttcgtat gccccgcgcc    5820

tcgaccaaga aaaagaagaa ttactacgca agaaattaca gttaaatccc acacctgcta    5880

acagaagcag ataccagtcc aggaaggtgg agaacatgaa agccataaca gctagacgta    5940

ttctgcaagg cctagggcat tatttgaagg cagaaggaaa agtggagtgc taccgaaccc    6000

tgcatcctgt tcctttgtat tcatctagtg tgaaccgtgc cttttcaagc cccaaggtcg    6060
```

-continued

```
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
```

aaaaccagca gagactttgg ccatgctcag cgttaacgtt gacaacccgg gctacgatga 8520
gctgctggaa gcagctgtta agtgccccgg aaggaaaagg agatccaccg aggagctgtt 8580
taaggagtat aagctaacgc gcccttacat ggccagatgc atcagatgtg cagttgggag 8640
ctgccatagt ccaatagcaa tcgaggcagt aaagagcgac gggcacgacg gttatgttag 8700
acttcagact tcctcgcagt atggcctgga ttcctccggc aacttaaagg gcaggaccat 8760
gcggtatgac atgcacggga ccattaaaga gataccacta catcaagtgt cactccatac 8820
atctcgcccg tgtcacattg tggatgggca cggttatttc ctgcttgcca ggtgcccggc 8880
aggggactcc atcaccatgg aatttaagaa agattccgtc acacactcct gctcggtgcc 8940
gtatgaagtg aaatttaatc ctgtaggcag agaactctat actcatcccc cagaacacgg 9000
agtagagcaa gcgtgccaag tctacgcaca tgatgcacag aacagaggag cttatgtcga 9060
gatgcacctc ccgggctcag aagtggacag cagtttggtt tccttgagcg gcagttcagt 9120
caccgtgaca cctcctgttg ggactagcgc cctggtggaa tgcgagtgtg gcggcacaaa 9180
gatctccgag accatcaaca agacaaaaca gttcagccag tgcacaaaga aggagcagtg 9240
cagagcatat cggctgcaga acgataagtg ggtgtataat tctgacaaac tgcccaaagc 9300
agcgggagcc accttaaaag gaaaactgca tgtcccattc ttgctggcag acggcaaatg 9360
caccgtgcct ctagcaccag aacctatgat aacctttggt ttcagatcag tgtcactgaa 9420
actgcaccct aagaatccca catatctaac cacccgccaa cttgctgatg agcctcacta 9480
cacgcacgag ctcatatctg aaccagctgt taggaatttt accgtcaccg aaaaagggtg 9540
ggagtttgta tggggaaacc acccgccgaa aaggttttgg gcacaggaaa cagcacccgg 9600
aaatccacat gggctaccgc acgaggtgat aactcattat taccacagat accctatgtc 9660
caccatcctg ggtttgtcaa tttgtgccgc cattgcaacc gtttccgttg cagcgtctac 9720
ctggctgttt tgcagatcta gagttgcgtg cctaactcct taccggctaa cacctaacgc 9780
taggatacca ttttgtctgg ctgtgctttg ctgcgcccgc actgcccggg ccgagaccac 9840
ctgggagtcc ttggatcacc tatggaacaa taaccaacag atgttctgga ttcaattgct 9900
gatccctctg gccgccttga tcgtagtgac tcgcctgctc aggtgcgtgt gctgtgtcgt 9960
gcctttttta gtcatggccg gcgccgcagg cgccggcgcc tacgagcacg cgaccacgat 10020
gccgagccaa gcgggaatct cgtataacac tatagtcaac agagcaggct acgcaccact 10080
ccctatcagc ataacaccaa caaagatcaa gctgatacct acagtgaact tggagtacgt 10140
cacctgccac tacaaaacag gaatggattc accagccatc aaatgctgcg gatctcagga 10200
atgcactcca acttacaggc ctgatgaaca gtgcaaagtc ttcacagggg tttacccgtt 10260
catgtggggt ggtgcatatt gcttttgcga cactgagaac acccaagtca gcaaggccta 10320
cgtaatgaaa tctgacgact gccttgcgga tcatgctgaa gcatataaag cgcacacagc 10380
ctcagtgcag gcgttcctca acatcacagt gggagaacac tctattgtga ctaccgtgta 10440
tgtgaatgga gaaactcctg tgaatttcaa tggggtcaaa ttaactgcag gtccgctttc 10500
cacagcttgg acaccctttg atcgcaaaat cgtgcagtat gccggggaga tctataatta 10560
tgattttcct gagtatgggg caggacaacc aggagcattt ggagatatac aatccagaac 10620
agtctcaagc tcagatctgt atgccaatac caacctagtg ctgcagagac ccaaagcagg 10680
agcgatccac gtgccataca ctcaggcacc ttcgggtttt gagcaatgga agaaagataa 10740
agctccatca ttgaaattta ccgccccttt cggatgcgaa atatatacaa accccattcg 10800
cgccgaaaac tgtgctgtag ggtcaattcc attagccttt gacattcccg acgccttgtt 10860
caccagggtg tcagaaacac cgacactttc agcggccgaa tgcactctta acgagtgcgt 10920
gtattcttcc gactttggtg ggatcgccac ggtcaagtac tcggccagca agtcaggcaa 10980
gtgcgcagtc catgtgccat cagggactgc taccctaaaa gaagcagcag tcgagctaac 11040
cgagcaaggg tcggcgacta tccatttctc gaccgcaaat atccacccgg agttcaggct 11100
ccaaatatgc acatcatatg ttacgtgcaa aggtgattgt caccccccga aagaccatat 11160
tgtgacacac cctcagtatc acgcccaaac atttacagcc gcggtgtcaa aaaccgcgtg 11220
gacgtggtta acatccctgc tgggaggatc agccgtaatt attataattg gcttggtgct 11280
ggctactatt gtggccatgt acgtgctgac caaccagaaa cataattgaa tacagcagca 11340
attggcaagc tgcttacata gaactcgcgg cgattggcat gccgccttaa aatttttatt 11400
ttattttttc ttttcttttc cgaatcggat tttgttttta atatttc 11447

<210> SEQ ID NO 4
<211> LENGTH: 9577
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380

-continued

```
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
```

-continued

```
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
```

-continued

```
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaagccacc atggcaggca tgtttcaggc gctgagcgaa ggctgcaccc cgtatgatat   7620
taaccagatg ctgaacgtgc tgggcgatca tcaggtctca ggccttgagc agcttgagag   7680
tataatcaac tttgaaaaac tgactgaatg gaccagttct aatgttatgc ctatcctgtc   7740
tcctctgaca aagggcatcc tgggcttcgt gtttaccctg accgtgcctt ctgagagagg   7800
acttagctgc attagcgaag cggatgcgac cacccccggaa agcgcgaacc tgggcgaaga   7860
aattctgagc cagctgtatc tttggccaag ggtgacctac cattccccta gttatgctta   7920
ccaccaattt gaaagacgag ccaaatataa aagacacttc cccggctttg gccagagcct   7980
gctgtttggc taccctgtgt acgtgttcgg cgattgcgtg cagggcgatt gggatgcgat   8040
tcgctttcgc tattgcgcgc cgccgggcta tgcgctgctg cgctgcaacg ataccaacta   8100
tagcgctctg ctggctgtgg gggccctaga aggacccagg aatcaggact ggcttggtgt   8160
cccaagacaa cttgtaactc ggatgcaggc tattcagaat gccggcctgt gtaccctggt   8220
ggccatgctg gaagagacaa tcttctggct gcaagcgttt ctgatggcgc tgaccgatag   8280
cggcccgaaa accaacatta ttgtggatag ccagtatgtg atgggcatta gcaaaccgag   8340
ctttcaggaa tttgtggatt gggaaaacgt gagcccggaa ctgaacagca ccgatcagcc   8400
gttttggcaa gccggaatcc tggccagaaa tctggtgcct atggtggcca cagtgcaggg   8460
ccagaacctg aagtaccagg gtcagtcact agtcatctct gcttctatca ttgtcttcaa   8520
```

```
cctgctggaa ctggaaggtg attatcgaga tgatggcaac gtgtgggtgc ataccccgct   8580
gagcccgcgc accctgaacg cgtgggtgaa agcggtggaa gaaaaaaaag gtattccagt   8640
tcacctagag ctggccagta tgaccaacat ggagctcatg agcagtattg tgcatcagca   8700
ggtcagaaca tacggccccg tgttcatgtg tctcggcgga ctgcttacaa tggtggctgg   8760
tgctgtgtgg ctgacagtgc gagtgctcga gctgttccgg gccgcgcagc tggccaacga   8820
cgtggtcctc cagatcatgg agctttgtgg tgcagcgttt cgccaggtgt gccataccac   8880
cgtgccgtgg ccgaacgcga gcctgacccc gaaatggaac aacgaaacca cccagcccca   8940
gatcgccaac tgcagcgtgt atgacttttt tgtgtggctc cattattatt ctgttcgaga   9000
cacactttgg ccaagggtga cctaccatat gaacaaatat gcgtatcata tgctggaaag   9060
acgagccaaa tataaaagag gaccaggacc tggcgctaaa tttgtggccg cctggacact   9120
gaaagccgct gctggtcctg gacctggcca gtacatcaag gccaacagca agttcatcgg   9180
catcaccgaa ctcggacccg gaccaggctg atgattcgaa cggccgtatc acgcccaaac   9240
atttacagcc gcggtgtcaa aaaccgcgtg gacgtggtta acatccctgc tgggaggatc   9300
agccgtaatt attataattg gcttggtgct ggctactatt gtggccatgt acgtgctgac   9360
caaccagaaa cataattgaa tacagcagca attggcaagc tgcttacata gaactcgcgg   9420
cgattggcat gccgccttaa aatttttatt ttattttttc ttttcttttc cgaatcggat   9480
tttgttttta atatttcaaa aaaaaaaaaa aaaaaaaaaa aaaaaaaaaa aaaaaaaaaa   9540
aaaaaaaaaa aaaaaaaaaa aaaaaaaaaa aaaaaaa                            9577
```

<210> SEQ ID NO 5
<211> LENGTH: 11447
<212> TYPE: DNA
<213> ORGANISM: Venezuelan equine encephalitis virus

<400> SEQUENCE: 5

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
```

-continued

```
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
```

```
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
```

```
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
```

-continued

```
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta agtgccccgg aaggaaaagg agatccaccg aggagctgtt   8580
taaggagtat aagctaacgc gcccttacat ggccagatgc atcagatgtg cagttgggag   8640
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
aggggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960
gccttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ttaactgcag gtccgctttc  10500
```

```
cacagcttgg acaccctttg atcgcaaaat cgtgcagtat gccggggaga tctataatta  10560
tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt cacccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg gcttggtgct  11280
ggctactatt gtggccatgt acgtgctgac caaccagaaa cataattgaa tacagcagca  11340
attggcaagc tgcttacata gaactcgcgg cgattggcat gccgccttaa aatttttatt  11400
ttattttttc ttttcttttc cgaatcggat tttgttttta atatttc               11447
```

<210> SEQ ID NO 6
<211> LENGTH: 7894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
```

-continued

```
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
```

-continued

```
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
```

-continued

```
tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gactatcacg cccaaacatt   7560

tacagccgcg gtgtcaaaaa ccgcgtggac gtggttaaca tccctgctgg gaggatcagc   7620

cgtaattatt ataattggct tggtgctggc tactattgtg gccatgtacg tgctgaccaa   7680

ccagaaacat aattgaatac agcagcaatt ggcaagctgc ttacatagaa ctcgcggcga   7740

ttggcatgcc gccttaaaat ttttatttta ttttttcttt tcttttccga atcggatttt   7800

gtttttaata tttcaaaaaa aaaaaaaaaa aaaaaaaaaa aaaaaaaaaa aaaaaaaaaa   7860

aaaaaaaaaa aaaaaaaaaa aaaaaaaaaa aaaa                               7894
```

<210> SEQ ID NO 7
<211> LENGTH: 7893
<212> TYPE: DNA
<213> ORGANISM: Artificial Sequence
<220> FEATURE:
<223> OTHER INFORMATION: Description of Artificial Sequence: Synthetic
polynucleotide -continued

<400> SEQUENCE: 7

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa catagggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
```

ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680

-continued

```
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
```

```
cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga ccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gactatcacg cccaaacatt   7560

tacagccgcg gtgtcaaaaa ccgcgtggac gtggttaaca tccctgctgg gaggatcagc   7620

cgtaattatt ataattggct tggtgctggc tactattgtg gccatgtacg tgctgaccaa   7680

ccagaaacat aattgaatac agcagcaatt ggcaagctgc ttacatagaa ctcgcggcga   7740

ttggcatgcc gccttaaaat ttttatttta tttttctttt cttttccgaa tcggattttg   7800

tttttaatat ttcaaaaaaa aaaaaaaaaa aaaaaaaaaa aaaaaaaaaa aaaaaaaaaa   7860

aaaaaaaaaa aaaaaaaaaa aaaaaaaaaa aaa                                7893
```

<210> SEQ ID NO 8
<211> LENGTH: 7927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
taatacgact cactatagga tgggcggcgc atgagagaag cccagaccaa ttacctaccc     60

aaaatggaga aagttcacgt tgacatcgag gaagacagcc cattcctcag agctttgcag    120

cggagcttcc cgcagtttga ggtagaagcc aagcaggtca ctgataatga ccatgctaat    180

gccagagcgt tttcgcatct ggcttcaaaa ctgatcgaaa cggaggtgga cccatccgac    240

acgatccttg acattggaag tgcgcccgcc cgcagaatgt attctaagca caagtatcat    300

tgtatctgtc cgatgagatg tgcggaagat ccggacagat tgtataagta tgcaactaag    360

ctgaagaaaa actgtaagga aataactgat aaggaattgg acaagaaaat gaaggagctc    420

gccgccgtca tgagcgaccc tgacctggaa actgagacta tgtgcctcca cgacgacgag    480

tcgtgtcgct acgaagggca agtcgctgtt taccaggatg tatacgcggt tgacggaccg    540

acaagtctct atcaccaagc caataaggga gttagagtcg cctactggat aggctttgac    600

accaccccctt ttatgtttaa gaacttggct ggagcatatc catcatactc taccaactgg    660

gccgacgaaa ccgtgttaac ggctcgtaac ataggcctat gcagctctga cgttatggag    720

cggtcacgta gagggatgtc cattcttaga aagaagtatt tgaaaccatc caacaatgtt    780

ctattctctg ttggctcgac catctaccac gagaagaggg acttactgag gagctggcac    840

ctgccgtctg tatttcactt acgtggcaag caaaattaca catgtcggtg tgagactata    900

gttagttgcg acgggtacgt cgttaaaaga atagctatca gtccaggcct gtatgggaag    960

ccttcaggct atgctgctac gatgcaccgc gagggattct tgtgctgcaa agtgacagac   1020

acattgaacg gggagagggt ctcttttccc gtgtgcacgt atgtgccagc tacattgtgt   1080

gaccaaatga ctggcatact ggcaacagat gtcagtgcgg acgacgcgca aaaactgctg   1140

gttgggctca accagcgtat agtcgtcaac ggtcgcaccc agagaaacac caataccatg   1200
```

```
aaaaattacc ttttgcccgt agtggcccag gcatttgcta ggtgggcaaa ggaatataag    1260

gaagatcaag aagatgaaag gccactagga ctacgagata gacagttagt catggggtgt    1320

tgttgggctt ttagaaggca caagataaca tctatttata agcgcccgga tacccaaacc    1380

atcatcaaag tgaacagcga tttccactca ttcgtgctgc ccaggatagg cagtaacaca    1440

ttggagatcg ggctgagaac aagaatcagg aaaatgttag aggagcacaa ggagccgtca    1500

cctctcatta ccgccgagga cgtacaagaa gctaagtgcg cagccgatga ggctaaggag    1560

gtgcgtgaag ccgaggagtt gcgcgcagct ctaccacctt tggcagctga tgttgaggag    1620

cccactctgg aagccgatgt cgacttgatg ttacaagagg ctggggccgg ctcagtggag    1680

acacctcgtg gcttgataaa ggttaccagc tacgctggcg aggacaagat cggctcttac    1740

gctgtgcttt ctccgcaggc tgtactcaag agtgaaaaat tatcttgcat ccaccctctc    1800

gctgaacaag tcatagtgat aacacactct ggccgaaaag ggcgttatgc cgtggaacca    1860

taccatggta aagtagtggt gccagaggga catgcaatac ccgtccagga ctttcaagct    1920

ctgagtgaaa gtgccaccat tgtgtacaac gaacgtgagt tcgtaaacag gtacctgcac    1980

catattgcca cacatggagg agcgctgaac actgatgaag aatattacaa aactgtcaag    2040

cccagcgagc acgacggcga atacctgtac gacatcgaca ggaaacagtg cgtcaagaaa    2100

gaactagtca ctgggctagg gctcacaggc gagctggtgg atcctccctt ccatgaattc    2160

gcctacgaga gtctgagaac acgaccagcc gctccttacc aagtaccaac cataggggtg    2220

tatggcgtgc caggatcagg caagtctggc atcattaaaa gcgcagtcac caaaaaagat    2280

ctagtggtga gcgccaagaa agaaaactgt gcagaaatta taagggacgt caagaaaatg    2340

aaagggctgg acgtcaatgc cagaactgtg gactcagtgc tcttgaatgg atgcaaacac    2400

cccgtagaga ccctgtatat tgacgaagct tttgcttgtc atgcaggtac tctcagagcg    2460

ctcatagcca ttataagacc taaaaaggca gtgctctgcg gggatcccaa acagtgcggt    2520

ttttttaaca tgatgtgcct gaaagtgcat tttaaccacg agatttgcac acaagtcttc    2580

cacaaaagca tctctcgccg ttgcactaaa tctgtgactt cggtcgtctc aaccttgttt    2640

tacgacaaaa aaatgagaac gacgaatccg aaagagacta agattgtgat tgacactacc    2700

ggcagtacca aacctaagca ggacgatctc attctcactt gtttcagagg gtgggtgaag    2760

cagttgcaaa tagattacaa aggcaacgaa ataatgacgg cagctgcctc tcaagggctg    2820

acccgtaaag gtgtgtatgc cgttcggtac aaggtgaatg aaaatcctct gtacgcaccc    2880

acctcagaac atgtgaacgt cctactgacc cgcacggagg accgcatcgt gtggaaaaca    2940

ctagccggcg acccatggat aaaaacactg actgccaagt accctgggaa tttcactgcc    3000

acgatagagg agtggcaagc agagcatgat gccatcatga ggcacatctt ggagagaccg    3060

gaccctaccg acgtcttcca gaataaggca aacgtgtgtt gggccaaggc tttagtgccg    3120

gtgctgaaga ccgctggcat agacatgacc actgaacaat ggaacactgt ggattatttt    3180

gaaacggaca aagctcactc agcagagata gtattgaacc aactatgcgt gaggttcttt    3240

ggactcgatc tggactccgg tctattttct gcacccactg ttccgttatc cattaggaat    3300

aatcactggg ataactcccc gtcgcctaac atgtacgggc tgaataaaga agtggtccgt    3360

cagctctctc gcaggtaccc acaactgcct cgggcagttg ccactggaag agtctatgac    3420

atgaacactg gtacactgcg caattatgat ccgcgcataa acctagtacc tgtaaacaga    3480

agactgcctc atgctttagt cctccaccat aatgaacacc cacagagtga cttttcttca    3540
```

ttcgtcagca aattgaaggg cagaactgtc ctggtggtcg gggaaaagtt gtccgtccca 3600
ggcaaaatgg ttgactggtt gtcagaccgg cctgaggcta ccttcagagc tcggctggat 3660
ttaggcatcc caggtgatgt gcccaaatat gacataatat ttgttaatgt gaggacccca 3720
tataaatacc atcactatca gcagtgtgaa gaccatgcca ttaagcttag catgttgacc 3780
aagaaagctt gtctgcatct gaatcccggc ggaacctgtg tcagcatagg ttatggttac 3840
gctgacaggg ccagcgaaag catcattggt gctatagcgc ggcagttcaa gttttcccgg 3900
gtatgcaaac cgaaatcctc acttgaagag acggaagttc tgtttgtatt cattgggtac 3960
gatcgcaagg cccgtacgca caatccttac aagctttcat caaccttgac caacatttat 4020
acaggttcca gactccacga agccggatgt gcaccctcat atcatgtggt gcgaggggat 4080
attgccacgg ccaccgaagg agtgattata aatgctgcta acagcaaagg acaacctggc 4140
ggaggggtgt gcggagcgct gtataagaaa ttcccggaaa gcttcgattt acagccgatc 4200
gaagtaggaa aagcgcgact ggtcaaaggt gcagctaaac atatcattca tgccgtagga 4260
ccaaacttca acaaagtttc ggaggttgaa ggtgacaaac agttggcaga ggcttatgag 4320
tccatcgcta agattgtcaa cgataacaat tacaagtcag tagcgattcc actgttgtcc 4380
accggcatct tttccgggaa caaagatcga ctaacccaat cattgaacca tttgctgaca 4440
gctttagaca ccactgatgc agatgtagcc atatactgca gggacaagaa atgggaaatg 4500
actctcaagg aagcagtggc taggagagaa gcagtggagg agatatgcat atccgacgac 4560
tcttcagtga cagaacctga tgcagagctg gtgagggtgc atccgaagag ttctttggct 4620
ggaaggaagg gctacagcac aagcgatggc aaaactttct catatttgga agggaccaag 4680
tttcaccagg cggccaagga tatagcagaa attaatgcca tgtggcccgt tgcaacggag 4740
gccaatgagc aggtatgcat gtatatcctc ggagaaagca tgagcagtat taggtcgaaa 4800
tgccccgtcg aagagtcgga agcctccaca ccacctagca cgctgccttg cttgtgcatc 4860
catgccatga ctccagaaag agtacagcgc ctaaaagcct cacgtccaga acaaattact 4920
gtgtgctcat cctttccatt gccgaagtat agaatcactg gtgtgcagaa gatccaatgc 4980
tcccagccta tattgttctc accgaaagtg cctgcgtata ttcatccaag gaagtatctc 5040
gtggaaacac caccggtaga cgagactccg gagccatcgg cagagaacca atccacagag 5100
gggacacctg aacaaccacc acttataacc gaggatgaga ccaggactag aacgcctgag 5160
ccgatcatca tcgaagagga agaagaggat agcataagtt tgctgtcaga tggcccgacc 5220
caccaggtgc tgcaagtcga ggcagacatt cacgggccgc cctctgtatc tagctcatcc 5280
tggtccattc ctcatgcatc cgactttgat gtggacagtt tatccatact tgacaccctg 5340
gagggagcta gcgtgaccag cggggcaacg tcagccgaga ctaactctta cttcgcaaag 5400
agtatggagt ttctggcgcg accggtgcct gcgcctcgaa cagtattcag gaaccctcca 5460
catcccgctc cgcgcacaag aacaccgtca cttgcaccca gcagggcctg ctcgagaacc 5520
agcctagttt ccaccccgcc aggcgtgaat agggtgatca ctagagagga gctcgaggcg 5580
cttaccccgt cacgcactcc tagcaggtcg gtctcgagaa ccagcctggt ctccaacccg 5640
ccaggcgtaa atagggtgat tacaagagag gagtttgagg cgttcgtagc acaacaacaa 5700
tgacggtttg atgcgggtgc atacatcttt tcctccgaca ccggtcaagg gcatttacaa 5760
caaaaatcag taaggcaaac ggtgctatcc gaagtggtgt tggagaggac cgaattggag 5820
atttcgtatg ccccgcgcct cgaccaagaa aaagaagaat tactacgcaa gaaattacag 5880
ttaaatccca cacctgctaa cagaagcaga taccagtcca ggaaggtgga gaacatgaaa 5940
gccataacag ctagacgtat tctgcaaggc ctagggcatt atttgaaggc agaaggaaaa 6000
gtggagtgct accgaaccct gcatcctgtt cctttgtatt catctagtgt gaaccgtgcc 6060
ttttcaagcc ccaaggtcgc agtggaagcc tgtaacgcca tgttgaaaga gaactttccg 6120
actgtggctt cttactgtat tattccagag tacgatgcct atttggacat ggttgacgga 6180
gcttcatgct gcttagacac tgccagtttt tgccctgcaa agctgcgcag ctttccaaag 6240
aaacactcct atttggaacc cacaatacga tcggcagtgc cttcagcgat ccagaacacg 6300
ctccagaacg tcctggcagc tgccacaaaa agaaattgca atgtcacgca aatgagagaa 6360
ttgcccgtat tggattcggc ggcctttaat gtggaatgct tcaagaaata tgcgtgtaat 6420
aatgaatatt gggaaacgtt taaagaaaac cccatcaggc ttactgaaga aaacgtggta 6480
aattacatta ccaaattaaa aggaccaaaa gctgctgctc tttttgcgaa gacacataat 6540
ttgaatatgt tgcaggacat accaatggac aggtttgtaa tggacttaaa gagagacgtg 6600
aaagtgactc caggaacaaa acatactgaa gaacggccca aggtacaggt gatccaggct 6660
gccgatccgc tagcaacagc gtatctgtgc ggaatccacc gagagctggt taggagatta 6720
aatgcggtcc tgcttccgaa cattcataca ctgtttgata tgtcggctga agactttgac 6780
gctattatag ccgagcactt ccagcctggg gattgtgttc tggaaactga catcgcgtcg 6840
tttgataaaa gtgaggacga cgccatggct ctgaccgcgt taatgattct ggaagactta 6900
ggtgtggacg cagagctgtt gacgctgatt gaggcggctt tcggcgaaat ttcatcaata 6960
catttgccca ctaaaactaa atttaaattc ggagccatga tgaaatctgg aatgttcctc 7020
acactgtttg tgaacacagt cattaacatt gtaatcgcaa gcagagtgtt gagagaacgg 7080
ctaaccggat caccatgtgc agcattcatt ggagatgaca atatcgtgaa aggagtcaaa 7140
tcggacaaat taatggcaga caggtgcgcc acctggttga atatggaagt caagattata 7200
gatgctgtgg tgggcgagaa agcgccttat ttctgtggag ggtttatttt gtgtgactcc 7260
gtgaccggca cagcgtgccg tgtggcagac cccctaaaaa ggctgtttaa gcttggcaaa 7320
cctctggcag cagacgatga acatgatgat gacaggagaa gggcattgca tgaagagtca 7380
acacgctgga accgagtggg tattctttca gagctgtgca aggcagtaga atcaaggtat 7440
gaaaccgtag gaacttccat catagttatg gccatgacta ctctagctag cagtgttaaa 7500
tcattcagct acctgagagg ggcccctata actctctacg gctaacctga atggactacg 7560
actatcacgc ccaaacattt acagccgcgg tgtcaaaaac cgcgtggacg tggttaacat 7620
ccctgctggg aggatcagcc gtaattatta taattggctt ggtgctggct actattgtgg 7680
ccatgtacgt gctgaccaac cagaaacata attgaataca gcagcaattg gcaagctgct 7740
tacatagaac tcgcggcgat tggcatgccg ccttaaaatt tttattttat tttttctttt 7800
cttttccgaa tcggattttg tttttaatat ttcaaaaaaa aaaaaaaaaa aaaaaaaaaa 7860
aaaaaaaaaa aaaaaaaaaa aaaaaaaaaa aaaaaaaaaa aaaaaaaaaa aaatacgtag 7920
tttaaac 7927

<210> SEQ ID NO 9
<211> LENGTH: 7926
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

-continued

```
taatacgact cactatagga taggcggcgc atgagagaag cccagaccaa ttacctaccc     60
aaaatggaga aagttcacgt tgacatcgag gaagacagcc cattcctcag agctttgcag    120
cggagcttcc cgcagtttga ggtagaagcc aagcaggtca ctgataatga ccatgctaat    180
gccagagcgt tttcgcatct ggcttcaaaa ctgatcgaaa cggaggtgga cccatccgac    240
acgatccttg acattggaag tgcgcccgcc cgcagaatgt attctaagca caagtatcat    300
tgtatctgtc cgatgagatg tgcggaagat ccggacagat tgtataagta tgcaactaag    360
ctgaagaaaa actgtaagga aataactgat aaggaattgg acaagaaaat gaaggagctc    420
gccgccgtca tgagcgaccc tgacctggaa actgagacta tgtgcctcca cgacgacgag    480
tcgtgtcgct acgaagggca agtcgctgtt taccaggatg tatacgcggt tgacggaccg    540
acaagtctct atcaccaagc caataaggga gttagagtcg cctactggat aggctttgac    600
accacccctt ttatgtttaa gaacttggct ggagcatatc catcatactc taccaactgg    660
gccgacgaaa ccgtgttaac ggctcgtaac ataggcctat gcagctctga cgttatggag    720
cggtcacgta gagggatgtc cattcttaga aagaagtatt tgaaaccatc caacaatgtt    780
ctattctctg ttggctcgac catctaccac gagaagaggg acttactgag gagctggcac    840
ctgccgtctg tatttcactt acgtggcaag caaaattaca catgtcggtg tgagactata    900
gttagttgcg acgggtacgt cgttaaaaga atagctatca gtccaggcct gtatgggaag    960
ccttcaggct atgctgctac gatgcaccgc gagggattct tgtgctgcaa agtgacagac   1020
acattgaacg gggagagggt ctcttttccc gtgtgcacgt atgtgccagc tacattgtgt   1080
gaccaaatga ctggcatact ggcaacagat gtcagtgcgg acgacgcgca aaaactgctg   1140
gttgggctca accagcgtat agtcgtcaac ggtcgcaccc agagaaacac caataccatg   1200
aaaaattacc ttttgcccgt agtggcccag gcatttgcta ggtgggcaaa ggaatataag   1260
gaagatcaag aagatgaaag gccactagga ctacgagata gacagttagt catggggtgt   1320
tgttgggctt ttagaaggca caagataaca tctatttata agcgcccgga tacccaaacc   1380
atcatcaaag tgaacagcga tttccactca ttcgtgctgc ccaggatagg cagtaacaca   1440
ttggagatcg ggctgagaac aagaatcagg aaaatgttag aggagcacaa ggagccgtca   1500
cctctcatta ccgccgagga cgtacaagaa gctaagtgcg cagccgatga ggctaaggag   1560
gtgcgtgaag ccgaggagtt gcgcgcagct ctaccacctt tggcagctga tgttgaggag   1620
cccactctgg aagccgatgt cgacttgatg ttacaagagg ctggggccgg ctcagtggag   1680
acacctcgtg gcttgataaa ggttaccagc tacgatggcg aggacaagat cggctcttac   1740
gctgtgcttt ctccgcaggc tgtactcaag agtgaaaaat tatcttgcat ccaccctctc   1800
gctgaacaag tcatagtgat aacacactct ggccgaaaag ggcgttatgc cgtggaacca   1860
taccatggta aagtagtggt gccagaggga catgcaatac ccgtccagga ctttcaagct   1920
ctgagtgaaa gtgccaccat tgtgtacaac gaacgtgagt tcgtaaacag gtacctgcac   1980
catattgcca cacatggagg agcgctgaac actgatgaag aatattacaa aactgtcaag   2040
cccagcgagc acgacggcga atacctgtac gacatcgaca ggaaacagtg cgtcaagaaa   2100
gaactagtca ctgggctagg gctcacaggc gagctggtgg atcctccctt ccatgaattc   2160
gcctacgaga gtctgagaac acgaccagcc gctccttacc aagtaccaac catagggggtg  2220
tatggcgtgc caggatcagg caagtctggc atcattaaaa gcgcagtcac caaaaaagat   2280
ctagtggtga gcgccaagaa agaaaactgt gcagaaatta taagggacgt caagaaaatg   2340
```

```
aaagggctgg acgtcaatgc cagaactgtg gactcagtgc tcttgaatgg atgcaaacac   2400
cccgtagaga ccctgtatat tgacgaagct tttgcttgtc atgcaggtac tctcagagcg   2460
ctcatagcca ttataagacc taaaaaggca gtgctctgcg gggatcccaa acagtgcggt   2520
ttttttaaca tgatgtgcct gaaagtgcat tttaaccacg agatttgcac acaagtcttc   2580
cacaaaagca tctctcgccg ttgcactaaa tctgtgactt cggtcgtctc aaccttgttt   2640
tacgacaaaa aaatgagaac gacgaatccg aaagagacta agattgtgat tgacactacc   2700
ggcagtacca aacctaagca ggacgatctc attctcactt gtttcagagg gtgggtgaag   2760
cagttgcaaa tagattacaa aggcaacgaa ataatgacgg cagctgcctc tcaagggctg   2820
acccgtaaag gtgtgtatgc cgttcggtac aaggtgaatg aaaatcctct gtacgcaccc   2880
acctcagaac atgtgaacgt cctactgacc cgcacggagg accgcatcgt gtggaaaaca   2940
ctagccggcg acccatggat aaaaacactg actgccaagt accctgggaa tttcactgcc   3000
acgatagagg agtggcaagc agagcatgat gccatcatga ggcacatctt ggagagaccg   3060
gaccctaccg acgtcttcca gaataaggca aacgtgtgtt gggccaaggc tttagtgccg   3120
gtgctgaaga ccgctggcat agacatgacc actgaacaat ggaacactgt ggattatttt   3180
gaaacggaca aagctcactc agcagagata gtattgaacc aactatgcgt gaggttcttt   3240
ggactcgatc tggactccgg tctattttct gcacccactg ttccgttatc cattaggaat   3300
aatcactggg ataactcccc gtcgcctaac atgtacgggc tgaataaaga agtggtccgt   3360
cagctctctc gcaggtaccc acaactgcct cgggcagttg ccactggaag agtctatgac   3420
atgaacactg gtacactgcg caattatgat ccgcgcataa acctagtacc tgtaaacaga   3480
agactgcctc atgctttagt cctccaccat aatgaacacc cacagagtga cttttcttca   3540
ttcgtcagca aattgaaggg cagaactgtc ctggtggtcg gggaaaagtt gtccgtccca   3600
ggcaaaatgg ttgactggtt gtcagaccgg cctgaggcta ccttcagagc tcggctggat   3660
ttaggcatcc caggtgatgt gcccaaatat gacataatat ttgttaatgt gaggacccca   3720
tataaatacc atcactatca gcagtgtgaa gaccatgcca ttaagcttag catgttgacc   3780
aagaaagctt gtctgcatct gaatcccggc ggaacctgtg tcagcatagg ttatggttac   3840
gctgacaggg ccagcgaaag catcattggt gctatagcgc ggcagttcaa gttttcccgg   3900
gtatgcaaac cgaaatcctc acttgaagag acggaagttc tgtttgtatt cattgggtac   3960
gatcgcaagg cccgtacgca caatccttac aagctttcat caaccttgac caacatttat   4020
acaggttcca gactccacga agccggatgt gcaccctcat atcatgtggt gcgaggggat   4080
attgccacgg ccaccgaagg agtgattata aatgctgcta acagcaaagg acaacctggc   4140
ggaggggtgt gcggagcgct gtataagaaa ttcccggaaa gcttcgattt acagccgatc   4200
gaagtaggaa aagcgcgact ggtcaaaggt gcagctaaac atatcattca tgccgtagga   4260
ccaaacttca acaaagtttc ggaggttgaa ggtgacaaac agttggcaga ggcttatgag   4320
tccatcgcta agattgtcaa cgataacaat tacaagtcag tagcgattcc actgttgtcc   4380
accggcatct tttccgggaa caaagatcga ctaacccaat cattgaacca tttgctgaca   4440
gctttagaca ccactgatgc agatgtagcc atatactgca gggacaagaa atgggaaatg   4500
actctcaagg aagcagtggc taggagagaa gcagtggagg agatatgcat atccgacgac   4560
tcttcagtga cagaacctga tgcagagctg gtgagggtgc atccgaagag ttctttggct   4620
ggaaggaagg gctacagcac aagcgatggc aaaactttct catatttgga agggaccaag   4680
tttcaccagg cggccaagga tatagcagaa attaatgcca tgtggcccgt tgcaacggag   4740
```

```
gccaatgagc aggtatgcat gtatatcctc ggagaaagca tgagcagtat taggtcgaaa   4800
tgccccgtcg aagagtcgga agcctccaca ccacctagca cgctgccttg cttgtgcatc   4860
catgccatga ctccagaaag agtacagcgc ctaaaagcct cacgtccaga acaaattact   4920
gtgtgctcat cctttccatt gccgaagtat agaatcactg gtgtgcagaa gatccaatgc   4980
tcccagccta tattgttctc accgaaagtg cctgcgtata ttcatccaag gaagtatctc   5040
gtggaaacac caccggtaga cgagactccg gagccatcgg cagagaacca atccacagag   5100
gggacacctg aacaaccacc acttataacc gaggatgaga ccaggactag aacgcctgag   5160
ccgatcatca tcgaagagga agaagaggat agcataagtt tgctgtcaga tggcccgacc   5220
caccaggtgc tgcaagtcga ggcagacatt cacgggccgc cctctgtatc tagctcatcc   5280
tggtccattc ctcatgcatc cgactttgat gtggacagtt tatccatact tgacaccctg   5340
gagggagcta gcgtgaccag cggggcaacg tcagccgaga ctaactctta cttcgcaaag   5400
agtatggagt ttctggcgcg accggtgcct gcgcctcgaa cagtattcag gaaccctcca   5460
catcccgctc cgcgcacaag aacaccgtca cttgcaccca gcagggcctg ctcgagaacc   5520
agcctagttt ccaccccgcc aggcgtgaat agggtgatca ctagagagga gctcgaggcg   5580
cttaccccgt cacgcactcc tagcaggtcg gtctcgagaa ccagcctggt ctccaacccg   5640
ccaggcgtaa atagggtgat tacaagagag gagtttgagg cgttcgtagc acaacaacaa   5700
tgacggtttg atgcgggtgc atacatcttt tcctccgaca ccggtcaagg gcatttacaa   5760
caaaaatcag taaggcaaac ggtgctatcc gaagtggtgt tggagaggac cgaattggag   5820
atttcgtatg ccccgcgcct cgaccaagaa aaagaagaat tactacgcaa gaaattacag   5880
ttaaatccca cacctgctaa cagaagcaga taccagtcca ggaaggtgga gaacatgaaa   5940
gccataacag ctagacgtat tctgcaaggc ctagggcatt atttgaaggc agaaggaaaa   6000
gtggagtgct accgaaccct gcatcctgtt cctttgtatt catctagtgt gaaccgtgcc   6060
ttttcaagcc ccaaggtcgc agtggaagcc tgtaacgcca tgttgaaaga gaactttccg   6120
actgtggctt cttactgtat tattccagag tacgatgcct atttggacat ggttgacgga   6180
gcttcatgct gcttagacac tgccagtttt tgccctgcaa agctgcgcag ctttccaaag   6240
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
aaagtgactc caggaacaaa acatactgaa gaacggccca aggtacaggt gatccaggct   6660
gccgatccgc tagcaacagc gtatctgtgc ggaatccacc gagagctggt taggagatta   6720
aatgcggtcc tgcttccgaa cattcataca ctgtttgata tgtcggctga agactttgac   6780
gctattatag ccgagcactt ccagcctggg gattgtgttc tggaaactga catcgcgtcg   6840
tttgataaaa gtgaggacga cgccatggct ctgaccgcgt taatgattct ggaagactta   6900
ggtgtggacg cagagctgtt gacgctgatt gaggcggctt tcggcgaaat ttcatcaata   6960
catttgccca ctaaaactaa atttaaattc ggagccatga tgaaatctgg aatgttcctc   7020
acactgtttg tgaacacagt cattaacatt gtaatcgcaa gcagagtgtt gagagaacgg   7080
```

-continued

```
ctaaccggat caccatgtgc agcattcatt ggagatgaca atatcgtgaa aggagtcaaa   7140

tcggacaaat taatggcaga caggtgcgcc acctggttga atatggaagt caagattata   7200

gatgctgtgg tgggcgagaa agcgccttat ttctgtggag ggtttatttt gtgtgactcc   7260

gtgaccggca cagcgtgccg tgtggcagac cccctaaaaa ggctgtttaa gcttggcaaa   7320

cctctggcag cagacgatga acatgatgat gacaggagaa gggcattgca tgaagagtca   7380

acacgctgga accgagtggg tattctttca gagctgtgca aggcagtaga atcaaggtat   7440

gaaaccgtag gaacttccat catagttatg gccatgacta ctctagctag cagtgttaaa   7500

tcattcagct acctgagagg ggcccctata actctctacg gctaacctga atggactacg   7560

actatcacgc ccaaacattt acagccgcgg tgtcaaaaac cgcgtggacg tggttaacat   7620

ccctgctggg aggatcagcc gtaattatta taattggctt ggtgctggct actattgtgg   7680

ccatgtacgt gctgaccaac cagaaacata attgaataca gcagcaattg gcaagctgct   7740

tacatagaac tcgcggcgat tggcatgccg ccttaaaatt tttattttat tttctttttc   7800

ttttccgaat cggattttgt ttttaatatt tcaaaaaaaa aaaaaaaaaa aaaaaaaaaa   7860

aaaaaaaaaa aaaaaaaaaa aaaaaaaaaa aaaaaaaaaa aaaaaaaaaa aatacgtagt   7920

ttaaac                                                              7926
```

<210> SEQ ID NO 10
<211> LENGTH: 36519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagatga ggcacctgag agacctgccc    600

gatgagaaaa tcatcatcgc ttccgggaac gagattctgg aactggtggt aaatgccatg    660

atgggcgacg accctccgga gccccccacc ccatttgaga caccttcgct gcacgatttg    720

tatgatctgg aggtggatgt gcccgaggac gatcccaatg aggaggcggt aaatgatttt    780

tttagcgatg ccgcgctgct agctgccgag gaggcttcga gctctagctc agacagcgac    840

tcttcactgc ataccccctag acccggcaga ggtgagaaaa agatccccga gcttaaaggg    900

gaagagatgg acttgcgctg ctatgaggaa tgcttgcccc cgagcgatga tgaggacgag    960

caggcgatcc agaacgcagc gagccaggga gtgcaagccg ccagcgagag ctttgcgctg   1020

gactgcccgc ctctgcccgg acacggctgt aagtcttgtg aatttcatcg catgaatact   1080

ggagataaag ctgtgttgtg tgcactttgc tatatgagag cttacaacca ttgtgtttac   1140
```

-continued

```
agtaagtgtg attaagttga actttagagg gaggcagaga gcagggtgac tgggcgatga   1200
ctggtttatt tatgtatata tgttctttat ataggtcccg tctctgacgc agatgatgag   1260
acccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gcctttttgg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggaggggta ttcagccctt atctgacggg   3540
```

-continued gcgtctcccc tcctgggcgg gagtgcgtca gaatgtgatg ggatccacgg tggacggccg 3600
gcccgtgcag cccgcgaact cttcaaccct gacctatgca accctgagct cttcgtcgtt 3660
ggacgcagct gccgccgcag ctgctgcatc tgccgccagc gccgtgcgcg gaatggccat 3720
gggcgccggc tactacggca ctctggtggc caactcgagt tccaccaata atcccgccag 3780
cctgaacgag gagaagctgt tgctgctgat ggcccagctc gaggccttga cccagcgcct 3840
gggcgagctg acccagcagg tggctcagct gcaggagcag acgcgggccg cggttgccac 3900
ggtgaaatcc aaataaaaaa tgaatcaata aataaacgga gacggttgtt gattttaaca 3960
cagagtctga atctttattt gatttttcgc gcgcggtagg ccctggacca ccggtctcga 4020
tcattgagca cccggtggat cttttccagg acccggtaga ggtgggcttg gatgttgagg 4080
tacatgggca tgagcccgtc ccgggggtgg aggtagctcc attgcagggc ctcgtgctcg 4140
ggggtggtgt tgtaaatcac ccagtcatag caggggcgca gggcatggtg ttgcacaata 4200
tctttgagga ggagactgat ggccacgggc agccctttgg tgtaggtgtt tacaaatctg 4260
ttgagctggg agggatgcat gcgggggggag atgaggtgca tcttggcctg gatcttgaga 4320
ttggcgatgt taccgcccag atcccgcctg gggttcatgt tgtgcaggac caccagcacg 4380
gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggagggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920
tcgcgcacca gttccgccag gaggcgctct ccccccaggg ataggagctc ctggagcgag 4980
gcgaagtttt tcagcggctt gagtccgtcg gccatgggca ttttggagag ggtttgttgc 5040
aagagttcca ggcggtccca gagctcggtg atgtgctcta cggcatctcg atccagcaga 5100
cctcctcgtt tcgcgggttg ggacggctgc gggagtaggg caccagacga tgggcgtcca 5160
gcgcagccag ggtccggtcc ttccagggtc gcagcgtccg cgtcagggtg gtctccgtca 5220
cggtgaaggg gtgcgcgccg ggctgggcgc ttgcgagggt gcgcttcagg ctcatccggc 5280
tggtcgaaaa ccgctcccga tcggcgccct gcgcgtcggc caggtagcaa ttgaccatga 5340
gttcgtagtt gagcgcctcg gccgcgtggc ctttggcgcg gagcttacct ttggaagtct 5400
gcccgcaggc gggacagagg agggacttga gggcgtagag cttgggggcg aggaagacgg 5460
actcgggggc gtaggcgtcc gcgccgcagt gggcgcagac ggtctcgcac tccacgagcc 5520
aggtgaggtc gggctggtcg gggtcaaaaa ccagtttccc gccgttcttt ttgatgcgtt 5580
tcttaccttt ggtctccatg agctcgtgtc cccgctgggt gacaaagagg ctgtccgtgt 5640
ccccgtagac cgactttatg ggccggtcct cgagcggtgt gccgcggtcc tcctcgtaga 5700
ggaaccccgc ccactccgag acgaaagccc gggtccaggc cagcacgaag gaggccacgt 5760
gggacgggta gcggtcgttg tccaccagcg ggtccacctt ttccagggta tgcaaacaca 5820
tgtccccctc gtccacatcc aggaaggtga ttggcttgta agtgtaggcc acgtgaccgg 5880

-continued

```
gggtcccggc cgggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg ggcagggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat tcgcgcacgg   6540
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agccccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg gggcacctcg gcccggttgt   7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
```

ggttgacttg caggagtttt tccagggcgc gcgggaggtc cagatggtac ttgatctcca 8340
ccgcgccatt ggtggcgacg tcgatggctt gcagggtccc gtgcccctgg ggtgtgacca 8400
ccgtcccccg tttcttcttg ggcggctggg gcgacggggg cggtgcctct tccatggtta 8460
gaagcggcgg cgaggacgcg cgccgggcgg caggggcggc tcggggcccg gaggcagggg 8520
cggcaggggc acgtcggcgc cgcgcgcggg taggttctgg tactgcgccc ggagaagact 8580
ggcgtgagcg acgacgcgac ggttgacgtc ctggatctga cgcctctggg tgaaggccac 8640
gggacccgtg agtttgaacc tgaaagagag ttcgacagaa tcaatctcgg tatcgttgac 8700
ggcggcctgc cgcaggatct cttgcacgtc gcccgagttg tcctggtagg cgatctcggt 8760
catgaactgc tcgatctcct cctcttgaag gtctccgcgg ccggcgcgct ccacggtggc 8820
cgcgaggtcg ttggagatgc ggcccatgag ctgcgagaag gcgttcatgc ccgcctcgtt 8880
ccagacgcgg ctgtagacca cgacgccctc gggatcgcgg gcgcgcatga ccacctgggc 8940
gaggttgagc tccacgtggc gcgtgaagac cgcgtagttg cagaggcgct ggtagaggta 9000
gttgagcgtg gtggcgatgt gctcggtgac gaagaaatac atgatccagc ggcggagcgg 9060
catctcgctg acgtcgccca gcgcctccaa acgttccatg gcctcgtaaa agtccacggc 9120
gaagttgaaa aactgggagt tgcgcgccga gacggtcaac tcctcctcca gaagacggat 9180
gagctcggcg atggtggcgc gcacctcgcg ctcgaaggcc cccgggagtt cctccacttc 9240
ctcttcttcc tcctccacta acatctcttc tacttcctcc tcaggcggca gtggtggcgg 9300
gggagggggc ctgcgtcgcc ggcggcgcac gggcagacgg tcgatgaagc gctcgatggt 9360
ctcgccgcgc cggcgtcgca tggtctcggt gacggcgcgc ccgtcctcgc ggggccgcag 9420
cgtgaagacg ccgccgcgca tctccaggtg gccggggggg tccccgttgg gcagggagag 9480
ggcgctgacg atgcatctta tcaattgccc cgtagggact ccgcgcaagg acctgagcgt 9540
ctcgagatcc acgggatctg aaaaccgctg aacgaaggct tcgagccagt cgcagtcgca 9600
aggtaggctg agcacggttt cttctggcgg gtcatgttgg ttgggagcgg ggcgggcgat 9660
gctgctggtg atgaagttga aataggcggt tctgagacgg cggatggtgg cgaggagcac 9720
caggtctttg ggcccggctt gctggatgcg cagacggtcg gccatgcccc aggcgtggtc 9780
ctgacacctg gccaggtcct tgtagtagtc ctgcatgagc cgctccacgg gcacctcctc 9840
ctcgcccgcg cggccgtgca tgcgcgtgag cccgaagccg cgctggggct ggacgagcgc 9900
caggtcggcg acgacgcgct cggcgaggat ggcttgctgg atctgggtga gggtggtctg 9960
gaagtcatca aagtcgacga agcggtggta ggctccggtg ttgatggtgt aggagcagtt 10020
ggccatgacg gaccagttga cggtctggtg gcccggacgc acgagctcgt ggtacttgag 10080
gcgcgagtag gcgcgcgtgt cgaagatgta gtcgttgcag gtgcgcacca ggtactggta 10140
gccgatgagg aagtgcggcg gcggctggcg gtagagcggc catcgctcgg tggcgggggc 10200
gccgggcgcg aggtcctcga gcatggtgcg gtggtagccg tagatgtacc tggacatcca 10260
ggtgatgccg gcggcggtgg tggaggcgcg cgggaactcg cggacgcggt tccagatgtt 10320
gcgcagcggc aggaagtagt tcatggtggg cacggtctgg cccgtgaggc gcgcgcagtc 10380
gtggatgctc tatacgggca aaaacgaaag cggtcagcgg ctcgactccg tggcctggag 10440
gctaagcgaa cgggttgggc tgcgcgtgta ccccggttcg aatctcgaat caggctggag 10500
ccgcagctaa cgtggtattg gcactcccgt ctcgacccaa gcctgcacca accctccagg 10560
atacggaggc gggtcgtttt gcaacttttt tttggaggcc ggatgagact agtaagcgcg 10620

-continued

```
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
```

```
ttcctgatgc aggagggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggaccccgt gaccgagctg gtcatgcccg  14580
gggtgtacac caacgaggct ttccatcccg atattgtctt gctgcccggc tgcggggtgg  14640
acttcaccga gagccgcctc agcaacctgc tgggcattcg caagaggcag cccttccagg  14700
aaggcttcca gatcatgtac gaggatctgg aggggggcaa catccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
```

-continued

```
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt gggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
```

ggccaaccag gccgtgcagc ggcagatcaa cagccgcctg gacccggtgc cgcccgccgg 17820
ctccgtggag atgccgcagg tggaggagga gctgcctccc ctggacaagc ggggcgagaa 17880
gcgaccccgc cccgatgcgg aggagacgct gctgacgcac acggacgagc cgcccccgta 17940
cgaggaggcg gtgaaactgg gtctgcccac cacgcggccc atcgcgcccc tggccaccgg 18000
ggtgctgaaa cccgaaaagc ccgcgaccct ggacttgcct cctccccagc cttcccgccc 18060
ctctacagtg gctaagcccc tgccgccggt ggccgtggcc cgcgcgcgac ccgggggcac 18120
cgcccgccct catgcgaact ggcagagcac tctgaacagc atcgtgggtc tgggagtgca 18180
gagtgtgaag cgccgccgct gctattaaac ctaccgtagc gcttaacttg cttgtctgtg 18240
tgtgtatgta ttatgtcgcc gccgccgctg tccaccagaa ggaggagtga agaggcgcgt 18300
cgccgagttg caagatggcc accccatcga tgctgcccca gtgggcgtac atgcacatcg 18360
ccggacagga cgcttcggag tacctgagtc cgggtctggt gcagtttgcc cgcgccacag 18420
acacctactt cagtctgggg aacaagttta ggaaccccac ggtggcgccc acgcacgatg 18480
tgaccaccga ccgcagccag cggctgacgc tgcgcttcgt gcccgtggac cgcgaggaca 18540
acacctactc gtacaaagtg cgctacacgc tggccgtggg cgacaaccgc gtgctggaca 18600
tggccagcac ctactttgac atccgcggcg tgctggatcg gggccctagc ttcaaaccct 18660
actccggcac cgcctacaac agtctggccc ccaagggagc acccaacact tgtcagtgga 18720
catataaagc cgatggtgaa actgccacag aaaaaaccta tacatatgga aatgcacccg 18780
tgcagggcat taacatcaca aaagatggta ttcaacttgg aactgacacc gatgatcagc 18840
caatctacgc agataaaacc tatcagcctg aacctcaagt gggtgatgct gaatggcatg 18900
acatcactgg tactgatgaa aagtatggag gcagagctct taagcctgat accaaaatga 18960
agccttgtta tggttctttt gccaagccta ctaataaaga aggaggtcag gcaaatgtga 19020
aaacaggaac aggcactact aaagaatatg acatagacat ggctttcttt gacaacagaa 19080
gtgcggctgc tgctggccta gctccagaaa ttgttttgta tactgaaaat gtggatttgg 19140
aaactccaga tacccatatt gtatacaaag caggcacaga tgacagcagc tcttctatta 19200
atttgggtca gcaagccatg cccaacagac ctaactacat tggtttcaga gacaacttta 19260
tcgggctcat gtactacaac agcactggca atatgggggt gctggccggt caggcttctc 19320
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100

-continued tctacgccac cttcttcccc atggcgcaca acacggcctc cacgctcgag gccatgctgc 20160
gcaacgacac caacgaccag tccttcaacg actacctctc ggcggccaac atgctctacc 20220
ccatcccggc caacgccacc aacgtgccca tctccatccc ctcgcgcaac tgggccgcct 20280
tccgcggctg gtccttcacg cgtctcaaga ccaaggagac gccctcgctg ggctccgggt 20340
tcgaccccta cttcgtctac tcgggctcca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctacaa ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760
ccatgcgcca gggccagccc taccccgcca actaccccta cccgctcatc ggcaagagcg 20820
ccgtcaccag cgtcacccag aaaaagttcc tctgcgacag ggtcatgtgg cgcatcccct 20880
tctccagcaa cttcatgtcc atgggcgcgc tcaccgacct cggccagaac atgctctatg 20940
ccaactccgc ccacgcgcta gacatgaatt tcgaagtcga ccccatggat gagtccaccc 21000
ttctctatgt tgtcttcgaa gtcttcgacg tcgtccgagt gcaccagccc caccgcggcg 21060
tcatcgaggc cgtctacctg cgcaccccct tctcggccgg taacgccacc acctaagctc 21120
ttgcttcttg caagccatgg ccgcgggctc cggcgagcag gagctcaggg ccatcatccg 21180
cgacctgggc tgcgggccct acttcctggg caccttcgat aagcgcttcc cgggattcat 21240
ggccccgcac aagctggcct gcgccatcgt caacacggcc ggccgcgaga ccgggggcga 21300
gcactggctg gccttcgcct ggaacccgcg ctcgaacacc tgctacctct tcgacccctt 21360
cgggttctcg gacgagcgcc tcaagcagat ctaccagttc gagtacgagg gcctgctgcg 21420
ccgcagcgcc ctggccaccg aggaccgctg cgtcaccctg gaaaagtcca cccagaccgt 21480
gcagggtccg cgctcggccg cctgcgggct cttctgctgc atgttcctgc acgccttcgt 21540
gcactggccc gaccgcccca tggacaagaa ccccaccatg aacttgctga cgggggtgcc 21600
caacggcatg ctccagtcgc cccaggtgga acccaccctg cgccgcaacc aggaggcgct 21660
ctaccgcttc ctcaactccc actccgccta ctttcgctcc caccgcgcgc gcatcgagaa 21720
ggccaccgcc ttcgaccgca tgaatcaaga catgtaaacc gtgtgtgtat gttaaatgtc 21780
tttaataaac agcactttca tgttacacat gcatctgaga tgatttattt agaaatcgaa 21840
agggttctgc cgggtctcgg catggcccgc gggcagggac acgttgcgga actggtactt 21900
ggccagccac ttgaactcgg ggatcagcag tttgggcagc ggggtgtcgg ggaaggagtc 21960
ggtccacagc ttccgcgtca gttgcagggc gcccagcagg tcgggcgcgg agatcttgaa 22020
atcgcagttg ggacccgcgt tctgcgcgcg ggagttgcgg tacacggggt tgcagcactg 22080
gaacaccatc agggccgggt gcttcacgct cgccagcacc gtcgcgtcgg tgatgctctc 22140
cacgtcgagg tcctcggcgt tggccatccc gaagggggtc atcttgcagg tctgccttcc 22200
catggtgggc acgcacccgg gcttgtggtt gcaatcgcag tgcaggggga tcagcatcat 22260
ctgggcctgg tcggcgttca tccccgggta catggccttc atgaaagcct ccaattgcct 22320
gaacgcctgc tgggccttgg ctccctcggt gaagaagacc ccgcaggact tgctagagaa 22380
ctggttggtg gcgcacccgg cgtcgtgcac gcagcagcgc gcgtcgttgt tggccagctg 22440
caccacgctg cgcccccagc ggttctgggt gatcttggcc cggtcggggt tctccttcag 22500
cgcgcgctgc ccgttctcgc tcgccacatc catctcgatc atgtgctcct tctggatcat 22560
ggtggtcccg tgcaggcacc gcagcttgcc ctcggcctcg gtgcacccgt gcagccacag 22620
cgcgcacccg gtgcactccc agttcttgtg ggcgatctgg gaatgcgcgt gcacgaagcc 22680
ctgcaggaag cggcccatca tggtggtcag ggtcttgttg ctagtgaagg tcagcggaat 22740
gccgcggtgc tcctcgttga tgtacaggtg gcagatgcgg cggtacacct cgccctgctc 22800
gggcatcagc tggaagttgg ctttcaggtc ggtctccacg cggtagcggt ccatcagcat 22860
agtcatgatt tccataccct tctcccaggc cgagacgatg ggcaggctca tagggttctt 22920
caccatcatc ttagcgctag cagccgcggc caggggggtcg ctctcgtcca gggtctcaaa 22980
gctccgcttg ccgtccttct cggtgatccg caccgggggg tagctgaagc ccacggccgc 23040
cagctcctcc tcggcctgtc tttcgtcctc gctgtcctgg ctgacgtcct gcaggaccac 23100
atgcttggtc ttgcggggtt tcttcttggg cggcagcggc ggcggagatg ttggagatgg 23160
cgagggggag cgcgagttct cgctcaccac tactatctct tcctcttctt ggtccgaggc 23220
cacgcggcgg taggtatgtc tcttcggggg cagaggcgga ggcgacgggc tctcgccgcc 23280
gcgacttggc ggatggctgg cagagcccct tccgcgttcg gggggtgcgct cccggcggcg 23340
ctctgactga cttcctccgc ggccggccat tgtgttctcc tagggaggaa caacaagcat 23400
ggagactcag ccatcgccaa cctcgccatc tgccccccacc gccgacgaga agcagcagca 23460
gcagaatgaa agcttaaccg ccccgccgcc cagccccgcc acctccgacg cggccgtccc 23520
agacatgcaa gagatggagg aatccatcga gattgacctg ggctatgtga cgcccgcgga 23580
gcacgaggag gagctggcag tgcgcttttc acaagaagag atacaccaag aacagccaga 23640
gcaggaagca gagaatgagc agagtcaggc tgggctcgag catgacggcg actacctcca 23700
cctgagcggg ggggaggacg cgctcatcaa gcatctggcc cggcaggcca ccatcgtcaa 23760
ggatgcgctg ctcgaccgca ccgaggtgcc cctcagcgtg gaggagctca gccgcgccta 23820
cgagttgaac ctcttctcgc cgcgcgtgcc ccccaagcgc cagcccaatg gcacctgcga 23880
gcccaacccg cgcctcaact tctacccggt cttcgcggtg cccgaggccc tggccaccta 23940
ccacatcttt ttcaagaacc aaaagatccc cgtctcctgc cgcgccaacc gcacccgcgc 24000
cgacgccctt ttcaacctgg gtcccggcgc ccgcctacct gatatcgcct ccttggaaga 24060
ggttcccaag atcttcgagg gtctgggcag cgacgagact cgggccgcga acgctctgca 24120
aggagaagga ggagagcatg agcaccacag cgccctggtc gagttggaag gcgacaacgc 24180
gcggctggcg gtgctcaaac gcacggtcga gctgacccat ttcgcctacc cggctctgaa 24240
cctgcccccc aaagtcatga gcgcggtcat ggaccaggtg ctcatcaagc gcgcgtcgcc 24300
catctccgag gacgagggca tgcaagactc cgaggagggc aagcccgtgg tcagcgacga 24360
gcagctggcc cggtggctgg gtcctaatgc tagtccccag agtttggaag agcggcgcaa 24420
actcatgatg gccgtggtcc tggtgaccgt ggagctggag tgcctgcgcc gcttcttcgc 24480
cgacgcggag accctgcgca aggtcgagga gaacctgcac tacctcttca ggcacgggtt 24540
cgtgcgccag gcctgcaaga tctccaacgt ggagctgacc aacctggtct cctacatggg 24600
catcttgcac gagaaccgcc tggggcagaa cgtgctgcac accaccctgc gcggggaggc 24660
ccggcgcgac tacatccgcg actgcgtcta cctctacctc tgccacacct ggcagacggg 24720
catgggcgtg tggcagcagt gtctggagga gcagaacctg aaagagctct gcaagctcct 24780
gcagaagaac ctcaagggtc tgtggaccgg gttcgacgag cgcaccaccg cctcggacct 24840

```
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
```

-continued

```
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
```

-continued

```
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgttggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaagg gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcacccccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
```

```
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aacccccccct tcgtctcttc agatggattc caagagaagc ccctgggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg ggctaactc ttatacctt tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
```

ctcgtacccg tggatcatct gggagctgaa caagtctatg ttggcacagc acaggcatat 34380
gctcatgcat ctcttcagca ctctcaactc ctcgggggtc aaaaccatat cccagggcac 34440
ggggaactct tgcaggacag cgaaccccgc agaacagggc aatcctcgca cagaacttac 34500
attgtgcatg gacagggtat cgcaatcagg cagcaccggg tgatcctcca ccagagaagc 34560
gcgggtctcg gtctcctcac agcgtggtaa gggggccggc cgatacgggt gatggcggga 34620
cgcggctgat cgtgttcgcg accgtgtcat gatgcagttg ctttcggaca ttttcgtact 34680
tgctgtagca gaacctggtc cgggcgctgc acaccgatcg ccggcggcgg tctcggcgct 34740
tggaacgctc ggtgttgaaa ttgtaaaaca gccactctct cagaccgtgc agcagatcta 34800
gggcctcagg agtgatgaag atcccatcat gcctgatggc tctgatcaca tcgaccaccg 34860
tggaatgggc cagacccagc cagatgatgc aattttgttg ggtttcggtg acggcggggg 34920
agggaagaac aggaagaacc atgattaact tttaatccaa acggtctcgg agtacttcaa 34980
aatgaagatc gcggagatgg cacctctcgc ccccgctgtg ttggtggaaa ataacagcca 35040
ggtcaaaggt gatacggttc tcgagatgtt ccacggtggc ttccagcaaa gcctccacgc 35100
gcacatccag aaacaagaca atagcgaaag cgggagggtt ctctaattcc tcaatcatca 35160
tgttacactc ctgcaccatc cccagataat tttcattttt ccagccttga atgattcgaa 35220
ctagttcctg aggtaaatcc aagccagcca tgataaagag ctcgcgcaga gcgccctcca 35280
ccggcattct taagcacacc ctcataattc caagatattc tgctcctggt tcacctgcag 35340
cagattgaca agcggaatat caaaatctct gccgcgatcc ctgagctcct ccctcagcaa 35400
taactgtaag tactctttca tatcctctcc gaaattttta gccataggac caccaggaat 35460
aagattaggg caagccacag tacagataaa ccgaagtcct ccccagtgag cattgccaaa 35520
tgcaagactg ctataagcat gctggctaga cccggtgata tcttccagat aactggacag 35580
aaaatcgccc aggcaatttt taagaaaatc aacaaaagaa aaatcctcca ggtggacgtt 35640
tagagcctcg ggaacaacga tgaagtaaat gcaagcggtg cgttccagca tggttagtta 35700
gctgatctgt agaaaaaaca aaaatgaaca ttaaaccatg ctagcctggc gaacaggtgg 35760
gtaaatcgtt ctctccagca ccaggcaggc cacggggtct ccggcgcgac cctcgtaaaa 35820
attgtcgcta tgattgaaaa ccatcacaga gagacgttcc cggtggccgg cgtgaatgat 35880
tcgacaagat gaatacaccc ccggaacatt ggcgtccgcg agtgaaaaaa agcgcccgag 35940
gaagcaataa ggcactacaa tgctcagtct caagtccagc aaagcgatgc catgcggatg 36000
aagcacaaaa ttctcaggtg cgtacaaaat gtaattactc ccctcctgca caggcagcaa 36060
agcccccgat ccctccaggt acacatacaa agcctcagcg tccatagctt accgagcagc 36120
agcacacaac aggcgcaaga gtcagagaaa ggctgagctc taacctgtcc acccgctctc 36180
tgctcaatat atagcccaga tctacactga cgtaaaggcc aaagtctaaa aatacccgcc 36240
aaataatcac acacgcccag cacacgccca gaaaccggtg acacactcaa aaaaatacgc 36300
gcacttcctc aaacgcccaa aactgccgtc atttccgggt tcccacgcta cgtcatcaaa 36360
acacgacttt caaattccgt cgaccgttaa aaacgtcacc cgccccgccc ctaacggtcg 36420
cccgtctctc agccaatcag cgccccgcat ccccaaattc aaacacctca tttgcatatt 36480
aacgcgcaca aaaagtttga ggtatattat tgatgatgg 36519

<210> SEQ ID NO 11
<211> LENGTH: 31867
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780
attgacgtca atgggtggag tatttacggt aaactgccca cttggcagta catcaagtgt 840
atcatatgcc aagtccgccc cctattgacg tcaatgacgg taaatggccc gcctggcatt 900
atgcccagta catgacctta cgggactttc ctacttggca gtacatctac gtattagtca 960
tcgctattac catggtgatg cggttttggc agtacaccaa tgggcgtgga tagcggtttg 1020
actcacgggg atttccaagt ctccacccca ttgacgtcaa tgggagtttg ttttggcacc 1080
aaaatcaacg ggactttcca aaatgtcgta ataaccccgc cccgttgacg caaatgggcg 1140
gtaggcgtgt acggtgggag gtctatataa gcagagctcg tttagtgaac cgtcagatcg 1200
cctggaacgc catccacgct gttttgacct ccatagaaga cagcgatcgc gccaccatgg 1260
tgagcaaggg cgaggagctg ttcaccgggg tggtgcccat cctggtcgag ctggacggcg 1320
acgtaaacgg ccacaagttc agcgtgtccg gcgagggcga gggcgatgcc acctacggca 1380
agctgaccct gaagttcatc tgcaccaccg gcaagctgcc cgtgccctgg cccaccctcg 1440
tgaccaccct gacctacggc gtgcagtgct tcagccgcta ccccgaccac atgaagcagc 1500
acgacttctt caagtccgcc atgcccgaag gctacgtcca ggagcgcacc atcttcttca 1560
aggacgacgg caactacaag acccgcgccg aggtgaagtt cgagggcgac accctggtga 1620
accgcatcga gctgaagggc atcgacttca aggaggacgg caacatcctg gggcacaagc 1680
tggagtacaa ctacaacagc cacaacgtct atatcatggc cgacaagcag aagaacggca 1740
tcaaggtgaa cttcaagatc cgccacaaca tcgaggacgg cagcgtgcag ctcgccgacc 1800
actaccagca gaacaccccc atcggcgacg gccccgtgct gctgcccgac aaccactacc 1860
tgagcaccca gtccgccctg agcaaagacc ccaacgagaa gcgcgatcac atggtcctgc 1920
tggagttcgt gaccgccgcc gggatcactc tcggcatgga cgagctttac aagtagtgag 1980
tttaaactcc catttaaatg tgagggttaa tgcttcgagc agacatgata agatacattg 2040
atgagtttgg acaaaccaca actagaatgc agtgaaaaaa atgctttatt tgtgaaattt 2100
gtgatgctat tgctttattt gtaaccatta taagctgcaa taaacaagtt aacaacaaca 2160
attgcattca ttttatgttt caggttcagg gggagatgtg ggaggttttt taaagcaagt 2220
aaaacctcta caaatgtggt aaaataacta taacggtcct aaggtagcga gtgagtagtg 2280
ttctggggcg ggggaggacc tgcatgaggg ccagaataac tgaaatctgt gcttttctgt 2340
gtgttgcagc agcatgagcg gaagcggctc ctttgaggga ggggtattca gcccttatct 2400
gacggggcgt ctcccctcct gggcgggagt gcgtcagaat gtgatgggat ccacggtgga 2460
cggccggccc gtgcagcccg cgaactcttc aaccctgacc tatgcaaccc tgagctcttc 2520
gtcgttggac gcagctgccg ccgcagctgc tgcatctgcc gccagcgccg tgcgcggaat 2580
ggccatgggc gccggctact acggcactct ggtggccaac tcgagttcca ccaataatcc 2640
cgccagcctg aacgaggaga agctgttgct gctgatggcc cagctcgagg ccttgaccca 2700
gcgcctgggc gagctgaccc agcaggtggc tcagctgcag gagcagacgc gggccgcggt 2760
tgccacggtg aaatccaaat aaaaaatgaa tcaataaata aacggagacg gttgttgatt 2820
ttaacacaga gtctgaatct ttatttgatt tttcgcgcgc ggtaggccct ggaccaccgg 2880
tctcgatcat tgagcacccg gtggatcttt tccaggaccc ggtagaggtg ggcttggatg 2940
ttgaggtaca tgggcatgag cccgtcccgg gggtggaggt agctccattg cagggcctcg 3000
tgctcggggg tggtgttgta aatcacccag tcatagcagg ggcgcagggc atggtgttgc 3060
acaatatctt tgaggaggag actgatggcc acgggcagcc ctttggtgta ggtgtttaca 3120
aatctgttga gctgggaggg atgcatgcgg ggggagatga ggtgcatctt ggcctggatc 3180
ttgagattgg cgatgttacc gcccagatcc cgcctggggt tcatgttgtg caggaccacc 3240
agcacggtgt atccggtgca cttggggaat ttatcatgca acttggaagg gaaggcgtga 3300
aagaatttgg cgacgccttt gtgcccgccc aggttttcca tgcactcatc catgatgatg 3360
gcgatgggcc cgtgggcggc ggcctgggca aagacgtttc gggggtcgga cacatcatag 3420
ttgtggtcct gggtgaggtc atcataggcc attttaatga atttggggcg gagggtgccg 3480
gactggggga caaaggtacc ctcgatcccg ggggcgtagt tcccctcaca gatctgcatc 3540
tcccaggctt tgagctcgga ggggggggatc atgtccacct gcggggcgat aaagaacacg 3600
gtttccgggg cgggggagat gagctgggcc gaaagcaagt tccggagcag ctgggacttg 3660
ccgcagccgg tggggccgta gatgaccccg atgaccggct gcaggtggta gttgagggag 3720
agacagctgc cgtcctcccg gaggaggggg gccacctcgt tcatcatctc gcgcacgtgc 3780
atgttctcgc gcaccagttc cgccaggagg cgctctcccc ccagggatag gagctcctgg 3840
agcgaggcga agtttttcag cggcttgagt ccgtcggcca tgggcatttt ggagagggtt 3900
tgttgcaaga gttccaggcg gtcccagagc tcggtgatgt gctctacggc atctcgatcc 3960
agcagacctc ctcgtttcgc gggttgggac ggctgcggga gtagggcacc agacgatggg 4020
cgtccagcgc agccagggtc cggtccttcc agggtcgcag cgtccgcgtc agggtggtct 4080
ccgtcacggt gaaggggtgc gcgccgggct gggcgcttgc gagggtgcgc ttcaggctca 4140
tccggctggt cgaaaaccgc tcccgatcgg cgccctgcgc gtcggccagg tagcaattga 4200
ccatgagttc gtagttgagc gcctcggccg cgtggccttt ggcgcggagc ttacctttgg 4260
aagtctgccc gcaggcggga cagaggaggg acttgagggc gtagagcttg ggggcgagga 4320
agacggactc gggggcgtag gcgtccgcgc cgcagtgggc gcagacggtc tcgcactcca 4380
cgagccaggt gaggtcgggc tggtcggggt caaaaaccag tttcccgccg ttcttttga 4440
tgcgtttctt acctttggtc tccatgagct cgtgtccccg ctgggtgaca aagaggctgt 4500
ccgtgtcccc gtagaccgac tttatgggcc ggtcctcgag cggtgtgccg cggtcctcct 4560

-continued cgtagaggaa ccccgcccac tccgagacga aagcccgggt ccaggccagc acgaaggagg 4620
ccacgtggga cgggtagcgg tcgttgtcca ccagcgggtc caccttttcc agggtatgca 4680
aacacatgtc cccctcgtcc acatccagga aggtgattgg cttgtaagtg taggccacgt 4740
gaccgggggt cccggccggg ggggtataaa agggtgcggg tccctgctcg tcctcactgt 4800
cttccggatc gctgtccagg agcgccagct gttggggtag gtattccctc tcgaaggcgg 4860
gcatgacctc ggcactcagg ttgtcagttt ctagaaacga ggaggatttg atattgacgg 4920
tgccggcgga gatgcctttc aagagcccct cgtccatctg gtcagaaaag acgatctttt 4980
tgttgtcgag cttggtggcg aaggagccgt agagggcgtt ggagaggagc ttggcgatgg 5040
agcgcatggt ctggtttttt tccttgtcgg cgcgctcctt ggcggcgatg ttgagctgca 5100
cgtactcgcg cgccacgcac ttccattcgg ggaagacggt ggtcagctcg tcgggcacga 5160
ttctgacctg ccagccccga ttatgcaggg tgatgaggtc cacactggtg gccacctcgc 5220
cgcgcagggg ctcattagtc cagcagaggc gtccgccctt gcgcgagcag aagggggggca 5280
gggggtccag catgacctcg tcgggggggt cggcatcgat ggtgaagatg ccgggcagga 5340
ggtcggggtc aaagtagctg atggaagtgg ccagatcgtc cagggcagct tgccattcgc 5400
gcacggccag cgcgctctcg tagggactga ggggcgtgcc ccagggcatg ggatgggtaa 5460
gcgcggaggc gtacatgccg cagatgtcgt agacgtagag gggctcctcg aggatgccga 5520
tgtaggtggg gtagcagcgc cccccgcgga tgctggcgcg cacgtagtca tacagctcgt 5580
gcgagggggc gaggagcccc gggcccaggt tggtgcgact gggcttttcg gcgcggtaga 5640
cgatctggcg gaaaatggca tgcgagttgg aggagatggt gggcctttgg aagatgttga 5700
agtgggcgtg gggcagtccg accgagtcgc ggatgaagtg ggcgtaggag tcttgcagct 5760
tggcgacgag ctcggcggtg actaggacgt ccagagcgca gtagtcgagg gtctcctgga 5820
tgatgtcata cttgagctgt ccctttttgtt tccacagctc gcggttgaga aggaactctt 5880
cgcggtcctt ccagtactct tcgaggggga acccgtcctg atctgcacgg taagagccta 5940
gcatgtagaa ctggttgacg gccttgtagg cgcagcagcc cttctccacg gggagggcgt 6000
aggcctgggc ggccttgcgc agggaggtgt gcgtgagggc gaaagtgtcc ctgaccatga 6060
ccttgaggaa ctggtgcttg aagtcgatat cgtcgcagcc cccctgctcc cagagctgga 6120
agtccgtgcg cttcttgtag gcggggttgg gcaaagcgaa agtaacatcg ttgaagagga 6180
tcttgcccgc gcggggcata aagttgcgag tgatgcggaa aggttggggc acctcggccc 6240
ggttgttgat gacctgggcg gcgagcacga tctcgtcgaa gccgttgatg ttgtggccca 6300
cgatgtagag ttccacgaat cgcggacggc ccttgacgtg gggcagtttc ttgagctcct 6360
cgtaggtgag ctcgtcgggg tcgctgagcc cgtgctgctc gagcgcccag tcggcgagat 6420
gggggttggc gcggaggaag gaagtccaga gatccacggc cagggcggtt tgcagacggt 6480
cccggtactg acggaactgc tgcccgacgg ccatttttttc gggggtgacg cagtagaagg 6540
tgcgggggtc cccgtgccag cgatcccatt tgagctggag ggcgagatcg agggcgagct 6600
cgacgagccg gtcgtccccg gagagtttca tgaccagcat gaaggggacg agctgcttgc 6660
cgaaggaccc catccaggtg taggtttcca catcgtaggt gaggaagagc ctttcggtgc 6720
gaggatgcga gccgatgggg aagaactgga tctcctgcca ccaattggag gaatggctgt 6780
tgatgtgatg gaagtagaaa tgccgacggc gcgccgaaca ctcgtgcttg tgtttataca 6840
agcggccaca gtgctcgcaa cgctgcacgg gatgcacgtg ctgcacgagc tgtacctgag 6900
ttcctttgac gaggaatttc agtgggaagt ggagtcgtgg cgcctgcatc tcgtgctgta 6960

-continued

```
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtgg tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cgggcaaaaa cgaaagcggt cagcggctcg actccgtggc   9300
```

-continued

```
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agccccctcc acagccggcg cttctgcccc cgccccagca   9780
gcaacttcca gccacgaccg ccgcggccgc cgtgagcggg gctggacaga gttatgatca   9840
ccagctggcc ttggaagagg gcgaggggct ggcgcgcctg gggggcgtcgt cgccggagcg   9900
gcacccgcgc gtgcagatga aaagggacgc tcgcgaggcc tacgtgccca agcagaacct   9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gccccttca cggacagcgg cagcatcaac  11640
cgcaactcgt acctgggcta cctgattaac ctgtaccgcg aggccatcgg ccaggcgcac  11700
```

gtggacgagc agacctacca ggagatcacc cacgtgagcc gcgccctggg ccaggacgac 11760
ccgggcaacc tggaagccac cctgaacttt ttgctgacca accggtcgca gaagatcccg 11820
ccccagtacg cgctcagcac cgaggaggag cgcatcctgc gttacgtgca gcagagcgtg 11880
ggcctgttcc tgatgcagga gggggccacc cccagcgccg cgctcgacat gaccgcgcgc 11940
aacatggagc ccagcatgta cgccagcaac cgcccgttca tcaataaact gatggactac 12000
ttgcatcggg cggccgccat gaactctgac tatttcacca acgccatcct gaatccccac 12060
tggctcccgc cgccggggtt ctacacgggc gagtacgaca tgcccgaccc caatgacggg 12120
ttcctgtggg acgatgtgga cagcagcgtg ttctcccccc gaccgggtgc taacgagcgc 12180
cccttgtgga agaaggaagg cagcgaccga cgcccgtcct cggcgctgtc cggccgcgag 12240
ggtgctgccg cggcggtgcc cgaggccgcc agtcctttcc cgagcttgcc cttctcgctg 12300
aacagtatcc gcagcagcga gctgggcagg atcacgcgcc cgcgcttgct gggcgaagag 12360
gagtacttga atgactcgct gttgagaccc gagcgggaga agaacttccc caataacggg 12420
atagaaagcc tggtggacaa gatgagccgc tggaagacgt atgcgcagga gcacagggac 12480
gatccccggg cgtcgcaggg ggccacgagc cggggcagcg ccgcccgtaa acgccggtgg 12540
cacgacaggc agcggggaca gatgtgggac gatgaggact ccgccgacga cagcagcgtg 12600
ttggacttgg gtgggagtgg taacccgttc gctcacctgc gcccccgtat cgggcgcatg 12660
atgtaagaga aaccgaaaat aaatgatact caccaaggcc atggcgacca gcgtgcgttc 12720
gtttcttctc tgttgttgtt gtatctagta tgatgaggcg tgcgtacccg gagggtcctc 12780
ctccctcgta cgagagcgtg atgcagcagg cgatggcggc ggcggcgatg cagcccccgc 12840
tggaggctcc ttacgtgccc ccgcggtacc tggcgcctac ggagggggcgg aacagcattc 12900
gttactcgga gctggcaccc ttgtacgata ccacccggtt gtacctggtg gacaacaagt 12960
cggcggacat cgcctcgctg aactaccaga acgaccacag caacttcctg accaccgtgg 13020
tgcagaacaa tgacttcacc cccacggagg ccagcaccca gaccatcaac tttgacgagc 13080
gctcgcggtg gggcggccag ctgaaaacca tcatgcacac caacatgccc aacgtgaacg 13140
agttcatgta cagcaacaag ttcaaggcgc gggtgatggt ctcccgcaag acccccaatg 13200
gggtgacagt gacagaggat tatgatggta gtcaggatga gctgaagtat gaatgggtgg 13260
aatttgagct gcccgaaggc aacttctcgg tgaccatgac catcgacctg atgaacaacg 13320
ccatcatcga caattacttg gcggtggggc ggcagaacgg ggtgctggag agcgacatcg 13380
gcgtgaagtt cgacactagg aacttcaggc tgggctggga ccccgtgacc gagctggtca 13440
tgcccggggt gtacaccaac gaggctttcc atcccgatat tgtcttgctg cccggctgcg 13500
ggtggactt caccgagagc cgcctcagca acctgctggg cattcgcaag aggcagccct 13560
tccaggaagg cttccagatc atgtacgagg atctggaggg gggcaacatc cccgcgctcc 13620
tggatgtcga cgcctatgag aaaagcaagg aggatgcagc agctgaagca actgcagccg 13680
tagctaccgc ctctaccgag gtcaggggcg ataattttgc aagcgccgca gcagtggcag 13740
cggccgaggc ggctgaaacc gaaagtaaga tagtcattca gccggtggag aaggatagca 13800
agaacaggag ctacaacgta ctaccggaca agataaacac cgcctaccgc agctggtacc 13860
tagcctacaa ctatggcgac cccgagaagg gcgtgcgctc ctggacgctg ctcaccacct 13920
cggacgtcac ctgcggcgtg gagcaagtct actggtcgct gcccgacatg atgcaagacc 13980
cggtcacctt ccgctccacg cgtcaagtta gcaactaccc ggtggtgggc gccgagctcc 14040
tgcccgtcta ctccaagagc ttcttcaacg agcaggccgt ctactcgcag cagctgcgcg 14100
ccttcacctc gcttacgcac gtcttcaacc gcttccccga gaaccagatc ctcgtccgcc 14160
cgcccgcgcc caccattacc accgtcagtg aaaacgttcc tgctctcaca gatcacggga 14220
ccctgccgct gcgcagcagt atccggggag tccagcgcgt gaccgttact gacgccagac 14280
gccgcacctg cccctacgtc tacaaggccc tgggcatagt cgcgccgcgc gtcctctcga 14340
gccgcacctt ctaaatgtcc attctcatct cgcccagtaa taacaccggt tggggcctgc 14400
gcgcgcccag caagatgtac ggaggcgctc gccaacgctc cacgcaacac cccgtgcgcg 14460
tgcgcgggca cttccgcgct ccctggggcg ccctcaaggg ccgcgtgcgg tcgcgcacca 14520
ccgtcgacga cgtgatcgac caggtggtgg ccgacgcgcg caactacacc cccgccgccg 14580
cgcccgtctc caccgtggac gccgtcatcg acagcgtggt ggccgacgcg cgccggtacg 14640
cccgcgccaa gagccggcgg cggcgcatcg cccggcggca ccggagcacc cccgccatgc 14700
gcgcggcgcg agccttgctg cgcagggcca ggcgcacggg acgcagggcc atgctcaggg 14760
cggccagacg cgcggcttca ggcgccagcg ccggcaggac ccggagacgc gcggccacgg 14820
cggcggcagc ggccatcgcc agcatgtccc gcccgcggcg agggaacgtg tactgggtgc 14880
gcgacgccgc caccggtgtg cgcgtgcccg tgcgcacccg ccccccctcgc acttgaagat 14940 gttcacttcg cgatgttgat gtgtcccagc ggcgaggagg atgtccaagc gcaaattcaa 15000
ggaagagatg ctccaggtca tcgcgcctga gatctacggc cctgcggtgg tgaaggagga 15060
aagaaagccc cgcaaaatca agcgggtcaa aaaggacaaa aaggaagaag aaagtgatgt 15120
ggacggattg gtggagtttg tgcgcgagtt cgccccccgg cggcgcgtgc agtggcgcgg 15180
gcggaaggtg caaccggtgc tgagacccgg caccaccgtg gtcttcacgc ccggcgagcg 15240
ctccggcacc gcttccaagc gctcctacga cgaggtgtac ggggatgatg atattctgga 15300
gcaggcggcc gagcgcctgg gcgagtttgc ttacggcaag cgcagccgtt ccgcaccgaa 15360
ggaagaggcg gtgtccatcc cgctggacca cggcaacccc acgccgagcc tcaagcccgt 15420
gaccttgcag caggtgctgc cgaccgcggc gccgcgccgg gggttcaagc gcgagggcga 15480
ggatctgtac cccaccatgc agctgatggt gcccaagcgc cagaagctgg aagacgtgct 15540
ggagaccatg aaggtggacc cggacgtgca gcccgaggtc aaggtgcggc ccatcaagca 15600
ggtggccccg ggcctgggcg tgcagaccgt ggacatcaag attcccacgg agcccatgga 15660
aacgcagacc gagcccatga tcaagcccag caccagcacc atggaggtgc agacggatcc 15720
ctggatgcca tcggctccta gtcgaagacc ccggcgcaag tacggcgcgg ccagcctgct 15780
gatgcccaac tacgcgctgc atccttccat catccccacg ccgggctacc gcggcacgcg 15840
cttctaccgc ggtcatacca gcagccgccg ccgcaagacc accactcgcc gccgccgtcg 15900
ccgcaccgcc gctgcaacca cccctgccgc cctggtgcgg agagtgtacc gccgcggccg 15960
cgcacctctg accctgccgc gcgcgcgcta ccacccgagc atcgccattt aaactttcgc 16020
ctgctttgca gatcaatggc cctcacatgc cgccttcgcg ttcccattac gggctaccga 16080
ggaagaaaac cgcgccgtag aaggctggcg gggaacggga tgcgtcgcca ccaccaccgg 16140
cggcggcgcg ccatcagcaa gcggttgggg ggaggcttcc tgcccgcgct gatccccatc 16200
atcgccgcgg cgatcggggc gatccccggc attgcttccg tggcggtgca ggcctctcag 16260
cgccactgag acacacttgg aaacatcttg taataaacca atggactctg acgctcctgg 16320
tcctgtgatg tgttttcgta gacagatgga agacatcaat tttcgtcccc tggctccgcg 16380
acacggcacg cggccgttca tgggcacctg gagcgacatc ggcaccagcc aactgaacgg 16440
gggcgccttc aattggagca gtctctggag cgggcttaag aatttcgggt ccacgcttaa 16500
aacctatggc agcaaggcgt ggaacagcac cacagggcag gcgctgaggg ataagctgaa 16560
agagcagaac ttccagcaga aggtggtcga tgggctcgcc tcgggcatca acggggtggt 16620
ggacctggcc aaccaggccg tgcagcggca gatcaacagc cgcctggacc cggtgccgcc 16680
cgccggctcc gtggagatgc cgcaggtgga ggaggagctg cctcccctgg acaagcgggg 16740
cgagaagcga ccccgccccg atgcggagga gacgctgctg acgcacacgg acgagccgcc 16800
cccgtacgag gaggcggtga aactgggtct gcccaccacg cggcccatcg cgcccctggc 16860
caccggggtg ctgaaacccg aaaagcccgc gaccctggac ttgcctcctc cccagccttc 16920
ccgcccctct acagtggcta agcccctgcc gccggtggcc gtggcccgcg cgcgacccgg 16980
gggcaccgcc cgccctcatg cgaactggca gagcactctg aacagcatcg tgggtctggg 17040
agtgcagagt gtgaagcgcc gccgctgcta ttaaacctac cgtagcgctt aacttgcttg 17100
tctgtgtgtg tatgtattat gtcgccgccg ccgctgtcca ccagaaggag gagtgaagag 17160
gcgcgtcgcc gagttgcaag atggccaccc catcgatgct gccccagtgg gcgtacatgc 17220
acatcgccgg acaggacgct tcggagtacc tgagtccggg tctggtgcag tttgcccgcg 17280
ccacagacac ctacttcagt ctggggaaca agtttaggaa ccccacggtg gcgcccacgc 17340
acgatgtgac caccgaccgc agccagcggc tgacgctgcg cttcgtgccc gtggaccgcg 17400
aggacaacac ctactcgtac aaagtgcgct acacgctggc cgtgggcgac aaccgcgtgc 17460
tggacatggc cagcacctac tttgacatcc gcggcgtgct ggatcggggc cctagcttca 17520
aaccctactc cggcaccgcc tacaacagtc tggcccccaa gggagcaccc aacacttgtc 17580
agtggacata taaagccgat ggtgaaactg ccacagaaaa aacctataca tatggaaatg 17640
cacccgtgca gggcattaac atcacaaaag atggtattca acttggaact gacaccgatg 17700
atcagccaat ctacgcagat aaaacctatc agcctgaacc tcaagtgggt gatgctgaat 17760
ggcatgacat cactggtact gatgaaaagt atggaggcag agctcttaag cctgatacca 17820
aaatgaagcc ttgttatggt tcttttgcca agcctactaa taaagaagga ggtcaggcaa 17880
atgtgaaaac aggaacaggc actactaaag aatatgacat agacatggct ttctttgaca 17940
acagaagtgc ggctgctgct ggcctagctc cagaaattgt tttgtatact gaaaatgtgg 18000
atttggaaac tccagatacc catattgtat acaaagcagg cacagatgac agcagctctt 18060
ctattaattt gggtcagcaa gccatgccca acagacctaa ctacattggt ttcagagaca 18120
actttatcgg gctcatgtac tacaacagca ctggcaatat gggggtgctg gccggtcagg 18180
cttctcagct gaatgctgtg gttgacttgc aagacagaaa caccgagctg tcctaccagc 18240
tcttgcttga ctctctgggt gacagaaccc ggtatttcag tatgtggaat caggcggtgg 18300
acagctatga tcctgatgtg cgcattattg aaaatcatgg tgtggaggat gaacttccca 18360
actattgttt ccctctggat gctgttggca gaacagatac ttatcaggga attaaggcta 18420
atggaactga tcaaaccaca tggaccaaag atgacagtgt caatgatgct aatgagatag 18480
gcaagggtaa tccattcgcc atggaaatca acatccaagc caacctgtgg aggaacttcc 18540
tctacgccaa cgtggccctg tacctgcccg actcttacaa gtacacgccg gccaatgtta 18600
ccctgcccac caacaccaac acctacgatt acatgaacgg ccgggtggtg gcgccctcgc 18660
tggtggactc ctacatcaac atcggggcgc gctggtcgct ggatcccatg gacaacgtga 18720 acccctcaa ccaccaccgc aatgcggggc tgcgctaccg ctccatgctc ctgggcaacg 18780

```
ggcgctacgt gcccttccac atccaggtgc cccagaaatt tttcgccatc aagagcctcc  18840
tgctcctgcc cgggtcctac acctacgagt ggaacttccg caaggacgtc aacatgatcc  18900
tgcagagctc cctcggcaac gacctgcgca cggacggggc ctccatctcc ttcaccagca  18960
tcaacctcta cgccaccttc ttccccatgg cgcacaacac ggcctccacg ctcgaggcca  19020
tgctgcgcaa cgacaccaac gaccagtcct tcaacgacta cctctcggcg gccaacatgc  19080
tctaccccat cccggccaac gccaccaacg tgcccatctc catcccctcg cgcaactggg  19140
ccgccttccg cggctggtcc ttcacgcgtc tcaagaccaa ggagacgccc tcgctgggct  19200
ccgggttcga cccctacttc gtctactcgg gctccatccc ctacctcgac ggcaccttct  19260
acctcaacca caccttcaag aaggtctcca tcaccttcga ctcctccgtc agctggcccg  19320
gcaacgaccg gctcctgacg cccaacgagt tcgaaatcaa gcgcaccgtc gacggcgagg  19380
gctacaacgt ggcccagtgc aacatgacca aggactggtt cctggtccag atgctggccc  19440
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcaccctg gcctaccagc acaacaactc gggcttcgtc ggctacctcg  19620
cgcccaccat gcgccagggc cagccctacc ccgccaacta cccctacccg ctcatcggca  19680
agagcgccgt caccagcgtc acccagaaaa agttcctctg cgacagggtc atgtggcgca  19740
tccccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccacccttct ctatgttgtc ttcgaagtct tcgacgtcgt ccgagtgcac cagccccacc  19920
gcggcgtcat cgaggccgtc tacctgcgca ccccctttctc ggccggtaac gccaccacct  19980
aagctcttgc ttcttgcaag ccatggccgc gggctccggc gagcaggagc tcagggccat  20040
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
ccccttcggg ttctcggacg agcgcctcaa gcagatctac cagttcgagt acgagggcct  20280
gctgcgccgc agcgccctgg ccaccgagga ccgctgcgtc accctggaaa agtccaccca  20340
gaccgtgcag ggtccgcgct cggccgcctg cgggctcttc tgctgcatgt tcctgcacgc  20400
cttcgtgcac tggcccgacc gccccatgga caagaacccc accatgaact tgctgacggg  20460
ggtgcccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg cagggcgccc agcaggtcgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag gggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
```

-continued ttgcctgaac gcctgctggg ccttggctcc ctcggtgaag aagaccccgc aggacttgct 21240
agagaactgg ttggtggcgc acccggcgtc gtgcacgcag cagcgcgcgt cgttgttggc 21300
cagctgcacc acgctgcgcc cccagcggtt ctgggtgatc ttggcccggt cggggttctc 21360
cttcagcgcg cgctgcccgt tctcgctcgc cacatccatc tcgatcatgt gctccttctg 21420
gatcatggtg gtcccgtgca ggcaccgcag cttgccctcg gcctcggtgc acccgtgcag 21480
ccacagcgcg cacccggtgc actcccagtt cttgtgggcg atctgggaat gcgcgtgcac 21540
gaagccctgc aggaagcggc ccatcatggt ggtcagggtc ttgttgctag tgaaggtcag 21600
cggaatgccg cggtgctcct cgttgatgta caggtggcag atgcggcggt acacctcgcc 21660
ctgctcgggc atcagctgga agttggcttt caggtcggtc tccacgcggt agcggtccat 21720
cagcatagtc atgatttcca tacccttctc ccaggccgag acgatgggca ggctcatagg 21780
gttcttcacc atcatcttag cgctagcagc cgcggccagg gggtcgctct cgtccagggt 21840
ctcaaagctc cgcttgccgt ccttctcggt gatccgcacc ggggggtagc tgaagcccac 21900
ggccgccagc tcctcctcgg cctgtctttc gtcctcgctg tcctggctga cgtcctgcag 21960
gaccacatgc ttggtcttgc ggggtttctt cttgggcggc agcggcggcg gagatgttgg 22020
agatggcgag gggagcgcg agttctcgct caccactact atctcttcct cttcttggtc 22080
cgaggccacg cggcggtagg tatgtctctt cgggggcaga ggcggaggcg acgggctctc 22140
gccgccgcga cttggcggat ggctggcaga gccccttccg cgttcggggg tgcgctcccg 22200
gcggcgctct gactgacttc ctccgcggcc ggccattgtg ttctcctagg gaggaacaac 22260
aagcatggag actcagccat cgccaacctc gccatctgcc cccaccgccg acgagaagca 22320
gcagcagcag aatgaaagct taaccgcccc gccgcccagc cccgccacct ccgacgcggc 22380
cgtcccagac atgcaagaga tggaggaatc catcgagatt gacctgggct atgtgacgcc 22440
cgcggagcac gaggaggagc tggcagtgcg cttttcacaa gaagagatac accaagaaca 22500
gccagagcag gaagcagaga atgagcagag tcaggctggg ctcgagcatg acggcgacta 22560
cctccacctg agcgggggg aggacgcgct catcaagcat ctggcccggc aggccaccat 22620
cgtcaaggat gcgctgctcg accgcaccga ggtgcccctc agcgtggagg agctcagccg 22680
cgcctacgag ttgaacctct tctcgccgcg cgtgcccccc aagcgccagc ccaatggcac 22740
ctgcgagccc aacccgcgcc tcaacttcta cccggtcttc gcggtgcccg aggccctggc 22800
cacctaccac atctttttca agaaccaaaa gatccccgtc tcctgccgcg ccaaccgcac 22860
ccgcgccgac gccctttca acctgggtcc cggcgcccgc ctacctgata tcgcctcctt 22920
ggaagaggtt cccaagatct tcgagggtct gggcagcgac gagactcggg ccgcgaacgc 22980
tctgcaagga gaaggaggag agcatgagca ccacagcgcc ctggtcgagt tggaaggcga 23040
caacgcgcgg ctggcggtgc tcaaacgcac ggtcgagctg acccatttcg cctacccggc 23100
tctgaacctg ccccccaaag tcatgagcgc ggtcatggac caggtgctca tcaagcgcgc 23160
gtcgcccatc tccgaggacg agggcatgca agactccgag gagggcaagc ccgtggtcag 23220
cgacgagcag ctggcccggt ggctgggtcc taatgctagt ccccagagtt tggaagagcg 23280
gcgcaaactc atgatggccg tggtcctggt gaccgtggag ctggagtgcc tgcgccgctt 23340
cttcgccgac gcggagaccc tgcgcaaggt cgaggagaac ctgcactacc tcttcaggca 23400
cgggttcgtg cgccaggcct gcaagatctc caacgtggag ctgaccaacc tggtctccta 23460
catgggcatc ttgcacgaga accgcctggg gcagaacgtg ctgcacacca ccctgcgcgg 23520
ggaggcccgg cgcgactaca tccgcgactg cgtctacctc tacctctgcc acacctggca 23580
gacgggcatg ggcgtgtggc agcagtgtct ggaggagcag aacctgaaag agctctgcaa 23640
gctcctgcag aagaacctca agggtctgtg gaccgggttc gacgagcgca ccaccgcctc 23700
ggacctggcc gacctcattt tccccgagcg cctcaggctg acgctgcgca acggcctgcc 23760
cgactttatg agccaaagca tgttgcaaaa ctttcgctct ttcatcctcg aacgctccgg 23820
aatcctgccc gccacctgct ccgcgctgcc ctcggacttc gtgccgctga ccttccgcga 23880
gtgccccccg ccgctgtgga gccactgcta cctgctgcgc ctggccaact acctggccta 23940
ccactcggac gtgatcgagg acgtcagcgg cgagggcctg ctcgagtgcc actgccgctg 24000
caacctctgc acgccgcacc gctccctggc ctgcaacccc cagctgctga gcgagaccca 24060
gatcatcggc accttcgagt tgcaagggcc cagcgaaggc gagggttcag ccgccaaggg 24120
gggtctgaaa ctcaccccgg ggctgtggac ctcggcctac ttgcgcaagt tcgtgcccga 24180
ggactaccat cccttcgaga tcaggttcta cgaggaccaa tcccatccgc ccaaggccga 24240
gctgtcggcc tgcgtcatca cccagggggc gatcctggcc caattgcaag ccatccagaa 24300
atcccgccaa gaattcttgc tgaaaaaggg ccgcggggtc tacctcgacc cccagaccgg 24360
tgaggagctc aaccccggct tcccccagga tgccccgagg aaacaagaag ctgaaagtgg 24420
agctgccgcc cgtggaggat ttggaggaag actgggagaa cagcagtcag gcagaggagg 24480
aggagatgga ggaagactgg gacagcactc aggcagagga ggacagcctg caagacagtc 24540
tggaggaaga cgaggaggag gcagaggagg aggtggaaga agcagccgcc gccagaccgt 24600
cgtcctcggc gggggagaaa gcaagcagca cggataccat ctccgctccg ggtcggggtc 24660
ccgctcgacc acacagtaga tgggacgaga ccggacgatt cccgaacccc accacccaga 24720
ccggtaagaa ggagcggcag ggatacaagt cctggcgggg gcacaaaaac gccatcgtct 24780
cctgcttgca ggcctgcggg ggcaacatct ccttcacccg gcgctacctg ctcttccacc 24840
gcggggtgaa ctttccccgc aacatcttgc attactaccg tcacctccac agcccctact 24900
acttccaaga agaggcagca gcagcagaaa aagaccagca gaaaaccagc agctagaaaa 24960
tccacagcgg cggcagcagg tggactgagg atcgcggcga acgagccggc gcaaacccgg 25020
gagctgagga accggatctt tcccaccctc tatgccatct tccagcagag tcgggggcag 25080
gagcaggaac tgaaagtcaa gaaccgttct ctgcgctcgc tcacccgcag ttgtctgtat 25140
cacaagagcg aagaccaact tcagcgcact ctcgaggacg ccgaggctct cttcaacaag 25200
tactgcgcgc tcactcttaa agagtagccc gcgcccgccc agtcgcagaa aaaggcggga 25260
attacgtcac ctgtgccctt cgccctagcc gcctccaccc atcatcatga gcaaagagat 25320
tcccacgcct tacatgtgga gctaccagcc ccagatgggc ctggccgccg gtgccgccca 25380
ggactactcc acccgcatga attggctcag cgccgggccc gcgatgatct cacgggtgaa 25440
tgacatccgc gcccaccgaa accagatact cctagaacag tcagcgctca ccgccacgcc 25500
ccgcaatcac ctcaatccgc gtaattggcc cgccgccctg gtgtaccagg aaattcccca 25560
gcccacgacc gtactacttc cgcgagacgc ccaggccgaa gtccagctga ctaactcagg 25620
tgtccagctg gcgggcggcg ccaccctgtg tcgtcaccgc cccgctcagg gtataaagcg 25680
gctggtgatc cggggcagag gcacacagct caacgacgag gtggtgagct cttcgctggg 25740
tctgcgacct gacggagtct tccaactcgc cggatcgggg agatcttcct tcacgcctcg 25800
tcaggccgtc ctgactttgg agagttcgtc ctcgcagccc cgctcgggtg gcatcggcac 25860
tctccagttc gtggaggagt tcactccctc ggtctacttc aacccettct ccggctcccc 25920

```
cggccactac ccggacgagt tcatcccgaa cttcgacgcc atcagcgagt cggtggacgg  25980
ctacgattga atgtcccatg gtggcgcagc tgacctagct cggcttcgac acctggacca  26040
ctgccgccgc ttccgctgct tcgctcggga tctcgccgag tttgcctact ttgagctgcc  26100
cgaggagcac cctcagggcc cggcccacgg agtgcggatc gtcgtcgaag gggcctcgga  26160
ctcccacctg cttcggatct tcagccagcg tccgatcctg gtcgagcgcg agcaaggaca  26220
gacccttctg actctgtact gcatctgcaa ccaccccggc ctgcatgaaa gtctttgttg  26280
tctgctgtgt actgagtata ataaaagctg agatcagcga ctactccgga cttccgtgtg  26340
ttcctgaatc catcaaccag tctttgttct tcaccgggaa cgagaccgag ctccagctcc  26400
agtgtaagcc ccacaagaag tacctcacct ggctgttcca gggctccccg atcgccgttg  26460
tcaaccactg cgacaacgac ggagtcctgc tgagcggccc tgccaacctt actttttcca  26520
cccgcagaag caagctccag ctcttccaac ccttcctccc cgggacctat cagtgcgtct  26580
cgggaccctg ccatcacacc ttccacctga tcccgaatac cacagcgtcg ctccccgcta  26640
ctaacaacca aactaacctc caccaacgcc accgtcgcga cggccacaat acatgcccat  26700
attagactat gaggccgagc cacagcgacc catgctcccc gctattagtt acttcaatct  26760
aaccggcgga gatgactgac ccactggcca acaacaacgt caacgacctt ctcctggaca  26820
tggacggccg cgcctcggag cagcgactcg cccaacttcg cattcgccag cagcaggaga  26880
gagccgtcaa ggagctgcag gatgcggtgg ccatccacca gtgcaagaga ggcatcttct  26940
gcctggtgaa acaggccaag atctcctacg aggtcactcc aaacgaccat cgcctctcct  27000
acgagctcct gcagcagcgc cagaagttca cctgcctggt cggagtcaac cccatcgtca  27060
tcacccagca gtctggcgat accaaggggt gcatccactg ctcctgcgac tcccccgact  27120
gcgtccacac tctgatcaag accctctgcg gcctccgcga cctcctcccc atgaactaat  27180
cacccccctta tccagtgaaa taaagatcat attgatgatg attttacaga aataaaaaat  27240
aatcatttga tttgaaataa agatacaatc atattgatga tttgagttta acaaaaaaat  27300
aaagaatcac ttacttgaaa tctgatacca ggtctctgtc catgttttct gccaacacca  27360
cttcactccc ctcttcccag ctctggtact gcaggccccg gcgggctgca aacttcctcc  27420
acacgctgaa ggggatgtca aattcctcct gtccctcaat cttcatttta tcttctatca  27480
gatgtccaaa aagcgcgtcc gggtggatga tgacttcgac cccgtctacc cctacgatgc  27540
agacaacgca ccgaccgtgc ccttcatcaa ccccccccttc gtctcttcag atggattcca  27600
agagaagccc ctgggggtgt tgtccctgcg actggccgac cccgtcacca ccaagaacgg  27660
ggaaatcacc ctcaagctgg gagagggggt ggacctcgat tcctcgggaa aactcatctc  27720
caacacggcc accaaggccg ccgcccctct cagtttttcc aacaacacca tttcccttaa  27780
catggatcac cccttttaca ctaaagatgg aaaattatcc ttacaagttt ctccaccatt  27840
aaatatactg agaacaagca ttctaaacac actagcttta ggttttggat caggtttagg  27900
actccgtggc tctgccttgg cagtacagtt agtctctcca cttacatttg atactgatgg  27960
aaacataaag cttaccttag acagaggttt gcatgttaca acaggagatg caattgaaag  28020
caacataagc tgggctaaag gtttaaaatt tgaagatgga gccatagcaa ccaacattgg  28080
aaatgggtta gagtttggaa gcagtagtac agaaacaggt gttgatgatg cttacccaat  28140
ccaagttaaa cttggatctg gccttagctt tgacagtaca ggagccataa tggctggtaa  28200
caaagaagac gataaactca ctttgtggac aacacctgat ccatcaccaa actgtcaaat  28260
```

-continued actcgcagaa aatgatgcaa aactaacact ttgcttgact aaatgtggta gtcaaatact 28320
ggccactgtg tcagtcttag ttgtaggaag tggaaaccta aaccccatta ctggcaccgt 28380
aagcagtgct caggtgtttc tacgttttga tgcaaacggt gttcttttaa cagaacattc 28440
tacactaaaa aaatactggg ggtataggca gggagatagc atagatggca ctccatatac 28500
caatgctgta ggattcatgc ccaatttaaa agcttatcca aagtcacaaa gttctactac 28560
taaaaataat atagtagggc aagtatacat gaatggagat gtttcaaaac ctatgcttct 28620
cactataacc ctcaatggta ctgatgacag caacagtaca tattcaatgt cattttcata 28680
cacctggact aatggaagct atgttggagc aacatttggg gctaactctt ataccttctc 28740
atacatcgcc caagaatgaa cactgtatcc caccctgcat gccaaccctt cccaccccac 28800
tctgtggaac aaactctgaa acacaaaata aaataaagtt caagtgtttt attgattcaa 28860
cagttttaca ggattcgagc agttattttt cctccaccct cccaggacat ggaatacacc 28920
accctctccc cccgcacagc cttgaacatc tgaatgccat tggtgatgga catgcttttg 28980
gtctccacgt tccacacagt ttcagagcga gccagtctcg ggtcggtcag ggagatgaaa 29040
ccctccgggc actcccgcat ctgcacctca cagctcaaca gctgaggatt gtcctcggtg 29100
gtcgggatca cggttatctg gaagaagcag aagagcggcg gtgggaatca tagtccgcga 29160
acgggatcgg ccggtggtgt cgcatcaggc cccgcagcag tcgctgccgc cgccgctccg 29220
tcaagctgct gctcaggggg tccgggtcca gggactccct cagcatgatg cccacggccc 29280
tcagcatcag tcgtctggtg cggcgggcgc agcagcgcat gcggatctcg ctcaggtcgc 29340
tgcagtacgt gcaacacaga accaccaggt tgttcaacag tccatagttc aacacgctcc 29400
agccgaaact catcgcggga aggatgctac ccacgtggcc gtcgtaccag atcctcaggt 29460
aaatcaagtg gtgccccctc cagaacacgc tgcccacgta catgatctcc ttgggcatgt 29520
ggcggttcac cacctcccgg taccacatca ccctctggtt gaacatgcag ccccggatga 29580
tcctgcggaa ccacagggcc agcaccgccc cgcccgccat gcagcgaaga gaccccgggt 29640
cccggcaatg gcaatggagg acccaccgct cgtacccgtg gatcatctgg gagctgaaca 29700
agtctatgtt ggcacagcac aggcatatgc tcatgcatct cttcagcact ctcaactcct 29760
cgggggtcaa aaccatatcc cagggcacgg ggaactcttg caggacagcg aaccccgcag 29820
aacagggcaa tcctcgcaca gaacttacat tgtgcatgga cagggtatcg caatcaggca 29880
gcaccgggtg atcctccacc agagaagcgc gggtctcggt ctcctcacag cgtggtaagg 29940
gggccggccg atacgggtga tggcgggacg cggctgatcg tgttcgcgac cgtgtcatga 30000
tgcagttgct ttcggacatt ttcgtacttg ctgtagcaga acctggtccg ggcgctgcac 30060
accgatcgcc ggcggcggtc tcggcgcttg gaacgctcgg tgttgaaatt gtaaaacagc 30120
cactctctca gaccgtgcag cagatctagg gcctcaggag tgatgaagat cccatcatgc 30180
ctgatggctc tgatcacatc gaccaccgtg gaatgggcca gacccagcca gatgatgcaa 30240
ttttgttggg tttcggtgac ggcgggggag ggaagaacag gaagaaccat gattaacttt 30300
taatccaaac ggtctcggag tacttcaaaa tgaagatcgc ggagatggca cctctcgccc 30360
ccgctgtgtt ggtggaaaat aacagccagg tcaaaggtga tacggttctc gagatgttcc 30420
acggtggctt ccagcaaagc ctccacgcgc acatccagaa acaagacaat agcgaaagcg 30480
ggagggttct ctaattcctc aatcatcatg ttacactcct gcaccatccc cagataattt 30540
tcatttttcc agccttgaat gattcgaact agttcgtgag gtaaatccaa gccagccatg 30600
ataaagagct cgcgcagagc gccctccacc ggcattctta agcacaccct cataattcca 30660
agatattctg ctcctggttc acctgcagca gattgacaag cggaatatca aaatctctgc 30720
cgcgatccct gagctcctcc ctcagcaata actgtaagta ctctttcata tcctctccga 30780
aatttttagc cataggacca ccaggaataa gattagggca agccacagta cagataaacc 30840
gaagtcctcc ccagtgagca ttgccaaatg caagactgct ataagcatgc tggctagacc 30900
cggtgatatc ttccagataa ctggacagaa aatcgcccag gcaattttta agaaaatcaa 30960
caaaagaaaa atcctccagg tggacgttta gagcctcggg aacaacgatg aagtaaatgc 31020
aagcggtgcg ttccagcatg gttagttagc tgatctgtag aaaaaaacaaa aatgaacatt 31080 aaaccatgct agcctggcga acaggtgggt aaatcgttct ctccagcacc aggcaggcca 31140
cggggtctcc ggcgcgaccc tcgtaaaaat tgtcgctatg attgaaaacc atcacagaga 31200
gacgttcccg gtggccggcg tgaatgattc gacaagatga atacaccccc ggaacattgg 31260
cgtccgcgag tgaaaaaaag cgcccgagga agcaataagg cactacaatg ctcagtctca 31320
agtccagcaa agcgatgcca tgcggatgaa gcacaaaatt ctcaggtgcg tacaaaatgt 31380
aattactccc ctcctgcaca ggcagcaaag cccccgatcc ctccaggtac acatacaaag 31440
cctcagcgtc catagcttac cgagcagcag cacacaacag gcgcaagagt cagagaaagg 31500
ctgagctcta acctgtccac ccgctctctg ctcaatatat agcccagatc tacactgacg 31560
taaaggccaa agtctaaaaa tacccgccaa ataatcacac acgcccagca cacgcccaga 31620
aaccggtgac acactcaaaa aaatacgcgc acttcctcaa acgcccaaaa ctgccgtcat 31680
ttccgggttc ccacgctacg tcatcaaaac acgactttca aattccgtcg accgttaaaa 31740
acgtcacccg ccccgcccct aacggtcgcc cgtctctcag ccaatcagcg ccccgcatcc 31800
ccaaattcaa acacctcatt tgcatattaa cgcgcacaaa aagtttgagg tatattattg 31860
atgatgg 31867

<210> SEQ ID NO 12
<211> LENGTH: 32788
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780

```
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
ccgggatgtt ccaggcactg tccgaaggct gcacacccta tgatattaac cagatgctga   1320
atgtcctggg agaccaccag gtctctggcc tggagcagct ggagagcatc atcaacttcg   1380
agaagctgac cgagtggaca agctccaatg tgatgcctat cctgtcccca ctgaccaagg   1440
gcatcctggg cttcgtgttt accctgacag tgccttctga gcggggcctg tcttgcatca   1500
gcgaggcaga cgcaaccaca ccagagtccg ccaatctggg cgaggagatc ctgtctcagc   1560
tgtacctgtg gccccgggtg acatatcact cccccttctta cgcctatcac cagttcgagc   1620
ggagagccaa gtacaagaga cacttcccag gctttggcca gtctctgctg ttcggctacc   1680
ccgtgtacgt gttcggcgat tgcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gcctttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctggc aaggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac cccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
```

```
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
cggtaggccc tggaccaccg gtctcgatca ttgagcaccc ggtggatctt ttccaggacc   3840
cggtagaggt gggcttggat gttgaggtac atgggcatga gcccgtcccg gggtggagg   3900
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg agggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
cccagggata ggagctcctg gagcgaggcg aagtttttca gcggcttgag tccgtcggcc   4800
atgggcattt tggagagggt ttgttgcaag agttccaggc ggtcccagag ctcggtgatg   4860
tgctctacgg catctcgatc cagcagacct cctcgtttcg cgggttggga cggctgcggg   4920
agtagggcac cagacgatgg gcgtccagcg cagccagggt ccggtccttc cagggtcgca   4980
gcgtccgcgt cagggtggtc tccgtcacgg tgaaggggtg cgcgccgggc tgggcgcttg   5040
cgagggtgcg cttcaggctc atccggctgg tcgaaaaccg ctcccgatcg gcgccctgcg   5100
cgtcggccag gtagcaattg accatgagtt cgtagttgag cgcctcggcc gcgtggcctt   5160
tggcgcggag cttacctttg gaagtctgcc cgcaggcggg acagaggagg gacttgaggg   5220
cgtagagctt gggggcgagg aagacggact cgggggcgta ggcgtccgcg ccgcagtggg   5280
cgcagacggt ctcgcactcc acgagccagg tgaggtcggg ctggtcgggg tcaaaaacca   5340
gtttcccgcc gttctttttg atgcgtttct tacctttggt ctccatgagc tcgtgtcccc   5400
gctgggtgac aaagaggctg tccgtgtccc cgtagaccga ctttatgggc cggtcctcga   5460
gcggtgtgcc gcggtcctcc tcgtagagga accccgccca ctccgagacg aaagcccggg   5520
```

tccaggccag cacgaaggag gccacgtggg acgggtagcg gtcgttgtcc accagcgggt 5580
ccaccttttc cagggtatgc aaacacatgt ccccctcgtc cacatccagg aaggtgattg 5640
gcttgtaagt gtaggccacg tgaccggggg tcccggccgg gggggtataa aagggtgcgg 5700
gtccctgctc gtcctcactg tcttccggat cgctgtccag gagcgccagc tgttggggta 5760
ggtattccct ctcgaaggcg ggcatgacct cggcactcag gttgtcagtt tctagaaacg 5820
aggaggattt gatattgacg gtgccggcgg agatgccttt caagagcccc tcgtccatct 5880
ggtcagaaaa gacgatcttt ttgttgtcga gcttggtggc gaaggagccg tagagggcgt 5940
tggagaggag cttggcgatg gagcgcatgg tctggttttt ttccttgtcg gcgcgctcct 6000
tggcggcgat gttgagctgc acgtactcgc gcgccacgca cttccattcg gggaagacgg 6060
tggtcagctc gtcgggcacg attctgacct gccagccccg attatgcagg gtgatgaggt 6120
ccacactggt ggccacctcg ccgcgcaggg gctcattagt ccagcagagg cgtccgccct 6180
tgcgcgagca gaagggggc agggggtcca gcatgacctc gtcggggggg tcggcatcga 6240
tggtgaagat gccgggcagg aggtcggggt caaagtagct gatggaagtg gccagatcgt 6300
ccagggcagc ttgccattcg cgcacggcca gcgcgctctc gtagggactg aggggcgtgc 6360
cccagggcat gggatgggta agcgcggagg cgtacatgcc gcagatgtcg tagacgtaga 6420
ggggctcctc gaggatgccg atgtaggtgg ggtagcagcg ccccccgcgg atgctggcgc 6480
gcacgtagtc atacagctcg tgcgaggggg cgaggagccc cgggcccagg ttggtgcgac 6540
tgggcttttc ggcgcggtag acgatctggc ggaaaatggc atgcgagttg gaggagatgg 6600
tgggcctttg gaagatgttg aagtgggcgt ggggcagtcc gaccgagtcg cggatgaagt 6660
gggcgtagga gtcttgcagc ttggcgacga gctcggcggt gactaggacg tccagagcgc 6720
agtagtcgag ggtctcctgg atgatgtcat acttgagctg tccctttttgt ttccacagct 6780
cgcggttgag aaggaactct tcgcggtcct tccagtactc ttcgaggggg aacccgtcct 6840
gatctgcacg gtaagagcct agcatgtaga actggttgac ggccttgtag gcgcagcagc 6900
ccttctccac ggggagggcg taggcctggg cggccttgcg cagggaggtg tgcgtgaggg 6960
cgaaagtgtc cctgaccatg accttgagga actggtgctt gaagtcgata tcgtcgcagc 7020
ccccctgctc ccagagctgg aagtccgtgc gcttcttgta ggcggggttg ggcaaagcga 7080
aagtaacatc gttgaagagg atcttgcccg cgcggggcat aaagttgcga gtgatgcgga 7140
aaggttgggg cacctcggcc cggttgttga tgacctgggc ggcgagcacg atctcgtcga 7200
agccgttgat gttgtggccc acgatgtaga gttccacgaa tcgcggacgg cccttgacgt 7260
ggggcagttt cttgagctcc tcgtaggtga gctcgtcggg gtcgctgagc ccgtgctgct 7320
cgagcgccca gtcggcgaga tgggggttgg cgcggaggaa ggaagtccag agatccacgg 7380
ccagggcggt ttgcagacgg tcccggtact gacggaactg ctgcccgacg gccatttttt 7440
cgggggtgac gcagtagaag gtgcgggggt ccccgtgcca gcgatcccat ttgagctgga 7500
gggcgagatc gagggcgagc tcgacgagcc ggtcgtcccc ggagagtttc atgaccagca 7560
tgaaggggac gagctgcttg ccgaaggacc ccatccaggt gtaggtttcc acatcgtagg 7620
tgaggaagag cctttcggtg cgaggatgcg agccgatggg gaagaactgg atctcctgcc 7680
accaattgga ggaatggctg ttgatgtgat ggaagtagaa atgccgacgg cgcgccgaac 7740
actcgtgctt gtgtttatac aagcggccac agtgctcgca acgctgcacg ggatgcacgt 7800
gctgcacgag ctgtacctga gttcctttga cgaggaattt cagtgggaag tggagtcgtg 7860

-continued

```
gcgcctgcat ctcgtgctgt actacgtcgt ggtggtcggc ctggccctct tctgcctcga    7920
tggtggtcat gctgacgagc ccgcgcggga ggcaggtcca gacctcggcg cgagcgggtc    7980
ggagagcgag gacgagggcg cgcaggccgg agctgtccag ggtcctgaga cgctgcggag    8040
tcaggtcagt gggcagcggc ggcgcgcggt tgacttgcag gagtttttcc agggcgcgcg    8100
ggaggtccag atggtacttg atctccaccg cgccattggt ggcgacgtcg atggcttgca    8160
gggtcccgtg cccctggggt gtgaccaccg tcccccgttt cttcttgggc ggctggggcg    8220
acgggggcgg tgcctcttcc atggttagaa gcggcggcga ggacgcgcgc cgggcggcag    8280
gggcggctcg gggcccggag gcaggggcgg caggggcacg tcggcgccgc gcgcgggtag    8340
gttctggtac tgcgcccgga gaagactggc gtgagcgacg acgcgacggt tgacgtcctg    8400
gatctgacgc ctctgggtga aggccacggg acccgtgagt ttgaacctga aagagagttc    8460
gacagaatca atctcggtat cgttgacggc ggcctgccgc aggatctctt gcacgtcgcc    8520
cgagttgtcc tggtaggcga tctcggtcat gaactgctcg atctcctcct cttgaaggtc    8580
tccgcggccg gcgcgctcca cggtggccgc gaggtcgttg gagatgcggc ccatgagctg    8640
cgagaaggcg ttcatgcccg cctcgttcca gacgcggctg tagaccacga cgccctcggg    8700
atcgcgggcg cgcatgacca cctgggcgag gttgagctcc acgtggcgcg tgaagaccgc    8760
gtagttgcag aggcgctggt agaggtagtt gagcgtggtg gcgatgtgct cggtgacgaa    8820
gaaatacatg atccagcggc ggagcggcat ctcgctgacg tcgcccagcg cctccaaacg    8880
ttccatggcc tcgtaaaagt ccacggcgaa gttgaaaaac tgggagttgc gcgccgagac    8940
ggtcaactcc tcctccagaa gacggatgag ctcggcgatg gtggcgcgca cctcgcgctc    9000
gaaggccccc gggagttcct ccacttcctc ttcttcctcc tccactaaca tctcttctac    9060
ttcctcctca ggcggcagtg gtggcggggg agggggcctg cgtcgccggc ggcgcacggg    9120
cagacggtcg atgaagcgct cgatggtctc gccgcgccgg cgtcgcatgg tctcggtgac    9180
ggcgcgcccg tcctcgcggg gccgcagcgt gaagacgccg ccgcgcatct ccaggtggcc    9240
gggggggtcc ccgttgggca gggagagggc gctgacgatg catcttatca attgccccgt    9300
agggactccg cgcaaggacc tgagcgtctc gagatccacg ggatctgaaa accgctgaac    9360
gaaggcttcg agccagtcgc agtcgcaagg taggctgagc acggtttctt ctggcgggtc    9420
atgttggttg ggagcggggc gggcgatgct gctggtgatg aagttgaaat aggcggttct    9480
gagacggcgg atggtggcga ggagcaccag gtctttgggc ccggcttgct ggatgcgcag    9540
acggtcggcc atgccccagg cgtggtcctg acacctggcc aggtccttgt agtagtcctg    9600
catgagccgc tccacgggca cctcctcctc gcccgcgcgg ccgtgcatgc gcgtgagccc    9660
gaagccgcgc tggggctgga cgagcgccag gtcggcgacg acgcgctcgg cgaggatggc    9720
ttgctggatc tgggtgaggg tggtctggaa gtcatcaaag tcgacgaagc ggtggtaggc    9780
tccggtgttg atggtgtagg agcagttggc catgacggac cagttgacgg tctggtggcc    9840
cggacgcacg agctcgtggt acttgaggcg cgagtaggcg cgcgtgtcga agatgtagtc    9900
gttgcaggtg cgcaccaggt actggtagcc gatgaggaag tgcggcggcg gctggcggta    9960
gagcggccat cgctcggtgg cgggggcgcc gggcgcgagg tcctcgagca tggtgcggtg   10020
gtagccgtag atgtacctgg acatccaggt gatgccggcg gcggtggtgg aggcgcgcgg   10080
gaactcgcgg acgcggttcc agatgttgcg cagcggcagg aagtagttca tggtgggcac   10140
ggtctggccc gtgaggcgcg cgcagtcgtg gatgctctat acgggcaaaa acgaaagcgg   10200
tcagcggctc gactccgtgg cctggaggct aagcgaacgg gttgggctgc gcgtgtaccc   10260
```

```
cggttcgaat ctcgaatcag gctggagccg cagctaacgt ggtattggca ctcccgtctc  10320
gacccaagcc tgcaccaacc ctccaggata cggaggcggg tcgttttgca acttttttt  10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggccccccttc  12540
acggacagcg gcagcatcaa ccgcaactcg tacctgggct acctgattaa cctgtaccgc  12600
```

gaggccatcg gccaggcgca cgtggacgag cagacctacc aggagatcac ccacgtgagc 12660
cgcgccctgg gccaggacga cccgggcaac ctggaagcca ccctgaactt tttgctgacc 12720
aaccggtcgc agaagatccc gccccagtac gcgctcagca ccgaggagga gcgcatcctg 12780
cgttacgtgc agcagagcgt gggcctgttc ctgatgcagg agggggccac ccccagcgcc 12840
gcgctcgaca tgaccgcgcg caacatggag cccagcatgt acgccagcaa ccgcccgttc 12900
atcaataaac tgatggacta cttgcatcgg gcggccgcca tgaactctga ctatttcacc 12960
aacgccatcc tgaatcccca ctggctcccg ccgccggggt tctacacggg cgagtacgac 13020
atgcccgacc ccaatgacgg gttcctgtgg gacgatgtgg acagcagcgt gttctccccc 13080
cgaccgggtg ctaacgagcg ccccttgtgg aagaaggaag gcagcgaccg acgcccgtcc 13140
tcggcgctgt ccggccgcga gggtgctgcc gcggcggtgc ccgaggccgc cagtcctttc 13200
ccgagcttgc ccttctcgct gaacagtatc cgcagcagcg agctgggcag gatcacgcgc 13260
ccgcgcttgc tgggcgaaga ggagtacttg aatgactcgc tgttgagacc cgagcgggag 13320
aagaacttcc ccaataacgg gatagaaagc ctggtggaca agatgagccg ctggaagacg 13380
tatgcgcagg agcacaggga cgatccccgg gcgtcgcagg gggccacgag ccggggcagc 13440
gccgcccgta aacgccggtg gcacgacagg cagcggggac agatgtggga cgatgaggac 13500
tccgccgacg acagcagcgt gttggacttg ggtgggagtg gtaacccgtt cgctcacctg 13560
cgcccccgta tcgggcgcat gatgtaagag aaaccgaaaa taaatgatac tcaccaaggc 13620
catggcgacc agcgtgcgtt cgtttcttct ctgttgttgt tgtatctagt atgatgaggc 13680
gtgcgtaccc ggagggtcct cctccctcgt acgagagcgt gatgcagcag gcgatggcgg 13740
cggcggcgat gcagcccccg ctggaggctc cttacgtgcc cccgcggtac ctggcgccta 13800
cggaggggcg gaacagcatt cgttactcgg agctggcacc cttgtacgat accacccggt 13860
tgtacctggt ggacaacaag tcggcggaca tcgcctcgct gaactaccag aacgaccaca 13920
gcaacttcct gaccaccgtg gtgcagaaca atgacttcac ccccacggag gccagcaccc 13980
agaccatcaa ctttgacgag cgctcgcggt ggggcggcca gctgaaaacc atcatgcaca 14040
ccaacatgcc caacgtgaac gagttcatgt acagcaacaa gttcaaggcg cgggtgatgg 14100
tctcccgcaa gacccccaat ggggtgacag tgacagagga ttatgatggt agtcaggatg 14160
agctgaagta tgaatgggtg gaatttgagc tgcccgaagg caacttctcg gtgaccatga 14220
ccatcgacct gatgaacaac gccatcatcg acaattactt ggcggtgggg cggcagaacg 14280
gggtgctgga gagcgacatc ggcgtgaagt tcgacactag gaacttcagg ctgggctggg 14340
accccgtgac cgagctggtc atgcccgggg tgtacaccaa cgaggctttc catcccgata 14400
ttgtcttgct gcccggctgc ggggtggact tcaccgagag ccgcctcagc aacctgctgg 14460
gcattcgcaa gaggcagccc ttccaggaag gcttccagat catgtacgag gatctggagg 14520
ggggcaacat ccccgcgctc ctggatgtcg acgcctatga gaaaagcaag gaggatgcag 14580
cagctgaagc aactgcagcc gtagctaccg cctctaccga ggtcaggggc gataattttg 14640
caagcgccgc agcagtggca gcggccgagg cggctgaaac cgaaagtaag atagtcattc 14700
agccggtgga gaaggatagc aagaacagga gctacaacgt actaccggac aagataaaca 14760
ccgcctaccg cagctggtac ctagcctaca actatggcga ccccgagaag ggcgtgcgct 14820
cctggacgct gctcaccacc tcggacgtca cctgcggcgt ggagcaagtc tactggtcgc 14880
tgcccgacat gatgcaagac ccggtcacct tccgctccac gcgtcaagtt agcaactacc 14940
cggtggtggg cgccgagctc ctgcccgtct actccaagag cttcttcaac gagcaggccg 15000

-continued tctactcgca gcagctgcgc gccttcacct cgcttacgca cgtcttcaac cgcttccccg 15060
agaaccagat cctcgtccgc ccgcccgcgc ccaccattac caccgtcagt gaaaacgttc 15120
ctgctctcac agatcacggg accctgccgc tgcgcagcag tatccgggga gtccagcgcg 15180
tgaccgttac tgacgccaga cgccgcacct gcccctacgt ctacaaggcc ctgggcatag 15240
tcgcgccgcg cgtcctctcg agccgcacct tctaaatgtc cattctcatc tcgcccagta 15300
ataacaccgg ttggggcctg cgcgcgccca gcaagatgta cggaggcgct cgccaacgct 15360
ccacgcaaca ccccgtgcgc gtgcgcgggc acttccgcgc tccctggggc gccctcaagg 15420
gccgcgtgcg gtcgcgcacc accgtcgacg acgtgatcga ccaggtggtg gccgacgcgc 15480
gcaactacac ccccgccgcc gcgcccgtct ccaccgtgga cgccgtcatc gacagcgtgg 15540
tggccgacgc gcgccggtac gcccgcgcca agagccggcg gcggcgcatc gcccggcggc 15600
accggagcac ccccgccatg cgcgcggcgc gagccttgct gcgcagggcc aggcgcacgg 15660
gacgcagggc catgctcagg gcggccagac gcgcggcttc aggcgccagc gccggcagga 15720
cccggagacg cgcggccacg gcggcggcag cggccatcgc cagcatgtcc cgcccgcggc 15780
gagggaacgt gtactgggtg cgcgacgccg ccaccggtgt gcgcgtgccc gtgcgcaccc 15840
gcccccctcg cacttgaaga tgttcacttc gcgatgttga tgtgtcccag cggcgaggag 15900
gatgtccaag cgcaaattca aggaagagat gctccaggtc atcgcgcctg agatctacgg 15960
ccctgcggtg gtgaaggagg aaagaaagcc ccgcaaaatc aagcgggtca aaaaggacaa 16020
aaaggaagaa gaaagtgatg tggacggatt ggtggagttt gtgcgcgagt tcgccccccg 16080
gcggcgcgtg cagtggcgcg ggcggaaggt gcaaccggtg ctgagacccg gcaccaccgt 16140
ggtcttcacg cccggcgagc gctccggcac cgcttccaag cgctcctacg acgaggtgta 16200
cggggatgat gatattctgg agcaggcggc cgagcgcctg ggcgagtttg cttacggcaa 16260
gcgcagccgt tccgcaccga aggaagaggc ggtgtccatc ccgctggacc acggcaaccc 16320
cacgccgagc ctcaagcccg tgaccttgca gcaggtgctg ccgaccgcgg cgccgcgccg 16380
ggggttcaag cgcgagggcg aggatctgta ccccaccatg cagctgatgg tgcccaagcg 16440
ccagaagctg gaagacgtgc tggagaccat gaaggtggac ccggacgtgc agcccgaggt 16500
caaggtgcgg cccatcaagc aggtggcccc gggcctgggc gtgcagaccg tggacatcaa 16560
gattcccacg gagcccatgg aaacgcagac cgagcccatg atcaagccca gcaccagcac 16620
catggaggtg cagacggatc cctggatgcc atcggctcct agtcgaagac cccggcgcaa 16680
gtacggcgcg gccagcctgc tgatgcccaa ctacgcgctg catccttcca tcatccccac 16740
gccgggctac cgcggcacgc gcttctaccg cggtcatacc agcagccgcc gccgcaagac 16800
caccactcgc cgccgccgtc gccgcaccgc cgctgcaacc acccctgccg ccctggtgcg 16860
gagagtgtac cgccgcggcc gcgcacctct gaccctgccg cgcgcgcgct accacccgag 16920
catcgccatt taaactttcg cctgctttgc agatcaatgg ccctcacatg ccgccttcgc 16980
gttcccatta cgggctaccg aggaagaaaa ccgcgccgta gaaggctggc ggggaacggg 17040
atgcgtcgcc accaccaccg gcggcggcgc gccatcagca agcggttggg gggaggcttc 17100
ctgcccgcgc tgatccccat catcgccgcg gcgatcgggg cgatccccgg cattgcttcc 17160
gtggcggtgc aggcctctca gcgccactga gacacacttg gaaacatctt gtaataaacc 17220
aatggactct gacgctcctg gtcctgtgat gtgttttcgt agacagatgg aagacatcaa 17280
tttttcgtcc ctggctccgc gacacggcac gcggccgttc atgggcacct ggagcgacat 17340

-continued

```
cggcaccagc caactgaacg ggggcgcctt caattggagc agtctctgga gcgggcttaa   17400

gaatttcggg tccacgctta aaacctatgg cagcaaggcg tggaacagca ccacagggca   17460

ggcgctgagg gataagctga aagagcagaa cttccagcag aaggtggtcg atgggctcgc   17520

ctcgggcatc aacggggtgg tggacctggc caaccaggcc gtgcagcggc agatcaacag   17580

ccgcctggac ccggtgccgc ccgccggctc cgtggagatg ccgcaggtgg aggaggagct   17640

gcctcccctg gacaagcggg gcgagaagcg accccgcccc gatgcggagg agacgctgct   17700

gacgcacacg gacgagccgc ccccgtacga ggaggcggtg aaactgggtc tgcccaccac   17760

gcggcccatc gcgcccctgg ccaccggggt gctgaaaccc gaaaagcccg cgaccctgga   17820

cttgcctcct ccccagcctt cccgcccctc tacagtggct aagcccctgc cgccggtggc   17880

cgtggcccgc gcgcgacccg ggggcaccgc ccgccctcat gcgaactggc agagcactct   17940

gaacagcatc gtgggtctgg gagtgcagag tgtgaagcgc cgccgctgct attaaaccta   18000

ccgtagcgct taacttgctt gtctgtgtgt gtatgtatta tgtcgccgcc gccgctgtcc   18060

accagaagga ggagtgaaga ggcgcgtcgc cgagttgcaa gatggccacc ccatcgatgc   18120

tgccccagtg ggcgtacatg cacatcgccg gacaggacgc ttcggagtac ctgagtccgg   18180

gtctggtgca gtttgcccgc gccacagaca cctacttcag tctggggaac aagtttagga   18240

accccacggt ggcgcccacg cacgatgtga ccaccgaccg cagccagcgg ctgacgctgc   18300

gcttcgtgcc cgtggaccgc gaggacaaca cctactcgta caaagtgcgc tacacgctgg   18360

ccgtgggcga caaccgcgtg ctggacatgg ccagcaccta ctttgacatc cgcggcgtgc   18420

tggatcgggg ccctagcttc aaaccctact ccggcaccgc ctacaacagt ctggccccca   18480

agggagcacc caacacttgt cagtggacat ataaagccga tggtgaaact gccacagaaa   18540

aaacctatac atatggaaat gcacccgtgc agggcattaa catcacaaaa gatggtattc   18600

aacttggaac tgacaccgat gatcagccaa tctacgcaga taaaacctat cagcctgaac   18660

ctcaagtggg tgatgctgaa tggcatgaca tcactggtac tgatgaaaag tatggaggca   18720

gagctcttaa gcctgatacc aaaatgaagc cttgttatgg ttcttttgcc aagcctacta   18780

ataaagaagg aggtcaggca aatgtgaaaa caggaacagg cactactaaa gaatatgaca   18840

tagacatggc tttctttgac aacagaagtg cggctgctgc tggcctagct ccagaaattg   18900

ttttgtatac tgaaaatgtg gatttggaaa ctccagatac ccatattgta tacaaagcag   18960

gcacagatga cagcagctct tctattaatt tgggtcagca agccatgccc aacagaccta   19020

actacattgg tttcagagac aactttatcg ggctcatgta ctacaacagc actggcaata   19080

tgggggtgct ggccggtcag gcttctcagc tgaatgctgt ggttgacttg caagacagaa   19140

acaccgagct gtcctaccag ctcttgcttg actctctggg tgacagaacc cggtatttca   19200

gtatgtggaa tcaggcggtg gacagctatg atcctgatgt gcgcattatt gaaaatcatg   19260

gtgtggagga tgaacttccc aactattgtt tccctctgga tgctgttggc agaacagata   19320

cttatcaggg aattaaggct aatggaactg atcaaaccac atggaccaaa gatgacagtg   19380

tcaatgatgc taatgagata ggcaaggta atccattcgc catggaaatc aacatccaag   19440

ccaacctgtg gaggaacttc ctctacgcca acgtggccct gtacctgccc gactcttaca   19500

agtacacgcc ggccaatgtt accctgccca ccaacaccaa cacctacgat tacatgaacg   19560

gccgggtggt ggcgccctcg ctggtggact cctacatcaa catcggggcg cgctggtcgc   19620

tggatcccat ggacaacgtg aaccccttca accaccaccg caatgcgggg ctgcgctacc   19680

gctccatgct cctgggcaac gggcgctacg tgcccttcca catccaggtg ccccagaaat   19740
```

```
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg acccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc ccgcacaag ctggcctgcg ccatcgtcaa  21060
cacggccggc cgcgagaccg gggcgagca ctggctggcc ttcgcctgga acccgcgctc  21120
gaacacctgc tacctcttcg acccttcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
```

-continued

```
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc atacccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
cgcggtgccc gaggccctgg ccacctacca catctttttc aagaaccaaa agatccccgt  23760
ctcctgccgc gccaaccgca cccgcgccga cgcccttttc aacctgggtc ccggcgcccg  23820
cctacctgat atcgcctcct tggaagaggt tcccaagatc ttcgagggtc tgggcagcga  23880
cgagactcgg gccgcgaacg ctctgcaagg agaaggagga gagcatgagc accacagcgc  23940
cctggtcgag ttggaaggcg acaacgcgcg gctggcggtg ctcaaacgca cggtcgagct  24000
gacccatttc gcctacccgg ctctgaacct gccccccaaa gtcatgagcg cggtcatgga  24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag  24180
tccccagagt ttggaagagc ggcgcaaact catgatggcc gtggtcctgg tgaccgtgga  24240
gctggagtgc ctgcgccgct tcttcgccga cgcggagacc ctgcgcaagg tcgaggagaa  24300
cctgcactac ctcttcaggc acgggttcgt gcgccaggcc tgcaagatct ccaacgtgga  24360
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
```

ctacctctgc cacacctggc agacgggcat gggcgtgtgg cagcagtgtc tggaggagca 24540
gaacctgaaa gagctctgca agctcctgca gaagaacctc aagggtctgt ggaccgggtt 24600
cgacgagcgc accaccgcct cggacctggc cgacctcatt ttccccgagc gcctcaggct 24660
gacgctgcgc aacggcctgc ccgactttat gagccaaagc atgttgcaaa actttcgctc 24720
tttcatcctc gaacgctccg gaatcctgcc cgccacctgc tccgcgctgc cctcggactt 24780
cgtgccgctg accttccgcg agtgcccccc gccgctgtgg agccactgct acctgctgcg 24840
cctggccaac tacctggcct accactcgga cgtgatcgag gacgtcagcg gcgagggcct 24900
gctcgagtgc cactgccgct gcaacctctg cacgccgcac cgctccctgg cctgcaaccc 24960
ccagctgctg agcgagaccc agatcatcgg caccttcgag ttgcaagggc ccagcgaagg 25020
cgagggttca gccgccaagg ggggtctgaa actcaccccg ggctgtgga cctcggccta 25080
cttgcgcaag ttcgtgcccg aggactacca tcccttcgag atcaggttct acgaggacca 25140
atcccatccg cccaaggccg agctgtcggc ctgcgtcatc acccaggggg cgatcctggc 25200
ccaattgcaa gccatccaga aatcccgcca agaattcttg ctgaaaaagg gccgcggggt 25260
ctacctcgac ccccagaccg gtgaggagct caaccccggc ttcccccagg atgccccgag 25320
gaaacaagaa gctgaaagtg gagctgccgc ccgtggagga tttggaggaa gactgggaga 25380
acagcagtca ggcagaggag gaggagatgg aggaagactg ggacagcact caggcagagg 25440
aggacagcct gcaagacagt ctggaggaag acgaggagga ggcagaggag gaggtggaag 25500
aagcagccgc cgccagaccg tcgtcctcgg cgggggagaa agcaagcagc acggatacca 25560
tctccgctcc gggtcggggt cccgctcgac cacacagtag atgggacgag accggacgat 25620
tcccgaaccc caccacccag accggtaaga aggagcggca gggatacaag tcctggcggg 25680
ggcacaaaaa cgccatcgtc tcctgcttgc aggcctgcgg gggcaacatc tccttcaccc 25740
ggcgctacct gctcttccac cgcggggtga actttccccg caacatcttg cattactacc 25800
gtcacctcca cagcccctac tacttccaag aagaggcagc agcagcagaa aaagaccagc 25860
agaaaaccag cagctagaaa atccacagcg gcggcagcag gtggactgag gatcgcggcg 25920
aacgagccgg cgcaaacccg ggagctgagg aaccggatct ttcccaccct ctatgccatc 25980
ttccagcaga gtcgggggca ggagcaggaa ctgaaagtca agaaccgttc tctgcgctcg 26040
ctcacccgca gttgtctgta tcacaagagc gaagaccaac ttcagcgcac tctcgaggac 26100
gccgaggctc tcttcaacaa gtactgcgcg ctcactctta aagagtagcc cgcgcccgcc 26160
cagtcgcaga aaaaggcggg aattacgtca cctgtgccct tcgccctagc cgcctccacc 26220
catcatcatg agcaaagaga ttcccacgcc ttacatgtgg agctaccagc cccagatggg 26280
cctggccgcc ggtgccgccc aggactactc cacccgcatg aattggctca gcgccgggcc 26340
cgcgatgatc tcacgggtga atgacatccg cgcccaccga aaccagatac tcctagaaca 26400
gtcagcgctc accgccacgc cccgcaatca cctcaatccg cgtaattggc ccgccgccct 26460
ggtgtaccag gaaattcccc agcccacgac cgtactactt ccgcgagacg cccaggccga 26520
agtccagctg actaactcag gtgtccagct ggcgggcggc gccaccctgt gtcgtcaccg 26580
ccccgctcag ggtataaagc ggctggtgat ccggggcaga ggcacacagc tcaacgacga 26640
ggtggtgagc tcttcgctgg gtctgcgacc tgacggagtc ttccaactcg ccggatcggg 26700
gagatcttcc ttcacgcctc gtcaggccgt cctgactttg gagagttcgt cctcgcagcc 26760
ccgctcgggt ggcatcggca ctctccagtt cgtggaggag ttcactccct cggtctactt 26820

-continued

```
caaccccttc tccggctccc ccggccacta cccggacgag ttcatcccga acttcgacgc  26880
catcagcgag tcggtggacg gctacgattg aatgtcccat ggtggcgcag ctgacctagc  26940
tcggcttcga cacctggacc actgccgccg cttccgctgc ttcgctcggg atctcgccga  27000
gtttgcctac tttgagctgc ccgaggagca ccctcagggc ccggcccacg gagtgcggat  27060
cgtcgtcgaa gggggcctcg actcccacct gcttcggatc ttcagccagc gtccgatcct  27120
ggtcgagcgc gagcaaggac agacccttct gactctgtac tgcatctgca accaccccgg  27180
cctgcatgaa agtctttgtt gtctgctgtg tactgagtat aataaaagct gagatcagcg  27240
actactccgg acttccgtgt gttcctgaat ccatcaacca gtctttgttc ttcaccggga  27300
acgagaccga gctccagctc cagtgtaagc cccacaagaa gtacctcacc tggctgttcc  27360
agggctcccc gatcgccgtt gtcaaccact gcgacaacga cggagtcctg ctgagcggcc  27420
ctgccaacct tactttttcc acccgcagaa gcaagctcca gctcttccaa cccttcctcc  27480
ccgggaccta tcagtgcgtc tcgggaccct gccatcacac cttccacctg atcccgaata  27540
ccacagcgtc gctccccgct actaacaacc aaactaacct ccaccaacgc caccgtcgcg  27600
acggccacaa tacatgccca tattagacta tgaggccgag ccacagcgac ccatgctccc  27660
cgctattagt tacttcaatc taaccggcgg agatgactga cccactggcc aacaacaacg  27720
tcaacgacct tctcctggac atggacggcc gcgcctcgga gcagcgactc gcccaacttc  27780
gcattcgcca gcagcaggag agagccgtca aggagctgca ggatgcggtg gccatccacc  27840
agtgcaagag aggcatcttc tgcctggtga aacaggccaa gatctcctac gaggtcactc  27900
caaacgacca tcgcctctcc tacgagctcc tgcagcagcg ccagaagttc acctgcctgg  27960
tcggagtcaa ccccatcgtc atcacccagc agtctggcga taccaagggg tgcatccact  28020
gctcctgcga ctcccccgac tgcgtccaca ctctgatcaa gaccctctgc ggcctccgcg  28080
acctcctccc catgaactaa tcaccccctt atccagtgaa ataaagatca tattgatgat  28140
gattttacag aaataaaaaa taatcatttg atttgaaata aagatacaat catattgatg  28200
atttgagttt aacaaaaaaa taaagaatca cttacttgaa atctgatacc aggtctctgt  28260
ccatgttttc tgccaacacc acttcactcc cctcttccca gctctggtac tgcaggcccc  28320
ggcgggctgc aaacttcctc cacacgctga aggggatgtc aaattcctcc tgtccctcaa  28380
tcttcatttt atcttctatc agatgtccaa aaagcgcgtc cgggtggatg atgacttcga  28440
ccccgtctac ccctacgatg cagacaacgc accgaccgtg cccttcatca acccccccctt  28500
cgtctcttca gatggattcc aagagaagcc cctgggggtg ttgtccctgc gactggccga  28560
ccccgtcacc accaagaacg gggaaatcac cctcaagctg ggagaggggg tggacctcga  28620
ttcctcggga aaactcatct ccaacacggc caccaaggcc gccgcccctc tcagtttttc  28680
caacaacacc atttccctta acatggatca ccccttttac actaaagatg gaaaattatc  28740
cttacaagtt tctccaccat taaatatact gagaacaagc attctaaaca cactagcttt  28800
aggttttgga tcaggtttag gactccgtgg ctctgccttg gcagtacagt tagtctctcc  28860
acttacattt gatactgatg gaaacataaa gcttacctta gacagaggtt tgcatgttac  28920
aacaggagat gcaattgaaa gcaacataag ctgggctaaa ggtttaaaat ttgaagatgg  28980
agccatagca accaacattg gaaatgggtt agagtttgga agcagtagta cagaaacagg  29040
tgttgatgat gcttacccaa tccaagttaa acttggatct ggccttagct ttgacagtac  29100
aggagccata atggctggta acaaagaaga cgataaactc actttgtgga caacacctga  29160
tccatcacca aactgtcaaa tactcgcaga aaatgatgca aaactaacac tttgcttgac  29220
```

-continued

```
taaatgtggt agtcaaatac tggccactgt gtcagtctta gttgtaggaa gtggaaacct   29280

aaaccccatt actggcaccg taagcagtgc tcaggtgttt ctacgttttg atgcaaacgg   29340

tgttctttta acagaacatt ctacactaaa aaaatactgg gggtataggc agggagatag   29400

catagatggc actccatata ccaatgctgt aggattcatg cccaatttaa aagcttatcc   29460

aaagtcacaa agttctacta ctaaaaataa tatagtaggg caagtataca tgaatggaga   29520

tgtttcaaaa cctatgcttc tcactataac cctcaatggt actgatgaca gcaacagtac   29580

atattcaatg tcattttcat acacctggac taatggaagc tatgttggag caacatttgg   29640

ggctaactct tataccttct catacatcgc ccaagaatga acactgtatc ccaccctgca   29700

tgccaaccct tcccacccca ctctgtggaa caaactctga aacacaaaat aaaataaagt   29760

tcaagtgttt tattgattca acagttttac aggattcgag cagttatttt tcctccaccc   29820

tcccaggaca tggaatacac caccctctcc ccccgcacag ccttgaacat ctgaatgcca   29880

ttggtgatgg acatgctttt ggtctccacg ttccacacag tttcagagcg agccagtctc   29940

gggtcggtca gggagatgaa accctccggg cactcccgca tctgcacctc acagctcaac   30000

agctgaggat tgtcctcggt ggtcgggatc acggttatct ggaagaagca gaagagcggc   30060

ggtgggaatc atagtccgcg aacgggatcg gccggtggtg tcgcatcagg ccccgcagca   30120

gtcgctgccg ccgccgctcc gtcaagctgc tgctcagggg gtccgggtcc agggactccc   30180

tcagcatgat gcccacggcc ctcagcatca gtcgtctggt gcggcgggcg cagcagcgca   30240

tgcggatctc gctcaggtcg ctgcagtacg tgcaacacag aaccaccagg ttgttcaaca   30300

gtccatagtt caacacgctc cagccgaaac tcatcgcggg aaggatgcta cccacgtggc   30360

cgtcgtacca gatcctcagg taaatcaagt ggtgccccct ccagaacacg ctgcccacgt   30420

acatgatctc cttgggcatg tggcggttca ccacctcccg gtaccacatc accctctggt   30480

tgaacatgca gccccggatg atcctgcgga accacagggc cagcaccgcc ccgcccgcca   30540

tgcagcgaag agaccccggg tcccggcaat ggcaatggag gacccaccgc tcgtacccgt   30600

ggatcatctg ggagctgaac aagtctatgt tggcacagca caggcatatg ctcatgcatc   30660

tcttcagcac tctcaactcc tcgggggtca aaaccatatc ccagggcacg gggaactctt   30720

gcaggacagc gaaccccgca gaacagggca atcctcgcac agaacttaca ttgtgcatgg   30780

acagggtatc gcaatcaggc agcaccgggt gatcctccac cagagaagcg cgggtctcgg   30840

tctcctcaca gcgtggtaag ggggccggcc gatacgggtg atggcgggac gcggctgatc   30900

gtgttcgcga ccgtgtcatg atgcagttgc tttcggacat tttcgtactt gctgtagcag   30960

aacctggtcc gggcgctgca caccgatcgc cggcggcggt ctcggcgctt ggaacgctcg   31020

gtgttgaaat tgtaaaacag ccactctctc agaccgtgca gcagatctag ggcctcagga   31080

gtgatgaaga tcccatcatg cctgatggct ctgatcacat cgaccaccgt ggaatgggcc   31140

agacccagcc agatgatgca attttgttgg gtttcggtga cggcggggga gggaagaaca   31200

ggaagaacca tgattaactt ttaatccaaa cggtctcgga gtacttcaaa atgaagatcg   31260

cggagatggc acctctcgcc cccgctgtgt tggtggaaaa taacagccag gtcaaaggtg   31320

atacggttct cgagatgttc cacggtggct tccagcaaag cctccacgcg cacatccaga   31380

aacaagacaa tagcgaaagc gggagggttc tctaattcct caatcatcat gttacactcc   31440

tgcaccatcc ccagataatt ttcatttttc cagccttgaa tgattcgaac tagttcgtga   31500

ggtaaatcca agccagccat gataaagagc tcgcgcagag cgccctccac cggcattctt   31560
```

aagcacaccc tcataattcc aagatattct gctcctggtt cacctgcagc agattgacaa 31620
gcggaatatc aaaatctctg ccgcgatccc tgagctcctc cctcagcaat aactgtaagt 31680
actctttcat atcctctccg aaatttttag ccataggacc accaggaata agattagggc 31740
aagccacagt acagataaac cgaagtcctc cccagtgagc attgccaaat gcaagactgc 31800
tataagcatg ctggctagac ccggtgatat cttccagata actggacaga aaatcgccca 31860
ggcaattttt aagaaaatca acaaaagaaa aatcctccag gtggacgttt agagcctcgg 31920
gaacaacgat gaagtaaatg caagcggtgc gttccagcat ggttagttag ctgatctgta 31980
gaaaaaacaa aaatgaacat taaaccatgc tagcctggcg aacaggtggg taaatcgttc 32040
tctccagcac caggcaggcc acggggtctc cggcgcgacc ctcgtaaaaa ttgtcgctat 32100
gattgaaaac catcacagag agacgttccc ggtggccggc gtgaatgatt cgacaagatg 32160
aatacacccc cggaacattg gcgtccgcga gtgaaaaaaa gcgcccgagg aagcaataag 32220
gcactacaat gctcagtctc aagtccagca aagcgatgcc atgcggatga agcacaaaat 32280
tctcaggtgc gtacaaaatg taattactcc cctcctgcac aggcagcaaa gcccccgatc 32340
cctccaggta cacatacaaa gcctcagcgt ccatagctta ccgagcagca gcacacaaca 32400
ggcgcaagag tcagagaaag gctgagctct aacctgtcca cccgctctct gctcaatata 32460
tagcccagat ctacactgac gtaaaggcca aagtctaaaa atacccgcca aataatcaca 32520
cacgcccagc acacgcccag aaaccggtga cacactcaaa aaaatacgcg cacttcctca 32580
aacgcccaaa actgccgtca tttccgggtt cccacgctac gtcatcaaaa cacgactttc 32640
aaattccgtc gaccgttaaa aacgtcaccc gccccgcccc taacggtcgc ccgtctctca 32700
gccaatcagc gccccgcatc cccaaattca aacacctcat ttgcatatta acgcgcacaa 32760
aaagtttgag gtatattatt gatgatgg 32788

<210> SEQ ID NO 13
<211> LENGTH: 30684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780

-continued

```
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
tgagcaaggg cgaggagctg ttcaccgggg tggtgcccat cctggtcgag ctggacggcg   1320
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg gggaggacc tgcatgaggg ccagaataac tgaaatctgt gcttttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
tctcgatcat tgagcacccg gtggatcttt tccaggaccc ggtagaggtg ggcttggatg   2940
ttgaggtaca tgggcatgag cccgtcccgg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acgggcagcc ctttggtgta ggtgtttaca   3120
aatctgttga gctgggaggg atgcatgcgg ggggagatga ggtgcatctt ggcctggatc   3180
```

-continued ttgagattgg cgatgttacc gcccagatcc cgcctggggt tcatgttgtg caggaccacc 3240
agcacggtgt atccggtgca cttggggaat ttatcatgca acttggaagg gaaggcgtga 3300
aagaatttgg cgacgccttt gtgcccgccc aggttttcca tgcactcatc catgatgatg 3360
gcgatgggcc cgtgggcggc ggcctgggca aagacgtttc gggggtcgga cacatcatag 3420
ttgtggtcct gggtgaggtc atcataggcc attttaatga atttggggcg gagggtgccg 3480
gactggggga caaaggtacc ctcgatcccg gggcgtagt tcccctcaca gatctgcatc 3540
tcccaggctt tgagctcgga gggggggatc atgtccacct gcggggcgat aaagaacacg 3600
gtttccgggg cgggggagat gagctgggcc gaaagcaagt tccggagcag ctgggacttg 3660
ccgcagccgg tggggccgta gatgaccccg atgaccggct gcaggtggta gttgagggag 3720
agacagctgc cgtcctcccg gaggaggggg gccacctcgt tcatcatctc gcgcacgtgc 3780
atgttctcgc gcaccagttc cgccaggagg cgctctcccc ccagggatag gagctcctgg 3840
agcgaggcga agtttttcag cggcttgagt ccgtcggcca tgggcatttt ggagagggtt 3900
tgttgcaaga gttccaggcg gtcccagagc tcggtgatgt gctctacggc atctcgatcc 3960
agcagacctc ctcgtttcgc gggttgggac ggctgcggga gtagggcacc agacgatggg 4020
cgtccagcgc agccagggtc cggtccttcc agggtcgcag cgtccgcgtc agggtggtct 4080
ccgtcacggt gaaggggtgc gcgccgggct gggcgcttgc gagggtgcgc ttcaggctca 4140
tccggctggt cgaaaaccgc tcccgatcgg cgccctgcgc gtcggccagg tagcaattga 4200
ccatgagttc gtagttgagc gcctcggccg cgtggccttt ggcgcggagc ttacctttgg 4260
aagtctgccc gcaggcggga cagaggaggg acttgagggc gtagagcttg ggggcgagga 4320
agacggactc gggggcgtag gcgtccgcgc cgcagtgggc gcagacggtc tcgcactcca 4380
cgagccaggt gaggtcgggc tggtcggggt caaaaaccag tttcccgccg ttctttttga 4440
tgcgtttctt acctttggtc tccatgagct cgtgtccccg ctgggtgaca aagaggctgt 4500
ccgtgtcccc gtagaccgac tttatgggcc ggtcctcgag cggtgtgccg cggtcctcct 4560
cgtagaggaa ccccgcccac tccgagacga aagcccgggt ccaggccagc acgaaggagg 4620
ccacgtggga cgggtagcgg tcgttgtcca ccagcgggtc caccttttcc agggtatgca 4680
aacacatgtc cccctcgtcc acatccagga aggtgattgg cttgtaagtg taggccacgt 4740
gaccgggggt cccggccggg ggggtataaa agggtgcggg tccctgctcg tcctcactgt 4800
cttccggatc gctgtccagg agcgccagct gttggggtag gtattccctc tcgaaggcgg 4860
gcatgacctc ggcactcagg ttgtcagttt ctagaaacga ggaggatttg atattgacgg 4920
tgccggcgga gatgcctttc aagagcccct cgtccatctg gtcagaaaag acgatctttt 4980
tgttgtcgag cttggtggcg aaggagccgt agagggcgtt ggagaggagc ttggcgatgg 5040
agcgcatggt ctggtttttt tccttgtcgg cgcgctcctt ggcggcgatg ttgagctgca 5100
cgtactcgcg cgccacgcac ttccattcgg ggaagacggt ggtcagctcg tcgggcacga 5160
ttctgacctg ccagccccga ttatgcaggg tgatgaggtc cacactggtg gccacctcgc 5220
cgcgcagggg ctcattagtc cagcagaggc gtccgccctt gcgcgagcag aagggggca 5280
gggggtccag catgacctcg tcgggggggt cggcatcgat ggtgaagatg ccgggcagga 5340
ggtcggggtc aaagtagctg atggaagtgg ccagatcgtc cagggcagct tgccattcgc 5400
gcacggccag cgcgcgctcg tagggactga ggggcgtgcc ccagggcatg ggatgggtaa 5460
gcgcggaggc gtacatgccg cagatgtcgt agacgtagag ggctcctcg aggatgccga 5520

-continued

```
tgtaggtggg gtagcagcgc cccccgcgga tgctggcgcg cacgtagtca tacagctcgt   5580
gcgagggggc gaggagcccc gggcccaggt tggtgcgact gggcttttcg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt ccctttttgtt tccacagctc gcggttgaga aggaactctt   5880
cgcggtcctt ccagtactct tcgaggggga acccgtcctg atctgcacgg taagagccta   5940
gcatgtagaa ctggttgacg gccttgtagg cgcagcagcc cttctccacg ggagggcgt   6000
aggcctgggc ggccttgcgc agggaggtgt gcgtgagggc gaaagtgtcc ctgaccatga   6060
ccttgaggaa ctggtgcttg aagtcgatat cgtcgcagcc cccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg ggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccattttttc gggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
```

```
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtgg tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cgggcaaaaa cgaaagcggt cagcggctcg actccgtggc   9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agccccctcc acagccggcg cttctgcccc cgccccagca   9780
gcaacttcca gccacgaccg ccgcggccgc cgtgagcggg gctggacaga gttatgatca   9840
ccagctggcc ttggaagagg gcgaggggct ggcgcgcctg gggcgtcgt cgccggagcg    9900
gcacccgcgc gtgcagatga aaagggacgc tcgcgaggcc tacgtgccca agcagaacct   9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
```

```
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gcccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctcccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
```

atgtaagaga aaccgaaaat aaatgatact caccaaggcc atggcgacca gcgtgcgttc 12720
gtttcttctc tgttgttgtt gtatctagta tgatgaggcg tgcgtacccg gagggtcctc 12780
ctccctcgta cgagagcgtg atgcagcagg cgatggcggc ggcggcgatg cagccccccgc 12840
tggaggctcc ttacgtgccc ccgcggtacc tggcgcctac ggaggggcgg aacagcattc 12900
gttactcgga gctggcaccc ttgtacgata ccacccggtt gtacctggtg gacaacaagt 12960
cggcggacat cgcctcgctg aactaccaga acgaccacag caacttcctg accaccgtgg 13020
tgcagaacaa tgacttcacc cccacggagg ccagcaccca gaccatcaac tttgacgagc 13080
gctcgcggtg gggcggccag ctgaaaacca tcatgcacac caacatgccc aacgtgaacg 13140
agttcatgta cagcaacaag ttcaaggcgc gggtgatggt ctcccgcaag acccccaatg 13200
gggtgacagt gacagaggat tatgatggta gtcaggatga gctgaagtat gaatgggtgg 13260
aatttgagct gcccgaaggc aacttctcgg tgaccatgac catcgacctg atgaacaacg 13320
ccatcatcga caattacttg gcggtggggc ggcagaacgg ggtgctggag agcgacatcg 13380
gcgtgaagtt cgacactagg aacttcaggc tgggctggga ccccgtgacc gagctggtca 13440
tgcccggggt gtacaccaac gaggctttcc atcccgatat tgtcttgctg cccggctgcg 13500
gggtggactt caccgagagc cgcctcagca acctgctggg cattcgcaag aggcagccct 13560
tccaggaagg cttccagatc atgtacgagg atctggaggg gggcaacatc cccgcgctcc 13620
tggatgtcga cgcctatgag aaaagcaagg aggatgcagc agctgaagca actgcagccg 13680
tagctaccgc ctctaccgag gtcaggggcg ataattttgc aagcgccgca gcagtggcag 13740
cggccgaggc ggctgaaacc gaaagtaaga tagtcattca gccggtggag aaggatagca 13800
agaacaggag ctacaacgta ctaccggaca agataaacac cgcctaccgc agctggtacc 13860
tagcctacaa ctatggcgac cccgagaagg gcgtgcgctc ctggacgctg ctcaccacct 13920
cggacgtcac ctgcggcgtg gagcaagtct actggtcgct gcccgacatg atgcaagacc 13980
cggtcacctt ccgctccacg cgtcaagtta gcaactaccc ggtggtgggc gccgagctcc 14040
tgcccgtcta ctccaagagc ttcttcaacg agcaggccgt ctactcgcag cagctgcgcg 14100
ccttcacctc gcttacgcac gtcttcaacc gcttccccga gaaccagatc ctcgtccgcc 14160
cgcccgcgcc caccattacc accgtcagtg aaaacgttcc tgctctcaca gatcacggga 14220
ccctgccgct gcgcagcagt atccggggag tccagcgcgt gaccgttact gacgccagac 14280
gccgcacctg cccctacgtc tacaaggccc tgggcatagt cgcgccgcgc gtcctctcga 14340
gccgcacctt ctaaatgtcc attctcatct cgcccagtaa taacaccggt tggggcctgc 14400
gcgcgcccag caagatgtac ggaggcgctc gccaacgctc cacgcaacac cccgtgcgcg 14460
tgcgcgggca cttccgcgct ccctggggcg ccctcaaggg ccgcgtgcgg tcgcgcacca 14520
ccgtcgacga cgtgatcgac caggtggtgg ccgacgcgcg caactacacc cccgccgccg 14580
cgcccgtctc caccgtggac gccgtcatcg acagcgtggt ggccgacgcg cgccggtacg 14640
cccgcgccaa gagccggcgg cggcgcatcg cccggcggca ccggagcacc cccgccatgc 14700
gcgcggcgcg agccttgctg cgcagggcca ggcgcacggg acgcagggcc atgctcaggg 14760
cggccagacg cgcggcttca ggcgccagcg ccggcaggac ccggagacgc gcggccacgg 14820
cggcggcagc ggccatcgcc agcatgtccc gcccgcggcg agggaacgtg tactgggtgc 14880
gcgacgccgc caccggtgtg cgcgtgcccg tgcgcacccg ccccccctcgc acttgaagat 14940
gttcacttcg cgatgttgat gtgtcccagc ggcgaggagg atgtccaagc gcaaattcaa 15000

```
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat tttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
```

aggacaacac ctactcgtac aaagtgcgct acacgctggc cgtgggcgac aaccgcgtgc 17460
tggacatggc cagcacctac tttgacatcc gcggcgtgct ggatcggggc cctagcttca 17520
aaccctactc cggcaccgcc tacaacagtc tggcccccaa gggagcaccc aacacttgtc 17580
agtggacata taaagccgat ggtgaaactg ccacagaaaa aacctataca tatggaaatg 17640
cacccgtgca gggcattaac atcacaaaag atggtattca acttggaact gacaccgatg 17700
atcagccaat ctacgcagat aaaacctatc agcctgaacc tcaagtgggt gatgctgaat 17760
ggcatgacat cactggtact gatgaaaagt atggaggcag agctcttaag cctgatacca 17820
aaatgaagcc ttgttatggt tcttttgcca agcctactaa taaagaagga ggtcaggcaa 17880
atgtgaaaac aggaacaggc actactaaag aatatgacat agacatggct ttctttgaca 17940
acagaagtgc ggctgctgct ggcctagctc cagaaattgt tttgtatact gaaaatgtgg 18000
atttggaaac tccagatacc catattgtat acaaagcagg cacagatgac agcagctctt 18060
ctattaattt gggtcagcaa gccatgccca acagacctaa ctacattggt ttcagagaca 18120
actttatcgg gctcatgtac tacaacagca ctggcaatat gggggtgctg gccggtcagg 18180
cttctcagct gaatgctgtg gttgacttgc aagacagaaa caccgagctg tcctaccagc 18240
tcttgcttga ctctctgggt gacagaaccc ggtatttcag tatgtggaat caggcggtgg 18300
acagctatga tcctgatgtg cgcattattg aaaatcatgg tgtggaggat gaacttccca 18360
actattgttt ccctctggat gctgttggca gaacagatac ttatcaggga attaaggcta 18420
atggaactga tcaaaccaca tggaccaaag atgacagtgt caatgatgct aatgagatag 18480
gcaagggtaa tccattcgcc atggaaatca acatccaagc caacctgtgg aggaacttcc 18540
tctacgccaa cgtggccctg tacctgcccg actcttacaa gtacacgccg gccaatgtta 18600
ccctgcccac caacaccaac acctacgatt acatgaacgg ccgggtggtg gcgccctcgc 18660
tggtggactc ctacatcaac atcggggcgc gctggtcgct ggatcccatg gacaacgtga 18720
accccttcaa ccaccaccgc aatgcggggc tgcgctaccg ctccatgctc ctgggcaacg 18780
ggcgctacgt gcccttccac atccaggtgc cccagaaatt tttcgccatc aagagcctcc 18840
tgctcctgcc cgggtcctac acctacgagt ggaacttccg caaggacgtc aacatgatcc 18900
tgcagagctc cctcggcaac gacctgcgca cggacggggc ctccatctcc ttcaccagca 18960
tcaacctcta cgccaccttc ttccccatgg cgcacaacac ggcctccacg ctcgaggcca 19020
tgctgcgcaa cgacaccaac gaccagtcct tcaacgacta cctctcggcg gccaacatgc 19080
tctaccccat cccggccaac gccaccaacg tgcccatctc catcccctcg cgcaactggg 19140
ccgccttccg cggctggtcc ttcacgcgtc tcaagaccaa ggagacgccc tcgctgggct 19200
ccgggttcga cccctacttc gtctactcgg gctccatccc ctacctcgac ggcaccttct 19260
acctcaacca caccttcaag aaggtctcca tcaccttcga ctcctccgtc agctggcccg 19320
gcaacgaccg gctcctgacg cccaacgagt tcgaaatcaa gcgcaccgtc gacggcgagg 19380
gctacaacgt ggcccagtgc aacatgacca aggactggtt cctggtccag atgctggccc 19440
actacaacat cggctaccag ggcttctacg tgcccgaggg ctacaaggac cgcatgtact 19500
ccttcttccg caacttccag cccatgagcc gccaggtggt ggacgaggtc aactacaagg 19560
actaccaggc cgtcaccctg gcctaccagc acaacaactc gggcttcgtc ggctacctcg 19620
cgcccaccat gcgccagggc cagccctacc ccgccaacta cccctacccg ctcatcggca 19680
agagcgccgt caccagcgtc acccagaaaa agttcctctg cgacagggtc atgtggcgca 19740
tccccttctc cagcaacttc atgtccatgg gcgcgctcac cgacctcggc cagaacatgc 19800
tctatgccaa ctccgcccac gcgctagaca tgaatttcga agtcgacccc atggatgagt 19860
ccacccttct ctatgttgtc ttcgaagtct tcgacgtcgt ccgagtgcac cagccccacc 19920
gcggcgtcat cgaggccgtc tacctgcgca ccccccttctc ggccggtaac gccaccacct 19980
aagctcttgc ttcttgcaag ccatggccgc gggctccggc gagcaggagc tcagggccat 20040
catccgcgac ctgggctgcg ggccctactt cctgggcacc ttcgataagc gcttcccggg 20100
attcatggcc ccgcacaagc tggcctgcgc catcgtcaac acggccggcc gcgagaccgg 20160
gggcgagcac tggctggcct tcgcctggaa cccgcgctcg aacacctgct acctcttcga 20220
ccccttcggg ttctcggacg agcgcctcaa gcagatctac cagttcgagt acgagggcct 20280
gctgcgccgc agcgccctgg ccaccgagga ccgctgcgtc accctggaaa agtccaccca 20340
gaccgtgcag ggtccgcgct cggccgcctg cgggctcttc tgctgcatgt tcctgcacgc 20400
cttcgtgcac tggcccgacc gccccatgga caagaacccc accatgaact tgctgacggg 20460
ggtgcccaac ggcatgctcc agtcgcccca ggtggaaccc accctgcgcc gcaaccagga 20520
ggcgctctac cgcttcctca actcccactc cgcctacttt cgctcccacc gcgcgcgcat 20580
cgagaaggcc accgccttcg accgcatgaa tcaagacatg taaaccgtgt gtgtatgtta 20640
aatgtcttta ataaacagca ctttcatgtt acacatgcat ctgagatgat ttatttagaa 20700
atcgaaaggg ttctgccggg tctcggcatg gcccgcgggc agggacacgt tgcggaactg 20760
gtacttggcc agccacttga actcggggat cagcagtttg ggcagcgggg tgtcggggaa 20820
ggagtcggtc cacagcttcc gcgtcagttg cagggcgccc agcaggtcgg gcgcggagat 20880
cttgaaatcg cagttgggac ccgcgttctg cgcgcgggag ttgcggtaca cggggttgca 20940
gcactggaac accatcaggg ccgggtgctt cacgctcgcc agcaccgtcg cgtcggtgat 21000
gctctccacg tcgaggtcct cggcgttggc catcccgaag gggtcatct tgcaggtctg 21060
ccttcccatg gtgggcacgc acccgggctt gtggttgcaa tcgcagtgca gggggatcag 21120
catcatctgg gcctggtcgg cgttcatccc cgggtacatg gccttcatga aagcctccaa 21180
ttgcctgaac gcctgctggg ccttggctcc ctcggtgaag aagaccccgc aggacttgct 21240
agagaactgg ttggtggcgc acccggcgtc gtgcacgcag cagcgcgcgt cgttgttggc 21300
cagctgcacc acgctgcgcc cccagcggtt ctgggtgatc ttggcccggt cggggttctc 21360
cttcagcgcg cgctgcccgt tctcgctcgc cacatccatc tcgatcatgt gctccttctg 21420
gatcatggtg gtcccgtgca ggcaccgcag cttgccctcg gcctcggtgc acccgtgcag 21480
ccacagcgcg cacccggtgc actcccagtt cttgtgggcg atctgggaat gcgcgtgcac 21540
gaagccctgc aggaagcggc ccatcatggt ggtcagggtc ttgttgctag tgaaggtcag 21600
cggaatgccg cggtgctcct cgttgatgta caggtggcag atgcggcggt acacctcgcc 21660
ctgctcgggc atcagctgga agttggcttt caggtcggtc tccacgcggt agcggtccat 21720
cagcatagtc atgatttcca tacccttctc ccaggccgag acgatgggca ggctcatagg 21780
gttcttcacc atcatcttag cgctagcagc cgcggccagg gggtcgctct cgtccagggt 21840
ctcaaagctc cgcttgccgt ccttctcggt gatccgcacc ggggggtagc tgaagcccac 21900
ggccgccagc tcctcctcgg cctgtctttc gtcctcgctg tcctggctga cgtcctgcag 21960
gaccacatgc ttggtcttgc ggggtttctt cttgggcggc agcggcggcg gagatgttgg 22020
agatggcgag gggagcgcg agttctcgct caccactact atctcttcct cttcttggtc 22080
cgaggccacg cggcggtagg tatgtctctt cgggggcaga ggcggaggcg acgggctctc 22140

-continued

```
gccgccgcga cttggcggat ggctggcaga gccccttccg cgttcggggg tgcgctcccg  22200
gcggcgctct gactgacttc ctccgcggcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
cgtcccagac atgcaagaga tggaggaatc catcgagatt gacctgggct atgtgacgcc  22440
cgcggagcac gaggaggagc tggcagtgcg cttttcacaa gaagagatac accaagaaca  22500
gccagagcag gaagcagaga atgagcagag tcaggctggg ctcgagcatg acggcgacta  22560
cctccacctg agcggggggg aggacgcgct catcaagcat ctggcccggc aggccaccat  22620
cgtcaaggat gcgctgctcg accgcaccga ggtgcccctc agcgtggagg agctcagccg  22680
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
cacctaccac atctttttca agaaccaaaa gatccccgtc tcctgccgcg ccaaccgcac  22860
ccgcgccgac gcccttttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgcgg ctggcggtgc tcaaacgcac ggtcgagctg acccatttcg cctacccggc  23100
tctgaacctg ccccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggcccggt ggctgggtcc taatgctagt ccccagagtt tggaagagcg  23280
gcgcaaactc atgatggccg tggtcctggt gaccgtggag ctggagtgcc tgcgccgctt  23340
cttcgccgac gcggagaccc tgcgcaaggt cgaggagaac ctgcactacc tcttcaggca  23400
cgggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggcccgg cgcgactaca tccgcgactg cgtctacctc tacctctgcc acacctggca  23580
gacgggcatg ggcgtgtggc agcagtgtct ggaggagcag aacctgaaag agctctgcaa  23640
gctcctgcag aagaacctca agggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc gccacctgct ccgcgctgcc ctcggacttc gtgccgctga ccttccgcga  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caacctctgc acgccgcacc gctccctggc ctgcaacccc cagctgctga gcgagaccca  24060
gatcatcggc accttcgagt tgcaagggcc cagcgaaggc gagggttcag ccgccaaggg  24120
gggtctgaaa ctcaccccgg ggctgtggac ctcggcctac ttgcgcaagt tcgtgcccga  24180
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
```

-continued

```
aggagatgga ggaagactgg gacagcactc aggcagagga ggacagcctg caagacagtc    24540

tggaggaaga cgaggaggag gcagaggagg aggtggaaga agcagccgcc gccagaccgt    24600

cgtcctcggc gggggagaaa gcaagcagca cggataccat ctccgctccg ggtcggggtc    24660

ccgctcgacc acacagtaga tgggacgaga ccggacgatt cccgaacccc accacccaga    24720

ccggtaagaa ggagcggcag ggatacaagt cctggcgggg gcacaaaaac gccatcgtct    24780

cctgcttgca ggcctgcggg ggcaacatct ccttcacccg cgcgctacctg ctcttccacc    24840

gcggggtgaa ctttccccgc aacatcttgc attactaccg tcacctccac agcccctact    24900

acttccaaga agaggcagca gcagcagaaa aagaccagca gaaaaccagc agctagaaaa    24960

tccacagcgg cggcagcagg tggactgagg atcgcggcga acgagccggc gcaaacccgg    25020

gagctgagga accggatctt tcccaccctc tatgccatct tccagcagag tcggggggcag    25080

gagcaggaac tgaaagtcaa gaaccgttct ctgcgctcgc tcacccgcag ttgtctgtat    25140

cacaagagcg aagaccaact tcagcgcact ctcgaggacg ccgaggctct cttcaacaag    25200

tactgcgcgc tcactcttaa agagtagccc gcgcccgccc agtcgcagaa aaaggcggga    25260

attacgtcac ctgtgccctt cgccctagcc gcctccaccc atcatcatga gcaaagagat    25320

tcccacgcct tacatgtgga gctaccagcc ccagatgggc ctggccgccg gtgccgccca    25380

ggactactcc acccgcatga attggctcag cgccgggccc gcgatgatct cacgggtgaa    25440

tgacatccgc gcccaccgaa accagatact cctagaacag tcagcgctca ccgccacgcc    25500

ccgcaatcac ctcaatccgc gtaattggcc cgccgccctg gtgtaccagg aaattcccca    25560

gcccacgacc gtactacttc cgcgagacgc ccaggccgaa gtccagctga ctaactcagg    25620

tgtccagctg gcgggcggcg ccaccctgtg tcgtcaccgc cccgctcagg gtataaagcg    25680

gctggtgatc cggggcagag gcacacagct caacgacgag gtggtgagct cttcgctggg    25740

tctgcgacct gacggagtct tccaactcgc cggatcgggg agatcttcct tcacgcctcg    25800

tcaggccgtc ctgactttgg agagttcgtc ctcgcagccc cgctcgggtg gcatcggcac    25860

tctccagttc gtggaggagt tcactccctc ggtctacttc aaccccttct ccggctcccc    25920

cggccactac ccggacgagt tcatcccgaa cttcgacgcc atcagcgagt cggtggacgg    25980

ctacgattga aactaatcac ccccttatcc agtgaaataa agatcatatt gatgatgatt    26040

ttacagaaat aaaaaataat catttgattt gaaataaaga tacaatcata ttgatgattt    26100

gagtttaaca aaaaaataaa gaatcactta cttgaaatct gataccaggt ctctgtccat    26160

gttttctgcc aacaccactt cactcccctc ttcccagctc tggtactgca ggccccggcg    26220

ggctgcaaac ttcctccaca cgctgaaggg gatgtcaaat tcctcctgtc cctcaatctt    26280

cattttatct tctatcagat gtccaaaaag cgcgtccggg tggatgatga cttcgacccc    26340

gtctacccct acgatgcaga caacgcaccg accgtgccct tcatcaaccc ccccttcgtc    26400

tcttcagatg gattccaaga gaagcccctg ggggtgttgt ccctgcgact ggccgacccc    26460

gtcaccacca agaacgggga aatcaccctc aagctgggag aggggtgga cctcgattcc    26520

tcgggaaaac tcatctccaa cacggccacc aaggccgccg cccctctcag tttttccaac    26580

aacaccattt cccttaacat ggatcacccc ttttacacta aagatggaaa attatcctta    26640

caagtttctc caccattaaa tatactgaga acaagcattc taaacacact agctttaggt    26700

tttggatcag gtttaggact ccgtggctct gccttggcag tacagttagt ctctccactt    26760

acatttgata ctgatggaaa cataaagctt accttagaca gaggtttgca tgttacaaca    26820

ggagatgcaa ttgaaagcaa cataagctgg gctaaaggtt taaaatttga agatggagcc    26880
```

atagcaacca acattggaaa tgggttagag tttggaagca gtagtacaga aacaggtgtt 26940
gatgatgctt acccaatcca agttaaactt ggatctggcc ttagctttga cagtacagga 27000
gccataatgg ctggtaacaa agaagacgat aaactcactt tgtggacaac acctgatcca 27060
tcaccaaact gtcaaatact cgcagaaaat gatgcaaaac taacactttg cttgactaaa 27120
tgtggtagtc aaatactggc cactgtgtca gtcttagttg taggaagtgg aaacctaaac 27180
cccattactg gcaccgtaag cagtgctcag gtgtttctac gttttgatgc aaacggtgtt 27240
cttttaacag aacattctac actaaaaaaa tactgggggt ataggcaggg agatagcata 27300
gatggcactc catataccaa tgctgtagga ttcatgccca atttaaaagc ttatccaaag 27360
tcacaaagtt ctactactaa aaataatata gtagggcaag tatacatgaa tggagatgtt 27420
tcaaaaccta tgcttctcac tataaccctc aatggtactg atgacagcaa cagtacatat 27480
tcaatgtcat tttcatacac ctggactaat ggaagctatg ttggagcaac atttggggct 27540
aactcttata ccttctcata catcgcccaa gaatgaacac tgtatcccac cctgcatgcc 27600
aacccttccc accccactct gtggaacaaa ctctgaaaca caaaataaaa taaagttcaa 27660
gtgttttatt gattcaacag ttttacagga ttcgagcagt tatttttcct ccaccctccc 27720
aggacatgga atacaccacc ctctccccc gcacagcctt gaacatctga atgccattgg 27780
tgatggacat gcttttggtc tccacgttcc acacagtttc agagcgagcc agtctcgggt 27840
cggtcaggga gatgaaaccc tccgggcact cccgcatctg cacctcacag ctcaacagct 27900
gaggattgtc ctcggtggtc gggatcacgg ttatctggaa gaagcagaag agcggcggtg 27960
ggaatcatag tccgcgaacg ggatcggccg gtggtgtcgc atcaggcccc gcagcagtcg 28020
ctgccgccgc cgctccgtca agctgctgct caggggtcc gggtccaggg actccctcag 28080
catgatgccc acggccctca gcatcagtcg tctggtgcgg cgggcgcagc agcgcatgcg 28140
gatctcgctc aggtcgctgc agtacgtgca acacagaacc accaggttgt tcaacagtcc 28200
atagttcaac acgctccagc cgaaactcat cgcgggaagg atgctaccca cgtggccgtc 28260
gtaccagatc ctcaggtaaa tcaagtggtg cccctccag aacacgctgc ccacgtacat 28320
gatctccttg ggcatgtggc ggttcaccac ctcccggtac cacatcaccc tctggttgaa 28380
catgcagccc cggatgatcc tgcggaacca cagggccagc accgccccgc ccgccatgca 28440
gcgaagagac cccgggtccc ggcaatggca atggaggacc caccgctcgt acccgtggat 28500
catctgggag ctgaacaagt ctatgttggc acagcacagg catatgctca tgcatctctt 28560
cagcactctc aactcctcgg gggtcaaaac catatcccag ggcacgggga actcttgcag 28620
gacagcgaac cccgcagaac agggcaatcc tcgcacagaa cttacattgt gcatggacag 28680
ggtatcgcaa tcaggcagca ccgggtgatc ctccaccaga gaagcgcggg tctcggtctc 28740
ctcacagcgt ggtaaggggg ccggccgata cgggtgatgg cgggacgcgg ctgatcgtgt 28800
tcgcgaccgt gtcatgatgc agttgctttc ggacattttc gtacttgctg tagcagaacc 28860
tggtccgggc gctgcacacc gatcgccggc ggcggtctcg gcgcttggaa cgctcggtgt 28920
tgaaattgta aaacagccac tctctcagac cgtgcagcag atctagggcc tcaggagtga 28980
tgaagatccc atcatgcctg atggctctga tcacatcgac caccgtggaa tgggccagac 29040
ccagccagat gatgcaattt tgttgggttt cggtgacggc gggggaggga agaacaggaa 29100
gaaccatgat taacttttaa tccaaacggt ctcggagtac ttcaaaatga agatcgcgga 29160
gatggcacct ctcgccccg ctgtgttggt ggaaaataac agccaggtca aaggtgatac 29220
ggttctcgag atgttccacg gtggcttcca gcaaagcctc cacgcgcaca tccagaaaca 29280
agacaatagc gaaagcggga gggttctcta attcctcaat catcatgtta cactcctgca 29340
ccatccccag ataattttca tttttccagc cttgaatgat tcgaactagt tcctgaggta 29400
aatccaagcc agccatgata aagagctcgc gcagagcgcc ctccaccggc attcttaagc 29460
acaccctcat aattccaaga tattctgctc ctggttcacc tgcagcagat tgacaagcgg 29520
aatatcaaaa tctctgccgc gatccctgag ctcctccctc agcaataact gtaagtactc 29580
tttcatatcc tctccgaaat ttttagccat aggaccacca ggaataagat tagggcaagc 29640
cacagtacag ataaaccgaa gtcctcccca gtgagcattg ccaaatgcaa gactgctata 29700
agcatgctgg ctagacccgg tgatatcttc cagataactg gacagaaaat cgcccaggca 29760
atttttaaga aaatcaacaa aagaaaaatc ctccaggtgg acgtttagag cctcgggaac 29820
aacgatgaag taaatgcaag cggtgcgttc cagcatggtt agttagctga tctgtagaaa 29880
aaacaaaaat gaacattaaa ccatgctagc ctggcgaaca ggtgggtaaa tcgttctctc 29940
cagcaccagg caggccacgg ggtctccggc gcgaccctcg taaaaattgt cgctatgatt 30000
gaaaaccatc acagagagac gttcccggtg gccggcgtga atgattcgac aagatgaata 30060
cacccccgga acattggcgt ccgcgagtga aaaaaagcgc ccgaggaagc aataaggcac 30120
tacaatgctc agtctcaagt ccagcaaagc gatgccatgc ggatgaagca caaaattctc 30180
aggtgcgtac aaaatgtaat tactcccctc ctgcacaggc agcaaagccc ccgatccctc 30240
caggtacaca tacaaagcct cagcgtccat agcttaccga gcagcagcac acaacaggcg 30300
caagagtcag agaaaggctg agctctaacc tgtccacccg ctctctgctc aatatatagc 30360
ccagatctac actgacgtaa aggccaaagt ctaaaaatac ccgccaaata atcacacacg 30420
cccagcacac gcccagaaac cggtgacaca ctcaaaaaaa tacgcgcact tcctcaaacg 30480
cccaaaactg ccgtcatttc cgggttccca cgctacgtca tcaaaacacg actttcaaat 30540
tccgtcgacc gttaaaaacg tcacccgccc cgcccctaac ggtcgcccgt ctctcagcca 30600
atcagcgccc cgcatcccca aattcaaaca cctcatttgc atattaacgc gcacaaaaag 30660
tttgaggtat attattgatg atgg 30684

<210> SEQ ID NO 14
<211> LENGTH: 8602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540

-continued

```
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
```

-continued

```
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

-continued

```
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaaagtccg ccatatgagg ccaccatgca gatcttcgtg aagaccctga ccggcaagac   7620
catcacccta gaggtggagc ccagtgacac catcgagaac gtgaaggcca agatccagga   7680
```

taaagagggc atccccccctg accagcagag gctgatcttt gccggcaagc agctggaaga 7740
tggccgcacc ctctctgatt acaacatcca gaaggagtca accctgcacc tggtccttcg 7800
cctgagaggt ggcgctgctt acagtataat caactttgaa aaactggctg cttacggcat 7860
cctgggcttt gtgtttacac tggctgccta cctgctgttt ggctatcctg tgtacgtggc 7920
cgcttatgga ctgtgtaccc tggtggccat gctggctgct tacaatctgg tgcctatggt 7980
ggccacagtg gccgcctatt gtcttggcgg actgctgaca atggtggcag cctacagccc 8040
gagctatgcg tatcatcagt ttgcagccta cggcccagga ccaggcgcta aatttgtggc 8100
tgcctggaca ctgaaagccg ccgctggacc aggtcctgga cagtacatca aggccaacag 8160
caagttcatc ggcatcaccg aactcggccc aggaccaggc tatccctacg atgtgcctga 8220
ttacgcctga tagtgatgat tcgaacggcc gtatcacgcc caaacattta cagccgcggt 8280
gtcaaaaacc gcgtggacgt ggttaacatc cctgctggga ggatcagccg taattattat 8340
aattggcttg gtgctggcta ctattgtggc catgtacgtg ctgaccaacc agaaacataa 8400
ttgaatacag cagcaattgg caagctgctt acatagaact cgcggcgatt ggcatgccgc 8460
cttaaaattt ttattttatt ttttcttttc ttttccgaat cggattttgt ttttaatatt 8520
tcaaaaaaaa aaaaaaaaaa aaaaaaaaaa aaaaaaaaaa aaaaaaaaaa aaaaaaaaaa 8580
aaaaaaaaaa aaaaaaaaaa aa 8602

<210> SEQ ID NO 15
<211> LENGTH: 9595
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa catagcccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080

```
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
```

-continued

```
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
```

tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gactctagaa tagtctttaa 7560
ttaaagtccg ccatatgaga tggaagatgc caaaaacatt aagaagggcc cagcgccatt 7620
ctacccactc gaagacggga ccgccggcga gcagctgcac aaagccatga agcgctacgc 7680
cctggtgccc ggcaccatcg cctttaccga cgcacatatc gaggtggaca ttacctacgc 7740
cgagtacttc gagatgagcg ttcggctggc agaagctatg aagcgctatg ggctgaatac 7800
aaaccatcgg atcgtggtgt gcagcgagaa tagcttgcag ttcttcatgc ccgtgttggg 7860
tgccctgttc atcggtgtgg ctgtggcccc agctaacgac atctacaacg agcgcgagct 7920
gctgaacagc atgggcatca gccagcccac cgtcgtattc gtgagcaaga aagggctgca 7980
aaagatcctc aacgtgcaaa agaagctacc gatcatacaa aagatcatca tcatggatag 8040
caagaccgac taccagggct tccaaagcat gtacaccttc gtgacttccc atttgccacc 8100
cggcttcaac gagtacgact tcgtgcccga gagcttcgac cgggacaaaa ccatcgccct 8160

```
gatcatgaac agtagtggca gtaccggatt gcccaagggc gtagccctac cgcaccgcac   8220

cgcttgtgtc cgattcagtc atgcccgcga ccccatcttc ggcaaccaga tcatccccga   8280

caccgctatc ctcagcgtgg tgccatttca ccacggcttc ggcatgttca ccacgctggg   8340

ctacttgatc tgcggctttc gggtcgtgct catgtaccgc ttcgaggagg agctattctt   8400

gcgcagcttg caagactata agattcaatc tgccctgctg gtgcccacac tatttagctt   8460

cttcgctaag agcactctca tcgacaagta cgacctaagc aacttgcacg agatcgccag   8520

cggcggggcg ccgctcagca aggaggtagg tgaggccgtg gccaaacgct tccacctacc   8580

aggcatccgc cagggctacg gcctgacaga aacaaccagc gccattctga tcacccccga   8640

aggggacgac aagcctggcg cagtaggcaa ggtggtgccc ttcttcgagg ctaaggtggt   8700

ggacttggac accggtaaga cactgggtgt gaaccagcgc ggcgagctgt gcgtccgtgg   8760

ccccatgatc atgagcggct acgttaacaa ccccgaggct acaaacgctc tcatcgacaa   8820

ggacggctgg ctgcacagcg gcgacatcgc ctactgggac gaggacgagc acttcttcat   8880

cgtggaccgg ctgaagagcc tgatcaaata caagggctac caggtagccc cagccgaact   8940

ggagagcatc ctgctgcaac accccaacat cttcgacgcc ggggtcgccg gcctgcccga   9000

cgacgatgcc ggcgagctgc ccgccgcagt cgtcgtgctg gaacacggta aaaccatgac   9060

cgagaaggag atcgtggact atgtggccag ccaggttaca accgccaaga agctgcgcgg   9120

tggtgttgtg ttcgtggacg aggtgcctaa aggactgacc ggcaagttgg acgcccgcaa   9180

gatccgcgag attctcatta aggccaagaa gggcggcaag atcgccgtgt aattcgaacg   9240

gccgtatcac gcccaaacat ttacagccgc ggtgtcaaaa accgcgtgga cgtggttaac   9300

atccctgctg ggaggatcag ccgtaattat tataattggc ttggtgctgg ctactattgt   9360

ggccatgtac gtgctgacca accagaaaca taattgaata cagcagcaat tggcaagctg   9420

cttacataga actcgcggcg attggcatgc cgccttaaaa tttttatttt atttttttctt   9480

ttcttttccg aatcggattt tgtttttaat atttcaaaaa aaaaaaaaaa aaaaaaaaaa   9540

aaaaaaaaaa aaaaaaaaaa aaaaaaaaaa aaaaaaaaaa aaaaaaaaaa aaaaa        9595
```

```
<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110
```

Pro Ser Asp Glu Gln Leu Lys Ser Gly Thr Ala Ser Val Val Cys Leu
115 120 125

Leu Asn Asn Phe Tyr Pro Arg Glu Ala Lys Val
130 135

<210> SEQ ID NO 17
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Gly Val Val Gln Pro Gly Arg Ser Leu Arg Leu Ser Cys Ala Ala Ser
1 5 10 15

Gly Phe Thr Phe Ser Ser Tyr Gly Met His Trp Val Arg Gln Ala Pro
20 25 30

Gly Lys Gly Leu Glu Trp Val Ala Val Ile Trp Tyr Asp Gly Ser Asn
35 40 45

Lys Tyr Tyr Ala Asp Ser Val Lys Gly Arg Phe Thr Ile Ser Arg Asp
50 55 60

Asn Ser Lys Asn Thr Leu Tyr Leu Gln Met Asn Ser Leu Arg Ala Glu
65 70 75 80

Asp Thr Ala Val Tyr Tyr Cys Ala Arg Asp Pro Arg Gly Ala Thr Leu
85 90 95

Tyr Tyr Tyr Tyr Tyr Gly Met Asp Val Trp Gly Gln Gly Thr Thr Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His
165

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gly Phe Thr Phe Ser Ser Tyr Gly Met His
1 5 10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Val Ile Trp Tyr Asp Gly Ser Asn Lys Tyr Tyr Ala Asp Ser Val
1 5 10 15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Asp Pro Arg Gly Ala Thr Leu Tyr Tyr Tyr Tyr Tyr Gly Met Asp Val
1 5 10 15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Arg Ala Ser Gln Ser Ile Asn Ser Tyr Leu Asp
1 5 10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ala Ala Ser Ser Leu Gln Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Gln Gln Tyr Tyr Ser Thr Pro Phe Thr
1 5

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys
100 105

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Gly Trp Phe Gly Glu Leu Ala Phe Asp Tyr Trp Gly
100 105 110

Gln Gly Thr Leu Val Thr Val Ser Ser
115 120

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Arg Tyr Trp Met Ser
1 5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Asn Ile Lys Gln Asp Gly Ser Glu Lys Tyr Tyr Val Asp Ser Val Lys
1 5 10 15

Gly

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Glu Gly Gly Trp Phe Gly Glu Leu Ala Phe Asp Tyr
1 5 10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Arg Ala Ser Gln Arg Val Ser Ser Ser Tyr Leu Ala
1 5 10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Asp Ala Ser Ser Arg Ala Thr
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Gln Gln Tyr Gly Ser Leu Pro Trp Thr
1 5

<210> SEQ ID NO 32
<211> LENGTH: 2019
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
gcccgggcat ttaaatgcga tcgcatcgat tacgactcta gaatagtcta gtccgcaggc 60
caccatgcag atcttcgtga agaccctgac cggcaagacc atcaccctag aggtggagcc 120
cagtgacacc atcgagaacg tgaaggccaa gatccaggat aaagagggca tcccccctga 180
ccagcagagg ctgatctttg ccggcaagca gctggaagat ggccgcaccc tctctgatta 240
caacatccag aaggagtcaa ccctgcacct ggtccttcgc ctgagaggtg ccatgtttca 300
ggcgctgagc gaaggctgca ccccgtatga tattaaccag atgctgaacg tgctgggcga 360
tcatcaggtc tcaggccttg agcagcttga gagtataatc aactttgaaa aactgactga 420
atggaccagt tctaatgtta tgcctatcct gtctcctctg acaaagggca tcctgggctt 480
cgtgtttacc ctgaccgtgc cttctgagag aggacttagc tgcattagcg aagcggatgc 540
gaccaccccg gaaagcgcga acctgggcga agaaattctg agccagctgt atctttggcc 600
aagggtgacc taccattccc ctagttatgc ttaccaccaa tttgaaagac gagccaaata 660
taaaagacac ttccccggct ttggccagag cctgctgttt ggctaccctg tgtacgtgtt 720
cggcgattgc gtgcagggcg attgggatgc gattcgcttt cgctattgcg cgccgccggg 780
ctatgcgctg ctgcgctgca acgataccaa ctatagcgct ctgctggctg tgggggccct 840
agaaggaccc aggaatcagg actggcttgg tgtcccaaga caacttgtaa ctcggatgca 900
ggctattcag aatgccggcc tgtgtaccct ggtggccatg ctggaagaga caatcttctg 960
gctgcaagcg tttctgatgg cgctgaccga tagcggcccg aaaaccaaca ttattgtgga 1020
tagccagtat gtgatgggca ttagcaaacc gagctttcag gaatttgtgg attgggaaaa 1080
cgtgagcccg gaactgaaca gcaccgatca gccgttttgg caagccggaa tcctggccag 1140
aaatctggtg cctatggtgg ccacagtgca gggccagaac ctgaagtacc agggtcagtc 1200
actagtcatc tctgcttcta tcattgtctt caacctgctg gaactggaag gtgattatcg 1260
agatgatggc aacgtgtggg tgcatacccc gctgagcccg cgcaccctga acgcgtgggt 1320
gaaagcggtg gaagaaaaaa aaggtattcc agttcaccta gagctggcca gtatgaccaa 1380
catggagctc atgagcagta ttgtgcatca gcaggtcaga acatacggcc ccgtgttcat 1440
gtgtctcggc ggactgctta caatggtggc tggtgctgtg tggctgacag tgcgagtgct 1500
cgagctgttc cgggccgcgc agctggccaa cgacgtggtc ctccagatca tggagctttg 1560
tggtgcagcg tttcgccagg tgtgccatac caccgtgccg tggccgaacg cgagcctgac 1620
cccgaaatgg aacaacgaaa ccacccagcc ccagatcgcc aactgcagcg tgtatgactt 1680
ttttgtgtgg ctccattatt attctgttcg agacacactt tggccaaggg tgacctacca 1740
tatgaacaaa tatgcgtatc atatgctgga aagacgagcc aaatataaaa gaggaccagg 1800
acctggcgct aaatttgtgg ccgcctggac actgaaagcc gctgctggtc ctggacctgg 1860
ccagtacatc aaggccaaca gcaagttcat cggcatcacc gaactcggac ccggaccagg 1920
ctgatgattt cgaaatttaa ataagcttgc ggccgctagg gataacaggg taattatcac 1980
gcccaaacat ttacagccgc ggtgtcaaaa accgcgtgg 2019

<210> SEQ ID NO 33
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Ala Met Phe Gln Ala
65 70 75 80

Leu Ser Glu Gly Cys Thr Pro Tyr Asp Ile Asn Gln Met Leu Asn Val
85 90 95

```
Leu Gly Asp His Gln Val Ser Gly Leu Glu Gln Leu Glu Ser Ile Ile
            100                 105                 110

Asn Phe Glu Lys Leu Thr Glu Trp Thr Ser Ser Asn Val Met Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510
```

-continued

```
Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

```
<210> SEQ ID NO 34
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

atggccggga tgttccaggc actgtccgaa ggctgcacac cctatgatat taaccagatg      60

ctgaatgtcc tgggagacca ccaggtctct ggcctggagc agctggagag catcatcaac     120

ttcgagaagc tgaccgagtg gacaagctcc aatgtgatgc ctatcctgtc cccactgacc     180

aagggcatcc tgggcttcgt gtttaccctg acagtgcctt ctgagcgggg cctgtcttgc     240

atcagcgagg cagacgcaac cacaccagag tccgccaatc tgggcgagga gatcctgtct     300

cagctgtacc tgtggccccg ggtgacatat cactccccttt cttacgccta tcaccagttc     360

gagcggagag ccaagtacaa gagacacttc ccaggctttg gccagtctct gctgttcggc     420

taccccgtgt acgtgttcgg cgattgcgtg cagggcgact gggatgccat ccggtttaga     480

tactgcgcac cacctggata tgcactgctg aggtgtaacg acaccaatta ttccgccctg     540

ctggcagtgg gcgccctgga gggccctcgc aatcaggatt ggctgggcgt gccaaggcag     600

ctggtgacac gcatgcaggc catccagaac gcaggcctgt gcaccctggt ggcaatgctg     660

gaggagacaa tcttctggct gcaggccttt ctgatggccc tgaccgacag cggccccaag     720

acaaacatca tcgtggattc ccagtacgtg atgggcatct ccaagccttc tttccaggag     780

tttgtggact gggagaacgt gagcccagag ctgaattcca ccgatcagcc attctggcag     840

gcaggaatcc tggcaaggaa cctggtgcct atggtggcca cagtgcaggg ccagaatctg     900

aagtaccagg gccagagcct ggtcatcagc gcctccatca tcgtgtttaa cctgctggag     960

ctggagggcg actatcggga cgatggcaac gtgtgggtgc acaccccact gagccccaga    1020

acactgaacg cctgggtgaa ggccgtggag gagaagaagg gcatcccagt gcacctggag    1080

ctggcctcca tgaccaatat ggagctgatg tctagcatcg tgcaccagca ggtgaggaca    1140

tacggacccg tgttcatgtg cctgggaggc ctgctgacca tggtggcagg agccgtgtgg    1200

ctgacagtgc gggtgctgga gctgttcaga gccgcccagc tggccaacga tgtggtgctg    1260

cagatcatgg agctgtgcgg agcagccttt cgccaggtgt gccacaccac agtgccatgg    1320

cccaatgcct ccctgacccc caagtggaac aatgagacaa cacagcctca gatcgccaac    1380

tgtagcgtgt acgacttctt cgtgtggctg cactactata gcgtgaggga taccctgtgg    1440
```

ccccgcgtga cataccacat gaataagtac gcctatcaca tgctggagag gcgcgccaag 1500
tataagagag gccctggccc aggcgcaaag tttgtggcag catggaccct gaaggccgcc 1560
gccggccccg gccccggcca gtatatcaag gctaacagta agttcattgg aatcacagag 1620
ctgggacccg gacctgga 1638

<210> SEQ ID NO 35
<211> LENGTH: 546
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Met Ala Gly Met Phe Gln Ala Leu Ser Glu Gly Cys Thr Pro Tyr Asp
1 5 10 15

Ile Asn Gln Met Leu Asn Val Leu Gly Asp His Gln Val Ser Gly Leu
20 25 30

Glu Gln Leu Glu Ser Ile Ile Asn Phe Glu Lys Leu Thr Glu Trp Thr
35 40 45

Ser Ser Asn Val Met Pro Ile Leu Ser Pro Leu Thr Lys Gly Ile Leu
50 55 60

Gly Phe Val Phe Thr Leu Thr Val Pro Ser Glu Arg Gly Leu Ser Cys
65 70 75 80

Ile Ser Glu Ala Asp Ala Thr Thr Pro Glu Ser Ala Asn Leu Gly Glu
85 90 95

Glu Ile Leu Ser Gln Leu Tyr Leu Trp Pro Arg Val Thr Tyr His Ser
100 105 110

Pro Ser Tyr Ala Tyr His Gln Phe Glu Arg Arg Ala Lys Tyr Lys Arg
115 120 125

His Phe Pro Gly Phe Gly Gln Ser Leu Leu Phe Gly Tyr Pro Val Tyr
130 135 140

Val Phe Gly Asp Cys Val Gln Gly Asp Trp Asp Ala Ile Arg Phe Arg
145 150 155 160

Tyr Cys Ala Pro Pro Gly Tyr Ala Leu Leu Arg Cys Asn Asp Thr Asn
165 170 175

Tyr Ser Ala Leu Leu Ala Val Gly Ala Leu Glu Gly Pro Arg Asn Gln
180 185 190

Asp Trp Leu Gly Val Pro Arg Gln Leu Val Thr Arg Met Gln Ala Ile
195 200 205

Gln Asn Ala Gly Leu Cys Thr Leu Val Ala Met Leu Glu Glu Thr Ile
210 215 220

Phe Trp Leu Gln Ala Phe Leu Met Ala Leu Thr Asp Ser Gly Pro Lys
225 230 235 240

Thr Asn Ile Ile Val Asp Ser Gln Tyr Val Met Gly Ile Ser Lys Pro
245 250 255

Ser Phe Gln Glu Phe Val Asp Trp Glu Asn Val Ser Pro Glu Leu Asn
260 265 270

Ser Thr Asp Gln Pro Phe Trp Gln Ala Gly Ile Leu Ala Arg Asn Leu
275 280 285

Val Pro Met Val Ala Thr Val Gln Gly Gln Asn Leu Lys Tyr Gln Gly
290 295 300

Gln Ser Leu Val Ile Ser Ala Ser Ile Ile Val Phe Asn Leu Leu Glu
305 310 315 320

```
Leu Glu Gly Asp Tyr Arg Asp Asp Gly Asn Val Trp Val His Thr Pro
                325                 330                 335

Leu Ser Pro Arg Thr Leu Asn Ala Trp Val Lys Ala Val Glu Glu Lys
            340                 345                 350

Lys Gly Ile Pro Val His Leu Glu Leu Ala Ser Met Thr Asn Met Glu
        355                 360                 365

Leu Met Ser Ser Ile Val His Gln Gln Val Arg Thr Tyr Gly Pro Val
    370                 375                 380

Phe Met Cys Leu Gly Gly Leu Leu Thr Met Val Ala Gly Ala Val Trp
385                 390                 395                 400

Leu Thr Val Arg Val Leu Glu Leu Phe Arg Ala Ala Gln Leu Ala Asn
                405                 410                 415

Asp Val Val Leu Gln Ile Met Glu Leu Cys Gly Ala Ala Phe Arg Gln
            420                 425                 430

Val Cys His Thr Thr Val Pro Trp Pro Asn Ala Ser Leu Thr Pro Lys
        435                 440                 445

Trp Asn Asn Glu Thr Thr Gln Pro Gln Ile Ala Asn Cys Ser Val Tyr
    450                 455                 460

Asp Phe Phe Val Trp Leu His Tyr Tyr Ser Val Arg Asp Thr Leu Trp
465                 470                 475                 480

Pro Arg Val Thr Tyr His Met Asn Lys Tyr Ala Tyr His Met Leu Glu
                485                 490                 495

Arg Arg Ala Lys Tyr Lys Arg Gly Pro Gly Pro Gly Ala Lys Phe Val
            500                 505                 510

Ala Ala Trp Thr Leu Lys Ala Ala Ala Gly Pro Gly Pro Gly Gln Tyr
        515                 520                 525

Ile Lys Ala Asn Ser Lys Phe Ile Gly Ile Thr Glu Leu Gly Pro Gly
    530                 535                 540

Pro Gly
545
```

<210> SEQ ID NO 36
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gcccgggcat ttaaatgcga tcgcatcgat tacgactcta gaatagtcta gtccgcaggc     60

caccatgcag atcttcgtga agaccctgac cggcaagacc atcaccctag aggtggagcc    120

cagtgacacc atcgagaacg tgaaggccaa gatccaggat aaagagggca tccccccctga    180

ccagcagagg ctgatctttg ccggcaagca gctggaagat ggccgcaccc tctctgatta    240

caacatccag aaggagtcaa ccctgcacct ggtccttcgc ctgagaggtg ccatgtttca    300

ggcgctgagc gaaggctgca ccccgtatga tattaaccag atgctgaacg tgctgggcga    360

tcatcagttt aagcacatca aagcctttga ccggacattt gctaacaacc caggtcccat    420

ggttgtgttt gccacacctg ggcctatcct gtctcctctg acaaagggca tcctgggctt    480

cgtgtttacc ctgaccgtgc cttctgagag aggacttagc tgcattagcg aagcggatgc    540

gaccaccccg gaaagcgcga acctgggcga agaaattctg agccagctgt atctttggcc    600

aagggtgacc taccattccc ctagttatgc ttaccaccaa tttgaaagac gagccaaata    660
```

```
taaaagacac ttccccggct ttggccagag cctgctgttt ggctaccctg tgtacgtgtt    720
cggcgattgc gtgcagggcg attgggatgc gattcgcttt cgctattgcg cgccgccggg    780
ctatgcgctg ctgcgctgca acgataccaa ctatagcgct ctgctggctg tgggggccct    840
agaaggaccc aggaatcagg actggcttgg tgtcccaaga caacttgtaa ctcggatgca    900
ggctattcag aatgccggcc tgtgtaccct ggtggccatg ctggaagaga caatcttctg    960
gctgcaagcg tttctgatgg cgctgaccga tagcggcccg aaaaccaaca ttattgtgga   1020
tagccagtat gtgatgggca ttagcaaacc gagctttcag gaatttgtgg attgggaaaa   1080
cgtgagcccg gaactgaaca gcaccgatca gccgttttgg caagccggaa tcctggccag   1140
aaatctggtg cctatggtgg ccacagtgca gggccagaac ctgaagtacc agggtcagtc   1200
actagtcatc tctgcttcta tcattgtctt caacctgctg gaactggaag gtgattatcg   1260
agatgatggc aacgtgtggg tgcatacccc gctgagcccg cgcaccctga acgcgtgggt   1320
gaaagcggtg gaagaaaaaa aaggtattcc agttcaccta gagctggcca gtatgaccaa   1380
catggagctc atgagcagta ttgtgcatca gcaggtcaga acatacggcc ccgtgttcat   1440
gtgtctcggc ggactgctta caatggtggc tggtgctgtg tggctgacag tgcgagtgct   1500
cgagctgttc cgggccgcgc agctggccaa cgacgtggtc ctccagatca tggagctttg   1560
tggtgcagcg tttcgccagg tgtgccatac caccgtgccg tggccgaacg cgagcctgac   1620
cccgaaatgg aacaacgaaa ccacccagcc ccagatcgcc aactgcagcg tgtatgactt   1680
ttttgtgtgg ctccattatt attctgttcg agacacactt tggccaaggg tgacctacca   1740
tatgaacaaa tatgcgtatc atatgctgga aagacgagcc aaatataaaa gaggaccagg   1800
acctggcgct aaatttgtgg ccgcctggac actgaaagcc gctgctggtc ctggacctgg   1860
ccagtacatc aaggccaaca gcaagttcat cggcatcacc gaactcggac ccggaccagg   1920
ctgatgattt cgaaatttaa ataagcttgc ggccgctagg gataacaggg taattatcac   1980
gcccaaacat ttacagccgc ggtgtcaaaa accgcgtgg                           2019
```

<210> SEQ ID NO 37
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Phe Lys His Ile Lys Ala Phe Asp Arg Thr Phe
            100                 105                 110

Ala Asn Asn Pro Gly Pro Met Val Val Phe Ala Thr Pro Gly Pro Ile
```

```
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540
```

Tyr Tyr Ser Val Arg Asp Thr Leu Trp Pro Arg Val Thr Tyr His Met
545 550 555 560

Asn Lys Tyr Ala Tyr His Met Leu Glu Arg Arg Ala Lys Tyr Lys Arg
565 570 575

Gly Pro Gly Pro Gly Ala Lys Phe Val Ala Ala Trp Thr Leu Lys Ala
580 585 590

Ala Ala Gly Pro Gly Pro Gly Gln Tyr Ile Lys Ala Asn Ser Lys Phe
595 600 605

Ile Gly Ile Thr Glu Leu Gly Pro Gly Pro Gly
610 615

<210> SEQ ID NO 38
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
atgcagatct tcgtgaagac cctgaccggc aagaccatca ccctagaggt ggagcccagt 60
gacaccatcg agaacgtgaa ggccaagatc caggataaag agggcatccc ccctgaccag 120
cagaggctga tctttgccgg caagcagctg gaagatggcc gcaccctctc tgattacaac 180
atccagaagg agtcaaccct gcacctggtc cttcgcctga gaggtggc 228

<210> SEQ ID NO 39
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
atgcagatct tcgtgaagac cctgaccggc aagaccatca ccctagaggt ggagcccagt 60
gacaccatcg agaacgtgaa ggccaagatc caggataaag agggcatccc ccctgaccag 120
cagaggctga tctttgccgg caagcagctg gaagatggcc gcaccctctc tgattacaac 180
atccagaagg agtcaaccct gcacctggtc cttcgcctga gaggtgcc 228

<210> SEQ ID NO 40
<211> LENGTH: 78
<212> TYPE: DNA
<213> ORGANISM: Homo sapiens

<400> SEQUENCE: 40
atggccgtca tggcgccccg aaccctcgtc ctgctactct cgggggctct ggccctgacc 60
cagacctggg cgggctct 78

<210> SEQ ID NO 41
<211> LENGTH: 201
<212> TYPE: DNA
<213> ORGANISM: Homo sapiens

<400> SEQUENCE: 41
ccgtcttccc agcccaccat ccccatcgtg ggcatcattg ctggcctggt tctctttgga 60
gctgtgatca ctggagctgt ggtcgctgct gtgatgtgga ggaggaagag ctcagataga 120
aaaggaggga gctactctca ggctgcaagc agtgacagtg cccagggctc tgatgtgtct 180
ctcacagctt gtaaagtgtg a 201

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
atggagaccg atacactgct gctgtgggtg ctgctcctgt gggtgccagg aagcacaggc 60

<210> SEQ ID NO 43
<211> LENGTH: 3178
<212> TYPE: DNA
<213> ORGANISM: Homo sapiens

<400> SEQUENCE: 43
ggcaccgatt cggggcctgc ccggacttcg ccgcacgctg cagaacctcg cccagcgccc 60
accatgcccc ggcagctcag cgcggcggcc gcgctcttcg cgtccctggc cgtaattttg 120
cacgatggca gtcaaatgag agcaaaagca tttccagaaa ccagagatta ttctcaacct 180
actgcagcag caacagtaca ggacataaaa aaacctgtcc agcaaccagc taagcaagca 240
cctcaccaaa ctttagcagc aagattcatg gatggtcata tcacctttca aacagcggcc 300
acagtaaaaa ttccaacaac taccccagca actacaaaaa acactgcaac caccagccca 360
attacctaca ccctggtcac aacccaggcc acacccaaca actcacacac agctcctcca 420
gttactgaag ttacagtcgg ccctagctta gccccttatt cactgccacc caccatcacc 480
ccaccagctc atacagctgg aaccagttca tcaaccgtca gccacacaac tgggaacacc 540
actcaaccca gtaaccagac caccccttcca gcaactttat cgatagcact gcacaaaagc 600
acaaccggtc agaagcctga tcaacccacc catgccccag gaacaacggc agctgcccac 660
aataccaccc gcacagctgc acctgcctcc acggttcctg ggcccaccct tgcacctcag 720
ccatcgtcag tcaagactgg aatttatcag gttctaaacg gaagcagact ctgtataaaa 780
gcagagatgg ggatacagct gattgttcaa gacaaggagt cggtttttc acctcggaga 840 tacttcaaca tcgaccccaa cgcaacgcaa gcctctggga actgtggcac ccgaaaatcc 900
aaccttctgt tgaattttca gggcggattt gtgaatctca catttaccaa ggatgaagaa 960
tcatattata tcagtgaagt gggagcctat ttgaccgtct cagatccaga gacagtttac 1020
caaggaatca aacatgcggt ggtgatgttc cagacagcag tcgggcattc cttcaagtgc 1080
gtgagtgaac agagcctcca gttgtcagcc cacctgcagg tgaaaacaac cgatgtccaa 1140
cttcaagcct ttgattttga agatgaccac tttggaaatg tggatgagtg ctcgtctgac 1200
tacacaattg tgcttcctgt gattggggcc atcgtggttg gtctctgcct tatgggtatg 1260
ggtgtctata aaatccgcct aaggtgtcaa tcatctggat accagagaat ctaattgttg 1320
cccgggggga atgaaaataa tggaatttag agaactcttt catcccttcc aggatggatg 1380
ttgggaaatt ccctcagagt gtgggtcctt caaacaatgt aaaccaccat cttctattca 1440
aatgaagtga gtcatgtgtg atttaagttc aggcagcaca tcaatttcta aatacttttt 1500
gtttatttta tgaaagatat agtgagctgt ttattttcta gtttccttta gaatatttta 1560
gccactcaaa gtcaacattt gagatatgtt gaattaacat aatatatgta aagtagaata 1620
agccttcaaa ttataaacca agggtcaatt gtaactaata ctactgtgtg tgcattgaag 1680
attttatttt acccttgatc ttaacaaagc ctttgctttg ttatcaaatg gactttcagt 1740
gcttttacta tctgtgtttt atggtttcat gtaacataca tattcctggt gtagcactta 1800
actccttttc cactttaaat ttgtttttgt tttttgagac ggagtttcac tcttgtcacc 1860
caggctggag tacagtggca cgatctcggc ttatggcaac ctccgcctcc cgggttcaag 1920
tgattctcct gcttcagctt cccgagtagc tgggattaca ggcacacact accacgcctg 1980
gctaattttt gtatttttat tatagacggg tttcaccatg ttggccagac tggtcttgaa 2040
ctcttgacct caggtgatcc acccacctca gcctcccaaa gtgctgggat tacaggcatg 2100
agccattgcg cccggcctta aatgtttttt ttaatcatca aaaagaacaa catatctcag 2160
gttgtctaag tgtttttatg taaaaccaac aaaaagaaca aatcagctta tattttttat 2220
cttgatgact cctgctccag aattgctaga ctaagaatta ggtggctaca gatggtagaa 2280
ctaaacaata agcaagagac aataataatg gcccttaatt attaacaaag tgccagagtc 2340
taggctaagc actttatcta tatctcattt cattctcaca acttataagt gaatgagtaa 2400
actgagactt aagggaactg aatcacttaa atgtcacctg gctaactgat ggcagagcca 2460
gagcttgaat tcatgttggt ctgacatcaa ggtctttggt cttctcccta caccaagtta 2520
cctacaagaa caatgacacc acactctgcc tgaaggctca cacctcatac cagcatacgc 2580
tcaccttaca gggaaatggg tttatccagg atcatgagac attagggtag atgaaaggag 2640
agctttgcag ataacaaaat agcctatcct taataaatcc tccactctct ggaaggagac 2700
tgaggggctt tgtaaaacat tagtcagttg ctcattttta tgggattgct tagctgggct 2760
gtaaagatga aggcatcaaa taaactcaaa gtatttttaa atttttttga taatagagaa 2820
acttcgctaa ccaactgttc tttcttgagt gtatagcccc atcttgtggt aacttgctgc 2880
ttctgcactt catatccata tttcctattg ttcactttat tctgtagagc agcctgccaa 2940
gaattttatt tctgctgttt tttttgctgc taaagaaagg aactaagtca ggatgttaac 3000
agaaaagtcc acataaccct agaattctta gtcaaggaat aattcaagtc agcctagaga 3060
ccatgttgac tttcctcatg tgtttcctta tgactcagta agttggcaag gtcctgactt 3120
tagtcttaat aaaacattga attgtagtaa aggtttttgc aataaaaact tactttgg 3178

<210> SEQ ID NO 44
<211> LENGTH: 1858
<212> TYPE: DNA
<213> ORGANISM: Mus sp.

<400> SEQUENCE: 44
attccggagg tgaaaaacaa tggcacaacg tgtataatgg ccagcttctc tgcctccttt 60
ctgaccacct acgagactgc gaatggttct cagatcgtga acatttccct gccagcctct 120
gcagaagtac tgaaaaatgg cagttcttgt ggtaaagaaa atgtttctga ccccagcctc 180
acaattactt ttggaagagg atatttactg acactcaact tcacaaaaaa tacaacacgt 240
tacagtgtcc agcatatgta ttttacatat aacttgtcag atacagaaca ttttcccaat 300
gccatcagca aagagatcta caccatggat tccacaactg acatcaaggc agacatcaac 360
aaagcatacc ggtgtgtcag tgatatccgg gtctacatga agaatgtgac cgttgtgctc 420
cgggatgcca ctatccaggc ctacctgtcg agtggcaact tcagcaagga agagacacac 480
tgcacacagg atggaccttc cccaaccact gggccaccca gcccctcacc accacttgtg 540
cccacaaacc ccactgtatc caagtacaat gttactggta acaacggaac ctgcctgctg 600

```
gcctctatgg cactgcaact gaatatcacc tacctgaaaa aggacaacaa gacggtgacc    660
agagcgttca acatcagccc aaatgacaca tctagtggga gttgcggtat caacttggtg    720
accctgaaag tggagaacaa gaacagagcc ctggaattgc agtttgggat gaatgccagc    780
tctagcctgt ttttcttgca aggagtgcgc ttgaatatga ctcttcctga tgccctagtg    840
cccacattca gcatctccaa ccattcactg aaagctcttc aggccactgt gggaaactca    900
tacaagtgca acactgagga acacatcttt gtcagcaaga tgctctccct caatgtcttc    960
agtgtgcagg tccaggcttt caaggtggac agtgacaggt ttgggtctgt ggaagagtgt   1020
gttcaggatg gtaacaacat gttgatcccc attgctgtgg gcggtgccct ggcagggctg   1080
atcctcatcg tcctcattgc ctacctcatt ggcaggaaga ggagtcacgc cggctatcag   1140
accatctagc ctggtgggca ggtgcaccag agatgcacag gggcctgttc tcacatcccc   1200
aagcttagat aggtgtggaa gggaggcaca ctttctggca aactgtttta aaatctgctt   1260
tatcaaatgt gaagttcatc ttgcaacatt tactatgcac aaaggaataa ctattgaaat   1320
gacggtgtta attttgctaa ctgggttaaa tattgatgag aaggctccac tgatttgact   1380
tttaagactt ggtgtttggt tcttcattct tttactcaga tttaagccta tcaaagggat   1440
actctggtcc agaccttggc ctggcaaggg tggctgatgg ttaggctgca cacacttaag   1500
aagcaacggg agcagggaag gcttgcacac aggcacgcac agggtcaacc tctggacact   1560
tggcttgggc tacctggcct tggggggggct gaactctggc atctggctgg gtacacaccc   1620
ccccaatttc tgtgctctgc cacccgtgag ctgccacttt cctaaataga aaatggcatt   1680
atttttattt actttttttgt aaagtgattt ccagtcttgt gttggcgttc agggtggccc   1740
tgtctctgca ctgtgtacaa taatagattc acactgctga cgtgtcttgc agcgtaggtg   1800
ggttgtacac tgggcatcag ctcacgtaat gcattgcctg taacgatgct aataaaaa     1858
```

<210> SEQ ID NO 45
<211> LENGTH: 2339
<212> TYPE: DNA
<213> ORGANISM: Homo sapiens

<400> SEQUENCE: 45

```
ggcccaaccg ccgcccgcgc ccccgctctc cgcaccgtac ccggccgcct cgcgccatgg     60
cggcccccgg cagcgcccgg cgacccctgc tgctgctact gctgttgctg ctgctcggcc    120
tcatgcattg tgcgtcagca gcaatgttta tggtgaaaaa tggcaacggg accgcgtgca    180
taatggccaa cttctctgct gccttctcag tgaactacga caccaagagt ggccctaaga    240
acatgacctt tgacctgcca tcagatgcca cagtggtgct caaccgcagc tcctgtggaa    300
aagagaacac ttctgacccc agtctcgtga ttgcttttgg aagaggacat acactcactc    360
tcaatttcac gagaaatgca acacgttaca gcgtccagct catgagtttt gtttataact    420
tgtcagacac acaccttttc cccaatgcga gctccaaaga aatcaagact gtggaatcta    480
taactgacat cagggcagat atagataaaa aatacagatg tgttagtggc acccaggtcc    540
acatgaacaa cgtgaccgta acgctccatg atgccaccat ccaggcgtac ctttccaaca    600
gcagcttcag caggggagag acacgctgtg aacaagacag gccttcccca accacagcgc    660
cccctgcgcc acccagcccc tcgccctcac ccgtgcccaa gagcccctct gtggacaagt    720
acaacgtgag cggcaccaac gggacctgcc tgctggccag catggggctg cagctgaacc    780
tcacctatga gaggaaggac aacacgacgg tgacaaggct tctcaacatc aaccccaaca    840
agacctcggc cagcgggagc tgcggcgccc acctggtgac tctggagctg cacagcgagg    900
```

gcaccaccgt cctgctcttc cagttcggga tgaatgcaag ttctagccgg tttttcctac 960
aaggaatcca gttgaataca attcttcctg acgccagaga ccctgccttt aaagctgcca 1020
acggctccct gcgagcgctg caggccacag tcggcaattc ctacaagtgc aacgcggagg 1080
agcacgtccg tgtcacgaag gcgttttcag tcaatatatt caaagtgtgg gtccaggctt 1140
tcaaggtgga aggtggccag tttggctctg tggaggagtg tctgctggac gagaacagca 1200
tgctgatccc catcgctgtg ggtggtgccc tggcggggct ggtcctcatc gtcctcatcg 1260
cctacctcgt cggcaggaag aggagtcacg caggctacca gactatctag cctggtgcac 1320
gcaggcacag cagctgcagg ggcctctgtt cctttctctg ggcttagggt cctgtcgaag 1380
gggaggcaca ctttctggca aacgtttctc aaatctgctt catccaatgt gaagttcatc 1440
ttgcagcatt tactatgcac aacagagtaa ctatcgaaat gacggtgtta attttgctaa 1500
ctgggttaaa tattttgcta actggttaaa cattaatatt taccaaagta ggattttgag 1560
ggtgggggtg ctctctctga gggggtgggg gtgccgctgt ctctgagggg tgggggtgcc 1620
gctgtctctg aggggtgggg gtgccgctct ctctgagggg gtgggggtgc cgctttctct 1680
gagggggtgg gggtgccgct ctctctgagg gggtgggggt gctgctctct ccgaggggtg 1740
gaatgccgct gtctctgagg ggtgggggtg ccgctctaaa ttggctccat atcatttgag 1800
tttagggttc tggtgtttgg tttcttcatt ctttactgca ctcagattta agccttacaa 1860
agggaaagcc tctggccgtc acacgtagga cgcatgaagg tcactcgtgg tgaggctgac 1920
atgctcacac attacaacag tagagaggga aaatcctaag acagaggaac tccagagatg 1980
agtgtctgga gcgcttcagt tcagctttaa aggccaggac gggccacacg tggctggcgg 2040
cctcgttcca gtggcggcac gtccttgggc gtctctaatg tctgcagctc aagggctggc 2100 actttttttaa atataaaaat gggtgttatt tttatttttt tttgtaaagt gatttttggt 2160
cttctgttga cattcggggt gatcctgttc tgcgctgtgt acaatgtgag atcggtgcgt 2220
tctcctgatg ttttgccgtg gcttggggat tgtacacggg accagctcac gtaatgcatt 2280
gcctgtaaca atgtaataaa aagcctcttt cttttaaaaa aaaaaaaaaa aaaaaaaaa 2339

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
cagtacatca aggccaacag caagttcatc ggcatcaccg aactc 45

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gln Tyr Ile Lys Ala Asn Ser Lys Phe Ile Gly Ile Thr Glu Leu
1 5 10 15

<210> SEQ ID NO 48
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
gctaaatttg tggctgcctg gacactgaaa gccgccgct 39

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Ala Lys Phe Val Ala Ala Trp Thr Leu Lys Ala Ala Ala
1 5 10

<210> SEQ ID NO 50
<211> LENGTH: 593
<212> TYPE: DNA
<213> ORGANISM: Woodchuck hepatitis virus

<400> SEQUENCE: 50
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tgt 593

<210> SEQ ID NO 51
<211> LENGTH: 589
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
tctccccccc cccctctcc ctcccccccc cctaacgtta ctggccgaag ccgcttggaa 60
taaggccggt gtgcgtttgt ctatatgtta ttttccacca tattgccgtc ttttggcaat 120
gtgagggccc ggaaacctgg ccctgtcttc ttgacgagca ttcctagggg tctttcccct 180
ctcgccaaag gaatgcaagg tctgttgaat gtcgtgaagg aagcagttcc tctggaagct 240
tcttgaagac aaacaacgtc tgtagcgacc ctttgcaggc agcggaaccc cccacctggc 300
gacaggtgcc tctgcggcca aaagccacgt gtataagata cacctgcaaa ggcggcacaa 360
ccccagtgcc acgttgtgag ttggatagtt gtggaaagag tcaaatggct ctcctcaagc 420
gtattcaaca aggggctgaa ggatgcccag aaggtacccc attgtatggg atctgatctg 480
gggcctcggt gcacatgctt tacatgtgtt tagtcgaggt taaaaaaacg tctaggcccc 540
ccgaaccacg ggacgtggt tttcctttga aaaacacgat gataatatg 589

<210> SEQ ID NO 52
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtag 720

<210> SEQ ID NO 53
<211> LENGTH: 1563
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
atgctgctgc tgctgctgct gctgggcctg aggctacagc tctccctggg catcatccca 60
gttgaggagg agaacccgga cttctggaac cgcgaggcag ccgaggccct gggtgccgcc 120
aagaagctgc agcctgcaca gacagccgcc aagaacctca tcatcttcct gggcgatggg 180
atgggggtgt ctacggtgac agctgccagg atcctaaaag ggcagaagaa ggacaaactg 240
gggcctgaga tacccctggc catggaccgc ttcccatatg tggctctgtc caagacatac 300
aatgtagaca aacatgtgcc agacagtgga gccacagcca cggcctacct gtgcggggtc 360
aagggcaact tccagaccat tggcttgagt gcagccgccc gctttaacca gtgcaacacg 420
acacgcggca acgaggtcat ctccgtgatg aatcgggcca agaaagcagg gaagtcagtg 480
ggagtggtaa ccaccacacg agtgcagcac gcctcgccag ccggcaccta cgcccacacg 540
gtgaaccgca actggtactc ggacgccgac gtgcctgcct cggcccgcca ggaggggtgc 600
caggacatcg ctacgcagct catctccaac atggacattg acgtgatcct aggtggaggc 660
cgaaagtaca tgtttcgcat gggaacccca gaccctgagt acccagatga ctacagccaa 720
ggtgggacca ggctggacgg gaagaatctg gtgcaggaat ggctggcgaa gcgccagggt 780
gcccggtatg tgtggaaccg cactgagctc atgcaggctt ccctggaccc gtctgtgacc 840
catctcatgg gtctctttga gcctggagac atgaaatacg agatccaccg agactccaca 900

```
ctggacccct ccctgatgga gatgacagag gctgccctgc gcctgctgag caggaacccc     960

cgcggcttct tcctcttcgt ggagggtggt cgcatcgacc atggtcatca tgaaagcagg    1020

gcttaccggg cactgactga gacgatcatg ttcgacgacg ccattgagag ggcgggccag    1080

ctcaccagcg aggaggacac gctgagcctc gtcactgccg accactccca cgtcttctcc    1140

ttcggaggct acccccctgcg agggagctcc atcttcgggc tggcccctgg caaggcccgg   1200

gacaggaagg cctacacggt cctcctatac ggaaacggtc caggctatgt gctcaaggac    1260

ggcgcccggc cggatgttac cgagagcgag agcgggagcc ccgagtatcg gcagcagtca    1320

gcagtgcccc tggacgaaga gacccacgca ggcgaggacg tggcggtgtt cgcgcgcggc    1380

ccgcaggcgc acctggttca cggcgtgcag gagcagacct tcatagcgca cgtcatggcc    1440

ttcgccgcct gcctggagcc ctacaccgcc tgcgacctgg cgccccccgc cggcaccacc    1500

gacgccgcgc acccgggtta ctctagagtc ggggcggccg gccgcttcga gcagacatga    1560

taa                                                                  1563
```

<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
atggaagatg ccaaaaacat taagaagggc ccagcgccat tctacccact cgaagacggg      60

accgccggcg agcagctgca caaagccatg aagcgctacg ccctggtgcc cggcaccatc     120

gcctttaccg acgcacatat cgaggtggac attacctacg ccgagtactt cgagatgagc     180

gttcggctgg cagaagctat gaagcgctat gggctgaata caaaccatcg gatcgtggtg     240

tgcagcgaga atagcttgca gttcttcatg cccgtgttgg gtgccctgtt catcggtgtg     300

gctgtggccc cagctaacga catctacaac gagcgcgagc tgctgaacag catgggcatc     360

agccagccca ccgtcgtatt cgtgagcaag aaagggctgc aaaagatcct caacgtgcaa     420

aagaagctac cgatcataca aaagatcatc atcatggata gcaagaccga ctaccagggc     480

ttccaaagca tgtacacctt cgtgacttcc catttgccac ccggcttcaa cgagtacgac     540

ttcgtgcccg agagcttcga ccgggacaaa accatcgccc tgatcatgaa cagtagtggc     600

agtaccggat tgcccaaggg cgtagcccta ccgcaccgca ccgcttgtgt ccgattcagt     660

catgcccgcg accccatctt cggcaaccag atcatccccg acaccgctat cctcagcgtg     720

gtgccatttc accacggctt cggcatgttc accacgctgg gctacttgat ctgcggcttt     780

cgggtcgtgc tcatgtaccg cttcgaggag gagctattct tgcgcagctt gcaagactat     840

aagattcaat ctgccctgct ggtgcccaca ctatttagct tcttcgctaa gagcactctc     900

atcgacaagt acgacctaag caacttgcac gagatcgcca gcggcggggc gccgctcagc     960

aaggaggtag gtgaggccgt ggccaaacgc ttccacctac caggcatccg ccagggctac    1020

ggcctgacag aaacaaccag cgccattctg atcacccccg aaggggacga caagcctggc    1080

gcagtaggca aggtggtgcc cttcttcgag gctaaggtgg tggacttgga caccggtaag    1140

acactgggtg tgaaccagcg cggcgagctg tgcgtccgtg gccccatgat catgagcggc    1200

tacgttaaca accccgaggc tacaaacgct ctcatcgaca aggacggctg gctgcacagc    1260

ggcgacatcg cctactggga cgaggacgag cacttcttca tcgtggaccg gctgaagagc    1320
```

ctgatcaaat acaagggcta ccaggtagcc ccagccgaac tggagagcat cctgctgcaa 1380
caccccaaca tcttcgacgc cggggtcgcc ggcctgcccg acgacgatgc cggcgagctg 1440
cccgccgcag tcgtcgtgct ggaacacggt aaaaccatga ccgagaagga gatcgtggac 1500
tatgtggcca gccaggttac aaccgccaag aagctgcgcg gtggtgttgt gttcgtggac 1560
gaggtgccta aaggactgac cggcaagttg gacgcccgca agatccgcga gattctcatt 1620
aaggccaaga agggcggcaa gatcgccgtg taa 1653

<210> SEQ ID NO 55
<211> LENGTH: 66
<212> TYPE: DNA
<213> ORGANISM: Foot-and-mouth disease virus

<400> SEQUENCE: 55
gtaaagcaaa cactgaactt tgaccttctc aagttggctg gagacgttga gtccaatcct 60
gggccc 66

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Gly Pro Gly Pro Gly
1 5

<210> SEQ ID NO 57
<211> LENGTH: 10
<212> TYPE: RNA
<213> ORGANISM: Artificial Sequence
<220> FEATURE:
<223> OTHER INFORMATION: polyA tail
<220> FEATURE:
<221> NAME/KEY: variation
<222> LOCATION: (1)..(1)
<223> OTHER INFORMATION: A residue can be repeated upto hundred times.

<400> SEQUENCE: 57
aaaaaaaaaa 10

<210> SEQ ID NO 58
<211> LENGTH: 20
<212> TYPE: DNA
<213> ORGANISM: Artificial Sequence
<220> FEATURE:
<223> OTHER INFORMATION: Primer1

<400> SEQUENCE: 58
gtggtgtgca gcgagaatag 20

<210> SEQ ID NO 59
<211> LENGTH: 22
<212> TYPE: DNA
<213> ORGANISM: Artificial Sequence
<220> FEATURE:
<223> OTHER INFORMATION: Primer2

<400> SEQUENCE: 59
cgctcgttgt agatgtcgtt ag 22

<210> SEQ ID NO 60
<211> LENGTH: 24
<212> TYPE: DNA
<213> ORGANISM: Artificial Sequence
<220> FEATURE:
<223> OTHER INFORMATION: Probe

<400> SEQUENCE: 60
ttgcagttct tcatgcccgt gttg 24

<210> SEQ ID NO 61
<211> LENGTH: 22
<212> TYPE: DNA
<213> ORGANISM: Artificial Sequence
<220> FEATURE:
<223> OTHER INFORMATION: Primer1

<400> SEQUENCE: 61
gtttttgatc cagacccaga tg 22

<210> SEQ ID NO 62
<211> LENGTH: 21
<212> TYPE: DNA
<213> ORGANISM: Artificial Sequence
<220> FEATURE:
<223> OTHER INFORMATION: Primer2

<400> SEQUENCE: 62
gcccattatt cagagcgagt a 21

<210> SEQ ID NO 63
<211> LENGTH: 23
<212> TYPE: DNA
<213> ORGANISM: Artificial Sequence
<220> FEATURE:
<223> OTHER INFORMATION: Probe

<400> SEQUENCE: 63
tgcagggttt caccaggatc cac 23

<210> SEQ ID NO 64
<211> LENGTH: 17
<212> TYPE: DNA
<213> ORGANISM: Artificial Sequence
<220> FEATURE:
<223> OTHER INFORMATION: Primer1

<400> SEQUENCE: 64
ccttgcacat gccggag 17

<210> SEQ ID NO 65
<211> LENGTH: 17
<212> TYPE: DNA
<213> ORGANISM: Artificial Sequence
<220> FEATURE:
<223> OTHER INFORMATION: Primer2

<400> SEQUENCE: 65
acagagcctc gcctttg 17

<210> SEQ ID NO 66
<211> LENGTH: 21
<212> TYPE: DNA
<213> ORGANISM: Artificial Sequence
<220> FEATURE:
<223> OTHER INFORMATION: Probe

<400> SEQUENCE: 66
tcatccatgg tgagctggcg g 21

<210> SEQ ID NO 67
<211> LENGTH: 22
<212> TYPE: DNA
<213> ORGANISM: Artificial Sequence
<220> FEATURE:
<223> OTHER INFORMATION: Primer1

<400> SEQUENCE: 67
ctgaaagctc ggtttgctaa tg 22

<210> SEQ ID NO 68
<211> LENGTH: 21
<212> TYPE: DNA
<213> ORGANISM: Artificial Sequence
<220> FEATURE:
<223> OTHER INFORMATION: Primer2

<400> SEQUENCE: 68
ccatgctgga agagacaatc t 21

<210> SEQ ID NO 69
<211> LENGTH: 24
<212> TYPE: DNA
<213> ORGANISM: Artificial Sequence
<220> FEATURE:
<223> OTHER INFORMATION: Probe

<400> SEQUENCE: 69
cgtttctgat ggcgctgacc gata 24

<210> SEQ ID NO 70
<211> LENGTH: 22
<212> TYPE: DNA
<213> ORGANISM: Artificial Sequence
<220> FEATURE:
<223> OTHER INFORMATION: Primer1

<400> SEQUENCE: 70
tatgcctatc ctgtctcctc tg 22

<210> SEQ ID NO 71
<211> LENGTH: 22
<212> TYPE: DNA
<213> ORGANISM: Artificial Sequence
<220> FEATURE:
<223> OTHER INFORMATION: Primer2

<400> SEQUENCE: 71
gctaatgcag ctaagtcctc tc 22

<210> SEQ ID NO 72
<211> LENGTH: 24
<212> TYPE: DNA
<213> ORGANISM: Artificial Sequence
<220> FEATURE:
<223> OTHER INFORMATION: Probe

<400> SEQUENCE: 72
tgtttaccct gaccgtgcct tctg 24

<210> SEQ ID NO 73

<211> LENGTH: 9
<212> TYPE: PRT
<213> ORGANISM: Artificial Sequence
<220> FEATURE:
<223> OTHER INFORMATION: Minimal epitope

<400> SEQUENCE: 73

Gly Ile Leu Gly Phe Val Phe Thr Leu
1 5

<210> SEQ ID NO 74
<211> LENGTH: 9
<212> TYPE: PRT
<213> ORGANISM: Artificial Sequence
<220> FEATURE:
<223> OTHER INFORMATION: Minimal epitope

<400> SEQUENCE: 74

Leu Leu Phe Gly Tyr Pro Val Tyr Val
1 5

<210> SEQ ID NO 75
<211> LENGTH: 9
<212> TYPE: PRT
<213> ORGANISM: Artificial Sequence
<220> FEATURE:
<223> OTHER INFORMATION: Minimal epitope

<400> SEQUENCE: 75

Gly Leu Cys Thr Leu Val Ala Met Leu
1 5

<210> SEQ ID NO 76
<211> LENGTH: 9
<212> TYPE: PRT
<213> ORGANISM: Artificial Sequence
<220> FEATURE:
<223> OTHER INFORMATION: Minimal epitope

<400> SEQUENCE: 76

Asn Leu Val Pro Met Val Ala Thr Val
1 5

<210> SEQ ID NO 77
<211> LENGTH: 9
<212> TYPE: PRT
<213> ORGANISM: Artificial Sequence
<220> FEATURE:
<223> OTHER INFORMATION: Minimal epitope

<400> SEQUENCE: 77

Cys Leu Gly Gly Leu Leu Thr Met Val
1 5

<210> SEQ ID NO 78
<211> LENGTH: 9
<212> TYPE: PRT
<213> ORGANISM: Artificial Sequence
<220> FEATURE:
<223> OTHER INFORMATION: Minimal epitope

<400> SEQUENCE: 78

Asn Thr Asp Asn Asn Leu Ala Val Tyr
1 5

<210> SEQ ID NO 79
<211> LENGTH: 9

<212> TYPE: PRT
<213> ORGANISM: Artificial Sequence
<220> FEATURE:
<223> OTHER INFORMATION: Minimal epitope

<400> SEQUENCE: 79

Glu Val Asp Pro Ile Gly His Val Tyr
1               5

<210> SEQ ID NO 80
<211> LENGTH: 9
<212> TYPE: PRT
<213> ORGANISM: Artificial Sequence
<220> FEATURE:
<223> OTHER INFORMATION: Minimal epitope

<400> SEQUENCE: 80

Leu Leu Ala Ser Ser Ile Leu Cys Ala
1               5

<210> SEQ ID NO 81
<211> LENGTH: 10
<212> TYPE: PRT
<213> ORGANISM: Artificial Sequence
<220> FEATURE:
<223> OTHER INFORMATION: Minimal epitope

<400> SEQUENCE: 81

Ala Ile Phe Pro Gly Ala Val Pro Ala Ala
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Minimal epitope

<400> SEQUENCE: 82

Val Tyr Asp Leu Ser Arg Asp Ile Leu
1               5

<210> SEQ ID NO 83
<211> LENGTH: 10
<212> TYPE: PRT
<213> ORGANISM: Artificial Sequence
<220> FEATURE:
<223> OTHER INFORMATION: Minimal epitope

<400> SEQUENCE: 83

Ala Ser Ser Leu Pro Thr Thr Met Asn Tyr
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Minimal epitope

<400> SEQUENCE: 84

Pro Lys Tyr Val Lys Gln Asn Thr Leu Lys Leu Ala Thr
1               5                   10

<210> SEQ ID NO 85
<211> LENGTH: 14
<212> TYPE: PRT

<213> ORGANISM: Artificial Sequence
<220> FEATURE:
<223> OTHER INFORMATION: Minimal epitope

<400> SEQUENCE: 85

Leu Pro Leu Lys Met Leu Asn Ile Pro Ser Ile Asn Val His
1 5 10

<210> SEQ ID NO 86
<211> LENGTH: 15
<212> TYPE: PRT
<213> ORGANISM: Artificial Sequence
<220> FEATURE:
<223> OTHER INFORMATION: Minimal epitope

<400> SEQUENCE: 86

Pro Glu Gln Trp Met Phe Gln Gly Ala Pro Pro Ser Gln Gly Thr
1 5 10 15

<210> SEQ ID NO 87
<211> LENGTH: 15
<212> TYPE: PRT
<213> ORGANISM: Artificial Sequence
<220> FEATURE:
<223> OTHER INFORMATION: Minimal epitope

<400> SEQUENCE: 87

Glu His Pro Thr Phe Thr Ser Gln Tyr Arg Ile Gln Gly Lys Leu
1 5 10 15

<210> SEQ ID NO 88
<211> LENGTH: 25
<212> TYPE: PRT
<213> ORGANISM: Artificial Sequence
<220> FEATURE:
<223> OTHER INFORMATION: 25mer

<400> SEQUENCE: 88

Pro Ile Leu Ser Pro Leu Thr Lys Gly Ile Leu Gly Phe Val Phe Thr
1 5 10 15

Leu Thr Val Pro Ser Glu Arg Gly Leu
20 25

<210> SEQ ID NO 89
<211> LENGTH: 25
<212> TYPE: PRT
<213> ORGANISM: Artificial Sequence
<220> FEATURE:
<223> OTHER INFORMATION: 25mer

<400> SEQUENCE: 89

His Phe Pro Gly Phe Gly Gln Ser Leu Leu Phe Gly Tyr Pro Val Tyr
1 5 10 15

Val Phe Gly Asp Cys Val Gln Gly Asp
20 25

<210> SEQ ID NO 90
<211> LENGTH: 25
<212> TYPE: PRT
<213> ORGANISM: Artificial Sequence
<220> FEATURE:
<223> OTHER INFORMATION: 25mer

<400> SEQUENCE: 90

Arg Met Gln Ala Ile Gln Asn Ala Gly Leu Cys Thr Leu Val Ala Met
1 5 10 15

Leu Glu Glu Thr Ile Phe Trp Leu Gln
20 25

<210> SEQ ID NO 91
<211> LENGTH: 25
<212> TYPE: PRT
<213> ORGANISM: Artificial Sequence
<220> FEATURE:
<223> OTHER INFORMATION: 25mer

<400> SEQUENCE: 91

Trp Gln Ala Gly Ile Leu Ala Arg Asn Leu Val Pro Met Val Ala Thr
1 5 10 15

Val Gln Gly Gln Asn Leu Lys Tyr Gln
20 25

<210> SEQ ID NO 92
<211> LENGTH: 25
<212> TYPE: PRT
<213> ORGANISM: Artificial Sequence
<220> FEATURE:
<223> OTHER INFORMATION: 25mer

<400> SEQUENCE: 92

Arg Thr Tyr Gly Pro Val Phe Met Cys Leu Gly Gly Leu Leu Thr Met
1 5 10 15

Val Ala Gly Ala Val Trp Leu Thr Val
20 25

<210> SEQ ID NO 93
<211> LENGTH: 25
<212> TYPE: PRT
<213> ORGANISM: Artificial Sequence
<220> FEATURE:
<223> OTHER INFORMATION: 25mer

<400> SEQUENCE: 93

Ser Ser Ser Gly Leu Ile Asn Ser Asn Thr Asp Asn Asn Leu Ala Val
1 5 10 15

Tyr Asp Leu Ser Arg Asp Ile Leu Asn
20 25

<210> SEQ ID NO 94
<211> LENGTH: 25
<212> TYPE: PRT
<213> ORGANISM: Artificial Sequence
<220> FEATURE:
<223> OTHER INFORMATION: 25mer

<400> SEQUENCE: 94

Leu Val Phe Gly Ile Glu Leu Met Glu Val Asp Pro Ile Gly His Val
1 5 10 15

Tyr Ile Phe Ala Thr Cys Leu Gly Leu
20 25

<210> SEQ ID NO 95
<211> LENGTH: 25
<212> TYPE: PRT
<213> ORGANISM: Artificial Sequence
<220> FEATURE:
<223> OTHER INFORMATION: 25mer

<400> SEQUENCE: 95

Met Asn Phe Tyr Leu Leu Leu Ala Ser Ser Ile Leu Cys Ala Leu Ile

-continued

```
1               5                   10                  15

Val Phe Trp Lys Tyr Arg Arg Phe Gln
            20                  25


<210> SEQ ID NO 96
<211> LENGTH: 25
<212> TYPE: PRT
<213> ORGANISM: Artificial Sequence
<220> FEATURE:
<223> OTHER INFORMATION: 25mer

<400> SEQUENCE: 96

Ala Ala Ala Ala Ala Ala Ala Ala Ile Phe Pro Gly Ala Val Pro Ala
1               5                   10                  15

Ala Arg Pro Pro Tyr Pro Gly Ala Val
            20                  25


<210> SEQ ID NO 97
<211> LENGTH: 25
<212> TYPE: PRT
<213> ORGANISM: Artificial Sequence
<220> FEATURE:
<223> OTHER INFORMATION: 25mer

<400> SEQUENCE: 97

Ser Asn Thr Asp Asn Asn Leu Ala Val Tyr Asp Leu Ser Arg Asp Ile
1               5                   10                  15

Leu Asn Asn Phe Pro His Ser Ile Ala
            20                  25


<210> SEQ ID NO 98
<211> LENGTH: 25
<212> TYPE: PRT
<213> ORGANISM: Artificial Sequence
<220> FEATURE:
<223> OTHER INFORMATION: 25mer

<400> SEQUENCE: 98

Asp Pro Pro Gln Ser Pro Gln Gly Ala Ser Ser Leu Pro Thr Thr Met
1               5                   10                  15

Asn Tyr Pro Leu Trp Ser Gln Ser Tyr
            20                  25


<210> SEQ ID NO 99
<211> LENGTH: 25
<212> TYPE: PRT
<213> ORGANISM: Artificial Sequence
<220> FEATURE:
<223> OTHER INFORMATION: 25mer

<400> SEQUENCE: 99

Ile Thr Tyr Gly Ala Cys Pro Lys Tyr Val Lys Gln Asn Thr Leu Lys
1               5                   10                  15

Leu Ala Thr Gly Met Arg Asn Val Pro
            20                  25


<210> SEQ ID NO 100
<211> LENGTH: 25
<212> TYPE: PRT
<213> ORGANISM: Artificial Sequence
<220> FEATURE:
<223> OTHER INFORMATION: 25mer

<400> SEQUENCE: 100
```

-continued

Ser Ile Tyr Val Tyr Ala Leu Pro Leu Lys Met Leu Asn Ile Pro Ser
1 5 10 15

Ile Asn Val His His Tyr Pro Ser Ala
20 25

<210> SEQ ID NO 101
<211> LENGTH: 25
<212> TYPE: PRT
<213> ORGANISM: Artificial Sequence
<220> FEATURE:
<223> OTHER INFORMATION: 25mer

<400> SEQUENCE: 101

Glu Gly Pro Trp Val Pro Glu Gln Trp Met Phe Gln Gly Ala Pro Pro
1 5 10 15

Ser Gln Gly Thr Asp Val Val Gln His
20 25

<210> SEQ ID NO 102
<211> LENGTH: 25
<212> TYPE: PRT
<213> ORGANISM: Artificial Sequence
<220> FEATURE:
<223> OTHER INFORMATION: 25mer

<400> SEQUENCE: 102

Arg Gly Pro Gln Tyr Ser Glu His Pro Thr Phe Thr Ser Gln Tyr Arg
1 5 10 15

Ile Gln Gly Lys Leu Glu Tyr Arg His
20 25

<210> SEQ ID NO 103
<211> LENGTH: 9
<212> TYPE: PRT
<213> ORGANISM: Artificial Sequence
<220> FEATURE:
<223> OTHER INFORMATION: Minimal epitope

<400> SEQUENCE: 103

Cys Thr Pro Tyr Asp Ile Asn Gln Met
1 5

<210> SEQ ID NO 104
<211> LENGTH: 8
<212> TYPE: PRT
<213> ORGANISM: Artificial Sequence
<220> FEATURE:
<223> OTHER INFORMATION: Minimal epitope

<400> SEQUENCE: 104

Thr Thr Pro Glu Ser Ala Asn Leu
1 5

<210> SEQ ID NO 105
<211> LENGTH: 9
<212> TYPE: PRT
<213> ORGANISM: Artificial Sequence
<220> FEATURE:
<223> OTHER INFORMATION: Minimal epitope

<400> SEQUENCE: 105

Cys Ala Pro Pro Gly Tyr Ala Leu Leu
1 5

<210> SEQ ID NO 106

<211> LENGTH: 9
<212> TYPE: PRT
<213> ORGANISM: Artificial Sequence
<220> FEATURE:
<223> OTHER INFORMATION: Minimal epitope

<400> SEQUENCE: 106

Ser Gly Pro Lys Thr Asn Ile Ile Val
1               5

<210> SEQ ID NO 107
<211> LENGTH: 9
<212> TYPE: PRT
<213> ORGANISM: Artificial Sequence
<220> FEATURE:
<223> OTHER INFORMATION: Minimal epitope

<400> SEQUENCE: 107

Leu Ser Pro Arg Thr Leu Asn Ala Trp
1               5

<210> SEQ ID NO 108
<211> LENGTH: 9
<212> TYPE: PRT
<213> ORGANISM: Artificial Sequence
<220> FEATURE:
<223> OTHER INFORMATION: Minimal epitope

<400> SEQUENCE: 108

Thr Val Pro Trp Pro Asn Ala Ser Leu
1               5

<210> SEQ ID NO 109
<211> LENGTH: 15
<212> TYPE: PRT
<213> ORGANISM: Artificial Sequence
<220> FEATURE:
<223> OTHER INFORMATION: Minimal epitope

<400> SEQUENCE: 109

Pro Asn Gly Thr His Ser Trp Glu Tyr Trp Gly Ala Gln Leu Asn
1               5                   10                  15

<210> SEQ ID NO 110
<211> LENGTH: 13
<212> TYPE: PRT
<213> ORGANISM: Artificial Sequence
<220> FEATURE:
<223> OTHER INFORMATION: Minimal epitope

<400> SEQUENCE: 110

Tyr Lys Tyr Lys Val Val Lys Ile Glu Pro Leu Gly Val
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Minimal epitope

<400> SEQUENCE: 111

Thr Glu Glu Ala Lys Gln Ile Val Gln Arg His Leu Val Val Glu
1               5                   10                  15

<210> SEQ ID NO 112
<211> LENGTH: 13

<212> TYPE: PRT
<213> ORGANISM: Artificial Sequence
<220> FEATURE:
<223> OTHER INFORMATION: Minimal epitope

<400> SEQUENCE: 112

Ala Gly Ser Leu Gln Gly Gln Trp Arg Gly Ala Ala Gly
1 5 10

<210> SEQ ID NO 113
<211> LENGTH: 16
<212> TYPE: PRT
<213> ORGANISM: Artificial Sequence
<220> FEATURE:
<223> OTHER INFORMATION: Minimal epitope

<400> SEQUENCE: 113

Glu Ile Ser Thr Asn Ile Arg Gln Ala Gly Val Gln Tyr Ser Arg Ala
1 5 10 15

<210> SEQ ID NO 114
<211> LENGTH: 9
<212> TYPE: PRT
<213> ORGANISM: Artificial Sequence
<220> FEATURE:
<223> OTHER INFORMATION: Minimal epitope

<400> SEQUENCE: 114

Arg Pro Lys Gln Ala Trp Cys Trp Phe
1 5

<210> SEQ ID NO 115
<211> LENGTH: 9
<212> TYPE: PRT
<213> ORGANISM: Artificial Sequence
<220> FEATURE:
<223> OTHER INFORMATION: Minimal epitope

<400> SEQUENCE: 115

Arg Pro Lys Val Pro Leu Arg Thr Met
1 5

<210> SEQ ID NO 116
<211> LENGTH: 9
<212> TYPE: PRT
<213> ORGANISM: Artificial Sequence
<220> FEATURE:
<223> OTHER INFORMATION: Minimal epitope

<400> SEQUENCE: 116

Gly Pro Arg Lys Pro Ile Lys Cys Trp
1 5

<210> SEQ ID NO 117
<211> LENGTH: 9
<212> TYPE: PRT
<213> ORGANISM: Artificial Sequence
<220> FEATURE:
<223> OTHER INFORMATION: Minimal epitope

<400> SEQUENCE: 117

Leu Asn Met Ala Asp Lys Lys Glu Thr
1 5

<210> SEQ ID NO 118
<211> LENGTH: 25
<212> TYPE: PRT

<213> ORGANISM: Artificial Sequence
<220> FEATURE:
<223> OTHER INFORMATION: 25mer

<400> SEQUENCE: 118

Met Phe Gln Ala Leu Ser Glu Gly Cys Thr Pro Tyr Asp Ile Asn Gln
1               5                   10                  15

Met Leu Asn Val Leu Gly Asp His Gln
            20                  25

<210> SEQ ID NO 119
<211> LENGTH: 25
<212> TYPE: PRT
<213> ORGANISM: Artificial Sequence
<220> FEATURE:
<223> OTHER INFORMATION: 25mer

<400> SEQUENCE: 119

Ser Cys Ile Ser Glu Ala Asp Ala Thr Thr Pro Glu Ser Ala Asn Leu
1               5                   10                  15

Gly Glu Glu Ile Leu Ser Gln Leu Tyr
            20                  25

<210> SEQ ID NO 120
<211> LENGTH: 25
<212> TYPE: PRT
<213> ORGANISM: Artificial Sequence
<220> FEATURE:
<223> OTHER INFORMATION: 25mer

<400> SEQUENCE: 120

Trp Asp Ala Ile Arg Phe Arg Tyr Cys Ala Pro Pro Gly Tyr Ala Leu
1               5                   10                  15

Leu Arg Cys Asn Asp Thr Asn Tyr Ser
            20                  25

<210> SEQ ID NO 121
<211> LENGTH: 25
<212> TYPE: PRT
<213> ORGANISM: Artificial Sequence
<220> FEATURE:
<223> OTHER INFORMATION: 25mer

<400> SEQUENCE: 121

Ala Phe Leu Met Ala Leu Thr Asp Ser Gly Pro Lys Thr Asn Ile Ile
1               5                   10                  15

Val Asp Ser Gln Tyr Val Met Gly Ile
            20                  25

<210> SEQ ID NO 122
<211> LENGTH: 25
<212> TYPE: PRT
<213> ORGANISM: Artificial Sequence
<220> FEATURE:
<223> OTHER INFORMATION: 25mer

<400> SEQUENCE: 122

Gly Asn Val Trp Val His Thr Pro Leu Ser Pro Arg Thr Leu Asn Ala
1               5                   10                  15

Trp Val Lys Ala Val Glu Glu Lys Lys
            20                  25

<210> SEQ ID NO 123
<211> LENGTH: 25

<212> TYPE: PRT
<213> ORGANISM: Artificial Sequence
<220> FEATURE:
<223> OTHER INFORMATION: 25mer

<400> SEQUENCE: 123

Ala Phe Arg Gln Val Cys His Thr Thr Val Pro Trp Pro Asn Ala Ser
1               5                   10                  15

Leu Thr Pro Lys Trp Asn Asn Glu Thr
            20                  25

<210> SEQ ID NO 124
<211> LENGTH: 25
<212> TYPE: PRT
<213> ORGANISM: Artificial Sequence
<220> FEATURE:
<223> OTHER INFORMATION: 25mer

<400> SEQUENCE: 124

Val Phe Asn Phe Pro Pro Asn Gly Thr His Ser Trp Glu Tyr Trp Gly
1               5                   10                  15

Ala Gln Leu Asn Ala Met Lys Gly Asp
            20                  25

<210> SEQ ID NO 125
<211> LENGTH: 25
<212> TYPE: PRT
<213> ORGANISM: Artificial Sequence
<220> FEATURE:
<223> OTHER INFORMATION: 25mer

<400> SEQUENCE: 125

Asn Trp Arg Ser Glu Leu Tyr Lys Tyr Lys Val Val Lys Ile Glu Pro
1               5                   10                  15

Leu Gly Val Ala Pro Thr Lys Ala Lys
            20                  25

<210> SEQ ID NO 126
<211> LENGTH: 25
<212> TYPE: PRT
<213> ORGANISM: Artificial Sequence
<220> FEATURE:
<223> OTHER INFORMATION: 25mer

<400> SEQUENCE: 126

Glu Lys Val Lys His Thr Glu Glu Ala Lys Gln Ile Val Gln Arg His
1               5                   10                  15

Leu Val Val Glu Thr Gly Thr Thr Glu
            20                  25

<210> SEQ ID NO 127
<211> LENGTH: 25
<212> TYPE: PRT
<213> ORGANISM: Artificial Sequence
<220> FEATURE:
<223> OTHER INFORMATION: 25mer

<400> SEQUENCE: 127

Asp Gln Val Glu Ser Thr Ala Gly Ser Leu Gln Gly Gln Trp Arg Gly
1               5                   10                  15

Ala Ala Gly Thr Ala Ala Gln Ala Ala
            20                  25

<210> SEQ ID NO 128

<211> LENGTH: 25
<212> TYPE: PRT
<213> ORGANISM: Artificial Sequence
<220> FEATURE:
<223> OTHER INFORMATION: 25mer

<400> SEQUENCE: 128

Gln Glu Leu Asp Glu Ile Ser Thr Asn Ile Arg Gln Ala Gly Val Gln
1               5                   10                  15

Tyr Ser Arg Ala Asp Glu Glu Gln Gln
            20                  25

<210> SEQ ID NO 129
<211> LENGTH: 25
<212> TYPE: PRT
<213> ORGANISM: Artificial Sequence
<220> FEATURE:
<223> OTHER INFORMATION: 25mer

<400> SEQUENCE: 129

Phe His Ser Gln Pro Ile Asn Glu Arg Pro Lys Gln Ala Trp Cys Trp
1               5                   10                  15

Phe Gly Gly Ser Trp Lys Glu Ala Ile
            20                  25

<210> SEQ ID NO 130
<211> LENGTH: 25
<212> TYPE: PRT
<213> ORGANISM: Artificial Sequence
<220> FEATURE:
<223> OTHER INFORMATION: 25mer

<400> SEQUENCE: 130

Asp Asp Ile Asp Glu Glu Asp Asp Asp Leu Val Gly Val Ser Val Arg
1               5                   10                  15

Pro Lys Val Pro Leu Arg Thr Met Ser
            20                  25

<210> SEQ ID NO 131
<211> LENGTH: 25
<212> TYPE: PRT
<213> ORGANISM: Artificial Sequence
<220> FEATURE:
<223> OTHER INFORMATION: 25mer

<400> SEQUENCE: 131

Pro Phe Ala Ala Ala Gln Gln Arg Gly Pro Arg Lys Pro Ile Lys Cys
1               5                   10                  15

Trp Asn Cys Gly Lys Glu Gly His Ser
            20                  25

<210> SEQ ID NO 132
<211> LENGTH: 24
<212> TYPE: PRT
<213> ORGANISM: Artificial Sequence
<220> FEATURE:
<223> OTHER INFORMATION: 25mer

<400> SEQUENCE: 132

Arg Arg Leu Thr Ala Arg Leu Leu Asn Met Ala Asp Lys Lys Glu Thr
1               5                   10                  15

Arg Thr Pro Lys Lys Ala Lys Ala
            20

<210> SEQ ID NO 133
<211> LENGTH: 8
<212> TYPE: PRT
<213> ORGANISM: Artificial Sequence
<220> FEATURE:
<223> OTHER INFORMATION: Minimal epitope

<400> SEQUENCE: 133

Ser Ile Ile Asn Phe Glu Lys Leu
1 5

<210> SEQ ID NO 134
<211> LENGTH: 9
<212> TYPE: PRT
<213> ORGANISM: Artificial Sequence
<220> FEATURE:
<223> OTHER INFORMATION: Minimal epitope

<400> SEQUENCE: 134

Glu Gly Pro Arg Asn Gln Asp Trp Leu
1 5

<210> SEQ ID NO 135
<211> LENGTH: 9
<212> TYPE: PRT
<213> ORGANISM: Artificial Sequence
<220> FEATURE:
<223> OTHER INFORMATION: Minimal epitope

<400> SEQUENCE: 135

Thr Ala Pro Asp Asn Leu Gly Tyr Met
1 5

<210> SEQ ID NO 136
<211> LENGTH: 9
<212> TYPE: PRT
<213> ORGANISM: Artificial Sequence
<220> FEATURE:
<223> OTHER INFORMATION: Minimal epitope

<400> SEQUENCE: 136

Ser Val Tyr Asp Phe Phe Val Trp Leu
1 5

<210> SEQ ID NO 137
<211> LENGTH: 9
<212> TYPE: PRT
<213> ORGANISM: Artificial Sequence
<220> FEATURE:
<223> OTHER INFORMATION: Minimal epitope

<400> SEQUENCE: 137

Ser Pro Ser Tyr Ala Tyr His Gln Phe
1 5

<210> SEQ ID NO 138
<211> LENGTH: 9
<212> TYPE: PRT
<213> ORGANISM: Artificial Sequence
<220> FEATURE:
<223> OTHER INFORMATION: Minimal epitope

<400> SEQUENCE: 138

Met Asn Lys Tyr Ala Tyr His Met Leu
1 5

<210> SEQ ID NO 139

<211> LENGTH: 8
<212> TYPE: PRT
<213> ORGANISM: Artificial Sequence
<220> FEATURE:
<223> OTHER INFORMATION: Minimal epitope

<400> SEQUENCE: 139

Ser Ile Ile Val Phe Asn Leu Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Minimal epitope

<400> SEQUENCE: 140

Ala Ser Met Thr Asn Met Glu Leu Met
1               5

<210> SEQ ID NO 141
<211> LENGTH: 9
<212> TYPE: PRT
<213> ORGANISM: Artificial Sequence
<220> FEATURE:
<223> OTHER INFORMATION: Minimal epitope

<400> SEQUENCE: 141

Ala Gln Leu Ala Asn Asp Val Val Leu
1               5

<210> SEQ ID NO 142
<211> LENGTH: 9
<212> TYPE: PRT
<213> ORGANISM: Artificial Sequence
<220> FEATURE:
<223> OTHER INFORMATION: Minimal epitope

<400> SEQUENCE: 142

Leu Pro Tyr Leu Gly Trp Leu Val Phe
1               5

<210> SEQ ID NO 143
<211> LENGTH: 10
<212> TYPE: PRT
<213> ORGANISM: Artificial Sequence
<220> FEATURE:
<223> OTHER INFORMATION: Minimal epitope

<400> SEQUENCE: 143

Gly Tyr Cys Gly Leu Arg Gly Thr Gly Val
1               5                   10

<210> SEQ ID NO 144
<211> LENGTH: 8
<212> TYPE: PRT
<213> ORGANISM: Artificial Sequence
<220> FEATURE:
<223> OTHER INFORMATION: Minimal epitope

<400> SEQUENCE: 144

Leu Ser Ile Phe Lys His Lys Leu
1               5

<210> SEQ ID NO 145
<211> LENGTH: 8

<212> TYPE: PRT
<213> ORGANISM: Artificial Sequence
<220> FEATURE:
<223> OTHER INFORMATION: Minimal epitope

<400> SEQUENCE: 145

Leu Ile Trp Ile Pro Ala Leu Leu
1               5

<210> SEQ ID NO 146
<211> LENGTH: 9
<212> TYPE: PRT
<213> ORGANISM: Artificial Sequence
<220> FEATURE:
<223> OTHER INFORMATION: Minimal epitope

<400> SEQUENCE: 146

Ser Ser Gly His Asn Glu Cys Pro Val
1               5

<210> SEQ ID NO 147
<211> LENGTH: 9
<212> TYPE: PRT
<213> ORGANISM: Artificial Sequence
<220> FEATURE:
<223> OTHER INFORMATION: Minimal epitope

<400> SEQUENCE: 147

Gly Gln Lys Met Asn Ala Gln Ala Ile
1               5

<210> SEQ ID NO 148
<211> LENGTH: 17
<212> TYPE: PRT
<213> ORGANISM: Artificial Sequence
<220> FEATURE:
<223> OTHER INFORMATION: Minimal epitope

<400> SEQUENCE: 148

Ile Ser Gln Ala Val His Ala Ala His Ala Glu Ile Asn Glu Ala Gly
1               5                   10                  15

Arg

<210> SEQ ID NO 149
<211> LENGTH: 19
<212> TYPE: PRT
<213> ORGANISM: Artificial Sequence
<220> FEATURE:
<223> OTHER INFORMATION: Minimal epitope

<400> SEQUENCE: 149

Met Thr Glu Gln Gln Trp Asn Phe Ala Gly Ile Glu Ala Ala Ala Ser
1               5                   10                  15

Ala Ile Gln

<210> SEQ ID NO 150
<211> LENGTH: 20
<212> TYPE: PRT
<213> ORGANISM: Artificial Sequence
<220> FEATURE:
<223> OTHER INFORMATION: Minimal epitope

<400> SEQUENCE: 150

Phe Asn Asn Phe Thr Val Ser Phe Trp Leu Arg Val Pro Lys Val Ser
1               5                   10                  15

Ala Ser His Leu
20

<210> SEQ ID NO 151
<211> LENGTH: 15
<212> TYPE: PRT
<213> ORGANISM: Artificial Sequence
<220> FEATURE:
<223> OTHER INFORMATION: Minimal epitope

<400> SEQUENCE: 151

Asp Gly Ser Thr Asp Tyr Gly Ile Leu Gln Ile Asn Ser Arg Trp
1 5 10 15

<210> SEQ ID NO 152
<211> LENGTH: 19
<212> TYPE: PRT
<213> ORGANISM: Artificial Sequence
<220> FEATURE:
<223> OTHER INFORMATION: Minimal epitope

<400> SEQUENCE: 152

Met Glu Val Gly Trp Tyr Arg Ser Pro Phe Ser Arg Val Val His Leu
1 5 10 15

Tyr Arg Asn

<210> SEQ ID NO 153
<211> LENGTH: 25
<212> TYPE: PRT
<213> ORGANISM: Artificial Sequence
<220> FEATURE:
<223> OTHER INFORMATION: 25mer

<400> SEQUENCE: 153

Val Ser Gly Leu Glu Gln Leu Glu Ser Ile Ile Asn Phe Glu Lys Leu
1 5 10 15

Thr Glu Trp Thr Ser Ser Asn Val Met
20 25

<210> SEQ ID NO 154
<211> LENGTH: 25
<212> TYPE: PRT
<213> ORGANISM: Artificial Sequence
<220> FEATURE:
<223> OTHER INFORMATION: 25mer

<400> SEQUENCE: 154

Ala Leu Leu Ala Val Gly Ala Leu Glu Gly Pro Arg Asn Gln Asp Trp
1 5 10 15

Leu Gly Val Pro Arg Gln Leu Val Thr
20 25

<210> SEQ ID NO 155
<211> LENGTH: 25
<212> TYPE: PRT
<213> ORGANISM: Artificial Sequence
<220> FEATURE:
<223> OTHER INFORMATION: 25mer

<400> SEQUENCE: 155

Val Thr Asn Thr Glu Met Phe Val Thr Ala Pro Asp Asn Leu Gly Tyr
1 5 10 15

Met Tyr Glu Val Gln Trp Pro Gly Gln
20 25

<210> SEQ ID NO 156
<211> LENGTH: 25
<212> TYPE: PRT
<213> ORGANISM: Artificial Sequence
<220> FEATURE:
<223> OTHER INFORMATION: 25mer

<400> SEQUENCE: 156

```
Thr Gln Pro Gln Ile Ala Asn Cys Ser Val Tyr Asp Phe Phe Val Trp
1               5                   10                  15

Leu His Tyr Tyr Ser Val Arg Asp Thr
            20                  25
```

<210> SEQ ID NO 157
<211> LENGTH: 25
<212> TYPE: PRT
<213> ORGANISM: Artificial Sequence
<220> FEATURE:
<223> OTHER INFORMATION: 25mer

<400> SEQUENCE: 157

```
Leu Trp Pro Arg Val Thr Tyr His Ser Pro Ser Tyr Ala Tyr His Gln
1               5                   10                  15

Phe Glu Arg Arg Ala Lys Tyr Lys Arg
            20                  25
```

<210> SEQ ID NO 158
<211> LENGTH: 25
<212> TYPE: PRT
<213> ORGANISM: Artificial Sequence
<220> FEATURE:
<223> OTHER INFORMATION: 25mer

<400> SEQUENCE: 158

```
Leu Trp Pro Arg Val Thr Tyr His Met Asn Lys Tyr Ala Tyr His Met
1               5                   10                  15

Leu Glu Arg Arg Ala Lys Tyr Lys Arg
            20                  25
```

<210> SEQ ID NO 159
<211> LENGTH: 25
<212> TYPE: PRT
<213> ORGANISM: Artificial Sequence
<220> FEATURE:
<223> OTHER INFORMATION: 25mer

<400> SEQUENCE: 159

```
Gly Gln Ser Leu Val Ile Ser Ala Ser Ile Ile Val Phe Asn Leu Leu
1               5                   10                  15

Glu Leu Glu Gly Asp Tyr Arg Asp Asp
            20                  25
```

<210> SEQ ID NO 160
<211> LENGTH: 25
<212> TYPE: PRT
<213> ORGANISM: Artificial Sequence
<220> FEATURE:
<223> OTHER INFORMATION: 25mer

<400> SEQUENCE: 160

```
Gly Ile Pro Val His Leu Glu Leu Ala Ser Met Thr Asn Met Glu Leu
1               5                   10                  15

Met Ser Ser Ile Val His Gln Gln Val
            20                  25
```

<210> SEQ ID NO 161
<211> LENGTH: 25
<212> TYPE: PRT
<213> ORGANISM: Artificial Sequence
<220> FEATURE:
<223> OTHER INFORMATION: 25mer

<400> SEQUENCE: 161

```
Arg Val Leu Glu Leu Phe Arg Ala Ala Gln Leu Ala Asn Asp Val Val
1               5                   10                  15

Leu Gln Ile Met Glu Leu Cys Gly Ala
            20                  25
```

<210> SEQ ID NO 162
<211> LENGTH: 25
<212> TYPE: PRT
<213> ORGANISM: Artificial Sequence
<220> FEATURE:
<223> OTHER INFORMATION: 25mer

<400> SEQUENCE: 162

```
His Arg Tyr Ser Leu Glu Glu Ile Leu Pro Tyr Leu Gly Trp Leu Val
1               5                   10                  15

Phe Ala Val Val Thr Thr Ser Phe Leu
            20                  25
```

<210> SEQ ID NO 163
<211> LENGTH: 25
<212> TYPE: PRT
<213> ORGANISM: Artificial Sequence
<220> FEATURE:
<223> OTHER INFORMATION: 25mer

<400> SEQUENCE: 163

```
Tyr Leu Ser Lys Asn Pro Asp Gly Tyr Cys Gly Leu Arg Gly Thr Gly
1               5                   10                  15

Val Ser Cys Pro Met Ala Ile Lys Lys
            20                  25
```

<210> SEQ ID NO 164
<211> LENGTH: 25
<212> TYPE: PRT
<213> ORGANISM: Artificial Sequence
<220> FEATURE:
<223> OTHER INFORMATION: 25mer

<400> SEQUENCE: 164

```
Asn Glu Ile Pro Phe Thr Tyr Glu Gln Leu Ser Ile Phe Lys His Lys
1               5                   10                  15

Leu Asp Lys Thr Tyr Pro Gln Gly Tyr
            20                  25
```

<210> SEQ ID NO 165
<211> LENGTH: 25
<212> TYPE: PRT
<213> ORGANISM: Artificial Sequence
<220> FEATURE:
<223> OTHER INFORMATION: 25mer

<400> SEQUENCE: 165

```
Ser Arg Ala Ser Leu Leu Gly Pro Gly Phe Val Leu Ile Trp Ile Pro
1               5                   10                  15

Ala Leu Leu Pro Ala Leu Arg Leu Ser
```

20 25

<210> SEQ ID NO 166
<211> LENGTH: 25
<212> TYPE: PRT
<213> ORGANISM: Artificial Sequence
<220> FEATURE:
<223> OTHER INFORMATION: 25mer

<400> SEQUENCE: 166

Asn Trp His Lys Gly Trp Asn Trp Ser Ser Gly His Asn Glu Cys Pro
1 5 10 15

Val Gly Ala Ser Cys His Pro Phe Thr
20 25

<210> SEQ ID NO 167
<211> LENGTH: 25
<212> TYPE: PRT
<213> ORGANISM: Artificial Sequence
<220> FEATURE:
<223> OTHER INFORMATION: 25mer

<400> SEQUENCE: 167

Lys Thr Leu Leu Lys Val Ser Lys Gly Gln Lys Met Asn Ala Gln Ala
1 5 10 15

Ile Ala Leu Val Ala Cys Tyr Leu Arg
20 25

<210> SEQ ID NO 168
<211> LENGTH: 25
<212> TYPE: PRT
<213> ORGANISM: Artificial Sequence
<220> FEATURE:
<223> OTHER INFORMATION: 25mer

<400> SEQUENCE: 168

Glu Ser Leu Lys Ile Ser Gln Ala Val His Ala Ala His Ala Glu Ile
1 5 10 15

Asn Glu Ala Gly Arg Glu Val Val Gly
20 25

<210> SEQ ID NO 169
<211> LENGTH: 25
<212> TYPE: PRT
<213> ORGANISM: Artificial Sequence
<220> FEATURE:
<223> OTHER INFORMATION: 25mer

<400> SEQUENCE: 169

Met Thr Glu Gln Gln Trp Asn Phe Ala Gly Ile Glu Ala Ala Ala Ser
1 5 10 15

Ala Ile Gln Gly Asn Val Thr Ser Ile
20 25

<210> SEQ ID NO 170
<211> LENGTH: 25
<212> TYPE: PRT
<213> ORGANISM: Artificial Sequence
<220> FEATURE:
<223> OTHER INFORMATION: 25mer

<400> SEQUENCE: 170

Asp Met Phe Asn Asn Phe Thr Val Ser Phe Trp Leu Arg Val Pro Lys
1 5 10 15

```
Val Ser Ala Ser His Leu Glu Gln Tyr
            20                  25


<210> SEQ ID NO 171
<211> LENGTH: 25
<212> TYPE: PRT
<213> ORGANISM: Artificial Sequence
<220> FEATURE:
<223> OTHER INFORMATION: 25mer

<400> SEQUENCE: 171

Thr Asn Arg Asn Thr Asp Gly Ser Thr Asp Tyr Gly Ile Leu Gln Ile
1               5                   10                  15

Asn Ser Arg Trp Trp Cys Asn Asp Gly
            20                  25


<210> SEQ ID NO 172
<211> LENGTH: 25
<212> TYPE: PRT
<213> ORGANISM: Artificial Sequence
<220> FEATURE:
<223> OTHER INFORMATION: 25mer

<400> SEQUENCE: 172

Thr Gly Met Glu Val Gly Trp Tyr Arg Ser Pro Phe Ser Arg Val Val
1               5                   10                  15

His Leu Tyr Arg Asn Gly Lys Asp Gln
            20                  25


<210> SEQ ID NO 173
<211> LENGTH: 14
<212> TYPE: PRT
<213> ORGANISM: Artificial Sequence
<220> FEATURE:
<223> OTHER INFORMATION: MHC-II

<400> SEQUENCE: 173

Gln Tyr Ile Lys Ala Asn Ser Lys Phe Ile Gly Ile Thr Glu
1               5                   10


<210> SEQ ID NO 174
<211> LENGTH: 9
<212> TYPE: PRT
<213> ORGANISM: Artificial Sequence
<220> FEATURE:
<223> OTHER INFORMATION: HLA A*02:01

<400> SEQUENCE: 174

Asp Leu Met Gly Tyr Ile Pro Ala Val
1               5


<210> SEQ ID NO 175
<211> LENGTH: 10
<212> TYPE: PRT
<213> ORGANISM: Artificial Sequence
<220> FEATURE:
<223> OTHER INFORMATION: HLA A*02:01

<400> SEQUENCE: 175

Phe Leu Pro Ser Asp Phe Phe Pro Ser Val
1               5                   10


<210> SEQ ID NO 176
<211> LENGTH: 9
<212> TYPE: PRT
<213> ORGANISM: Artificial Sequence
```

-continued

<220> FEATURE:
<223> OTHER INFORMATION: HLA A*02:01

<400> SEQUENCE: 176

Phe Leu Leu Thr Arg Ile Leu Thr Ile
1               5

<210> SEQ ID NO 177
<211> LENGTH: 9
<212> TYPE: PRT
<213> ORGANISM: Artificial Sequence
<220> FEATURE:
<223> OTHER INFORMATION: HLA A*02:01

<400> SEQUENCE: 177

Trp Leu Ser Leu Leu Val Pro Phe Val
1               5

<210> SEQ ID NO 178
<211> LENGTH: 9
<212> TYPE: PRT
<213> ORGANISM: Artificial Sequence
<220> FEATURE:
<223> OTHER INFORMATION: HLA A*02:01

<400> SEQUENCE: 178

Phe Leu Leu Ser Leu Gly Ile His Leu
1               5

<210> SEQ ID NO 179
<211> LENGTH: 9
<212> TYPE: PRT
<213> ORGANISM: Artificial Sequence
<220> FEATURE:
<223> OTHER INFORMATION: HLA A*02:01

<400> SEQUENCE: 179

Ile Leu Lys Glu Pro Val His Gly Val
1               5

<210> SEQ ID NO 180
<211> LENGTH: 10
<212> TYPE: PRT
<213> ORGANISM: Artificial Sequence
<220> FEATURE:
<223> OTHER INFORMATION: HLA A*02:01

<400> SEQUENCE: 180

Tyr Met Leu Asp Leu Gln Pro Glu Thr Thr
1               5                   10

<210> SEQ ID NO 181
<211> LENGTH: 9
<212> TYPE: PRT
<213> ORGANISM: Artificial Sequence
<220> FEATURE:
<223> OTHER INFORMATION: HLA A*02:01

<400> SEQUENCE: 181

Cys Ile Asn Gly Val Cys Trp Thr Val
1               5

<210> SEQ ID NO 182
<211> LENGTH: 10
<212> TYPE: PRT
<213> ORGANISM: Artificial Sequence
<220> FEATURE:

<223> OTHER INFORMATION: HLA A*02:01

<400> SEQUENCE: 182

Tyr Leu Leu Pro Arg Arg Gly Pro Arg Leu
1 5 10

<210> SEQ ID NO 183
<211> LENGTH: 9
<212> TYPE: PRT
<213> ORGANISM: Artificial Sequence
<220> FEATURE:
<223> OTHER INFORMATION: HLA A*02:01

<400> SEQUENCE: 183

Phe Leu Tyr Ala Leu Ala Leu Leu Leu
1 5

<210> SEQ ID NO 184
<211> LENGTH: 9
<212> TYPE: PRT
<213> ORGANISM: Artificial Sequence
<220> FEATURE:
<223> OTHER INFORMATION: HLA A*02:01

<400> SEQUENCE: 184

Ala Ala Gly Ile Gly Ile Leu Thr Val
1 5

<210> SEQ ID NO 185
<211> LENGTH: 9
<212> TYPE: PRT
<213> ORGANISM: Artificial Sequence
<220> FEATURE:
<223> OTHER INFORMATION: HLA A*02:01

<400> SEQUENCE: 185

Ser Leu Leu Met Trp Ile Thr Gln Val
1 5

<210> SEQ ID NO 186
<211> LENGTH: 9
<212> TYPE: PRT
<213> ORGANISM: Artificial Sequence
<220> FEATURE:
<223> OTHER INFORMATION: HLA A*03:01

<400> SEQUENCE: 186

Lys Leu Gly Gly Ala Leu Gln Ala Lys
1 5

<210> SEQ ID NO 187
<211> LENGTH: 9
<212> TYPE: PRT
<213> ORGANISM: Artificial Sequence
<220> FEATURE:
<223> OTHER INFORMATION: HLA A*03:01

<400> SEQUENCE: 187

Arg Leu Arg Ala Glu Ala Gln Val Lys
1 5

<210> SEQ ID NO 188
<211> LENGTH: 10
<212> TYPE: PRT
<213> ORGANISM: Artificial Sequence
<220> FEATURE:
<223> OTHER INFORMATION: HLA B*44:05

<400> SEQUENCE: 188

Glu Glu Asn Leu Leu Asp Phe Val Arg Phe
1 5 10

<210> SEQ ID NO 189
<211> LENGTH: 9
<212> TYPE: PRT
<213> ORGANISM: Artificial Sequence
<220> FEATURE:
<223> OTHER INFORMATION: HLA B*44:05

<400> SEQUENCE: 189

Glu Glu Tyr Leu Gln Ala Phe Thr Tyr
1 5

<210> SEQ ID NO 190
<211> LENGTH: 9
<212> TYPE: PRT
<213> ORGANISM: Artificial Sequence
<220> FEATURE:
<223> OTHER INFORMATION: MHC H~2KB

<400> SEQUENCE: 190

Asp Trp Glu Asn Val Ser Pro Glu Leu
1 5

<210> SEQ ID NO 191
<211> LENGTH: 8
<212> TYPE: PRT
<213> ORGANISM: Artificial Sequence
<220> FEATURE:
<223> OTHER INFORMATION: Peptide

<400> SEQUENCE: 191

Gln Gly Gln Asn Leu Lys Tyr Gln
1 5

<210> SEQ ID NO 192
<211> LENGTH: 8
<212> TYPE: PRT
<213> ORGANISM: Artificial Sequence
<220> FEATURE:
<223> OTHER INFORMATION: Peptide

<400> SEQUENCE: 192

Trp Gln Ala Gly Ile Leu Ala Arg
1 5

<210> SEQ ID NO 193
<211> LENGTH: 10
<212> TYPE: PRT
<213> ORGANISM: Artificial Sequence
<220> FEATURE:
<223> OTHER INFORMATION: Peptide

<400> SEQUENCE: 193

Tyr Val Tyr Val Ala Asp Val Ala Ala Lys
1 5 10

<210> SEQ ID NO 194
<211> LENGTH: 8
<212> TYPE: PRT
<213> ORGANISM: Artificial Sequence
<220> FEATURE:
<223> OTHER INFORMATION: Peptide -continued

```
<400> SEQUENCE: 194

Phe Leu Leu Thr Arg Ile Cys Thr
1               5


<210> SEQ ID NO 195
<211> LENGTH: 8
<212> TYPE: PRT
<213> ORGANISM: Artificial Sequence
<220> FEATURE:
<223> OTHER INFORMATION: Peptide

<400> SEQUENCE: 195

Ser Ile Asn Asn Phe Glu Lys Leu
1               5


<210> SEQ ID NO 196
<211> LENGTH: 9
<212> TYPE: PRT
<213> ORGANISM: Artificial Sequence
<220> FEATURE:
<223> OTHER INFORMATION: Peptide

<400> SEQUENCE: 196

Ser Pro Ser Tyr Val Tyr His Gln Phe
1               5
```

ALPHAVIRUS NEOANTIGEN VECTORS AND INTERFERON INHIBITORS

CROSS REFERENCE TO RELATED APPLICATIONS

This application is a U.S. National Phase Application of International Application No. PCT/US2019/060355, filed Nov. 7, 2019, which claims the benefit of U.S. Provisional Application No. 62/756,980 filed Nov. 7, 2018, each of which is hereby incorporated in its entirety by reference for all purposes.

SEQUENCE LISTING

The instant application contains a Sequence Listing which has been submitted via Patent Center and is hereby incorporated herein by reference in its entirety. Said ASCII copy, created on Oct. 8, 2024 is named GSO-023WOUS_ST25.txt, and is 455,929 bytes in size.

BACKGROUND

Therapeutic vaccines based on tumor-specific antigens hold great promise as a next-generation of personalized cancer immunotherapy. 1-3 For example, cancers with a high mutational burden, such as non-small cell lung cancer (NSCLC) and melanoma, are particularly attractive targets of such therapy given the relatively greater likelihood of neoantigen generation.[4,5] Early evidence shows that neoantigen-based vaccination can elicit T-cell responses[6] and that neoantigen targeted cell-therapy can cause tumor regression under certain circumstances in selected patients.[7]

In addition to the challenges of current neoantigen prediction methods certain challenges also exist with the available vector systems that can be used for neoantigen delivery in humans, many of which are derived from humans. For example, many humans have pre-existing immunity to human viruses as a result of previous natural exposure, and this immunity can be a major obstacle to the use of recombinant human viruses for neoantigen delivery for cancer treatment.

Alphavirus-based vectors have been used a delivery platform. However, immune responses to the alphavirus-based vectors may reduce the efficacy as a delivery platform.

Improved delivery methods, particularly in the case of alphavirus-based vectors, such as in the case of cancer vaccines, are still needed.

SUMMARY

Disclosed herein is a method for stimulating an immune response in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence (SEQ ID NO: 57); and (b) a cassette, wherein the cassette comprises: (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence; (ii) optionally, a second promoter nucleotide sequence operably linked to the at least one nucleic acid sequence; and (iii) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus.

Also disclosed herein is a method for stimulating an immune response in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises the nucleic acid sequence set forth in SEQ ID NO: 6, wherein the RNA alphavirus backbone sequence comprises a 26S promoter nucleotide sequence and a poly(A) sequence (SEQ ID NO: 57), wherein the 26S promoter sequence is endogenous to the RNA alphavirus backbone, and wherein the poly(A) sequence (SEQ ID NO: 57) is endogenous to the RNA alphavirus backbone; and (b) a cassette integrated between the 26S promoter nucleotide sequence and the poly(A) sequence (SEQ ID NO: 57), wherein the cassette is operably linked to the 26S promoter nucleotide sequence, and wherein the cassette comprises at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that takes the encoded epitope sequence distinct from the corresponding peptide sequence encoded by a wild-type nucleic acid sequence, b. optionally a 5' linker sequence, and c. optionally a 3' linker sequence; and wherein the inhibitor of Type I interferon signaling comprises an anti-IFNαβ receptor (IFNAR) blocking antibody.

Also disclosed herein is a method for treating a subject with cancer, the method comprising administering to the subject a therapeutically effective amount of a composition for delivery of an expression system and administering to the subject therapeutically effective amount of an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence (SEQ ID NO: 57); and (b) a cassette, wherein the cassette comprises: (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence; (ii) optionally, a second promoter nucleotide sequence operably linked to the at least one nucleic acid sequence; and (iii) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus.

Also disclosed herein is a method for reducing tumor volume in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence (SEQ ID NO: 57); and (b) a cassette, wherein the cassette comprises: (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence; (ii) optionally, a second promoter nucleotide sequence operably linked to the at least one nucleic acid sequence; and (iii) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus.

Also disclosed herein is a method for stimulating a tumor specific immune response in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence (SEQ ID NO: 57); and (b) a cassette, wherein the cassette comprises: (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence; (ii) optionally, a second promoter nucleotide sequence operably linked to the at least one nucleic acid sequence; and (iii) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus.

Also disclosed herein is a method of enhancing delivery of an alphavirus-based expression system, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence (SEQ ID NO: 57); and (b) a cassette, wherein the cassette comprises: (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence; (ii) optionally, a second promoter nucleotide sequence operably linked to the at least one nucleic acid sequence; and (iii) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus.

In some aspects, the at least one nucleic acid sequence comprises the polypeptide-encoding nucleic acid sequence. In some aspects, the polypeptide-encoding nucleic acid sequence encodes the antigen-encoding nucleic acid sequence. In some aspects, the antigen-encoding nucleic acid sequence is the epitope-encoding nucleic acid sequence. In some aspects, the antigen-encoding nucleic acid sequence encodes a polypeptide sequence capable of undergoing antigen processing into the encoded epitope. In some aspects, the epitope-encoding nucleic acid sequence encodes an epitope known or suspected to be presented by MHC class I on a surface of a cell, optionally wherein the surface of the cell is a tumor cell surface or an infected cell surface, and optionally wherein the cell is the subject's cell. In some aspects, the cell is a tumor cell selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T cell lymphocytic leukemia, non-small cell lung cancer, and small cell lung cancer, or wherein the cell is an infected cell selected from the group consisting of: a pathogen infected cell, a virally infected cell, a bacterially infected cell, an fungally infected cell, and a parasitically infected cell. In some aspects, the virally infected cell is an HIV infected cell.

In some aspects, the polypeptide-encoding nucleic acid sequence encodes a full-length protein or functional portion thereof. In some aspects, the full-length protein or functional portion thereof is selected from the group consisting of: an antibody, a cytokine, a chimeric antigen receptor (CAR), a T-cell receptor, and a genome-editing system nuclease.

In some aspects, the at least one nucleic acid sequence comprises a non-coding nucleic acid sequence. In some aspects, the non-coding nucleic acid sequence is an RNA interference (RNAi) polynucleotide or genome-editing system polynucleotide.

In some aspects, the cassette comprises: i) the at least one nucleic acid sequence comprising the polypeptide-encoding nucleic acid sequence, wherein the polypeptide-encoding nucleic acid sequence is an antigen-encoding nucleic acid sequence comprising: a. an epitope-encoding nucleic acid sequence, optionally comprising at least one alteration that makes the encoded epitope sequence distinct from the corresponding peptide sequence encoded by a wild-type nucleic acid sequence b. optionally a 5' linker sequence, and c. optionally a 3' linker sequence; (ii) optionally, a second promoter nucleotide sequence operably linked to the antigen-encoding nucleic acid sequence; (iii) optionally, at least one MHC class II epitope-encoding nucleic acid sequence; (iv) optionally, at least one nucleic acid sequence encoding a GPGPG amino acid linker sequence (SEQ ID NO: 56); and (v) optionally, at least one second poly(A) sequence (SEQ ID NO: 57), wherein the second poly(A) sequence (SEQ ID NO: 57) is a native poly(A) sequence (SEQ ID NO: 57) or an exogenous poly(A) sequence (SEQ ID NO: 57) to the alphavirus. In some aspects, an ordered sequence of each element of the cassette is described in the formula, from 5' to 3', comprising $$P_a\text{-}(L5_b\text{-}N_c\text{-}L3_d)_X\text{-}(G5_e\text{-}U_f)_Y\text{-}G3_g$$

wherein P comprises the second promoter nucleotide sequence, where a=0 or 1, N comprises one of the epitope-encoding nucleic acid sequences, wherein the epitope-encoding nucleic acid sequence comprises an MHC class I epitope-encoding nucleic acid sequence, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker (SEQ ID NO: 56), where e=0 or 1, G3 comprises one of the at least one nucleic acid sequences encoding a GPGPG amino acid linker (SEQ ID NO: 56), where g=0 or 1, U comprises one of the at least one MHC class II epitope-encoding nucleic acid sequence, where f=1, X=1 to 400, where for each X the corresponding $N_c$ is an epitope-encoding nucleic acid sequence, and Y=0, 1, or 2, where for each Y the corresponding $U_f$ is an epitope-encoding nucleic acid sequence. In some aspects, for each X the corresponding $N_c$ is a distinct MHC class I epitope-encoding nucleic acid sequence. In some aspects, for each Y the corresponding $U_f$ is a distinct MHC class II epitope-encoding nucleic acid sequence. In some aspects, a=0, b=1, d=1, e=1, g=1, h=1, X=20, Y=2, the at least one promoter nucleotide sequence is a single 26S promoter nucleotide sequence provided by the RNA alphavirus backbone, the at least one polyadenylation poly(A) sequence (SEQ ID NO: 57) is a poly(A) sequence (SEQ ID NO: 57) of at least 100 consecutive A nucleotides provided by the RNA alphavirus backbone, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native C-terminal amino acid sequence of the MHC I epitope, and wherein the 3' linker sequence encodes a peptide that is at least 3 amino acids in length, U is each of a PADRE class II sequence and a Tetanus toxoid MHC class II sequence, the RNA alphavirus backbone is the sequence set forth in SEQ ID NO: 6, and each of the MHC class I epitope-encoding nucleic acid sequences encodes a polypeptide that is between 13 and 25 amino acids in length.

In some aspects, the composition for delivery of the expression system further comprises a nanoparticulate delivery vehicle. In some aspects, the nanoparticulate delivery vehicle is a lipid nanoparticle (LNP). In some aspects, the LNP comprises ionizable amino lipids. In some aspects, the ionizable amino lipids comprise MC3-like (dilinoleylmethyl-4-dimethylaminobutyrate) molecules. In some aspects, the nanoparticulate delivery vehicle encapsulates the expression system.

In some aspects, the composition for delivery of the expression system further comprises a plurality of LNPs, wherein the LNPs comprise: the neoantigen expression system; a cationic lipid; a non-cationic lipid; and a conjugated lipid that inhibits aggregation of the LNPs, wherein at least about 95% of the LNPs in the plurality of LNPs either: have a non-lamellar morphology; or are electron-dense. In some aspects, the non-cationic lipid is a mixture of (1) a phospholipid and (2) cholesterol or a cholesterol derivative.

In some aspects, the conjugated lipid that inhibits aggregation of the LNPs is a polyethyleneglycol (PEG)-lipid conjugate. In some aspects, the PEG-lipid conjugate is selected from the group consisting of: a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof. In some aspects the PEG-DAA conjugate is a member selected from the group consisting of: a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In some aspects, the composition for delivery of the expression system is fully encapsulated in the LNPs.

In some aspects, the non-lamellar morphology of the LNPs comprises an inverse hexagonal ($H_{II}$) or cubic phase structure.

In some aspects, the cationic lipid comprises from about 10 mol % to about 50 mol % of the total lipid present in the LNPs. In some aspects, the cationic lipid comprises from about 20 mol % to about 50 mol % of the total lipid present in the LNPs. In some aspects, the cationic lipid comprises from about 20 mol % to about 40 mol % of the total lipid present in the LNPs.

In some aspects, the non-cationic lipid comprises from about 10 mol % to about 60 mol % of the total lipid present in the LNPs. In some aspects, the non-cationic lipid comprises from about 20 mol % to about 55 mol % of the total lipid present in the LNPs. In some aspects, the non-cationic lipid comprises from about 25 mol % to about 50 mol % of the total lipid present in the LNPs.

In some aspects, the conjugated lipid comprises from about 0.5 mol % to about 20 mol % of the total lipid present in the LNPs. In some aspects, the conjugated lipid comprises from about 2 mol % to about 20 mol % of the total lipid present in the LNPs. In some aspects, the conjugated lipid comprises from about 1.5 mol % to about 18 mol % of the total lipid present in the LNPs.

In some aspects, greater than 95% of the LNPs have a non-lamellar morphology. In some aspects, greater than 95% of the LNPs are electron dense.

In some aspects, the composition for delivery of the expression system further comprises a plurality of LNPs, wherein the LNPs comprise: a cationic lipid comprising from 50 mol % to 65 mol % of the total lipid present in the LNPs; a conjugated lipid that inhibits aggregation of LNPs comprising from 0.5 mol % to 2 mol % of the total lipid present in the LNPs; and a non-cationic lipid comprising either: a mixture of a phospholipid and cholesterol or a derivative thereof, wherein the phospholipid comprises from 4 mol % to 10 mol % of the total lipid present in the LNPs and the cholesterol or derivative thereof comprises from 30 mol % to 40 mol % of the total lipid present in the LNPs; a mixture of a phospholipid and cholesterol or a derivative thereof, wherein the phospholipid comprises from 3 mol % to 15 mol % of the total lipid present in the LNPs and the cholesterol or derivative thereof comprises from 30 mol % to 40 mol % of the total lipid present in the LNPs; or up to 49.5 mol % of the total lipid present in the LNPs and comprising a mixture of a phospholipid and cholesterol or a derivative thereof, wherein the cholesterol or derivative thereof comprises from 30 mol % to 40 mol % of the total lipid present in the LNPs.

In some aspects, the composition for delivery of the expression system further comprises a plurality of LNPs, wherein the LNPs comprise: a cationic lipid comprising from 50 mol % to 85 mol % of the total lipid present in the LNPs; a conjugated lipid that inhibits aggregation of LNPs comprising from 0.5 mol % to 2 mol % of the total lipid present in the LNPs; and a non-cationic lipid comprising from 13 mol % to 49.5 mol % of the total lipid present in the LNPs.

In some aspects, the phospholipid comprises dipalmitoylphosphatidylcholine (DPPC), distearoylphosphatidylcholine (DSPC), or a mixture thereof.

In some aspects, the conjugated lipid comprises a polyethyleneglycol (PEG)-lipid conjugate. In some aspects, the PEG-lipid conjugate comprises a PEG-diacylglycerol (PEG-DAG) conjugate, a PEG-dialkyloxypropyl (PEG-DAA) conjugate, or a mixture thereof. In some aspects, the PEG-DAA conjugate comprises a PEG-dimyristyloxypropyl (PEG-DMA) conjugate, a PEG-distearyloxypropyl (PEG-DSA) conjugate, or a mixture thereof. In some aspects, the PEG portion of the conjugate has an average molecular weight of about 2,000 daltons.

In some aspects, the conjugated lipid comprises from 1 mol % to 2 mol % of the total lipid present in the LNPs.

In some aspects, the LNP comprises a compound having a structure of Formula I:

I

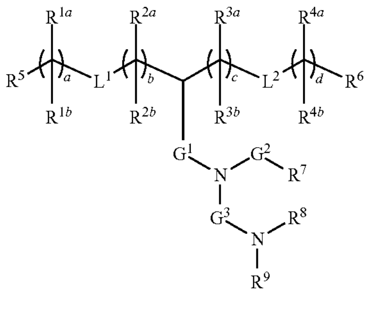

or a pharmaceutically acceptable salt, tautomer, prodrug or stereoisomer thereof, wherein: L' and L2 are each independently —O(C═O)—, —(C═O)O—, —C(═O)—, —O—, —$S(O)_x$—, —S—S—, —C(═O)S—, —SC(═O)—, —$R^aC$(═O)—, —C(═O)$R^a$—, —$R^aC$(═O)$R^a$—, —OC(═O)$R^a$—, —$R^aC$(═O)O— or a direct bond; $G^1$ is Ci-$C_2$ alkylene, —(C═O)—, —O(C═O)—, —SC(═O)—, —$R^aC$(═O)— or a direct bond: —C(═O)—, —(C═O)O—, —C(═O)S—, —C(═O)$R^a$— or a direct bond; G is Ci-$C_6$ alkylene; $R^a$ is H or C1-C12 alkyl; $R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond; $R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently H or methyl; $R^7$ is $C_4$-$C_{20}$ alkyl; $R^8$ and $R^9$ are each independently $C_1$-$C_{12}$ alkyl; or $R^8$ and $R^9$, together with the nitrogen atom to which they are attached, form a 5, 6 or 7-membered heterocyclic ring; a, b, c and d are each independently an integer from 1 to 24; and x is 0, 1 or 2.

In some aspects, the LNP comprises a compound having a structure of Formula II:

II

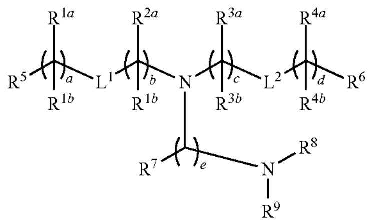

or a pharmaceutically acceptable salt, tautomer, prodrug or stereoisomer thereof, wherein:

$L^1$ and $L^2$ are each independently —O(C═O)—, —(C═O)O— or a carbon-carbon double bond; $R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl; $R^7$ is, at each occurrence, independently H or $C_1$-$C_{12}$ alkyl; $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom; a and d are each independently an integer from 0 to 24; b and c are each independently an integer from 1 to 24; and e is 1 or 2, provided that: at least one of $R^{1a}$, $R^{2a}$, $R^{3a}$ or $R^{4a}$ is C1-C12 alkyl, or at least one of $L^1$ or $L^2$ is-O(C═O)— or —(C═O)O—; and $R^{1a}$ and $R^{1b}$ are not isopropyl when a is 6 or n-butyl when a is 8.

In some aspects, any of the above compositions further comprise one or more excipients comprising a neutral lipid, a steroid, and a polymer conjugated lipid. In some aspects, the neutral lipid comprises at least one of 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), and 1,2-Dioleoyl-sn-glycero-3-phosphoethanolamine (DOPE). In some aspects, the neutral lipid is DSPC.

In some aspects, the molar ratio of the compound to the neutral lipid ranges from about 2:1 to about 8:1.

In some aspects, the steroid is cholesterol. In some aspects, the molar ratio of the compound to cholesterol ranges from about 2:1 to 1:1.

In some aspects, the polymer conjugated lipid is a pegylated lipid. In some aspects, the molar ratio of the compound to the pegylated lipid ranges from about 100:1 to about 25:1. In some aspects, the pegylated lipid is PEG-DAG, a PEG polyethylene (PEG-PE), a PEG-succinoyl-diacylglycerol (PEG-S-DAG), PEG-cer or a PEG dialkoxypropylcarbamate. In some aspects, the pegylated lipid has the following structure III:

III

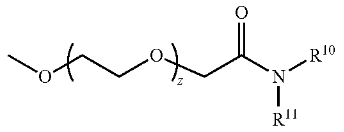

or a pharmaceutically acceptable salt, tautomer or stereoisomer thereof, wherein: $R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60. In some aspects, $R^{10}$ and $R^{11}$ are each independently straight, saturated alkyl chains having 12 to 16 carbon atoms. In some aspects, the average z is about 45.

In some aspects, the LNP self-assembles into non-bilayer structures when mixed with polyanionic nucleic acid. In some aspects, the non-bilayer structures have a diameter between 60 nm and 120 nm. In some aspects, the non-bilayer structures have a diameter of about 70 nm, about 80 nm, about 90 nm, or about 100 nm. In some aspects, wherein the nanoparticulate delivery vehicle has a diameter of about 100 nm.

In some aspects, the inhibitor of Type I interferon signaling is selected from the group consisting of: an IFNα inhibitor, an IFNβ inhibitor, an IFNAR inhibitor, and a Type I interferon signaling pathway inhibitor. In some aspects, the inhibitor of Type I interferon signaling is selected from the group consisting of: an antibody or an antigen-binding fragment thereof, a small molecule inhibitor, a RNAi polynucleotide, a genome-editing system, and an Fc-fusion protein. In some aspects, antibody is selected from the group consisting of: an anti-IFNα antibody, an anti-IFNαβ antibody, an anti-IFNαβ receptor (IFNAR) blocking antibody. In some aspects, the anti-IFNα antibody is selected from the group consisting of: Sifalimumab, Rontalizumab, and ASG-009. In some aspects, the anti-IFNAR blocking antibody is selected from the group consisting of: MAR1-5A3, Anifrolumab, AmS3A5-1, 64G12, H2K6, H2K1, H3K6, H3K1 3F11, 4G5, 11E2, and 9D4. In some aspects, the Type I interferon signaling pathway inhibitor comprises a JAK kinase inhibitor. In some aspects, the JAK kinase inhibitor comprises a small molecule. In some aspects, the JAK kinase inhibitor comprises a JAK1/2 inhibitor or a JAK1/3 inhibitor. In some aspects, the JAK1/3 inhibitor is Tofacitinib.

In some aspects, the inhibitor of Type I interferon signaling is administered before, concurrently with, or after administration of the composition for delivery of the expression system. In some aspects, the inhibitor of Type I interferon signaling is administered 24 hours or less before administration of the composition for delivery of the expression system. In some aspects, the inhibitor of Type I interferon signaling is administered less than 12 hours after administration of the composition for delivery of the expression system. In some aspects, the inhibitor of Type I interferon signaling is administered 6 hours or less after administration of the composition for delivery of the expression system. In some aspects, the inhibitor of Type I interferon signaling is administered between 24 hours before and 6 hours or less after administration of the composition for delivery of the expression system.

In some aspects, the composition for delivery of the expression system is administered intramuscularly (IM), intradermally (ID), subcutaneously (SC), or intravenously (IV). In some aspects, the composition for delivery of the expression system is administered intramuscularly (IM).

In some aspects, the inhibitor of Type I interferon signaling is administered intramuscularly (IM), intradermally (ID), subcutaneously (SC), or intravenously (IV). In some aspects, the inhibitor of Type I interferon signaling is administered intramuscularly (IM). In some aspects, the inhibitor of Type I interferon signaling is administered intravenously (IV).

In some aspects, a single administration of the inhibitor of Type I interferon signaling is administered.

In some aspects, the cassette is integrated between the at least one promoter nucleotide sequence and the at least one poly(A) sequence (SEQ ID NO: 57). In some aspects, the at least one promoter nucleotide sequence is operably linked to the cassette.

In some aspects, the one or more vectors comprise one or more +-stranded RNA vectors. In some aspects, the one or more +-stranded RNA vectors comprise a 5',7-methylguanosine (m7 g) cap. In some aspects, the one or more +-stranded RNA vectors are produced by in vitro transcription.

In some aspects, the one or more vectors are self-replicating within a mammalian cell.

In some aspects, the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the RNA alphavirus backbone comprises at least one nucleotide sequence of a Venezuelan equine encephalitis virus. In some aspects, the RNA alphavirus backbone comprises at least sequences for nonstructural protein-mediated amplification, a 26S promoter sequence, a poly(A) sequence (SEQ ID NO: 57), a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the RNA alphavirus backbone comprises at least sequences for nonstructural protein-mediated amplification, a 26S promoter sequence, and a poly(A) sequence (SEQ ID NO: 57) encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof. In some aspects, the RNA alphavirus backbone does not encode structural virion proteins capsid, E2 and E1. In some aspects, the cassette is inserted in place of structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus.

In some aspects, the Venezuelan equine encephalitis virus comprises the sequence of SEQ ID NO: 3 or SEQ ID NO: 5. In some aspects, the Venezuelan equine encephalitis virus comprises the sequence of SEQ ID NO: 3 or SEQ ID NO: 5 further comprising a deletion between base pair 7544 and 11175. In some aspects, the RNA alphavirus backbone comprises the sequence set forth in SEQ ID NO: 6 or SEQ ID NO: 7. In some aspects, the cassette is inserted at position 7544 to replace the deletion between base pairs 7544 and 11175 as set forth in the sequence of SEQ ID NO: 3 or SEQ ID NO: 5 In some aspects, the insertion of the cassette provides for transcription of a polycistronic RNA comprising the nsP1-4 genes and the at least one nucleic acid sequence, wherein the nsP1-4 genes and the at least one nucleic acid sequence are in separate open reading frames.

In some aspects, the at least one promoter nucleotide sequence is the native 26S promoter nucleotide sequence encoded by the RNA alphavirus backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more vectors are each at least 300 nt in size. In some aspects, the one or more vectors are each at least 1 kb in size. In some aspects, the one or more vectors are each 2 kb in size. In some aspects, the one or more vectors are each less than 5 kb in size.

In some aspects, at least one of the epitope-encoding nucleic acid sequences encodes an epitope that, when expressed and translated, is capable of being presented by MHC class I on a cell of the subject. In some aspects, at least one of the epitope-encoding nucleic acid sequences encodes an epitope that, when expressed and translated, is capable of being presented by MHC class II on a cell of the subject.

In some aspects, the at least one nucleic acid sequence comprises two or more nucleic acid sequences. In some aspects, the at least one nucleic acid sequence comprises two or more polypeptide-encoding nucleic acid sequences. In some aspects, each polypeptide-encoding nucleic acid sequence is linked directly to one another.

In some aspects, each polypeptide-encoding nucleic acid sequence is linked to a distinct polypeptide-encoding nucleic acid sequence with a nucleic acid sequence encoding a linker. In some aspects, the polypeptide-encoding nucleic acid sequence is an antigen-encoding nucleic acid sequence, and wherein the linker links two MHC class I epitope-encoding nucleic acid sequences or an MHC class I epitope-encoding nucleic acid sequence to an MHC class II epitope-encoding nucleic acid sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the polypeptide-encoding nucleic acid sequence is an antigen-encoding nucleic acid sequence, and wherein the linker links two MHC class II epitope-encoding nucleic acid sequences or an MHC class II sequence to an MHC class I epitope-encoding nucleic acid sequence. In some aspects, the linker comprises the sequence GPGPG (SEQ ID NO: 56).

In some aspects, the polypeptide-encoding nucleic acid sequence is an antigen-encoding nucleic acid sequence, and wherein the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, the epitope-encoding nucleic acid sequence comprises at least one alteration that makes the encoded epitope have increased binding affinity to its corresponding MHC allele relative to the translated, corresponding wild-type nucleic acid sequence. In some aspects, the epitope-encoding nucleic acid sequence comprises at least one alteration that makes the encoded epitope have increased binding stability to its corresponding MHC allele relative to the translated, corresponding wild-type nucleic acid sequence. In some aspects, the epitope-encoding nucleic acid sequence comprises at least one alteration that makes the encoded epitope have an increased likelihood of presentation on its corresponding MHC allele relative to the translated, corresponding wild-type nucleic acid sequence. In some aspects, the at least one alteration comprises a point mutation, a frameshift mutation, a non-frameshift mutation, a deletion mutation, an insertion mutation, a splice variant, a genomic rearrangement, or a proteasome-generated spliced antigen.

In some aspects, the subject is known or suspected to have cancer. In some aspects, stimulating the immune response treats the cancer. In some aspects, the cancer is selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer In some aspects, the subject has one or more tumors. In some aspects, stimulating the immune response reduces tumor volume of the one or more tumors.

In some aspects, the at least one nucleic acid sequence comprises at least 2-10, 2, 3, 4, 5, 6, 7, 8, 9, or 10 nucleic acid sequences, optionally wherein each nucleic acid sequence encodes a distinct non-coding nucleic acid sequence, a distinct polypeptide-encoding nucleic acid sequence, or a combination thereof. In some aspects, the at least one nucleic acid sequence comprises at least 11-20, 15-20, 11-100, 11-200, 11-300, 11-400, 11, 12, 13, 14, 15, 16, 17, 18, 19, 20 or up to 400 nucleic acid sequences, optionally wherein each nucleic acid sequence encodes a distinct non-coding nucleic acid sequence, a distinct polypeptide-encoding nucleic acid sequence, or a combination thereof. In some aspects, In some aspects, the at least one nucleic acid sequence comprises at least 2-10, 2, 3, 4, 5, 6, 7, 8, 9, or 10 polypeptide-encoding nucleic acid sequences. In some aspects, the at least one nucleic acid sequence comprises at least 11-20, 15-20, 11-100, 11-200, 11-300, 11-400, 11, 12, 13, 14, 15, 16, 17, 18, 19, 20 or up to 400 polypeptide-encoding nucleic acid sequences. In some aspects, the at least one nucleic acid sequence comprises at least 2-10, 2, 3, 4, 5, 6, 7, 8, 9, or 10 antigen-encoding nucleic acid sequences. In some aspects, the at least one nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one nucleic acid sequence comprises at least 2-400 antigen-encoding nucleic acid sequences and wherein at least two of the antigen-encoding nucleic acid sequences encode polypeptide sequences or portions thereof that are presented by MHC class I on a cell surface. In some aspects, at least two of the MHC class I epitopes are presented by MHC class I on the tumor cell surface.

In some aspects, when administered to the subject and translated, at least one of the epitopes encoded by the epitope-encoding nucleic acid sequence are presented on antigen presenting cells resulting in an immune response targeting a cell presenting at least one of the epitopes on the cell surface.

In some aspects, the epitope-encoding nucleic acid sequences comprises at least one MHC class I epitope-encoding nucleic acid sequence or MHC class II epitope-encoding nucleic acid sequence, and, when administered to the subject and translated, at least one of the MHC class I or class II epitopes are presented on antigen presenting cells resulting in an immune response targeting a cell presenting at least one of the epitopes on the cell surface, and optionally wherein the expression of each of the MHC class I and/or class II epitope-encoding nucleic acid sequences is driven by the at least one promoter nucleotide sequence.

In some aspects, the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence.

In some aspects, the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length.

In some aspects, the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible.

In some aspects, the at least one poly(A) sequence (SEQ ID NO: 57) comprises a poly(A) sequence (SEQ ID NO: 57) native to the alphavirus. In some aspects, the at least one poly(A) sequence (SEQ ID NO: 57) comprises a poly(A) sequence (SEQ ID NO: 57) exogenous to the alphavirus. In some aspects, the at least one poly(A) sequence is operably linked to at least one of the at least one nucleic acid sequences. In some aspects, the at least one poly(A) sequence (SEQ ID NO: 57) is at least 20, at least 30, at least 40, at least 50, at least 60, at least 70, at least 80, or at least 90 consecutive A nucleotides. In some aspects, the at least one poly(A) sequence (SEQ ID NO: 57) is at least 100 consecutive A nucleotides.

In some aspects, the cassette further comprises at least one of: an intron sequence, a woodchuck hepatitis virus post-transcriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one nucleic acid sequences.

In some aspects, the cassette further comprises a reporter gene, including but not limited to, green fluorescent protein (GFP), a GFP variant, secreted alkaline phosphatase, luciferase, a luciferase variant, or a detectable peptide or epitope.

In some aspects, the detectable peptide or epitope is selected from the group consisting of an HA tag, a Flag tag, a His-tag, or a V5 tag.

In some aspects, the one or more vectors further comprises one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES; or the heavy and light chain sequences of the antibody are linked by a flexible linker such as consecutive glycine residues. In some aspects, the immune modulator is a cytokine. In some aspects, the cytokine is at least one of IL-2, IL-7, IL-12, IL-15, or IL-21 or variants thereof of each.

In some aspects, the epitope-encoding nucleic acid sequence comprises a MHC class I epitope-encoding nucleic acid sequence, and wherein the MHC class I epitope-encoding nucleic acid sequence is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the tumor cell surface of the tumor, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence.

In some aspects, each of the MHC class I epitope-encoding nucleic acid sequences is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of epitopes; (b) inputting the peptide sequence of each epitope into a presentation model to generate a set of numerical likelihoods that each of the epitopes is presented by one or more of the MHC alleles on the tumor cell surface of the tumor, the set of numerical likelihoods having been identified at least based on received mass spectrometry data; and (c) selecting a subset of the set of epitopes based on the set of numerical likelihoods to generate a set of selected epitopes which are used to generate the at least 20 MHC class I epitope-encoding nucleic acid sequences. In some aspects, a number of the set of selected epitopes is 2-20. In some aspects, the presentation model represents dependence between: (a) presence of a pair of a particular one of the MHC alleles and a particular amino acid at a particular position of a peptide sequence; and (b) likelihood of presentation on the tumor cell surface, by the particular one of the MHC alleles of the pair, of such a peptide sequence comprising the particular amino acid at the particular position.

In some aspects, selecting the set of selected epitopes comprises selecting epitopes that have an increased likelihood of being presented on the tumor cell surface relative to unselected epitopes based on the presentation model. In some aspects, selecting the set of selected epitopes comprises selecting epitopes that have an increased likelihood of being capable of inducing a tumor-specific immune response in the subject relative to unselected epitopes based on the presentation model. In some aspects, selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC). In some aspects, selecting the set of selected epitopes comprises selecting epitopes that have a decreased likelihood of being subject to inhibition via central or peripheral tolerance relative to unselected epitopes based on the presentation model. In some aspects, selecting the set of selected epitopes comprises selecting epitopes that have a decreased likelihood of being capable of inducing an autoimmune response to normal tissue in the subject relative to unselected epitopes based on the presentation model. In some aspects, exome or transcriptome nucleotide sequencing data is obtained by performing sequencing on the tumor tissue. In some aspects, the sequencing is next generation sequencing (NGS) or any massively parallel sequencing approach.

In some aspects, the cassette comprises junctional epitope sequences formed by adjacent sequences in the cassette. In some aspects, at least one or each junctional epitope sequence has an affinity of greater than 500 nM for MHC. In some aspects, each junctional epitope sequence is non-self.

In some aspects, the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the cassette. In some aspects, the prediction is based on presentation likelihoods generated by inputting sequences of the non-therapeutic epitopes into a presentation model. In some aspects, an order of the antigen-encoding nucleic acid sequences in the cassette is determined by a series of steps comprising: (a) generating a set of candidate cassette sequences corresponding to different orders of the antigen-encoding nucleic acid sequences; (b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine.

In some aspects, the composition for delivery of the expression system and/or the inhibitor of Type I interferon signaling are formulated in a pharmaceutical composition comprising a pharmaceutically acceptable carrier. In some aspects, the method further comprises administering an adjuvant.

Also disclosed herein is a kit comprising the composition for delivery of the expression system and the inhibitor of Type I interferon signaling of any of the methods described herein, and instructions for use.

In some aspects, the epitope-encoding nucleic acid sequences derived are derived from a tumor of the subject. In some aspects, the epitope-encoding nucleic acid sequences are not derived from a tumor of the subject.

In some aspects, the method further comprises administration of one or more immune modulators, optionally wherein the immune modulator is administered before, concurrently with, or after administration of the composition for delivery of the expression system and/or the inhibitor of Type I interferon signaling, or pharmaceutical compositions thereof. In some aspects, the one or more immune modulators are selected from the group consisting of: an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the immune modulator is administered intravenously (IV), intramuscularly (IM), intradermally (ID), or subcutaneously (SC). In some aspects, the subcutaneous administration is near the site of the expression system administration site or in close proximity to one or more draining lymph nodes for the expression system.

In some aspects, the method further comprises administering to the subject a second vaccine composition. In some aspects, the second vaccine composition is administered prior to the administration of the composition for delivery of the expression system and/or the inhibitor of Type I interferon signaling, or pharmaceutical compositions thereof. In some aspects, the second vaccine composition is administered subsequent to the administration of the composition for delivery of the expression system and/or the inhibitor of Type I interferon signaling, or pharmaceutical compositions thereof. In some aspects, the second vaccine composition is the same as the composition for delivery of the expression system or pharmaceutical compositions thereof. In some aspects, the second vaccine composition is different from the composition for delivery of the expression system or pharmaceutical compositions thereof. In some aspects, the second vaccine composition comprises a chimpanzee adenovirus vector encoding at least one antigen-encoding nucleic acid sequence. In some aspects, the at least one antigen-encoding nucleic acid sequence encoded by the chimpanzee adenovirus vector is the same as the antigen-encoding nucleic acid sequence of any of the above method claims. In some aspects, a second administration of the inhibitor of Type I interferon signaling, or pharmaceutical compositions thereof, is administered before, concurrently with, or after administration of the second vaccine composition.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5B (SEQ ID NOs: 73-77, SEQ ID NOs: 174-189) illustrates in vivo evaluation of the impact of epitope position in long 21-mer cassettes and shows the sequence information on the T cell epitopes used.

FIG. 6B (SEQ ID NO: 49, SEQ ID NOs: 73-77, SEQ ID NOs: 103-108, SEQ ID NOs: 133-134, SEQ ID NOs: 136-141, SEQ ID NO: 173, SEQ ID NO: 190) illustrates final cassette design for preclinical IND-enabling studies and shows the sequence information for the T cell epitopes used that are presented on class I MHC of non-human primate, mouse and human origin, as well as sequences of 2 universal MHC class II epitopes PADRE and Tetanus toxoid.

DETAILED DESCRIPTION

I. Definitions

Figure 1:
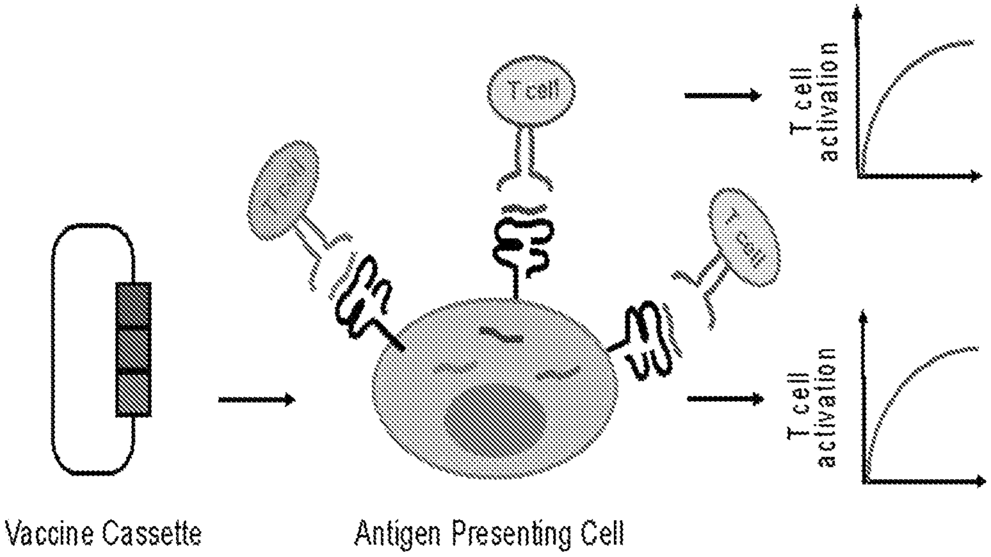
FIG. 1 illustrates development of an in vitro T cell activation assay. Schematic of the assay in which the delivery of a vaccine cassette to antigen presenting cells, leads to expression, epitope-processing and MHC-restricted presentation of distinct peptide antigens. Reporter T cells engineered with T cell receptors that match the specific peptide-MHC combination become activated resulting in luciferase expression.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response. An antigen can be a neoantigen. An antigen can be a "shared antigen" that is an antigen found among a specific population, e.g., a specific population of cancer patients.

As used herein the term "neoantigen" is an antigen that has at least one alteration that makes it distinct from the corresponding wild-type antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354(6310):354-358. Such shared neoantigens are useful for inducing an immune response in a subject via administration. The subject can be identified for administration through the use of various diagnostic methods, e.g., patient selection methods described further below.

As used herein the term "tumor antigen" is a antigen present in a subject's tumor cell or tissue but not in the subject's corresponding normal cell or tissue, or derived from a polypeptide known to or have been found to have altered expression in a tumor cell or cancerous tissue in comparison to a normal cell or tissue.

As used herein the term "antigen-based vaccine" is a vaccine composition based on one or more antigens, e.g., a plurality of antigens. The vaccines can be nucleotide-based (e.g., virally based, RNA based, or DNA based), protein-based (e.g., peptide based), or a combination thereof.

As used herein the term "candidate antigen" is a mutation or other aberration giving rise to a sequence that may represent a antigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay-which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or energizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

The term "antigen-encoding nucleic acid sequences derived from a tumor" refers to nucleic acid sequences directly extracted from the tumor, e.g. via RT-PCR; or sequence data obtained by sequencing the tumor and then synthesizing the nucleic acid sequences using the sequencing data, e.g., via various synthetic or PCR-based methods known in the art.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a 26S promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, or other 26S subgenomic promoter sequence, a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Antigens

Methods for identifying shared antigens (e.g., neoantigens) include identifying antigens from a tumor of a subject that are likely to be presented on the cell surface of the tumor or immune cells, including professional antigen presenting cells such as dendritic cells, and/or are likely to be immunogenic. As an example, one such method may comprise the steps of: obtaining at least one of exome, transcriptome or whole genome tumor nucleotide sequencing and/or expression data from the tumor cell of the subject, wherein the tumor nucleotide sequencing and/or expression data is used to obtain data representing peptide sequences of each of a set of antigens (e.g., in the case of neoantigens wherein the peptide sequence of each neoantigen comprises at least one alteration that makes it distinct from the corresponding wild-type peptide sequence or in cases of shared antigens without a mutation where peptides are derived from any polypeptide known to or have been found to have altered expression in a tumor cell or cancerous tissue in comparison to a normal cell or tissue); inputting the peptide sequence of each antigen into one or more presentation models to generate a set of numerical likelihoods that each of the antigens is presented by one or more MHC alleles on the tumor cell surface of the tumor cell of the subject or cells present in the tumor, the set of numerical likelihoods having been identified at least based on received mass spectrometry data; and selecting a subset of the set of antigens based on the set of numerical likelihoods to generate a set of selected antigens.

The presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have a tumor, and wherein the set of reference data comprises at least one of: data representing exome nucleotide sequences from tumor tissue, data representing exome nucleotide sequences from normal tissue, data representing transcriptome nucleotide sequences from tumor tissue, data representing proteome sequences from tumor tissue, and data representing MHC peptidome sequences from tumor tissue, and data representing MHC peptidome sequences from normal tissue. The reference data can further comprise mass spectrometry data, sequencing data, RNA sequencing data, expression profiling data, and proteomics data for single-allele cell lines engineered to express a predetermined MHC allele that are subsequently exposed to synthetic protein, normal and tumor human cell lines, and fresh and frozen primary samples, and T cell assays (e.g., ELISPOT). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Methods for identifying shared antigens also include generating an output for constructing a personalized cancer vaccine by identifying one or more antigens from one or more tumor cells of a subject that are likely to be presented on a surface of the tumor cells. As an example, one such method may comprise the steps of: obtaining at least one of exome, transcriptome, or whole genome nucleotide sequencing and/or expression data from the tumor cells and normal cells of the subject, wherein the nucleotide sequencing and/or expression data is used to obtain data representing peptide sequences of each of a set of antigens identified by comparing the nucleotide sequencing and/or expression data from the tumor cells and the nucleotide sequencing and/or expression data from the normal cells (e.g., in the case of neoantigens wherein the peptide sequence of each neoantigen comprises at least one alteration that makes it distinct from the corresponding wild-type peptide sequence or in cases of shared antigens without a mutation where peptides are derived from any polypeptide known to or have been found to have altered expression in a tumor cell or cancerous tissue in comparison to a normal cell or tissue), peptide sequence identified from the normal cells of the subject; encoding the peptide sequences of each of the antigens into a corresponding numerical vector, each numerical vector including information regarding a plurality of amino acids that make up the peptide sequence and a set of positions of the amino acids in the peptide sequence; inputting the numerical vectors, using a computer processor, into a deep learning presentation model to generate a set of presentation likelihoods for the set of antigens, each presentation likelihood in the set representing the likelihood that a corresponding antigen is presented by one or more class II MHC alleles on the surface of the tumor cells of the subject, the deep learning presentation model; selecting a subset of the set of antigens based on the set of presentation likelihoods to generate a set of selected antigens; and generating the output for constructing the personalized cancer vaccine based on the set of selected antigens.

Specific methods for identifying antigens, including neoantigens, are known to those skilled in the art, for example the methods described in more detail in international patent application publications WO/2017/106638, WO/2018/195357, and WO/2018/208856, each herein incorporated by reference, in their entirety, for all purposes.

A method of treating a subject having a tumor is disclosed herein, comprising performing the steps of any of the antigen identification methods described herein, and further comprising obtaining a tumor vaccine comprising the set of selected antigens, and administering the tumor vaccine to the subject.

A method disclosed herein can also include identifying one or more T cells that are antigen-specific for at least one of the antigens in the subset. In some embodiments, the identification comprises co-culturing the one or more T cells with one or more of the antigens in the subset under conditions that expand the one or more antigen-specific T cells. In further embodiments, the identification comprises contacting the one or more T cells with a tetramer comprising one or more of the antigens in the subset under conditions that allow binding between the T cell and the tetramer. In even further embodiments, the method disclosed herein can also include identifying one or more T cell receptors (TCR) of the one or more identified T cells. In certain embodiments, identifying the one or more T cell receptors comprises sequencing the T cell receptor sequences of the one or more identified T cells. The method disclosed herein can further comprise genetically engineering a plurality of T cells to express at least one of the one or more identified T cell receptors; culturing the plurality of T cells under conditions that expand the plurality of T cells; and infusing the expanded T cells into the subject. In some embodiments, genetically engineering the plurality of T cells to express at least one of the one or more identified T cell receptors comprises cloning the T cell receptor sequences of the one or more identified T cells into an expression vector; and transfecting each of the plurality of T cells with the expression vector. In some embodiments, the method disclosed herein further comprises culturing the one or more identified T cells under conditions that expand the one or more identified T cells; and infusing the expanded T cells into the subject.

Also disclosed herein is an isolated T cell that is antigen-specific for at least one selected antigen in the subset.

Also disclosed herein is a methods for manufacturing a tumor vaccine, comprising the steps of: obtaining at least one of exome, transcriptome or whole genome tumor nucleotide sequencing and/or expression data from the tumor cell of the subject, wherein the tumor nucleotide sequencing and/or expression data is used to obtain data representing peptide sequences of each of a set of antigens (e.g., in the case of neoantigens wherein the peptide sequence of each neoantigen comprises at least one alteration that makes it distinct from the corresponding wild-type peptide sequence or in cases of shared antigens without a mutation where peptides are derived from any polypeptide known to or have been found to have altered expression in a tumor cell or cancerous tissue in comparison to a normal cell or tissue); inputting the peptide sequence of each antigen into one or more presentation models to generate a set of numerical likelihoods that each of the antigens is presented by one or more MHC alleles on the tumor cell surface of the tumor cell of the subject, the set of numerical likelihoods having been identified at least based on received mass spectrometry data; and selecting a subset of the set of antigens based on the set of numerical likelihoods to generate a set of selected antigens; and producing or having produced a tumor vaccine comprising the set of selected antigens.

Also disclosed herein is a tumor vaccine including a set of selected antigens selected by performing the method comprising the steps of: obtaining at least one of exome, transcriptome or whole genome tumor nucleotide sequencing and/or expression data from the tumor cell of the subject, wherein the tumor nucleotide sequencing and/or expression data is used to obtain data representing peptide sequences of each of a set of antigens, and wherein the peptide sequence of each antigen (e.g., in the case of neoantigens wherein the peptide sequence of each neoantigen comprises at least one alteration that makes it distinct from the corresponding wild-type peptide sequence or in other cases of shared antigens without a mutation where peptides are derived from any polypeptide known to or have been found to have altered expression in a tumor cell or cancerous tissue in comparison to a normal cell or tissue); inputting the peptide sequence of each antigen into one or more presentation models to generate a set of numerical likelihoods that each of the antigens is presented by one or more MHC alleles on the tumor cell surface of the tumor cell of the subject, the set of numerical likelihoods having been identified at least based on received mass spectrometry data; and selecting a subset of the set of antigens based on the set of numerical likelihoods to generate a set of selected antigens; and producing or having produced a tumor vaccine comprising the set of selected antigens.

The tumor vaccine may include one or more of a nucleotide sequence, a polypeptide sequence, RNA, DNA, a cell, a plasmid, or a vector.

The tumor vaccine may include one or more antigens presented on the tumor cell surface.

The tumor vaccine may include one or more antigens that is immunogenic in the subject.

The tumor vaccine may not include one or more antigens that induce an autoimmune response against normal tissue in the subject.

The tumor vaccine may include an adjuvant.

The tumor vaccine may include an excipient.

A method disclosed herein may also include selecting antigens that have an increased likelihood of being presented on the tumor cell surface relative to unselected antigens based on the presentation model.

A method disclosed herein may also include selecting antigens that have an increased likelihood of being capable of inducing a tumor-specific immune response in the subject relative to unselected antigens based on the presentation model.

A method disclosed herein may also include selecting antigens that have an increased likelihood of being capable of being presented to naïve T cells by professional antigen presenting cells (APCs) relative to unselected antigens based on the presentation model, optionally wherein the APC is a dendritic cell (DC).

A method disclosed herein may also include selecting antigens that have a decreased likelihood of being subject to inhibition via central or peripheral tolerance relative to unselected antigens based on the presentation model.

A method disclosed herein may also include selecting antigens that have a decreased likelihood of being capable of inducing an autoimmune response to normal tissue in the subject relative to unselected antigens based on the presentation model.

The exome or transcriptome nucleotide sequencing and/or expression data may be obtained by performing sequencing on the tumor tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the antigen encoded peptide bind; the predicted stability of the antigen encoded peptide-MHC complex; the sequence and length of the antigen encoded peptide; the probability of presentation of antigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall neoantigen encoded peptide-sequence-independent probability of presentation by the particular MHC allele in other distinct subjects who express the particular MHC allele; the overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the neoantigen encoded peptide within its source protein sequence; the presence of protease cleavage motifs in the neoantigen encoded peptide, optionally weighted according to the expression of corresponding proteases in the tumor cells (as measured by RNA-seq or mass spectrometry); the turnover rate of the source protein as measured in the appropriate cell type; the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data; the level of expression of the proteasome, immunoproteasome, thioprotease, or other proteases in the tumor cells (which may be measured by RNA-seq, proteome mass spectrometry, or immunohistochemistry); the expression of the source gene of the neoantigen encoded peptide (e.g., as measured by RNA-seq or mass spectrometry); the typical tissue-specific expression of the source gene of the neoantigen encoded peptide during various stages of the cell cycle; a comprehensive catalog of features of the source protein and/or its domains as can be found in e.g. uniProt or PDB http://www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the neoantigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the tumor cells, stroma, or tumor-infiltrating lymphocytes (TILs); the copy number of the source gene of the neoantigen encoded peptide in the tumor cells; the probability that the peptide binds to the TAP or the measured or predicted binding affinity of the peptide to the TAP; the expression level of TAP in the tumor cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2 M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA- DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2 M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); tumor type (e.g., NSCLC, melanoma); clinical tumor subtype (e.g., squamous lung cancer vs. non-squamous); smoking history; the typical expression of the source gene of the peptide in the relevant tumor type or clinical subtype, optionally stratified by driver mutation.

The at least one alteration may be a frameshift or non-frameshift indel, missense or nonsense substitution, splice site alteration, genomic rearrangement or gene fusion, or any genomic or expression alteration giving rise to a neoORF.

The tumor cell may be selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

A method disclosed herein may also include obtaining a tumor vaccine comprising the set of selected neoantigens or a subset thereof, optionally further comprising administering the tumor vaccine to the subject.

At least one of neoantigens in the set of selected neoantigens, when in polypeptide form, may include at least one of: a binding affinity with MHC with an IC50 value of less than 1000 nM, for MHC Class I polypeptides a length of 8-15, 8, 9, 10, 11, 12, 13, 14, or 15 amino acids, for MHC Class II polypeptides a length of 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the polypeptide in the parent protein sequence promoting proteasome cleavage, and presence of sequence motifs promoting TAP transport. For MHC Class II, presence of sequence motifs within or near the peptide promoting cleavage by extracellular or lysosomal proteases (e.g., cathepsins) or HLA-DM catalyzed HLA binding.

Disclosed herein is are methods for identifying one or more neoantigens that are likely to be presented on a tumor cell surface of a tumor cell, comprising executing the steps of: receiving mass spectrometry data comprising data associated with a plurality of isolated peptides eluted from major histocompatibility complex (MHC) derived from a plurality of fresh or frozen tumor samples; obtaining a training data set by at least identifying a set of training peptide sequences present in the tumor samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

The presentation model may represent dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include selecting a subset of neoantigens, wherein the subset of neoantigens is selected because each has an increased likelihood that it is presented on the cell surface of the tumor relative to one or more distinct tumor neoantigens.

A method disclosed herein can also include selecting a subset of neoantigens, wherein the subset of neoantigens is selected because each has an increased likelihood that it is capable of inducing a tumor-specific immune response in the subject relative to one or more distinct tumor neoantigens.

A method disclosed herein can also include selecting a subset of neoantigens, wherein the subset of neoantigens is selected because each has an increased likelihood that it is capable of being presented to naïve T cells by professional antigen presenting cells (APCs) relative to one or more distinct tumor neoantigens, optionally wherein the APC is a dendritic cell (DC).

A method disclosed herein can also include selecting a subset of neoantigens, wherein the subset of neoantigens is selected because each has a decreased likelihood that it is subject to inhibition via central or peripheral tolerance relative to one or more distinct tumor neoantigens.

A method disclosed herein can also include selecting a subset of neoantigens, wherein the subset of neoantigens is selected because each has a decreased likelihood that it is capable of inducing an autoimmune response to normal tissue in the subject relative to one or more distinct tumor neoantigens.

A method disclosed herein can also include selecting a subset of neoantigens, wherein the subset of neoantigens is selected because each has a decreased likelihood that it will be differentially post-translationally modified in tumor cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3rd Ed. (Plenum Press) Vols A and B (1992).

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject. Specific methods for identifying neoantigens, including shared neoantigens, that are specific to tumors are known to those skilled in the art, for example the methods described in more detail in international patent application publications WO/2017/106638, WO/2018/195357, and WO/2018/208856, each herein incorporated by reference, in their entirety, for all purposes.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A. C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLID system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Antigens

Antigens can include nucleotides or polypeptides. For example, a antigen can be an RNA sequence that encodes for a polypeptide sequence. Antigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

Also disclosed herein are peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. Suitable polypeptides from which the antigenic peptides can be derived can be found for example in the COSMIC database. COSMIC curates comprehensive information on somatic mutations in human cancer. The peptide contains the tumor specific mutation.

One or more polypeptides encoded by a antigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more antigens can be presented on the surface of a tumor.

One or more antigens can be is immunogenic in a subject having a tumor, e.g., capable of eliciting a T cell response or a B cell response in the subject.

One or more antigens that induce an autoimmune response in a subject can be excluded from consideration in the context of vaccine generation for a subject having a tumor.

The size of at least one antigenic peptide molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the antigenic peptide molecules are equal to or less than 50 amino acids.

Antigenic peptides and polypeptides can be: for MHC Class I 15 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses.

Antigenic peptides and polypeptides can be presented on an HLA protein. In some aspects antigenic peptides and polypeptides are presented on an HLA protein with greater affinity than a wild-type peptide. In some aspects, a antigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, antigenic peptides and polypeptides do not induce an autoimmune response and/or invoke immunological tolerance when administered to a subject.

Also provided are compositions comprising at least two or more antigenic peptides. In some embodiments the composition contains at least two distinct peptides. At least two distinct peptides can be derived from the same polypeptide. By distinct polypeptides is meant that the peptide vary by length, amino acid sequence, or both. The peptides are derived from any polypeptide known to or have been found to contain a tumor specific mutation or peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. Suitable polypeptides from which the antigenic peptides can be derived can be found for example in the COSMIC database or the AACR Genomics Evidence Neoplasia Information Exchange (GENIE) database. COSMIC curates comprehensive information on somatic mutations in human cancer. AACR GENIE aggregates and links clinical-grade cancer genomic data with clinical outcomes from tens of thousands of cancer patients. The peptide contains the tumor specific mutation. In some aspects the tumor specific mutation is a driver mutation for a particular cancer type.

Antigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, antigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A antigenic peptide can be linked to the T helper peptide either directly or via a spacer either at the amino or carboxy terminus of the peptide. The amino terminus of either the antigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect a antigen includes a nucleic acid (e.g. polynucleotide) that encodes a antigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

V. Vaccine Compositions

Also disclosed herein is an immunogenic composition, e.g., a vaccine composition, capable of raising a specific immune response, e.g., a tumor-specific immune response. Vaccine compositions typically comprise one or a plurality of antigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 antigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen sequences, 6, 7, 8, 9, 10 11, 12, 13, or 14 different antigen sequences, or 12, 13 or 14 different antigen sequences.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to a antigen. Carriers can be scaffold structures, for example a polypeptide or a polysaccharide, to which a antigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP- EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186 (1): 18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6): 414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C) (e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a sub-cellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13):3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

V.A. Antigen Cassette

The methods employed for the selection of one or more antigens, the cloning and construction of a "cassette" and its insertion into a viral vector are within the skill in the art given the teachings provided herein. By "antigen cassette" is meant the combination of a selected antigen or plurality of antigens and the other regulatory elements necessary to transcribe the antigen(s) and express the transcribed product. A antigen or plurality of antigens can be operatively linked to regulatory components in a manner which permits transcription. Such components include conventional regulatory elements that can drive expression of the antigen(s) in a cell transfected with the viral vector. Thus the antigen cassette can also contain a selected promoter which is linked to the antigen(s) and located, with other, optional regulatory elements, within the selected viral sequences of the recombinant vector.

Useful promoters can be constitutive promoters or regulated (inducible) promoters, which will enable control of the amount of antigen(s) to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art.

The antigen cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the antigen-based sequences and before the viral vector sequences. A common intron sequence can also be derived from SV-40, and is referred to as the SV-40 T intron sequence. A antigen cassette can also contain such an intron, located between the promoter/enhancer sequence and the antigen(s). Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

A antigen cassette can have one or more antigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more antigens. Antigens can be linked directly to one another. Antigens can also be linked to one another with linkers. Antigens can be in any orientation relative to one another including N to C or C to N.

As above stated, the antigen cassette can be located in the site of any selected deletion in the viral vector, such as the site of the E1 gene region deletion or E3 gene region deletion, among others which may be selected.

The antigen cassette can be described using the following formula to describe the ordered sequence of each element, from 5' to 3':

$$(P_a\text{-}(L5_b\text{-}N_c\text{-}L3_d)_X)_Z\text{-}(P2_h\text{-}(G5_e\text{-}U_f)_Y)_W\text{-}G3_g$$

wherein P and P2 comprise promoter nucleotide sequences, N comprises an MHC class I epitope encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding Nc is a epitope encoding nucleic acid sequence, where for each Y the corresponding $U_f$ is an antigen-encoding nucleic acid sequence. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (i.e. only the promoter nucleotide sequence provided by a vector backbone (e.g., a viral backbone such as an alphavirus backbone) is present), 20 MHC class I epitope are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to a vector backbone (e.g., a viral backbone such as an alphavirus backbone). Examples of linking the 3' end of the antigen cassette to a vector backbone (e.g., a viral backbone such as an alphavirus backbone) include linking directly to the 3' UTR elements provided by a vector backbone (e.g., a viral backbone such as an alphavirus backbone), such as a 3' 19-nt CSE. Examples of linking the 5' end of the antigen cassette to a vector backbone (e.g., a viral backbone such as an alphavirus backbone) include linking directly to a 26S promoter sequence, an alphavirus 5' UTR, a 51-nt CSE, or a 24-nt CSE.

Other examples include: where a=1 describing where a promoter other than the promoter nucleotide sequence provided by a vector backbone (e.g., a viral backbone such as an alphavirus backbone) is present; where a=1 and Z is greater than 1 where multiple promoters other than the promoter nucleotide sequence provided by a vector backbone (e.g., a viral backbone such as an alphavirus backbone) are present each driving expression of 1 or more distinct MHC class I epitope encoding nucleic acid sequences; where h=1 describing where a separate promoter is present to drive expression of the MHC class II antigen-encoding nucleic acid sequences; and where g=0 describing the MHC class II antigen-encoding nucleic acid sequence, if present, is directly linked to a vector backbone (e.g., a viral backbone such as an alphavirus backbone).

Other examples include where each MHC class I epitope that is present can have a 5' linker, a 3' linker, neither, or both. In examples where more than one MHC class I epitope is present in the same antigen cassette, some MHC class I epitopes may have both a 5' linker and a 3' linker, while other MHC class I epitopes may have either a 5' linker, a 3' linker, or neither. In other examples where more than one MHC class I epitope is present in the same antigen cassette, some MHC class I epitopes may have either a 5' linker or a 3' linker, while other MHC class I epitopes may have either a 5' linker, a 3' linker, or neither.

In examples where more than one MHC class II epitope is present in the same antigen cassette, some MHC class II epitopes may have both a 5' linker and a 3' linker, while other MHC class II epitopes may have either a 5' linker, a 3' linker, or neither. In other examples where more than one MHC class II epitope is present in the same antigen cassette, some MHC class II epitopes may have either a 5' linker or a 3' linker, while other MHC class II epitopes may have either a 5' linker, a 3' linker, or neither.

The promoter nucleotide sequences P and/or P2 can be the same as a promoter nucleotide sequence provided by a vector backbone (e.g., a viral backbone such as an alphavirus backbone). For example, the promoter sequence provided by a vector backbone (e.g., a viral backbone such as an alphavirus backbone), Pn and P2, can each comprise a 26S subgenomic promoter. The promoter nucleotide sequences P and/or P2 can be different from the promoter nucleotide sequence provided by a vector backbone (e.g., a viral backbone such as an alphavirus backbone), as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encodes a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

V.B. Immune Checkpoints

Vectors described herein, such as C68 vectors described herein or alphavirus vectors described herein, can comprise a nucleic acid which encodes at least one antigen and the same or a separate vector can comprise a nucleic acid which encodes at least one immune modulator (e.g., an antibody such as an scFv) which binds to and blocks the activity of an immune checkpoint molecule. Vectors can comprise a antigen cassette and one or more nucleic acid molecules encoding a checkpoint inhibitor.

Illustrative immune checkpoint molecules that can be targeted for blocking or inhibition include, but are not limited to, CTLA-4, 4-1BB (CD137), 4-1BBL (CD137 L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. *Nat Biotechnol.* 2005 May; 23(5):584-90. Epub 2005 Apr. 17; herein incorporated by reference for all purposes.

Immune modulators (e.g., checkpoint inhibitor antibodies such as anti-CTLA4 antibodies or anti-PD1 antibodies) encoded in the same vector system as the antigen encoding cassette can also be encoded such that the nucleic acid sequence encoding the immune modulator is transcribed as part of the same transcript as the antigen-encoding nucleic acid sequence(s). Additional elements can be incorporated into the nucleic acid sequence cassette that allow for translation of both the antigens and the immune modulator. For example, an internal ribosome entry sequence (IRES) sequence can be used to separate sequences encoding antigens and immune modulator(s), allowing separate translation of the antigens and the immune modulator(s). In another example, a sequence encoding a self-cleaving 2A peptide can be incorporated between antigens and immune modulator(s), allowing translation of both the antigens and the immune modulator(s) as part of the same protein, followed by cleavage of the 2A peptide; resulting in separate proteins for the antigens and the immune modulator(s). These examples are not meant to be limiting, and it is also understood that multiple elements can be combined to facilitate co-expression of both antigens and immune modulator(s), such as use of both an IRES sequence and a 2A peptide encoding sequence. Additionally, a Furin cleavage site encoding sequence can be incorporated 5' of the 2A peptide encoding sequence. The Furin cleavage site allows for removal of the 2A peptide residues following self-cleavage.

In examples where antigens and immune modulator(s) are encoded on the same transcript, the order of the antigens and the immune modulator can be in any order. For example, in the case of using an IRES sequence to separate the antigens and the immune modulator, the order, from 5' to 3'; can either be in an antigen-IRES-immune modulator orientation, or in a immune modulator-IRES-antigen orientation.

In addition, immune modulators encoded in the same vector system as the antigen encoding cassette can also be encoded such that the nucleic acid sequence encoding the immune modulator is transcribed on a different transcript from the antigen-encoding nucleic acid sequence(s). For example, separate promoters can be incorporated to independently drive transcription of the immune modulator and the antigen-encoding nucleic acid sequence(s). The separate promoters can be the same or different promoters, and each can be an inducible or constitutive promoter. Exemplary promoter sequences include, but are not limited to, CMV, SV40, EF-1, RSV, PGK, MCK, HSA, and EBV promoter sequences. In another example, the antigen encoding cassette and the nucleic acid sequence encoding the immune modulator can be inserted into different regions, including deleted regions, of the same viral vector such that each are independently transcribed. In one example, a vector is designed with an expression cassette introduced into the deleted E1 region and the immune checkpoint inhibitor is introduced into the deleted E3 region in an E1/E3 deleted ChAdV68 viral vector.

V.C. Additional Considerations for Vaccine Design and Manufacture

V.C.1. Determination of a Set of Peptides that Cover all Tumor Subclones

Truncal peptides, meaning those presented by all or most tumor subclones, can be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.[54]

V.C.2. Antigen Prioritization

After all of the above antigen filters are applied, more candidate antigens may still be available for vaccine inclusion than the vaccine technology can support. Additionally, uncertainty about various aspects of the antigen analysis may remain and tradeoffs may exist between different properties of candidate vaccine antigens. Thus, in place of predetermined filters at each step of the selection process, an integrated multi-dimensional model can be considered that places candidate antigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of antigens may lower the probability that a tumor will escape immune attack via downregulation or mutation of HLA molecules)
7. Coverage of HLA classes (covering both HLA-I and HLA-II may increase the probability of therapeutic response and decrease the probability of tumor escape)

Additionally, optionally, antigens can be deprioritized (e.g., excluded) from the vaccination if they are predicted to be presented by HLA alleles lost or inactivated in either all or part of the patient's tumor. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010). Antigens can also be deprioritized if mass-spectrometry data indicates a predicted antigen is not presented by a predicted HLA allele.

V.D. Alphavirus

V.D.1. Alphavirus Biology

Alphaviruses are members of the family Togaviridae, and are positive-sense single stranded RNA viruses. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbial Review 1994). A natural alphavirus genome is typically around 12 kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' polyA tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

V.D.2. Alphavirus as a Delivery Vector

Alphaviruses (including alphavirus sequences, features, and other elements) can be used to generate alphavirus-based delivery vectors (also be referred to as alphavirus vectors, alphavirus viral vectors, alphavirus vaccine vectors, self-replicating RNA (srRNA) vectors, or self-amplifying RNA (samRNA) vectors). Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly illicit an immune response to the heterologous antigen expressed. However, the degree of desired cytotoxicity can be a balancing act, and thus several attenuated alphaviruses have been developed, including the TC-83 strain of VEE. Thus, an example of a antigen expression vector described herein can utilize an alphavirus backbone that allows for a high level of antigen expression, elicits a robust immune response to antigen, does not elicit an immune response to the vector itself, and can be used in a safe manner. Furthermore, the antigen expression cassette can be designed to elicit different levels of an immune response through optimization of which alphavirus sequences the vector uses, including, but not limited to, sequences derived from VEE or its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of a antigen expression vector described herein can utilize an alphavirus backbone wherein the structural proteins are replaced by a antigen cassette, the resulting vector both reducing biosafety concerns, while at the same time promoting efficient expression due to the reduction in overall expression vector size.

V.D.3. Alphavirus Production In Vitro

Alphavirus delivery vectors are generally positive-sense RNA polynucleotides. A convenient technique well-known in the art for RNA production is in vitro transcription IVT. In this technique, a DNA template of the desired vector is first produced by techniques well-known to those in the art, including standard molecular biology techniques such as cloning, restriction digestion, ligation, gene synthesis, and polymerase chain reaction (PCR). The DNA template contains a RNA polymerase promoter at the 5' end of the sequence desired to be transcribed into RNA. Promoters include, but are not limited to, bacteriophage polymerase promoters such as T3, T7, or SP6. The DNA template is then incubated with the appropriate RNA polymerase enzyme, buffer agents, and nucleotides (NTPs). The resulting RNA polynucleotide can optionally be further modified including, but limited to, addition of a 5' cap structure such as 7-methylguanosine or a related structure, and optionally modifying the 3' end to include a polyadenylate (polyA) tail. The RNA can then be purified using techniques well-known in the field, such as phenol-chloroform extraction.

V.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different antigen cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver antigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soluable vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

V.E. Chimpanzee Adenovirus (ChAd)

V.E.1. Viral Delivery with Chimpanzee Adenovirus

Vaccine compositions for delivery of one or more antigens (e.g., via a antigen cassette and including one or more neoantigens) can be created by providing adenovirus nucleotide sequences of chimpanzee origin, a variety of novel vectors, and cell lines expressing chimpanzee adenovirus genes. A nucleotide sequence of a chimpanzee C68 adenovirus (also referred to herein as ChAdV68) can be used in a vaccine composition for antigen delivery (See SEQ ID NO: 1). Use of C68 adenovirus derived vectors is described in further detail in U.S. Pat. No. 6,083,716, which is herein incorporated by reference in its entirety, for all purposes.

In a further aspect, provided herein is a recombinant adenovirus comprising the DNA sequence of a chimpanzee adenovirus such as C68 and a antigen cassette operatively linked to regulatory sequences directing its expression. The recombinant virus is capable of infecting a mammalian, preferably a human, cell and capable of expressing the antigen cassette product in the cell. In this vector, the native chimpanzee E1 gene, and/or E3 gene, and/or E4 gene can be deleted. A antigen cassette can be inserted into any of these sites of gene deletion. The antigen cassette can include a antigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering a antigen cassette into a mammalian cell comprising the step of introducing into the cell an effective amount of a chimpanzee adenovirus, such as C68, that has been engineered to express the antigen cassette.

Still another aspect provides a method for eliciting an immune response in a mammalian host to treat cancer. The method can comprise the step of administering to the host an effective amount of a recombinant chimpanzee adenovirus, such as C68, comprising a antigen cassette that encodes one or more antigens from the tumor against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and a antigen cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the antigen cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a host cell transfected with a vector disclosed herein such as a C68 vector engineered to expression a antigen cassette. Also disclosed herein is a human cell that expresses a selected gene introduced therein through introduction of a vector disclosed herein into the cell.

Also disclosed herein is a method for delivering a antigen cassette to a mammalian cell comprising introducing into said cell an effective amount of a vector disclosed herein such as a C68 vector engineered to expression the antigen cassette.

Also disclosed herein is a method for producing a antigen comprising introducing a vector disclosed herein into a mammalian cell, culturing the cell under suitable conditions and producing the antigen.

V.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38 [CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

V.E.3. Recombinant Viral Particles as Vectors

The compositions disclosed herein can comprise viral vectors, that deliver at least one antigen to cells. Such vectors comprise a chimpanzee adenovirus DNA sequence such as C68 and a antigen cassette operatively linked to regulatory sequences which direct expression of the cassette. The C68 vector is capable of expressing the cassette in an infected mammalian cell. The C68 vector can be functionally deleted in one or more viral genes. A antigen cassette comprises at least one antigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

V.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of a antigen cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

V.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

V.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene E1a and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express antigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising antigen(s) be inserted optionally into any deleted region of the chimpanzee C68 Ad virus. Alternatively, the cassette can be inserted into an existing gene region to disrupt the function of that region, if desired.

V.E.7. Helper Viruses

Depending upon the chimpanzee adenovirus gene content of the viral vectors employed to carry the antigen cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the "helper" virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the antigen cassette on the adenovirus vector allows both the Ad vector and the helper virus to be independently monitored. This second reporter is used to enable separation between the resulting recombinant virus and the helper virus upon purification.

V.E.8. Assembly of Viral Particle and Infection of a Cell Line

Assembly of the selected DNA sequences of the adenovirus, the antigen cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleotide sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired antigen cassette-containing viral vector, the vector can be transfected in vitro in the presence of a helper virus into the packaging cell line. Homologous recombination occurs between the helper and the vector sequences, which permits the adenovirus-antigen sequences in the vector to be replicated and packaged into virion capsids, resulting in the recombinant viral vector particles.

The resulting recombinant chimpanzee C68 adenoviruses are useful in transferring a antigen cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

V.E.9. Use of the Recombinant Virus Vectors

The resulting recombinant chimpanzee C68 adenovirus containing the antigen cassette (produced by cooperation of the adenovirus vector and helper virus or adenoviral vector and packaging cell line, as described above) thus provides an efficient gene transfer vehicle which can deliver antigen(s) to a subject in vivo or ex vivo.

The above-described recombinant vectors are administered to humans according to published methods for gene therapy. A chimpanzee viral vector bearing a antigen cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of antigen transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of antigen(s) can be monitored to determine the frequency of dosage administration.

Recombinant, replication defective adenoviruses can be administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising a antigen cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to antigen(s) can be monitored to determine the need, if any, for boosters. Following an assessment of antibody titers in the serum, for example, optional booster immunizations may be desired

VI. Therapeutic and Manufacturing Methods

Also provided is a method of stimulating an immune response in a subject (e.g., inducing, increasing, or enhancing an immune response, such as inducing, increasing, or enhancing a T cell response), stimulating a tumor specific immune response in a subject, vaccinating against a tumor, treating and or alleviating a symptom of cancer in a subject by administering to the subject one or more antigens such as a plurality of antigens identified using methods disclosed herein (e.g., administering a cassette containing an antigen-encoding nucleic acid sequence that has an epitope-encoding nucleic acid sequence and optionally a 5' and/or 3' linker sequence). For example, the methods described herein can induce, increase, or enhance an epitope-specific T cell response, such as inducing, increasing, or enhancing epitope-specific T cell proliferation, T cell activation, T cell cytokine production and/or secretion, T cell differentiation, T cell longevity, or any combination thereof. The methods described herein include stimulating an immune response in a subject (e.g., inducing, increasing, or enhancing an immune response through a combined administration of an alphavirus-based expression system (e.g., administering one or more alphavirus-based vectors encoding a cassette containing an antigen-encoding nucleic acid sequence that has an epitope-encoding nucleic acid sequence and optionally a 5' and/or 3' linker sequence) in combination with an inhibitor of Type I interferon signaling.

Also provided is a method of enhancing delivery of a payload by an alphavirus-based expression system by administering one or more vectors having an RNA alphavirus backbone and an encoded payload (e.g., a cassette) in combination with an inhibitor of Type I interferon signaling. A payload can be any nucleotide sequence desired to be delivered to a cell of interest. In general, the payload is a cassette operably linked to a promoter to drive expression of the nucleotide sequence. The nucleotide sequence can be coding (i.e., a polypeptide-encoding nucleic acid sequence capable of being transcribed and translated into a protein). In general, the polypeptide-encoding nucleic acid sequence can encode any protein desired to be expressed in a cell. Examples of proteins include, but are not limited to, an antibody, a cytokine, a chimeric antigen receptor (CAR), a T-cell receptor, or a genome-editing system component (e.g., a nuclease used in a genome-editing system). Genome-editing systems include, but are not limited to, a CRISPR system, a zinc-finger system, a meganuclease system, or a TALEN system. The nucleotide sequence can be non-coding (i.e., nucleic acid sequence capable of being transcribed but is not translated into a protein). In general, the non-coding nucleic acid sequence can encode any non-coding polynucleotide desired to be expressed in a cell. Examples of non-coding polynucleotides include, but are not limited to, RNA interference (RNAi) polynucleotides (e.g., antisense oligonucleotides, shRNAs, siRNAs, miRNAs etc.) or genome-editing system polynucleotide (e.g., a guide RNA [gRNA], a single-guide RNA [sgRNA], a trans-activating CRISPR [tracrRNA], and/or a CRISPR RNA [crRNA]).

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

A antigen can be administered in an amount sufficient to induce a CTL response.

A antigen can be administered alone or in combination with other therapeutic agents. The therapeutic agent is for example, a chemotherapeutic agent, radiation, or immunotherapy. Any suitable therapeutic treatment for a particular cancer can be administered.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each antigen to be included in a vaccine composition and the optimum dosing regimen can be determined. For example, a antigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of antigens present in the composition is/are tissue, cancer, and/or patient-specific. For instance, the exact selection of peptides can be guided by expression patterns of the parent proteins in a given tissue or guided by mutation status of a patient. The selection can be dependent on the specific type of cancer, the status of the disease, earlier treatment regimens, the immune status of the patient, and, of course, the HLA-haplotype of the patient. Furthermore, a vaccine can contain individualized components, according to personal needs of the particular patient. Examples include varying the selection of antigens according to the expression of the antigen in the particular patient or adjustments for secondary treatments following a first round or scheme of treatment.

A patient can be identified for administration of an antigen vaccine through the use of various diagnostic methods, e.g., patient selection methods described further below. Patient selection can involve identifying mutations in, or expression patterns of, one or more genes. In some cases, patient selection involves identifying the haplotype of the patient. The various patient selection methods can be performed in parallel, e.g., a sequencing diagnostic can identify both the mutations and the haplotype of a patient. The various patient selection methods can be performed sequentially, e.g., one diagnostic test identifies the mutations and separate diagnostic test identifies the haplotype of a patient, and where each test can be the same (e.g., both high-throughput sequencing) or different (e.g., one high-throughput sequencing and the other Sanger sequencing) diagnostic methods.

For a composition to be used as a vaccine for cancer, antigens with similar normal self-peptides that are expressed in high amounts in normal tissues can be avoided or be present in low amounts in a composition described herein. On the other hand, if it is known that the tumor of a patient expresses high amounts of a certain antigen, the respective pharmaceutical composition for treatment of this cancer can be present in high amounts and/or more than one antigen specific for this particularly antigen or pathway of this antigen can be included.

Compositions comprising a antigen can be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of a antigen, it is possible and can be felt desirable by the treating physician to administer substantial excesses of these compositions.

For therapeutic use, administration can begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at the site of surgical excision to induce a local immune response to the tumor. Disclosed herein are compositions for parenteral administration which comprise a solution of the antigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Antigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the antigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired antigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247:1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6 (7): 682-691 (1988); U.S. Pat. No. 5,279,833 Rose U.S. Pat. Nos. 5,279,833; 9,106,309WOAWO 91/06309; and Felgner et al., Proc. Natl. Acad. Sci. USA 84:7413-7414 (1987).

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev*. (2011) 239(1):45-61, Sakuma et al., Lentiviral vectors: basic to translational, *Biochem J*. (2012) 443(3):603-18, Cooper et al., Rescue of splicing-mediated intron loss maximizes expression in lentiviral vectors containing the human ubiquitin C promoter, *Nucl. Acids Res*. (2015) 43 (1): 682-690, Zufferey et al., Self-Inactivating Lentivirus Vector for Safe and Efficient In Vivo Gene Delivery, *J. Virol*. (1998) 72 (12): 9873-9880). Dependent on the packaging capacity of the above mentioned viral vector-based vaccine platforms, this approach can deliver one or more nucleotide sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med*. (2016) 22 (4):433-8, Stronen et al., Targeting of cancer neoantigens with donor-derived T cell receptor repertoires, *Science*. (2016) 352 (6291):1337-41, Lu et al., Efficient identification of mutated cancer antigens recognized by T cells associated with durable tumor regressions, *Clin Cancer Res*. (2014) 20(13): 3401-10). Upon introduction into a host, infected cells express the antigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a tumor vaccine, comprising performing the steps of a method disclosed herein; and producing a tumor vaccine comprising a plurality of antigens or a subset of the plurality of antigens.

Antigens disclosed herein can be manufactured using methods known in the art. For example, a method of producing a antigen or a vector (e.g., a vector including at least one sequence encoding one or more antigens) disclosed herein can include culturing a host cell under conditions suitable for expressing the antigen or vector wherein the host cell comprises at least one polynucleotide encoding the antigen or vector, and purifying the antigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NS0 cell, yeast, or a HEK293 cell. Host cells can be transformed with one or more polynucleotides comprising at least one nucleic acid sequence that encodes a antigen or vector disclosed herein, optionally wherein the isolated polynucleotide further comprises a promoter sequence operably linked to the at least one nucleic acid sequence that encodes the antigen or vector. In certain embodiments the isolated polynucleotide can be cDNA.

VIIA. Antigen and Payload Use and Administration

A vaccination protocol can be used to dose a subject with one or more antigens (e.g., administering a cassette containing an antigen-encoding nucleic acid sequence that has an epitope-encoding nucleic acid sequence and optionally a 5' and/or 3' linker sequence). A priming vaccine and a boosting vaccine can be used to dose the subject. The priming vaccine can be based on C68 (e.g., the sequences shown in SEQ ID NO: 1 or 2) or srRNA (e.g., the sequences shown in SEQ ID NO: 3 or 4) and the boosting vaccine can be based on C68 (e.g., the sequences shown in SEQ ID NO: 1 or 2) or srRNA (e.g., the sequences shown in SEQ ID NO: 3 or 4). Each vector typically includes a cassette that includes antigens. Cassettes can include about 20 antigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab.

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 μg RNA, in particular 10 or 100 μg can be used.

Anti-CTLA-4 (e.g., tremelimumab) can also be administered to the subject. For example, anti-CTLA4 can be administered subcutaneously near the site of the intramuscular vaccine injection (ChAdV68 prime or srRNA low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

T cell responses can be assessed as part of an immune monitoring protocol. T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELISpot assay. Specific CD4 or CD8 T cell responses to epitopes encoded in vaccines can be monitored from PBMCs by measuring induction of cytokines captured intracellularly or extracellularly, such as IFN-gamma, using flow cytometry. Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluorescein-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

A protocol can be used to dose a subject with one or more alphavirus-based expression systems (i.e., administering one or more vectors having an RNA alphavirus backbone and an encoded payload [e.g., a cassette]). In general, the protocols above directed to a vaccination can be followed to administered any of the alphavirus-based expression systems described herein.

VIIB. Inhibitor of Type I Interferon Signaling Use and Administration

The methods described herein include a method of enhancing delivery of a payload by an alphavirus-based expression system through a combined administration of one or more vectors having an RNA alphavirus backbone and an encoded payload (e.g., a cassette) and administration of an inhibitor of Type I interferon signaling. In some embodiments, administration of an inhibitor of Type I interferon signaling improves self-replication/self-amplification of the alphavirus-based vector in vivo following administration to a subject. Self-replication/self-amplification of the alphavirus-based vector can lead to improved expression of the encoded payload (e.g., the cassette). The inhibitor of Type I interferon signaling can be formulated as a pharmaceutical composition.

The inhibitor of Type I interferon signaling can be an IFNα inhibitor, an IFNβ inhibitor, an IFNAR inhibitor, or other Type I interferon signaling pathway inhibitor. The inhibitor of Type I interferon signaling can be an antibody or an antigen-binding fragment thereof, a small molecule inhibitor, a RNAi polynucleotide, a genome-editing system, an Fc-fusion protein. The inhibitor of Type I interferon signaling can be an antibody or an antigen-binding fragment thereof. The inhibitor of Type I interferon signaling can be an anti-IFNAR antibody or an antigen-binding fragment thereof, including, but not limited to, MAR1-5A3, Anifrolumab (also referred to as MEDI546), AmS3A5-1, 64G12, H2K6, H2K1, H3K6, H3K1 3F11, 4G5, 11E2, and 9D4, details of which can be found in U.S. Pat. Nos. 7,662,381 and 7,619,070, each herein incorporated by reference for all purposes. The inhibitor of Type I interferon signaling can be an anti-IFNα antibody or an antigen-binding fragment thereof, including, but not limited to, Sifalimumab, Rontalizumab, or ASG-009. The Type I interferon signaling pathway inhibitor can be a JAK kinase inhibitor, including small molecule inhibitors of JAK kinase. JAK kinase inhibitors include, but are not limited to, a JAK1/2 inhibitor or a JAK1/3 inhibitor. An example of a JAK1/3 inhibitor is Tofacitinib (trade names Xeljanz, Jakvinus, and Tofacinix) or Filgotinib (GLPG0634). An example of a JAK1/2 inhibitor is Ruxolitinib, Baricitinib, or Momelotinib (CYT387).

The inhibitor of Type I interferon signaling can be administered before, concurrently with, or after administration of the composition for delivery of the expression system (i.e., the alphavirus-based delivery platform). The inhibitor of Type I interferon signaling can be administered 24 hours or less before administration of the composition for delivery of the expression system. The inhibitor of Type I interferon signaling can be administered 24, 23, 22, 21, 20, 19, 18, 17, 16, 15, 14, 13, 12, 11, 10, 9, 8, 7, 6, 5, 4, 3, 2, or 1 hour or less before administration of the composition for delivery of the expression system. The inhibitor of Type I interferon signaling can be administered less than 12 hours after administration of the composition for delivery of the expression system. The inhibitor of Type I interferon signaling can be administered less than 12, 11, 10, 9, 8, 7, 6, 5, 4, 3, 2, or 1 hour after administration of the composition for delivery of the expression system. The inhibitor of Type I interferon signaling can be administered 6 hours or less after administration of the composition for delivery of the expression system. The inhibitor of Type I interferon signaling can be administered 6, 5, 4, 3, 2, or 1 hour or less after administration of the composition for delivery of the expression system. The inhibitor of Type I interferon signaling can be administered between 24 hours before and 6 hours or less after administration of the composition for delivery of the expression system.

The inhibitor of Type I interferon signaling can be administered intramuscularly (IM), intradermally (ID), subcutaneously (SC), or intravenously (IV). The inhibitor of Type I interferon signaling can be administered intramuscularly (IM), intradermally (ID), subcutaneously (SC), or intravenously (IV) and the composition for delivery of the expression system can be administered intramuscularly (IM), intradermally (ID), subcutaneously (SC), or intravenously (IV). The inhibitor of Type I interferon signaling can be administered intravenously (IV). The inhibitor of Type I interferon signaling can be administered intravenously (IV) and the composition for delivery of the expression system can be administered intramuscularly (IM), intradermally (ID), subcutaneously (SC), or intravenously (IV). The inhibitor of Type I interferon signaling can be administered IM. The inhibitor of Type I interferon signaling can be administered IM and the composition for delivery of the expression system can be administered intramuscularly (IM), intradermally (ID), subcutaneously (SC), or intravenously (IV). The inhibitor of Type I interferon signaling can be administered intravenously (IV) and the composition for delivery of the expression system can be administered intramuscularly (IM). The inhibitor of Type I interferon signaling can be administered IM and the composition for delivery of the expression system can be administered intramuscularly (IM).

A single administration of the inhibitor of Type I interferon signaling can be administered. Multiple administrations of the inhibitor of Type I interferon signaling can be administered. Multiple administrations of the inhibitor of Type I interferon signaling can be administered in combination with multiple administrations of an expression delivery platform, such as multiple administrations of alphavirus-based delivery platform. Multiple administrations of the inhibitor of Type I interferon signaling can be administered in the same manner or a different manner, such as by a different route, timing, or dose.

VIII. Antigen Identification

VIII.A. Antigen Candidate Identification

Research methods for NGS analysis of tumor and normal exome and transcriptomes have been described and applied in the antigen identification space.[6,14,15] Certain optimizations for greater sensitivity and specificity for antigen identification in the clinical setting can be considered. These optimizations can be grouped into two areas, those related to laboratory processes and those related to the NGS data analysis. Examples of optimizations are known to those skilled in the art, for example the methods described in more detail in international patent application publications WO/2017/106638, WO/2018/195357, and WO/2018/208856, each herein incorporated by reference, in their entirety, for all purposes.

VIII.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II-HLA-DR |
| Tu36 | Class II-HLA-DR |
| LN3 | Class II-HLA-DR |
| Tu39 | Class II-HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by Speed Vac evaporation and in some instances are stored at −20° C. prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector. MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97).

Figure 24A:
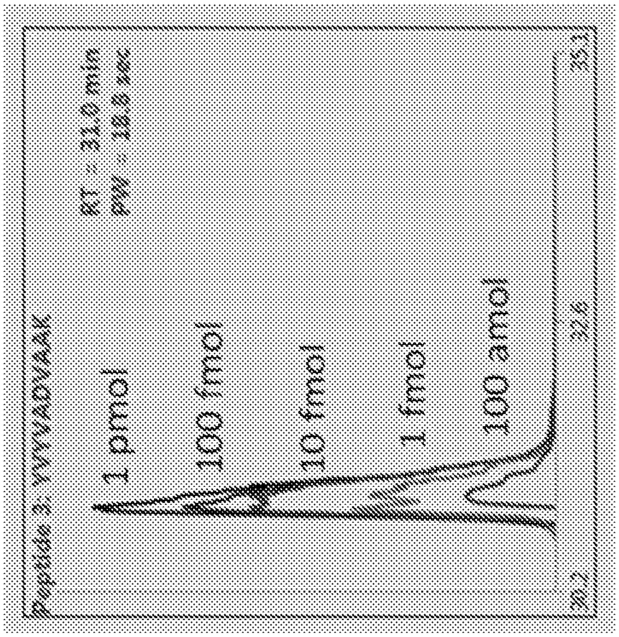
FIG. 24A (SEQ ID NO: 193) and FIG. 24B show example peptide spectrums generated from Promega's dynamic range standard.
Figure 24B:
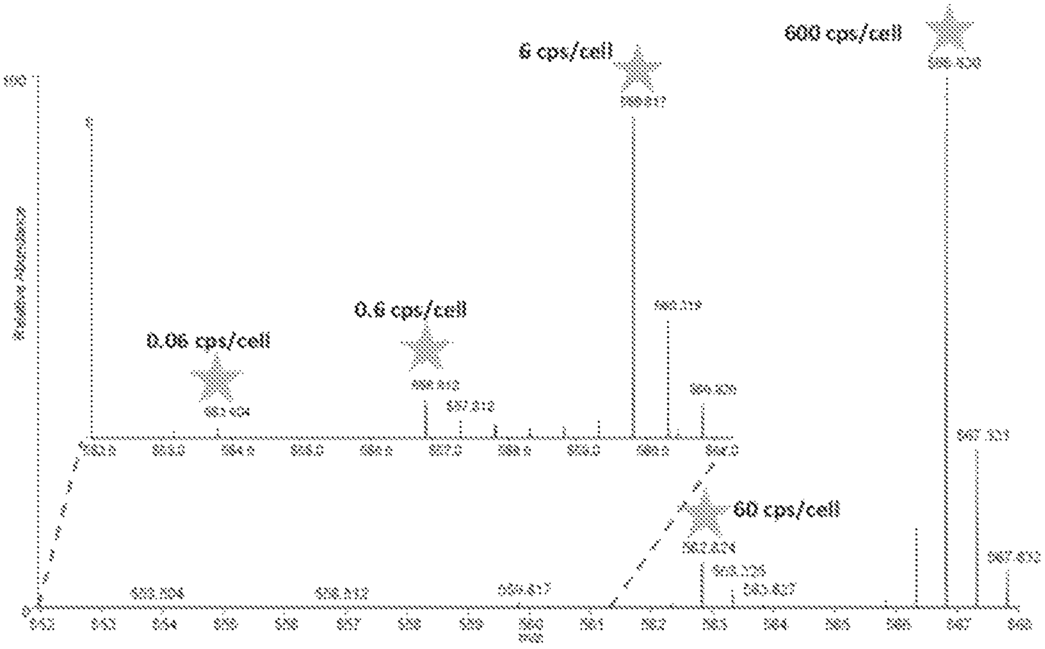
Figure 25:
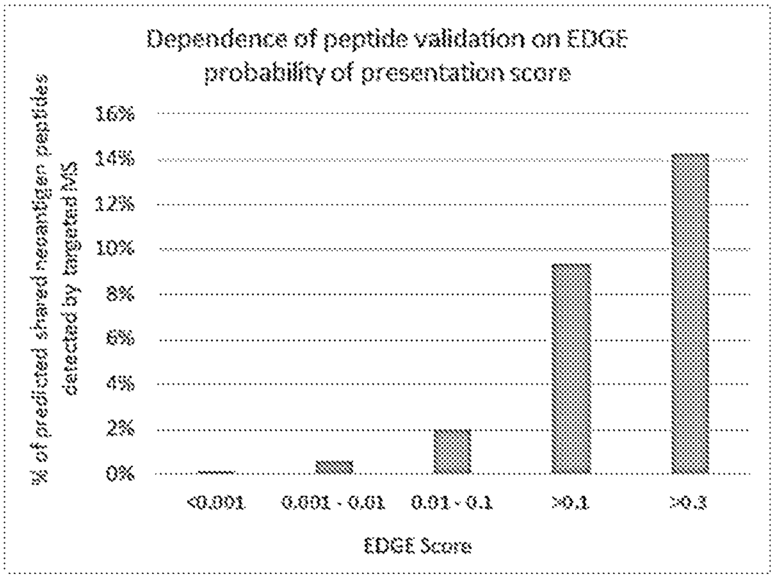
FIG. 25 shows the correlation between EDGE score and the probability of detection of candidate shared neoantigen peptides by targeted MS.

VIII.B.1. MS Limit of Detection Studies in Support of Comprehensive HLA Peptide Sequencing Using the peptide YVYVADVAAK (SEQ ID NO: 193) it was determined what the limits of detection are using different amounts of peptide loaded onto the LC column. The amounts of peptide tested were 1 μmol, 100 fmol, 10 fmol, 1 fmol, and 100 amol. (Table 1) The results are shown in FIGS. 24A and 24B. These results indicate that the lowest limit of detection (LoD) is in the attomol range ($10^{-18}$), that the dynamic range spans five orders of magnitude, and that the signal to noise appears sufficient for sequencing at low femtomole ranges ($10^{-15}$). Mass spectrometry can be used in conjunction with prediction algorithms described herein to validate HLA presentation. For example, mass spectrometry can be used to validate epitope candidates generated by EDGE prediction model (a deep learning model trained on HLA presented peptides sequenced by MS/MS, as described in international patent application publications WO/2017/106638, WO/2018/195357, and WO/2018/208856). An example of the correlation between EDGE score and the probability of detection of candidate shared neoantigen peptides by targeted MS is shown in FIG. 25.

TABLE 1

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

IX. Presentation Model

Presentation models can be used to identify likelihoods of peptide presentation in patients. Various presentation models are known to those skilled in the art, for example the presentation models described in more detail in international patent application publications WO/2017/106638, WO/2018/195357, WO/2018/208856, WO2016187508, and US patent application US20110293637, each herein incorporated by reference, in their entirety, for all purposes.

X. Training Module

Training modules can be used to construct one or more presentation models based on training data sets that generate likelihoods of whether peptide sequences will be presented by MHC alleles associated with the peptide sequences. Various training modules are known to those skilled in the art, for example the presentation models described in more detail in international patent application publications WO/2017/106638, WO/2018/195357, and WO/2018/208856, each herein incorporated by reference, in their entirety, for all purposes. A training module can construct a presentation model to predict presentation likelihoods of peptides on a per-allele basis. A training module can also construct a presentation model to predict presentation likelihoods of peptides in a multiple-allele setting where two or more MHC alleles are present.

XI. Prediction Module

A prediction module can be used to receive sequence data and select candidate antigens in the sequence data using a presentation model. Specifically, the sequence data may be DNA sequences, RNA sequences, and/or protein sequences extracted from tumor tissue cells of patients. A prediction module may identify candidate neoantigens that are mutated peptide sequences by comparing sequence data extracted from normal tissue cells of a patient with the sequence data extracted from tumor tissue cells of the patient to identify portions containing one or more mutations. A prediction module may identify candidate antigens that have altered expression in a tumor cell or cancerous tissue in comparison to a normal cell or tissue by comparing sequence data extracted from normal tissue cells of a patient with the sequence data extracted from tumor tissue cells of the patient to identify improperly expressed candidate antigens.

A presentation module can apply one or more presentation model to processed peptide sequences to estimate presentation likelihoods of the peptide sequences. Specifically, the prediction module may select one or more candidate antigen peptide sequences that are likely to be presented on tumor HLA molecules by applying presentation models to the candidate antigens. In one implementation, the presentation module selects candidate antigen sequences that have estimated presentation likelihoods above a predetermined threshold. In another implementation, the presentation model selects the N candidate antigen sequences that have the highest estimated presentation likelihoods (where N is generally the maximum number of epitopes that can be delivered in a vaccine). A vaccine including the selected candidate antigens for a given patient can be injected into the patient to induce immune responses.

XI.B.Cassette Design Module

XI.B.1 Overview

A cassette design module can be used to generate a vaccine cassette sequence based on selected candidate peptides for injection into a patient. Various cassette design modules are known to those skilled in the art, for example the cassette design modules described in more detail in international patent application publications WO/2017/106638, WO/2018/195357, and WO/2018/208856, each herein incorporated by reference, in their entirety, for all purposes.

A set of therapeutic epitopes may be generated based on the selected peptides determined by a prediction module associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

Therapeutic epitopes may correspond to selected peptides themselves Therapeutic epitopes may also include C- and/or N-terminal flanking sequences in addition to the selected peptides. N- and C-terminal flanking sequences can be the native N- and C-terminal flanking sequences of the therapeutic vaccine epitope in the context of its source protein. Therapeutic epitopes can represent a fixed-length epitope Therapeutic epitopes can represent a variable-length epitope, in which the length of the epitope can be varied depending on, for example, the length of the C- or N-flanking sequence. For example, the C-terminal flanking sequence and the N-terminal flanking sequence can each have varying lengths of 2-5 residues, resulting in 16 possible choices for the epitope.

A cassette design module can also generate cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves.

A cassette design module can generate a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

A cassette design module can iterate through one or more candidate cassettes, and determine a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, a cassette design module may determine a cassette sequence associated with the lowest junction epitope presentation score among the candidate cassette sequences.

A cassette design module may iterate through one or more candidate cassette sequences, determine the junction epitope presentation score for the candidate cassettes, and identify an optimal cassette sequence associated with a junction epitope presentation score below the threshold.

A cassette design module may further check the one or more candidate cassette sequences to identify if any of the junction epitopes in the candidate cassette sequences are self-epitopes for a given patient for whom the vaccine is being designed. To accomplish this, the cassette design module checks the junction epitopes against a known database such as BLAST. In one embodiment, the cassette design module may be configured to design cassettes that avoid junction self-epitopes.

A cassette design module can perform a brute force approach and iterate through all or most possible candidate cassette sequences to select the sequence with the smallest junction epitope presentation score. However, the number of such candidate cassettes can be prohibitively large as the capacity of the vaccine increases. For example, for a vaccine capacity of 20 epitopes, the cassette design module has to iterate through ~$10^{18}$ possible candidate cassettes to determine the cassette with the lowest junction epitope presentation score. This determination may be computationally burdensome (in terms of computational processing resources required), and sometimes intractable, for the cassette design module to complete within a reasonable amount of time to generate the vaccine for the patient. Moreover, accounting for the possible junction epitopes for each candidate cassette can be even more burdensome. Thus, a cassette design module may select a cassette sequence based on ways of iterating through a number of candidate cassette sequences that are significantly smaller than the number of candidate cassette sequences for the brute force approach.

A cassette design module can generate a subset of randomly or at least pseudo-randomly generated candidate cassettes, and selects the candidate cassette associated with a junction epitope presentation score below a predetermined threshold as the cassette sequence. Additionally, the cassette design module may select the candidate cassette from the subset with the lowest junction epitope presentation score as the cassette sequence. For example, the cassette design module may generate a subset of ~1 million candidate cassettes for a set of 20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective. A cassette design module can determine an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the “distance” for traveling from node A to node B may be different from the “distance” for traveling from node B to node A. By solving for an improved optimal cassette using an asymmetric TSP, the cassette design module can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. A cassette sequence determined through this approach can result in a sequence with significantly less presentation of junction epitopes while potentially requiring significantly less computational resources than the random sampling approach, especially when the number of generated candidate cassette sequences is large. Illustrative examples of different computational approaches and comparisons for optimizing cassette design are described in more detail in international patent application publications WO/2017/106638, WO/2018/195357, and WO/2018/208856, each herein incorporated by reference, in their entirety, for all purposes.

XIII. Example Computer

A computer can be used for any of the computational methods described herein. One skilled in the art will recognize a computer can have different architectures. Examples of computers are known to those skilled in the art, for example the computers described in more detail in international patent application publications WO/2017/106638, WO/2018/195357, and WO/2018/208856, each herein incorporated by reference, in their entirety, for all purposes.

XIV. Antigen Delivery Vector Example

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3rd Ed. (Plenum Press) Vols A and B (1992).

XIV.A. Neoantigen Cassette Design

Through vaccination, multiple class I MHC restricted tumor-specific neoantigens (TSNAs) that stimulate the corresponding cellular immune response(s) can be delivered. In one example, a vaccine cassette was engineered to encode multiple epitopes as a single gene product where the epitopes were either embedded within their natural, surrounding peptide sequence or spaced by non-natural linker sequences. Several design parameters were identified that could potentially impact antigen processing and presentation and therefore the magnitude and breadth of the TSNA specific CD8 T cell responses. In the present example, several model cassettes were designed and constructed to evaluate: (1) whether robust T cell responses could be generated to multiple epitopes incorporated in a single expression cassette; (2) what makes an optimal linker placed between the TSNAs within the expression cassette—that leads to optimal processing and presentation of all epitopes; (3) if the relative position of the epitopes within the cassette impact T cell responses; (4) whether the number of epitopes within a cassette influences the magnitude or quality of the T cell responses to individual epitopes; (5) if the addition of cellular targeting sequences improves T cell responses.

Two readouts were developed to evaluate antigen presentation and T cell responses specific for marker epitopes within the model cassettes: (1) an in vitro cell-based screen which allowed assessment of antigen presentation as gauged by the activation of specially engineered reporter T cells (Aarnoudse et al., 2002; Nagai et al., 2012); and (2) an in vivo assay that used HLA-A2 transgenic mice (Vitiello et al., 1991) to assess post-vaccination immunogenicity of cassette-derived epitopes of human origin by their corresponding epitope-specific T cell responses (Cornet et al., 2006; Depla et al., 2008; Ishioka et al., 1999).

XIV.B. Antigen Cassette Design Evaluation

XIV.B.1. Methods and Materials

TCR and Cassette Design and Cloning

The selected TCRs recognize peptides NLVPMVATV (SEQ ID NO: 76) (PDB #5D2N), CLGGLLTMV (SEQ ID NO: 77) (PDB #3REV), GILGFVFTL (SEQ ID NO: 75) (PDB #1OGA) LLFGYPVYV (SEQ ID NO: 74) (PDB #1A07) when presented by A*0201. Transfer vectors were constructed that contain 2A peptide-linked TCR subunits (beta followed by alpha), the EMCV IRES, and 2A-linked CD8 subunits (beta followed by alpha and by the puromycin resistance gene). Open reading frame sequences were codon-optimized and synthesized by GeneArt.

Cell Line Generation for In Vitro Epitope Processing and Presentation Studies

Peptides were purchased from ProImmune or Genscript diluted to 10 mg/mL with 10 mM tris(2-carboxyethyl) phosphine (TCEP) in water/DMSO (2:8, v/v). Cell culture medium and supplements, unless otherwise noted, were from Gibco. Heat inactivated fetal bovine serum (FBShi) was from Seradigm. QUANTI-Luc Substrate, Zeocin, and Puromycin were from InvivoGen. Jurkat-Lucia NFAT Cells (InvivoGen) were maintained in RPMI 1640 supplemented with 10% FBShi, Sodium Pyruvate, and 100 μg/mL Zeocin. Once transduced, these cells additionally received 0.3 μg/mL Puromycin. T2 cells (ATCC CRL-1992) were cultured in Iscove's Medium (IMDM) plus 20% FBShi. U-87 MG (ATCC HTB-14) cells were maintained in MEM Eagles Medium supplemented with 10% FBShi.

Jurkat-Lucia NFAT cells contain an NFAT-inducible Lucia reporter construct. The Lucia gene, when activated by the engagement of the T cell receptor (TCR), causes secretion of a coelenterazine-utilizing luciferase into the culture medium. This luciferase can be measured using the QUANTI-Luc luciferase detection reagent. Jurkat-Lucia cells were transduced with lentivirus to express antigen-specific TCRs. The HIV-derived lentivirus transfer vector was obtained from GeneCopoeia, and lentivirus support plasmids expressing VSV-G (pCMV-VsvG), Rev (pRSV-Rev) and Gag-pol (pCgpV) were obtained from Cell Design Labs.

Lentivirus was prepared by transfection of 50-80% confluent T75 flasks of HEK293 cells with Lipofectamine 2000 (Thermo Fisher), using 40 μl of lipofectamine and 20 μg of the DNA mixture (4:2:1:1 by weight of the transfer plasmid: pCgpV: pRSV-Rev:pCMV-VsvG). 8-10 mL of the virus-containing media were concentrated using the Lenti-X system (Clontech), and the virus resuspended in 100-200 μl of fresh medium. This volume was used to overlay an equal volume of Jurkat-Lucia cells (5x10E4-1x10E6 cells were used in different experiments). Following culture in 0.3 μg/ml puromycin-containing medium, cells were sorted to obtain clonality. These Jurkat-Lucia TCR clones were tested for activity and selectivity using peptide loaded T2 cells.

In Vitro Epitope Processing and Presentation Assay

T2 cells are routinely used to examine antigen recognition by TCRs. T2 cells lack a peptide transporter for antigen processing (TAP deficient) and cannot load endogenous peptides in the endoplasmic reticulum for presentation on the MHC. However, the T2 cells can easily be loaded with exogenous peptides. The five marker peptides (NLVPMVATV (SEQ ID NO: 76), CLGGLLTMV (SEQ ID NO: 77), GLCTLVAML (SEQ ID NO: 75), LLFGYPVYV (SEQ ID NO: 74), GILGFVFTL (SEQ ID NO: 75)) and two irrelevant peptides (WLSLLVPFV (SEQ ID NO: 178), FLLTRICT (SEQ ID NO: 194)) were loaded onto T2 cells. Briefly, T2 cells were counted and diluted to 1×106 cells/mL with IMDM plus 1% FBShi. Peptides were added to result in 10 μg peptide/1×106 cells. Cells were then incubated at 37° C. for 90 minutes. Cells were washed twice with IMDM plus 20% FBShi, diluted to 5x10E5 cells/mL and 100 μL plated into a 96-well Costar tissue culture plate. Jurkat-Lucia TCR clones were counted and diluted to 5x10E5 cells/mL in RPMI 1640 plus 10% FBShi and 100 μL added to the T2 cells. Plates were incubated overnight at 37° C., 5% CO2. Plates were then centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

To test marker epitope presentation by the adenoviral cassettes, U-87 MG cells were used as surrogate antigen presenting cells (APCs) and were transduced with the adenoviral vectors. U-87 MG cells were harvested and plated in culture media as 5x10E5 cells/100 μl in a 96-well Costar tissue culture plate. Plates were incubated for approximately 2 hours at 37° C. Adenoviral cassettes were diluted with MEM plus 10% FBShi to an MOI of 100, 50, 10, 5, 1 and 0 and added to the U-87 MG cells as 5 μl/well. Plates were again incubated for approximately 2 hours at 37° C. Jurkat-Lucia TCR clones were counted and diluted to 5x10E5 cells/mL in RPMI plus 10% FBShi and added to the U-87 MG cells as 100 μL/well. Plates were then incubated for approximately 24 hours at 37° C., 5% CO2. Plates were centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

Mouse Strains for Immunogenicity Studies

Transgenic HLA-A2.1 (HLA-A2 Tg) mice were obtained from Taconic Labs, Inc. These mice carry a transgene consisting of a chimeric class I molecule comprised of the human HLA-A2.1 leader, α1, and α2 domains and the murine H2-Kb α3, transmembrane, and cytoplasmic domains (Vitiello et al., 1991). Mice used for these studies were the first generation offspring (F1) of wild type BALB/cAnNTac females and homozygous HLA-A2.1 Tg males on the C57Bl/6 background.

Adenovirus Vector (Ad5v) Immunizations

HLA-A2 Tg mice were immunized with $1\times10^{10}$ to $1\times10^{6}$ viral particles of adenoviral vectors via bilateral intramuscular injection into the tibialis anterior. Immune responses were measured at 12 days post-immunization.

Lymphocyte Isolation

Lymphocytes were isolated from freshly harvested spleens and lymph nodes of immunized mice. Tissues were dissociated in RPMI containing 10% fetal bovine serum with penicillin and streptomycin (complete RPMI) using the GentleMACS tissue dissociator according to the manufacturer's instructions.

Ex Vivo Enzyme-Linked Immunospot (ELISPOT) Analysis

ELISPOT analysis was performed according to ELISPOT harmonization guidelines (Janetzki et al., 2015) with the mouse IFNg ELISpotPLUS kit (MABTECH). $1\times10^{5}$ splenocytes were incubated with 10 uM of the indicated peptides for 16 hours in 96-well IFNg antibody coated plates. Spots were developed using alkaline phosphatase. The reaction was timed for 10 minutes and was quenched by running the plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count x % confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Ex Vivo Intracellular Cytokine Staining (ICS) and Flow Cytometry Analysis

Freshly isolated lymphocytes at a density of $2\text{-}5\times10^{6}$ cells/mL were incubated with 10 uM of the indicated peptides for 2 hours. After two hours, brefeldin A was added to a concentration of 5 ug/ml and cells were incubated with stimulant for an additional 4 hours. Following stimulation, viable cells were labeled with fixable viability dye eFluor780 according to manufacturer's protocol and stained with anti-CD8 APC (clone 53-6.7, BioLegend) at 1:400 dilution. Anti-IFNg PE (clone XMG1.2, BioLegend) was used at 1:100 for intracellular staining. Samples were collected on an Attune NxT Flow Cytometer (Thermo Scientific). Flow cytometry data was plotted and analyzed using FlowJo. To assess degree of antigen-specific response, both the percent IFNg+ of CD8+ cells and the total IFNg+ cell number/$1\times10^{6}$ live cells were calculated in response to each peptide stimulant.

XIV.B.2. In Vitro Evaluation of Antigen Cassette Designs

As an example of antigen cassette design evaluation, an in vitro cell-based assay was developed to assess whether selected human epitopes within model vaccine cassettes were being expressed, processed, and presented by antigen-presenting cells (FIG. 1). Upon recognition, Jurkat-Lucia reporter T cells that were engineered to express one of five TCRs specific for well-characterized peptide-HLA combinations become activated and translocate the nuclear factor of activated T cells (NFAT) into the nucleus which leads to transcriptional activation of a luciferase reporter gene. Antigenic stimulation of the individual reporter CD8 T cell lines was quantified by bioluminescence.

Individual Jurkat-Lucia reporter lines were modified by lentiviral transduction with an expression construct that includes an antigen-specific TCR beta and TCR alpha chain separated by a P2A ribosomal skip sequence to ensure equimolar amounts of translated product (Banu et al., 2014). The addition of a second CD8 beta-P2A-CD8 alpha element to the lentiviral construct provided expression of the CD8 co-receptor, which the parent reporter cell line lacks, as CD8 on the cell surface is crucial for the binding affinity to target pMHC molecules and enhances signaling through engagement of its cytoplasmic tail (Lyons et al., 2006; Yachi et al., 2006).

After lentiviral transduction, the Jurkat-Lucia reporters were expanded under puromycin selection, subjected to single cell fluorescence assisted cell sorting (FACS), and the monoclonal populations tested for luciferase expression. This yielded stably transduced reporter cell lines for specific peptide antigens 1, 2, 4, and 5 with functional cell responses. (Table 2).

TABLE 2

Development of an in vitro T cell activation assay. Peptide-specific T cell recognition as measured by induction of luciferase indicates effective processing and presentation of the vaccine cassette antigens.

| Epitope | Short Cassette Design AAY |
|---|---|
| 1 | 24.5 ± 0.5 |
| 2 | 11.3 ± 0.4 |
| 3* | n/a |
| 4 | 26.1 ± 3.1 |
| 5 | 46.3 ± 1.9 |

*Reporter T cell for epitope 3 not yet generated

In another example, a series of short cassettes, all marker epitopes were incorporated in the same position (FIG. 2A) and only the linkers separating the HLA-A*0201 restricted epitopes (FIG. 2B) were varied. Reporter T cells were individually mixed with U-87 antigen-presenting cells (APCs) that were infected with adenoviral constructs expressing these short cassettes, and luciferase expression was measured relative to uninfected controls. All four antigens in the model cassettes were recognized by matching reporter T cells, demonstrating efficient processing and presentation of multiple antigens. The magnitude of T cell responses follow largely similar trends for the natural and AAY-linkers. The antigens released from the RR-linker based cassette show lower luciferase inductions (Table 3). The DPP-linker, designed to disrupt antigen processing, produced a vaccine cassette that led to low epitope presentation (Table 3).

TABLE 3

Evaluation of linker sequences in short cassettes. Luciferase induction in the in vitro T cell activation assay indicated that, apart from the DPP-based cassette, all linkers facilitated efficient release of the cassette antigens. T cell epitope only (no linker) = 9AA, natural linker one side = 17AA, natural linker both sides = 25AA, non-natural linkers = AAY, RR, DPP

| | Short Cassette Designs | | | | | |
|---|---|---|---|---|---|---|
| Epitope | 9AA | 17AA | 25AA | AAY | RR | DPP |
| 1 | 33.6 ± 0.9 | 42.8 ± 2.1 | 42.3 ± 2.3 | 24.5 ± 0.5 | 21.7 ± 0.9 | 0.9 ± 0.1 |
| 2 | 12.0 ± 0.9 | 10.3 ± 0.6 | 14.6 ± 04 | 11.3 ± 0.4 | 8.5 ± 0.3 | 1.1 ± 0.2 |
| 3* | n/a | n/a | n/a | n/a | n/a | n/a |
| 4 | 26.6 ± 2.5 | 16.1 ± 0.6 | 16.6 ± 0.8 | 26.1 ± 3.1 | 12.5 ± 0.8 | 1.3 ± 0.2 |
| 5 | 29.7 ± 0.6 | 21.2 ± 0.7 | 24.3 ± 1.4 | 46.3 ± 1.9 | 19.7 ± 0.4 | 1.3 ± 0.1 |

*Reporter T cell for epitope 3 not yet generated

Figure 3:
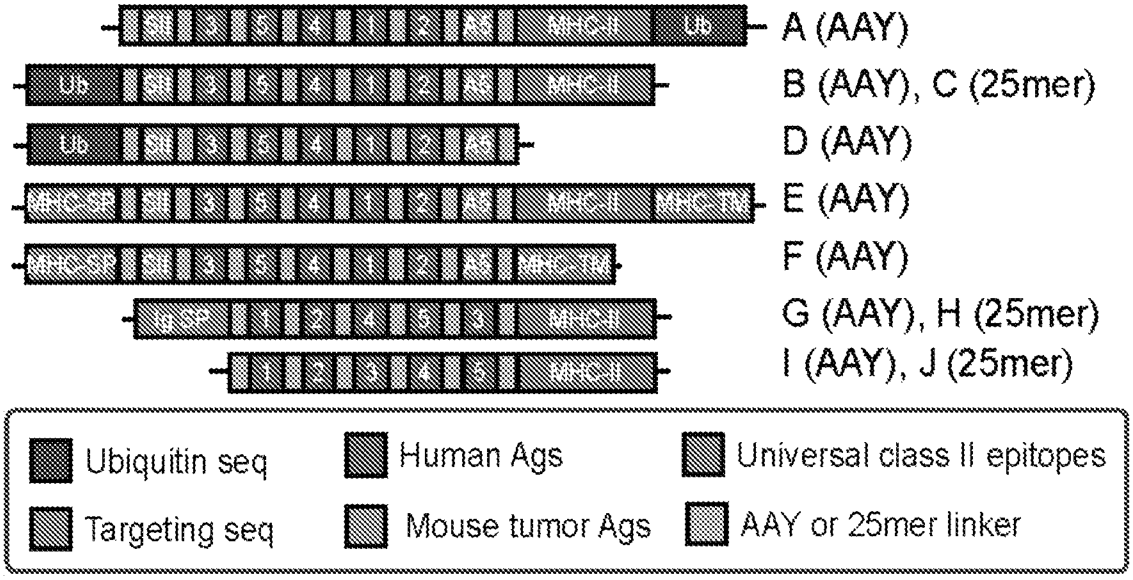
FIG. 3 illustrates evaluation of cellular targeting sequences added to model vaccine cassettes. The targeting cassettes extend the short cassette designs with ubiquitin (Ub), signal peptides (SP) and/or transmembrane (TM) domains, feature next to the five marker human T cell epitopes (epitopes 1 through 5) also two mouse T cell epitopes SIINFEKL (SEQ ID NO: 133) (SII) and SPSYAYHQF (SEQ ID NO: 137) (A5), and use either the non natural linker AAY- or natural linkers flanking the T cell epitopes on both sides (25mer).

In another example, an additional series of short cassettes were constructed that, besides human and mouse epitopes, contained targeting sequences such as ubiquitin (Ub), MHC and Ig-kappa signal peptides (SP), and/or MHC transmembrane (TM) motifs positioned on either the N- or C-terminus of the cassette. (FIG. 3). When delivered to U-87 APCs by adenoviral vector, the reporter T cells again demonstrated efficient processing and presentation of multiple cassette-derived antigens. However, the magnitude of T cell responses were not substantially impacted by the various targeting features (Table 4).

TABLE 4

Evaluation of cellular targeting sequences added to model vaccine cassettes. Employing the in vitro T cell activation assay demonstrated that the four HLA-A*0201 restricted marker epitopes are liberated efficiently from the model cassettes and targeting sequences did not substantially improve T cell recognition and activation.

| | Short Cassette Designs | | | | | | | | | |
|---|---|---|---|---|---|---|---|---|---|---|
| Epitope | A | B | C | D | E | F | G | H | I | J |
| 1 | 32.5 ± 1.5 | 31.8 ± 0.8 | 29.1 ± 1.2 | 29.1 ± 1.1 | 28.4 ± 0.7 | 20.4 ± 0.5 | 35.0 ± 1.3 | 30.3 ± 2.0 | 22.5 ± 0.9 | 38.1 ± 1.6 |
| 2 | 6.1 ± 0.2 | 6.3 ± 0.2 | 7.6 ± 0.4 | 7.0 ± 0.5 | 5.9 ± 0.2 | 3.7 ± 0.2 | 7.6 ± 0.4 | 5.4 ± 0.3 | 6.2 ± 0.4 | 6.4 ± 0.3 |
| 3* | n/a | n/a | n/a | n/a | n/a | n/a | n/a | n/a | n/a | n/a |
| 4 | 12.3 ± 1.1 | 14.1 ± 0.7 | 12.2 ± 0.8 | 13.7 ± 1.0 | 11.7 ± 0.8 | 10.6 ± 0.4 | 11.0 ± 0.6 | 7.6 ± 0.6 | 16.1 ± 0.5 | 8.7 ± 0.5 |
| 5 | 44.4 ± 2.8 | 53.6 ± 1.6 | 49.9 ± 3.3 | 50.5 ± 2.8 | 41.7 ± 2.8 | 36.1 ± 1.1 | 46.5 ± 2.1 | 31.4 ± 0.6 | 75.4 ± 1.6 | 35.7 ± 2.2 |

*Reporter T cell for epitope 3 not yet generated

XIV.B.3. In Vivo Evaluation of Antigen Cassette Designs

Figures 2A, 2B:
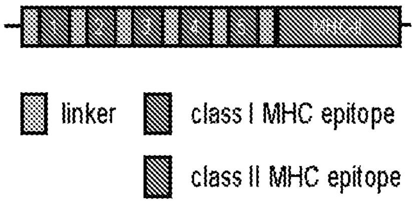
FIG. 2A illustrates evaluation of linker sequences in short cassettes and shows five class I MHC restricted epitopes (epitopes 1 through 5) concatenated in the same position relative to each other followed by two universal class II MHC epitopes (MHC-II). Various iterations were generated using different linkers. In some cases the T cell epitopes are directly linked to each other. In others, the T cell epitopes are flanked on one or both sides by its natural sequence. In other iterations, the T cell epitopes are linked by the non-natural sequences AAY, RR, and DPP.
FIG. 2B (SEQ ID NO: 49, SEQ ID NO: 73-77, SEQ ID NO: 173) illustrates evaluation of linker sequences in short cassettes and shows sequence information on the T cell epitopes embedded in the short cassettes.
Figure 4:
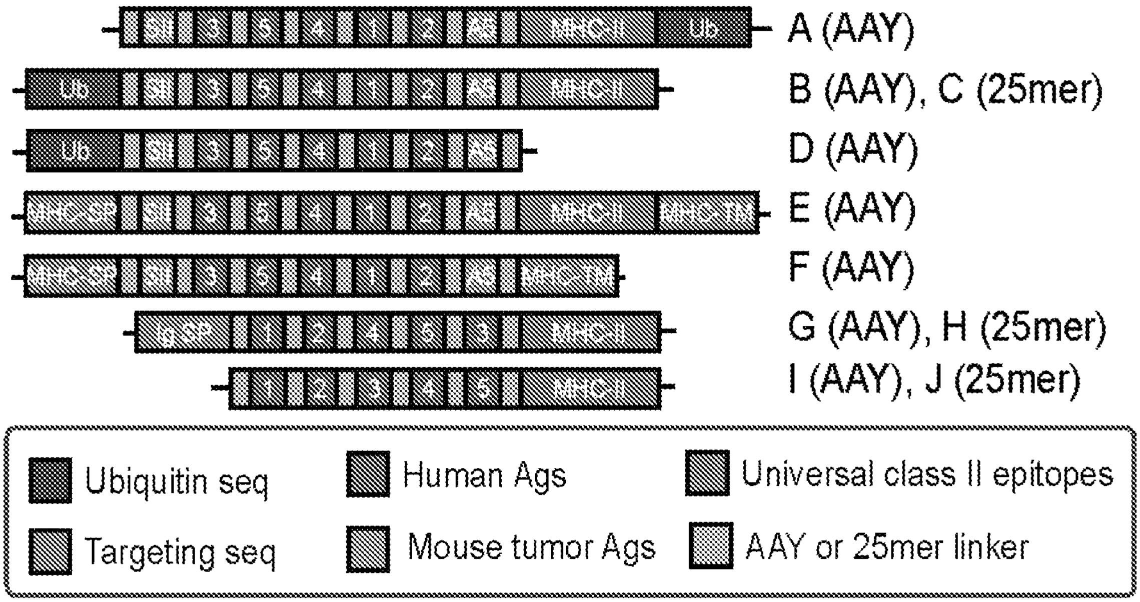
FIG. 4 illustrates in vivo evaluation of linker sequences in short cassettes. A) Experimental design of the in vivo evaluation of vaccine cassettes using HLA-A2 transgenic mice.
Figure 5A:
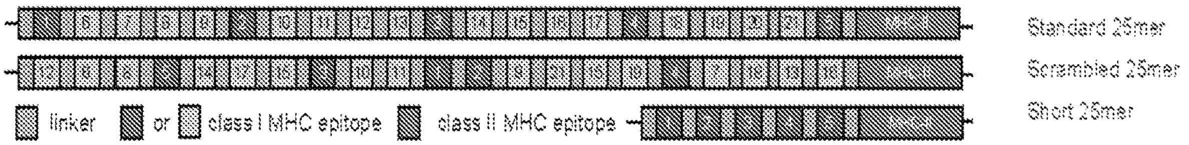
FIG. 5A illustrates in vivo evaluation of the impact of epitope position in long 21-mer cassettes and shows the design of long cassettes entails five marker class I epitopes (epitopes 1 through 5) contained in their 25-mer natural sequence (linker=natural flanking sequences), spaced with additional well-known T cell class I epitopes (epitopes 6 through 21) contained in their 25-mer natural sequence, and two universal class II epitopes (MHC-II0, with only the relative position of the class I epitopes varied.

As another example of antigen cassette design evaluation, vaccine cassettes were designed to contain 5 well-characterized human class I MHC epitopes known to stimulate CD8 T cells in an HLA-A*02:01 restricted fashion (FIG. 2A, 3, 5A). For the evaluation of their in vivo immunogenicity, vaccine cassettes containing these marker epitopes were incorporated in adenoviral vectors and used to infect HLA-A2 transgenic mice (FIG. 4). This mouse model carries a transgene consisting partly of human HLA-A*0201 and mouse H2-Kb thus encoding a chimeric class I MHC molecule consisting of the human HLA-A2.1 leader, α1 and α2 domains ligated to the murine α3, transmembrane and cytoplasmic H2-Kb domain (Vitiello et al., 1991). The chimeric molecule allows HLA-A*02:01-restricted antigen presentation whilst maintaining the species-matched interaction of the CD8 co-receptor with the α3 domain on the MHC.

For the short cassettes, all marker epitopes generated a T cell response, as determined by IFN-gamma ELISPOT, that was approximately 10-50× stronger of what has been commonly reported (Cornet et al., 2006; Depla et al., 2008; Ishioka et al., 1999). Of all the linkers evaluated, the concatamer of 25mer sequences, each containing a minimal epitope flanked by their natural amino acids sequences, generated the largest and broadest T cell response (Table 5). Intracellular cytokine staining (ICS) and flow cytometry analysis revealed that the antigen-specific T cell responses are derived from CD8 T cells.

TABLE 5

In vivo evaluation of linker sequences in short cassettes. ELISPOT data indicated that HLA-A2 transgenic mice, 17 days post-infection with 1e11 adenovirus viral particles, generated a T cell response to all class I MHC restricted epitopes in the cassette.

| | Short Cassette Designs | | | | | |
|---|---|---|---|---|---|---|
| Epitope | 9AA | 17AA | 25AA | AAY | RR | DPP |
| 1 | 2020 +/− 583 | 2505 +/− 1281 | 6844 +/− 956 | 1489 +/− 762 | 1675 +/− 690 | 1781 +/− 774 |
| 2 | 4472 +/− 755 | 3792 +/− 1319 | 7629 +/− 996 | 3851 +/− 1748 | 4726 +/− 1715 | 5868 +/− 1427 |
| 3 | 5830 +/− 315 | 3629 +/− 862 | 7253 +/− 491 | 4813 +/− 1761 | 6779 +/− 1033 | 7328 +/− 1700 |
| 4 | 5536 +/− 375 | 2446 +/− 955 | 2961 +/− 1487 | 4230 +/− 1759 | 6518 +/− 909 | 7222 +/− 1824 |
| 5 | 8800 +/− 0 | 7943 +/− 821 | 8423 +/− 442 | 8312 +/− 696 | 8800 +/− 0 | 1836 +/− 328 |

In another example, a series of long vaccine cassettes was constructed and incorporated in adenoviral vectors that, next to the original 5 marker epitopes, contained an additional 16 HLA-A*02:01, A*03:01 and B*44:05 epitopes with known CD8 T cell reactivity (FIG. 5A, B). The size of these long cassettes closely mimicked the final clinical cassette design, and only the position of the epitopes relative to each other was varied. The CD8 T cell responses were comparable in magnitude and breadth for both long and short vaccine cassettes, demonstrating that (a) the addition of more epitopes did not substantially impact the magnitude of immune response to the original set of epitopes, and (b) the position of an epitope in a cassette did not substantially influence the ensuing T cell response to it (Table 6).

TABLE 6

In vivo evaluation of the impact of epitope position in long cassettes. ELISPOT data indicated that HLA-A2 transgenic mice, 17 days post-infection with 5e10 adenovirus viral particles, generated a T cell response comparable in magnitude for both long and short vaccine cassettes.

| | Long Cassette Designs | | |
|---|---|---|---|
| Epitope | Standard | Scrambled | Short |
| 1 | 863 +/− 1080 | 804 +/− 1113 | 1871 +/− 2859 |
| 2 | 6425 +/− 1594 | 28 +/− 62 | 5390 +/− 1357 |
| 3* | 23 +/− 30 | 36 +/− 18 | 0 +/− 48 |
| 4 | 2224 +/− 1074 | 2727 +/− 644 | 2637 +/− 1673 |
| 5 | 7952 +/− 297 | 8100 +/− 0 | 8100 +/− 0 |

*Suspected technical error caused an absence of a T cell response.

XIV.B.4. Antigen Cassette Design for Immunogenicity and Toxicology Studies

In summary, the findings of the model cassette evaluations (FIG. 2-5, Tables 2-6) demonstrated that, for model vaccine cassettes, robust immunogenicity was achieved when a "string of beads" approach was employed that encodes around 20 epitopes in the context of an adenovirus-based vector. The epitopes were assembled by concatenating 25mer sequences, each embedding a minimal CD8 T cell epitope (e.g. 9 amino acid residues) that were flanked on both sides by its natural, surrounding peptide sequence (e.g. 8 amino acid residues on each side). As used herein, a "natural" or "native" flanking sequence refers to the N- and/or C-terminal flanking sequence of a given epitope in the naturally occurring context of that epitope within its source protein. For example, the HCMV pp65 MHC I epitope NLVPMVATV (SEQ ID NO: 76) is flanked on its 5' end by the native 5' sequence WQAGILAR (SEQ ID NO: 192) and on its 3' end by the native 3' sequence QGQNLKYQ (SEQ ID NO: 191), thus generating the WQAGILARNLVPMVATVQGQNLKYQ (SEQ ID NO: 91) 25mer peptide found within the HCMV pp65 source protein. The natural or native sequence can also refer to a nucleotide sequence that encodes an epitope flanked by native flanking sequence(s). Each 25mer sequence is directly connected to the following 25mer sequence. In instances where the minimal CD8 T cell epitope is greater than or less than 9 amino acids, the flanking peptide length can be adjusted such that the total length is still a 25mer peptide sequence. For example, a 10 amino acid CD8 T cell epitope can be flanked by an 8 amino acid sequence and a 7 amino acid. The concatamer was followed by two universal class II MHC epitopes that were included to stimulate CD4 T helper cells and improve overall in vivo immunogenicity of the vaccine cassette antigens. (Alexander et al., 1994; Panina-Bordignon et al., 1989) The class II epitopes were linked to the final class I epitope by a GPGPG amino acid linker (SEQ ID NO: 56). The two class II epitopes were also linked to each other by a GPGPG amino acid linker (SEQ ID NO: 56), as a well as flanked on the C-terminus by a GPGPG amino acid linker (SEQ ID NO: 56). Neither the position nor the number of epitopes appeared to substantially impact T cell recognition or response. Targeting sequences also did not appear to substantially impact the immunogenicity of cassette-derived antigens.

Figure 6A:
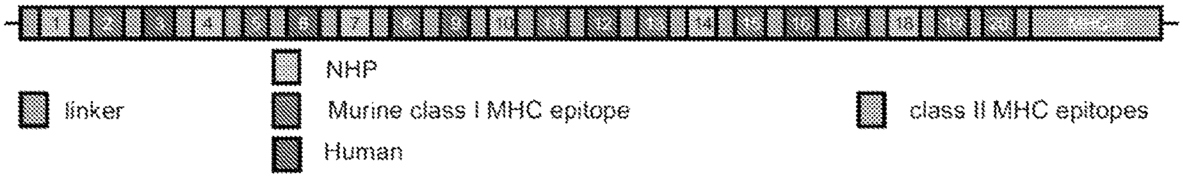
FIG. 6A illustrates final cassette design for preclinical IND-enabling studies and shows the design of the final cassettes comprises 20 MHC I epitopes contained in their 25-mer natural sequence (linker=natural flanking sequences), composed of 6 non-human primate (NHP) epitopes, 5 human epitopes, 9 murine epitopes, as well as 2 universal MHC class II epitopes.

As a further example, based on the in vitro and in vivo data obtained with model cassettes (FIG. 2-5, Tables 2-6), a cassette design was generated that alternates well-characterized T cell epitopes known to be immunogenic in non-human primates (NHPs), mice and humans. The 20 epitopes, all embedded in their natural 25mer sequences, are followed by the two universal class II MHC epitopes that were present in all model cassettes evaluated (FIG. 6). This cassette design was used to study immunogenicity as well as pharmacology and toxicology studies in multiple species.

XIV.B.5. Antigen Cassette Design and Evaluation for 30, 40, and 50 Antigens

Figure 29:
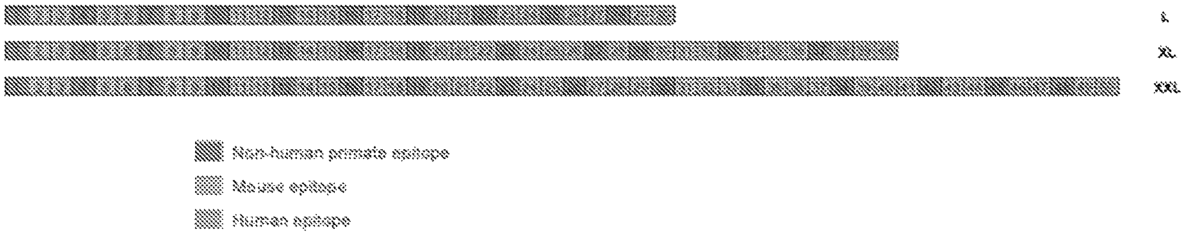
FIG. 29 illustrates the general organization of the model epitopes from the various species for large antigen cassettes that had either 30 (L), 40 (XL) or 50 (XXL) epitopes.

Large antigen cassettes were designed that had either 30 (L), 40 (XL) or 50 (XXL) epitopes, each 25 amino acids in length. The epitopes were a mix of human, NHP and mouse epitopes to model disease antigens including tumor antigens. FIG. 29 illustrates the general organization of the epitopes from the various species. The model antigens used are described in Tables 37, 38 and 39 for human, primate, and mouse model epitopes, respectively. Each of Tables 37, 38 and 39 described the epitope position, name, minimal epitope description, and MHC class.

Figure 30:
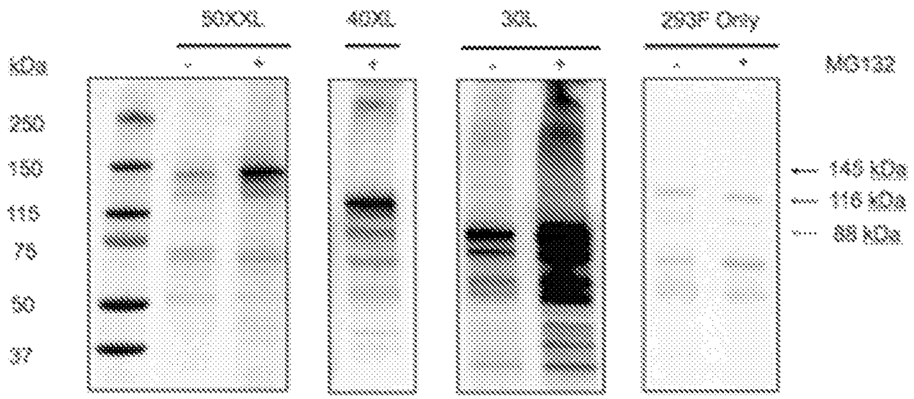
FIG. 30 shows ChAd vectors express long cassettes as indicated by the above Western blot using an anti-class II (PADRE) antibody that recognizes a sequence common to all cassettes. HEK293 cells were infected with chAd68 vectors expressing large cassettes (chAd68-50XXL, chAd68-40XL & chAd68-30 L) of variable size. Infections were set up at a MOI of 0.2. Twenty-four hours post infection MG132 a proteasome inhibitor was added to a set of the infected wells (indicated by the plus sign). Another set of virus treated wells were not treated with MG132 (indicated by minus sign). Uninfected HEK293 cells (293F) were used as a negative control. Forty-eight hours post infection cell pellets were harvested and analyzed by SDS/PAGE electrophoresis, and immunoblotting using a rabbit anti-Class II PADRE antibody. A HRP anti-rabbit antibody and ECL chemiluminescent substrate was used for detection.

These cassettes were cloned into the chAd68 and srRNA vaccine vectors as described to evaluate the efficacy of longer multiple-epitope cassettes. FIG. 30 shows that each of the large antigen cassettes were expressed from a ChAdV vector as indicated by at least one major band of the expected size by Western blot.

Figure 31:
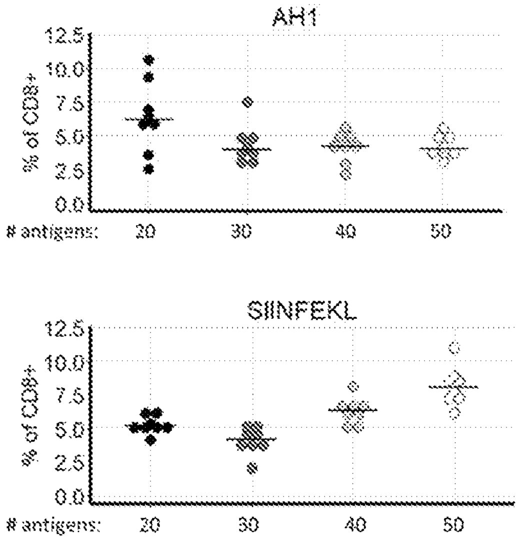
FIG. 31 shows CD8+ immune responses in chAd68 large cassette immunized mice, detected against AH1 (top) and SIINFEKL (SEQ ID NO: 133) (bottom) by ICS. Data is presented as IFNg+ cells against the model epitope as % of total CD8 cells
Figure 32:
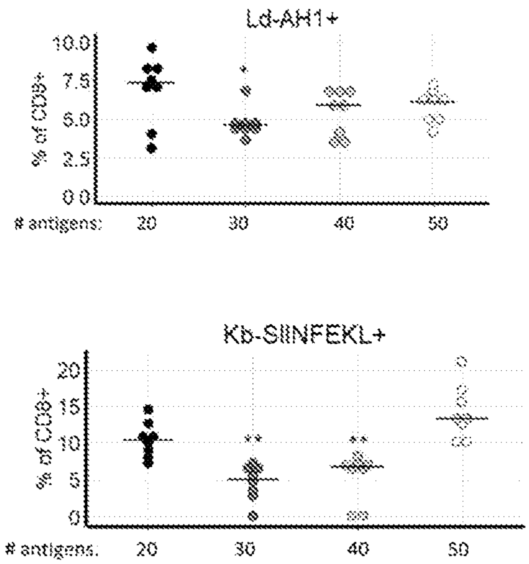
FIG. 32 shows CD8+ responses to LD-AH1+ (top) and Kb-SIINFEKL (SEQ ID NO: 133)+ (bottom) Tetramers post chAd68 large cassette vaccination. Data is presented as % of total CD8 cells reactive against the model Tetramer peptide complex. *p<0.05, **p<0.01 by ANOVA with Tukey's test. All p-values compared to MAG 20-antigen cassette.
Figure 33:
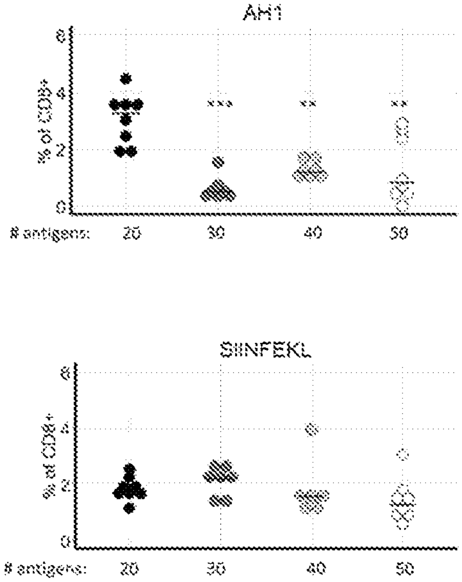
FIG. 33 shows CD8+ immune responses in alphavirus large cassette treated mice, detected against AH1 (top) and SIINFEKL (SEQ ID NO: 133) (bottom) by ICS. Data is presented as IFNg+ cells against the model epitope as % of total CD8 cells. *$p<0.05$, $p<0.01$, *$p<0.001$ by ANOVA with Tukey's test. All p-values compared to MAG 20-antigen cassette.

Mice were immunized as described to evaluate the efficacy of the large cassettes. T cell responses were analyzed by ICS and tetramer staining following immunization with a chAd68 vector (FIG. 31/Table 40 and FIG. 32/Table 41, respectively) and by ICS following immunization with a srRNA vector (FIG. 33/Table 42) for epitopes AH1 (top panels) and SINNFEKL (SEQ ID NO: 195) (bottom panels). Immunizations using chAd68 and srRNA vaccine vectors expressing either 30 (L), 40 (XL) or 50 (XXL) epitopes induced CD8+ immune responses to model disease epitopes.

TABLE 37

Human epitopes in large cassettes

| Epitope position in each cassette | | | | | | | | | |
|---|---|---|---|---|---|---|---|---|---|
| L | XL | XXL | Name | Minimal epitope | 25mer | MHC | Restriction | Strain | Species |
| 3 | 3 | 3 | 5. influenza M | GILGFVFTL | PILSPLTKGILGFVFTLTVPSERGL | Class I | A*02:01 | Human | Human |
| 6 | 6 | 6 | 4. HTLV-1 Tax | LLFGYPVYV | HFPGFGQSLLFGYPVYVFGDCVQGD | Class I | A*02:01 | Human | Human |
| 9 | 9 | 9 | 3. EBV BMLF1 | GLCTLVAML | RMQAIQNAGLCTLVAMLEETIFWLQ | Class I | A*02:01 | Human | Human |
| 12 | 12 | 12 | 1. HCMV pp65 | NLVPMVATV | WQAGILARNLVPMVATVQGQNLKYQ | Class I | A*02:01 | Human | Human |
| 15 | 15 | 15 | 2. EBV LMP2A | CLGGLLTMV | RTYGPVFMCLGGLLTMVAGAVWLTV | Class I | A*02:01 | Human | Human |

TABLE 37-continued

Human epitopes in large cassettes

| Epitope position in each cassette L | XL | XXL | Name | Minimal epitope | 25mer | MHC | Restriction | Strain | Species |
|---|---|---|---|---|---|---|---|---|---|
| 18 | 18 | 18 | CT83 | NTDNNLAVY | SSSGLINSNTDNNLAVYDLS RDILN | Class I | A*01:01 | Human | Human |
| | 21 | 21 | MAGEA6 | EVDPIGHVY | LVFGIELMEVDPIGHVYIFA TCLGL | Class I | B*35:01 | Human | Human |
| 21 | 25 | 25 | CT83 | LLASSILCA | MNFYLLLASSILCALIVFWK YRRFQ | Class I | A*02:01 | Human | Human |
| 24 | 31 | 28 | FOXE1 | AIFPGAVPAA | AAAAAAAAIFPGAVPAARPP YPGAV | Class I | A*02:01 | Human | Human |
| 27 | 35 | 32 | CT83 | VYDLSRDIL | SNTDNNLAVYDLSRDILNNF PHSIA | Class I | A*24:02 | Human | Human |
| | 38 | 36 | MAGE3/6 | ASSLPTTMNY | DPPQSPQGASSLPTTMNYPL WSQSY | Class I | A*01:01 | Human | Human |
| 30 | 40 | 40 | Influenza HA | PKYVKQNTLKLAT | ITYGACPKYVKQNTLKLATG MRNVP | Class II | DRB1*0101 | Human | Human |
| | | 44 | CMV pp65 | LPLKMLNIPSINVH | SIYVYALPLKMLNIPSINVH HYPSA | Class II | DRB1*0101 | Human | Human |
| | | 47 | EBV EBNA3A | PEQWMFQGAPPSQGT | EGPWVPEQWMFQGAPPSQGT DVVQH | Class II | DRB1*0102 | Human | Human |
| | | 50 | CMV pp65 | EHPTFTSQYRIQGKL | RGPQYSEHPTFTSQYRIQGK LEYRH | Class II | DRB1*1101 | Human | Human |

TABLE 38

NHP epitopes in large cassettes

| Epitope position in each cassette L | XL | XXL | Name | Minimal epitope | 25mer | MHC | Restriction | Strain | Species |
|---|---|---|---|---|---|---|---|---|---|
| 1 | 1 | 1 | Gag CM9 | CTPYDINQM | MFQALSEGCTPYDINQMLNV LGDHQ | Class I | Mamu-A*01 | Rhesus | NHP |
| 4 | 4 | 4 | Tat TL8 | TTPESANL | SCISEADATTPESANLGEEI LSQLY | Class I | Mamu-A*01 | Rhesus | NHP |
| 7 | 7 | 7 | Env CL9 | CAPPGYALL | WDAIRFRYCAPPGYALLRCN DTNYS | Class I | Mamu-A*01 | Rhesus | NHP |
| 10 | 10 | 10 | Pol SV9 | SGPKTNIIV | AFLMALTDSGPKTNIIVDSQ YVMGI | Class I | Mamu-A*01 | Rhesus | NHP |
| 13 | 13 | 13 | Gag LW9 | LSPRTLNAW | GNVWVHTPLSPRTLNAWVKA VEEKK | Class I | Mamu-A*01 | Rhesus | NHP |
| | | 16 | Env_TL9 | TVPWPNASL | AFRQVCHTTVPWPNASLTPK WNNET | Class I | Mamu-A*01 | Rhesus | NHP |
| 16 | 16 | 19 | Ag85B | PNGTHSWEYWGAQLN | VFNFPPNGTHSWEYWGAQLN AMKGD | Class II | Mamu-DR*W | Rhesus | NHP |
| 19 | 19 | 23 | HIV-1 Env | YKYKVVKIEPLGV | NWRSELYKYKVVKIEPLGVA PTKAK | Class II | Mamu-DR*W | Rhesus | NHP |

TABLE 38-continued

NHP epitopes in large cassettes

| Epitope position in each cassette L | XL | XXL | Name | Minimal epitope | 25mer | MHC | Restriction | Strain | Species |
|---|---|---|---|---|---|---|---|---|---|
| | | 26 | Gag TE15 | TEEAKQIVQRHLVVE | EKVKHTEEAKQIVQRHLVVE TGTTE | Class II | Mamu-DRB* | Rhesus | NHP |
| | 23 | 30 | CFP-10 36-48 | AGSLQGQWRGAAG | DQVESTAGSLQGQWRGAAGT AAQAA | Class II | Mafa-DRB1* | Cyno | NHP |
| | 27 | 34 | CFP-10 71-86 | EISTNIRQAGVQYSRA | QELDEISTNIRQAGVQYSRA DEEQQ | Class II | Mafa-DRB1* | Cyno | NHP |
| 22 | 29 | 38 | Env 338-346 | RPKQAWCWF | FHSQPINERPKQAWCWFGGS WKEAI | Class I | Mafa-A1*06: | Cyno | NHP |
| 25 | 33 | 42 | Nef 103-111 | RPKVPLRTM | DDIDEEDDDLVGVSVRPKVP LRTMS | Class I | Mafa-A1*06: | Cyno | NHP |
| 28 | 37 | 45 | Gag 386-394 | GPRKPIKCW | PFAAAQQRGPRKPIKCWNCG KEGHS | Class I | Mafa-A1*06: | Cyno | NHP |
| | | 48 | Nef LT9 | LNMADKKET | RRLTARGLLNMADKKETRTP KKAKA | Class I | Mafa-B*104: | Cyno | NHP |

TABLE 39

Mouse epitopes in large cassettes

| Epitope position in each cassette L | XL | XXL | Name | Minimal epitope | 25mer | MHC | Restriction | Strain | Species |
|---|---|---|---|---|---|---|---|---|---|
| 2 | 2 | 2 | OVA257 | SIINFEKL | VSGLEQLESIINFEKLTEWT SSNVM | Class I | H2-Kb | B6 | Mouse |
| | | 5 | B16-EGP | EGPRNQDWL | ALLAVGALEGPRNQDWLGVP RQLVT | Class I | H2-Db | B6 | Mouse |
| | | 8 | B16-TRP1 455-463 | TAPDNLGYM | VTNTEMFVTAPDNLGYMYEV QWPGQ | Class I | H2-Db | B6 | Mouse |
| | | 11 | Trp2180-188 | SVYDFFVWL | TQPQIANCSVYDFFVWLHYY SVRDT | Class I | H2-Kb | B6 | Mouse |
| 5 | 5 | 14 | CT26 AH1-A5 | SPSYAYHQF | LWPRVTYHSPSYAYHQFERR AKYKR | Class I | H2-Ld | Balb/C | Mouse |
| | 8 | 17 | CT26 AH1-39 | MNKYAYHML | LWPRVTYHMNKYAYHMLERR AKYKR | Class I | H2-Ld | Balb/C | Mouse |
| | 11 | 20 | MC38 Dpagt1 | SIIVFNLL | GQSLVISASIIVFNLLELEG DYRDD | Class I | H2-Kb | B6 | Mouse |
| | 14 | 22 | MC38 Adpgk | ASMTNMELM | GIPVHLELASMTNMELMSSI VHQQV | Class I | H2-Db | B6 | Mouse |
| | 17 | 24 | MC38 Reps1 | AQLANDVVL | RVLELFRAAQLANDVVLQIM ELCGA | Class I | H2-Db | B6 | Mouse |
| 8 | 20 | 27 | P815 P1A 35-44 | LPYLGWLVF | HRYSLEEILPYLGWLVFAVV TTSFL | Class I | H2-Ld | DBA/2 | Mouse |
| 11 | 22 | 29 | P815 P1E | GYCGLRGTGV | YLSKNPDGYCGLRGTGVSCP MAIKK | Class I | H2-Kd | DBA/2 | Mouse |
| 14 | 24 | 31 | Panc02 Mesothelir | LSIFKHKL | NEIPFTYEQLSIFKHKLDKT YPQGY | Class I | H2-Kb | B6 | Mouse |

TABLE 39-continued

| Mouse epitopes in large cassettes | | | | | | | | | |
|---|---|---|---|---|---|---|---|---|---|
| Epitope position in each cassette | | | | | | | | | |
| L | XL | XXL | Name | Minimal epitope | 25mer | MHC | Restriction | Strain | Species |
| 17 | 26 | 33 | Panc02 Mesothelir | LIWIPALL | SRASLLGPGFVLIWIPALLP ALRLS | Class I | H2-Kb | B6 | Mouse |
| 20 | 28 | 35 | ID8 FRa 161-169 | SSGHNECPV | NWHKGWNWSSGHNECPVGAS CHPFT | Class I | H2-Kb | B6 | Mouse |
| 23 | 30 | 37 | ID8 Meso-thelin 40 | GQKMNAQAI | KTLLKVSKGQKMNAQAIALV ACYLR | Class I | H2-Db | B6 | Mouse |
| 26 | 32 | 39 | OVA-II | ISQAVHAAHAEINEAGR | ESLKISQAVHAAHAEINEAG REVVG | Class II | I-Ab, I-Ad | B6 | Mouse |
| 29 | 34 | 41 | ESAT-6 | MTEQQWNFAGIEAAASAIQ | MTEQQWNFAGIEAAASAIQG NVTSI | Class II | I-Ab | B6 | Mouse |
| | 36 | 43 | TT p30 | FNNFTVSFWLRVPKVSASHL | DMFNNFTVSFWLRVPKVSAS HLEQY | Class II | I-Ad | Balb/C | Mouse |
| | 39 | 46 | HEL | DGSTDYGILQINSRW | TNRNTDGSTDYGILQINSRW WCNDG | Class II | I-Ak | CBA | Mouse |
| | | 49 | MOG | MEVGWYRSPFSRVVHLYRN | TGMEVGWYRSPFSRVVHLYR NGKDQ | Class II | I-Ab | B6 | Mouse |

TABLE 40

Average IFNg+ cells in response to AH1 and SIINFEKL (SEQ ID NO: 133) peptides in ChAd large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL (SEQ ID NO: 133) | 5.308 | 0.660 | n/a | 8 |
| 30 | SIINFEKL (SEQ ID NO: 133) | 4.119 | 1.019 | 0.978 | 8 |
| 40 | SIINFEKL (SEQ ID NO: 133) | 6.324 | 0.954 | 0.986 | 8 |
| 50 | SIINFEKL (SEQ ID NO: 133) | 8.169 | 1.469 | 0.751 | 8 |
| 20 | AH1 | 6.405 | 2.664 | n/a | 8 |
| 30 | AH1 | 4.373 | 1.442 | 0.093 | 8 |
| 40 | AH1 | 4.126 | 1.135 | 0.050 | 8 |
| 50 | AH1 | 4.216 | 0.808 | 0.063 | 8 |

TABLE 41

Average tetramer+ cells for AH1 and SIINFEKL (SEQ ID NO: 133) antigens in ChAd large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL (SEQ ID NO: 133) | 10.314 | 2.384 | n/a | 8 |
| 30 | SIINFEKL (SEQ ID NO: 133) | 4.551 | 2.370 | 0.003 | 8 |

TABLE 41-continued

Average tetramer+ cells for AH1 and SIINFEKL (SEQ ID NO: 133) antigens in ChAd large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 40 | SIINFEKL (SEQ ID NO: 133) | 5.186 | 3.254 | 0.009 | 8 |
| 50 | SIINFEKL (SEQ ID NO: 133) | 14.113 | 3.660 | 0.072 | 8 |
| 20 | AH1 | 6.864 | 2.207 | n/a | 8 |
| 30 | AH1 | 4.713 | 0.922 | 0.036 | 8 |
| 40 | AH1 | 5.393 | 1.452 | 0.223 | 8 |
| 50 | AH1 | 5.860 | 1.041 | 0.543 | 8 |

TABLE 42

Average IFNg+ cells in response to AH1 and SIINFEKL (SEQ ID NO: 133) peptides in SAM large cassette treated mice. Data is presented as % of total CD8 cells. Shown is average and standard deviation per group and p-value by ANOVA with Tukey's test. All p-values compared to MAG 20-antigen cassette.

| # antigens | Antigen | Average | Standard deviation | p-value | N |
|---|---|---|---|---|---|
| 20 | SIINFEKL | 1.843 | 0.422 | n/a | 8 |
| 30 | SIINFEKL | 2.112 | 0.522 | 0.879 | 7 |
| 40 | SIINFEKL | 1.754 | 0.978 | 0.995 | 7 |
| 50 | SIINFEKL | 1.409 | 0.766 | 0.606 | 8 |
| 20 | AH1 | 3.050 | 0.909 | n/a | 8 |
| 30 | AH1 | 0.618 | 0.427 | 1.91E−05 | 7 |
| 40 | AH1 | 1.286 | 0.284 | 0.001 | 7 |
| 50 | AH1 | 1.309 | 1.149 | 0.001 | 8 |

XV. ChAd Antigen Cassette Delivery Vector

XV.A. ChAd Antigen Cassette Delivery Vector Construction

In one example, Chimpanzee adenovirus (ChAd) was engineered to be a delivery vector for antigen cassettes. In a further example, a full-length ChAdV68 vector was synthesized based on AC_000011.1 (sequence 2 from Patent U.S. Pat. No. 6,083,716) with E1 (nt 457 to 3014) and E3 (nt 27,816-31,332) sequences deleted. Reporter genes under the control of the CMV promoter/enhancer were inserted in place of the deleted E1 sequences. Transfection of this clone into HEK293 cells did not yield infectious virus. To confirm the sequence of the wild-type C68 virus, isolate VR-594 was obtained from the ATCC, passaged, and then independently sequenced (SEQ ID NO: 10). When comparing the AC_000011.1 sequence to the ATCC VR-594 sequence (SEQ ID NO: 10) of wild-type ChAdV68 virus, 6 nucleotide differences were identified. In one example, a modified ChAdV68 vector was generated based on AC_000011.1, with the corresponding ATCC VR-594 nucleotides substituted at five positions (ChAdV68.5WTnt SEQ ID NO: 1).

In another example, a modified ChAdV68 vector was generated based on AC_000011.1 with E1 (nt 577 to 3403) and E3 (nt 27,816-31,332) sequences deleted and the corresponding ATCC VR-594 nucleotides substituted at four positions. A GFP reporter (ChAdV68.4WTnt.GFP; SEQ ID NO: 11) or model neoantigen cassette (ChAdV68.4WTnt.MAG25mer; SEQ ID NO: 12) under the control of the CMV promoter/enhancer was inserted in place of deleted E1 sequences.

In another example, a modified ChAdV68 vector was generated based on AC_000011.1 with E1 (nt 577 to 3403) and E3 (nt 27,125-31,825) sequences deleted and the corresponding ATCC VR-594 nucleotides substituted at five positions. A GFP reporter (ChAdV68.5WTnt.GFP; SEQ ID NO: 13) or model neoantigen cassette (ChAdV68.5WTnt.MAG25mer; SEQ ID NO: 2) under the control of the CMV promoter/enhancer was inserted in place of deleted E1 sequences Relevant Vectors are Described Below:

- Full-Length ChAdVC68 sequence "ChAdV68.5WTnt" (SEQ ID NO: 1); AC_000011.1 sequence with corresponding ATCC VR-594 nucleotides substituted at five positions.
- ATCC VR-594 C68 (SEQ ID NO: 10); Independently sequenced; Full-Length C68
- ChAdV68.4WTnt.GFP (SEQ ID NO: 11); AC_000011.1 with E1 (nt 577 to 3403) and E3 (nt 27,816-31.332) sequences deleted; corresponding ATCC VR-594 nucleotides substituted at four positions; GFP reporter under the control of the CMV promoter/enhancer inserted in place of deleted E1
- ChAdV68.4WTnt.MAG25mer (SEQ ID NO: 12); AC_000011.1 with E1 (nt 577 to 3403) and E3 (nt 27.816-31,332) sequences deleted; corresponding ATCC VR-594 nucleotides substituted at four positions; model neoantigen cassette under the control of the CMV promoter/enhancer inserted in place of deleted E1
- ChAdV68.SWTnt.GFP (SEQ ID NO: 13); AC_000011.1 with E1 (nt 577 to 3403) and E3 (nt 27,125-31,825) sequences deleted; corresponding ATCC VR-594 nucleotides substituted at five positions; GFP reporter under the control of the CMV promoter/enhancer inserted in place of deleted E1

XV.B. ChAd Antigen Cassette Delivery Vector Testing

XV.B.1. ChAd Vector Evaluation Methods and Materials

Transfection of HEK293A Cells Using Lipofectamine

DNA for the ChAdV68 constructs (ChAdV68.4WTnt.GFP, ChAdV68.5WTnt.GFP, ChAdV68.4WTnt.MAG25mer and ChAdV68.5WTnt.MAG25mer) was prepared and transfected into HEK293A cells using the following protocol.

10 ug of plasmid DNA was digested with PacI to liberate the viral genome. DNA was then purified using GeneJet DNA cleanup Micro columns (Thermo Fisher) according to manufacturer's instructions for long DNA fragments, and eluted in 20 ul of pre-heated water; columns were left at 37 degrees for 0.5-1 hours before the elution step.

HEK293A cells were introduced into 6-well plates at a cell density of $10^6$ cells/well 14-18 hours prior to transfection. Cells were overlaid with 1 ml of fresh medium (DMEM-10% hiFBS with pen/strep and glutamate) per well. 1-2 ug of purified DNA was used per well in a transfection with twice the ul volume (2-4 ul) of Lipofectamine2000, according to the manufacturer's protocol. 0.5 ml of OPTI-MEM medium containing the transfection mix was added to the 1 ml of normal growth medium in each well, and left on cells overnight.

Transfected cell cultures were incubated at 37° C. for at least 5-7 days. If viral plaques were not visible by day 7 post-transfection, cells were split 1:4 or 1:6, and incubated at 37° C. to monitor for plaque development. Alternatively, transfected cells were harvested and subjected to 3 cycles of freezing and thawing and the cell lysates were used to infect HEK293A cells and the cells were incubated until virus plaques were observed.

Transfection of ChAdV68 Vectors into HEK293A Cells Using Calcium Phosphate and Generation of the Tertiary Viral Stock DNA for the ChAdV68 constructs (ChAdV68.4WTnt.GFP, ChAdV68.5WTnt.GFP, ChAdV68.4WTnt.MAG25mer, ChAdV68.5WTnt.MAG25mer) was prepared and transfected into HEK293A cells using the following protocol.

HEK293A cells were seeded one day prior to the transfection at $10^6$ cells/well of a 6 well plate in 5% BS/DMEM/1×P/S, 1×Glutamax. Two wells are needed per transfection. Two to four hours prior to transfection the media was changed to fresh media. The ChAdV68.4WTnt.GFP plasmid was linearized with PacI. The linearized DNA was then phenol chloroform extracted and precipitated using one tenth volume of 3 M Sodium acetate pH 5.3 and two volumes of 100% ethanol. The precipitated DNA was pelleted by centrifugation at 12,000×g for 5 min before washing 1× with 70% ethanol. The pellet was air dried and re-suspended in 50 μL of sterile water. The DNA concentration was determined using a NanoDrop™ (ThermoFisher) and the volume adjusted to 5 μg of DNA/50 μL.

169 μL of sterile water was added to a microfuge tube. 5 μL of 2 M $CaCl_2$) was then added to the water and mixed gently by pipetting. 50 μL of DNA was added dropwise to the $CaCl_2$) water solution. Twenty six μL of 2 M $CaCl_2$) was then added and mixed gently by pipetting twice with a micro-pipettor. This final solution should consist of 5 μg of DNA in 250 μL of 0.25 M $CaCl_2$). A second tube was then prepared containing 250 μL of 2×HBS (Hepes buffered solution). Using a 2 mL sterile pipette attached to a Pipet- Aid air was slowly bubbled through the 2×HBS solution. At the same time the DNA solution in the 0.25 M $CaCl_2$) solution was added in a dropwise fashion. Bubbling was continued for approximately 5 seconds after addition of the final DNA droplet. The solution was then incubated at room temperature for up to 20 minutes before adding to 293A cells. 250 μL of the DNA/Calcium phosphate solution was added dropwise to a monolayer of 293A cells that had been seeded one day prior at $10^6$ cells per well of a 6 well plate. The cells were returned to the incubator and incubated overnight. The media was changed 24 h later. After 72 h the cells were split 1:6 into a 6 well plate. The monolayers were monitored daily by light microscopy for evidence of cytopathic effect (CPE). 7-10 days post transfection viral plaques were observed and the monolayer harvested by pipetting the media in the wells to lift the cells. The harvested cells and media were transferred to a 50 mL centrifuge tube followed by three rounds of freeze thawing (at −80° C. and 37° C.). The subsequent lysate, called the primary virus stock was clarified by centrifugation at full speed on a bench top centrifuge (4300×g) and a proportion of the lysate 10-50%) used to infect 293A cells in a T25 flask. The infected cells were incubated for 48 h before harvesting cells and media at complete CPE. The cells were once again harvested, freeze thawed and clarified before using this secondary viral stock to infect a T150 flask seeded at $1.5\times10^7$ cells per flask. Once complete CPE was achieved at 72 h the media and cells were harvested and treated as with earlier viral stocks to generate a tertiary stock.

Production in 293F Cells

ChAdV68 virus production was performed in 293F cells grown in 293 FreeStyle™ (ThermoFisher) media in an incubator at 8% CO2. On the day of infection cells were diluted to $10^6$ cells per mL, with 98% viability and 400 mL were used per production run in 1 L Shake flasks (Corning). 4 mL of the tertiary viral stock with a target MOI of >3.3 was used per infection. The cells were incubated for 48-72 h until the viability was <70% as measured by Trypan blue. The infected cells were then harvested by centrifugation, full speed bench top centrifuge and washed in 1×PBS, re-centrifuged and then re-suspended in 20 mL of 10 mM Tris pH7.4. The cell pellet was lysed by freeze thawing 3× and clarified by centrifugation at 4,300×g for 5 minutes.

Purification by CsCl Centrifugation

Viral DNA was purified by CsCl centrifugation. Two discontinuous gradient runs were performed. The first to purify virus from cellular components and the second to further refine separation from cellular components and separate defective from infectious particles.

10 mL of 1.2 (26.8 g CsCl dissolved in 92 mL of 10 mM Tris pH 8.0) CsCl was added to polyallomer tubes. Then 8 mL of 1.4 CsCl (53 g CsCl dissolved in 87 mL of 10 mM Tris pH 8.0) was carefully added using a pipette delivering to the bottom of the tube. The clarified virus was carefully layered on top of the 1.2 layer. If needed more 10 mM Tris was added to balance the tubes. The tubes were then placed in a SW-32Ti rotor and centrifuged for 2 h 30 min at 10° C. The tube was then removed to a laminar flow cabinet and the virus band pulled using an 18 gauge needle and a 10 mL syringe. Care was taken not to remove contaminating host cell DNA and protein. The band was then diluted at least 2× with 10 mM Tris pH 8.0 and layered as before on a discontinuous gradient as described above. The run was performed as described before except that this time the run was performed overnight. The next day the band was pulled with care to avoid pulling any of the defective particle band. The virus was then dialyzed using a Slide-a-Lyzer™ Cassette (Pierce) against ARM buffer (20 mM Tris pH 8.0, 25 mM NaCl, 2.5% Glycerol). This was performed 3×, 1 h per buffer exchange. The virus was then aliquoted for storage at −80° C.

Viral Assays

VP concentration was performed by using an OD 260 assay based on the extinction coefficient of $1.1\times10^{12}$ viral particles (VP) is equivalent to an Absorbance value of 1 at OD260 nm. Two dilutions (1:5 and 1:10) of adenovirus were made in a viral lysis buffer (0.1% SDS, 10 mM Tris pH 7.4, 1 mM EDTA). OD was measured in duplicate at both dilutions and the VP concentration/mL was measured by multiplying the OD260 value X dilution factor X $1.1\times10^{12}$ VP.

An infectious unit (IU) titer was calculated by a limiting dilution assay of the viral stock. The virus was initially diluted 100× in DMEM/5% NS/1×PS and then subsequently diluted using 10-fold dilutions down to $1\times10^{-7}$. 100 μL of these dilutions were then added to 293A cells that were seeded at least an hour before at 3e5 cells/well of a 24 well plate. This was performed in duplicate. Plates were incubated for 48 h in a $CO_2$ (5%) incubator at 37° C. The cells were then washed with 1×PBS and were then fixed with 100% cold methanol (−20° C.). The plates were then incubated at −20° C. for a minimum of 20 minutes. The wells were washed with 1×PBS then blocked in 1×PBS/0.1% BSA for 1 h at room temperature. A rabbit anti-Ad antibody (Abcam, Cambridge, MA) was added at 1:8,000 dilution in blocking buffer (0.25 ml per well) and incubated for 1 h at room temperature. The wells were washed 4× with 0.5 mL PBS per well. A HRP conjugated Goat anti-Rabbit antibody (Bethyl Labs, Montgomery Texas) diluted 1000× was added per well and incubated for 1 h prior to a final round of washing. 5 PBS washes were performed and the plates were developed using DAB (Diaminobenzidine tetrahydrochloride) substrate in Tris buffered saline (0.67 mg/mL DAB in 50 mM Tris pH 7.5, 150 mM NaCl) with 0.01% $H_2O_2$. Wells were developed for 5 min prior to counting. Cells were counted under a 10× objective using a dilution that gave between 4-40 stained cells per field of view. The field of view that was used was a 0.32 $mm^2$ grid of which there are equivalent to 625 per field of view on a 24 well plate. The number of infectious viruses/mL can be determined by the number of stained cells per grid multiplied by the number of grids per field of view multiplied by a dilution factor 10. Similarly, when working with GFP expressing cells florescent can be used rather than capsid staining to determine the number of GFP expressing virions per mL.

Immunizations

C57BL/6J female mice and Balb/c female mice were injected with $1\times10^8$ viral particles (VP) of ChAdV68.5WTnt.MAG25mer in 100 μL volume, bilateral intramuscular injection (50 μL per leg).

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+ 2×(spot count x % confluence/[100%-% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Figure 7A:
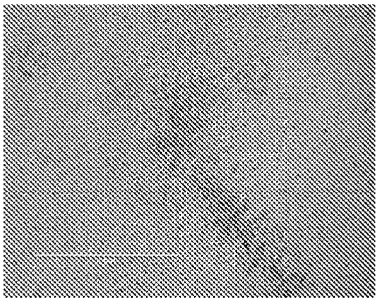
FIG. 7A illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using light microscopy (40× magnification).
Figure 7B:
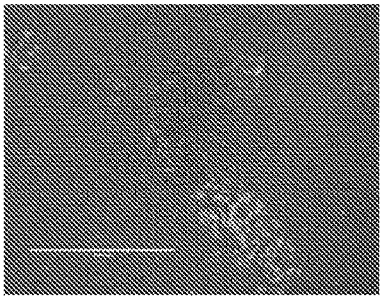
FIG. 7B illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 40× magnification.
Figure 7C:
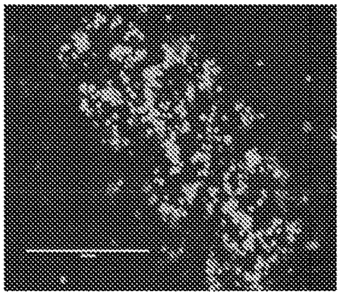
FIG. 7C illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 100× magnification.
Figure 8A:
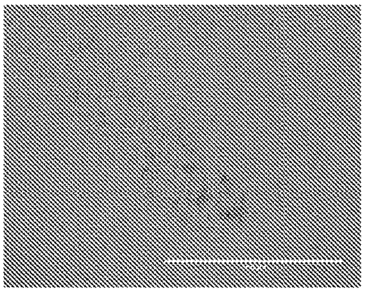
FIG. 8A illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using light microscopy (40× magnification)
Figure 8B:
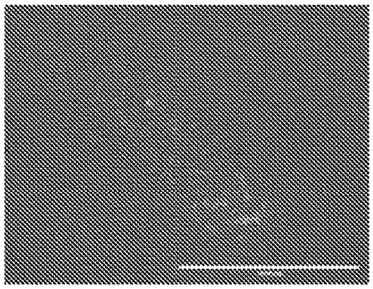
FIG. 8B illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 40× magnification.
Figure 8C:
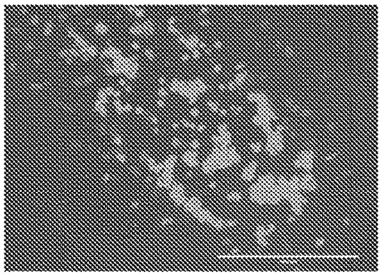
FIG. 8C illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 100× magnification.

XV.B.2. Production of ChAdV68 Viral Delivery Particles after DNA Transfection In one example, ChAdV68.4WTnt.GFP (FIG. 7) and ChAdV68.5WTnt.GFP (FIG. 8) DNA was transfected into HEK293A cells and virus replication (viral plaques) was observed 7-10 days after transfection. ChAdV68 viral plaques were visualized using light (FIGS. 7A and 8A) and fluorescent microscopy (FIGS. 7B-C and FIG. 8B-C). GFP denotes productive ChAdV68 viral delivery particle production.

XV.B.3. ChAdV68 Viral Delivery Particles Expansion

Figure 9:
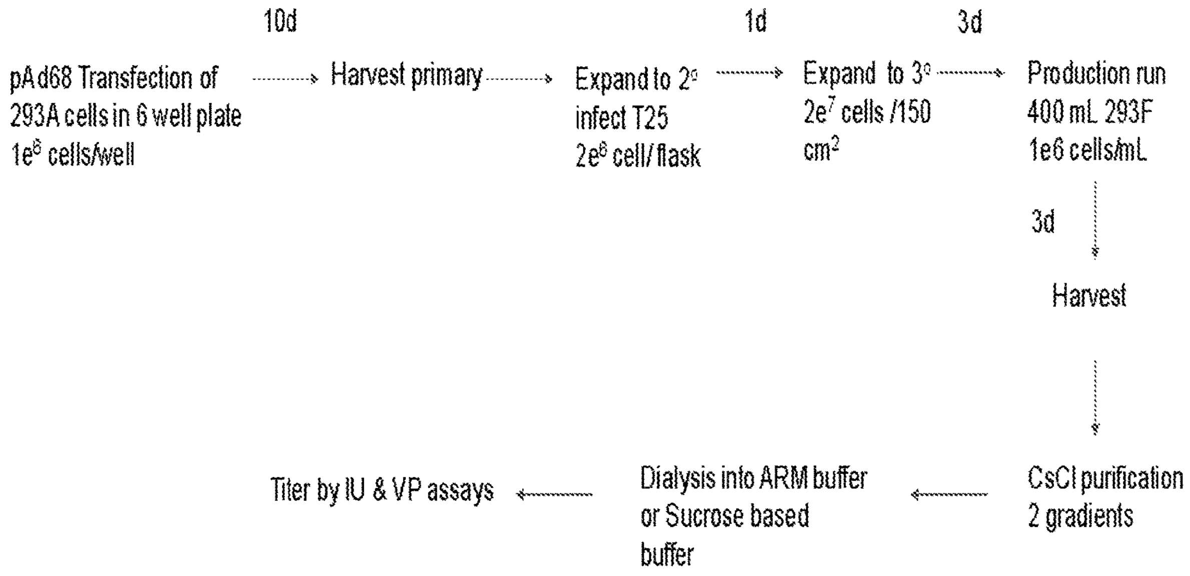
FIG. 9 illustrates the viral particle production scheme.

In one example, ChAdV68.4WTnt.GFP, ChAdV68.5WTnt.GFP, and ChAdV68.5WTnt.MAG25mer viruses were expanded in HEK293F cells and a purified virus stock produced 18 days after transfection (FIG. 9). Viral particles were quantified in the purified ChAdV68 virus stocks and compared to adenovirus type 5 (Ad5) and ChAdVY25 (a closely related ChAdV; Dicks, 2012, PloS ONE 7, e40385) viral stocks produced using the same protocol. ChAdV68 viral titers were comparable to Ad5 and ChAdVY25 (Table 7).

TABLE 7

Adenoviral vector production in 293F suspension cells

| Construct | Average VP/cell+/−SD |
|---|---|
| Ad5-Vectors (Multiple vectors) | 2.96e4 +/− 2.26e4 |
| Ad5-GFP | 3.89e4 |
| chAdY25-GFP | 1.75e3 +/− 6.03e1 |
| ChAdV68.4WTnt.GFP | 1.2e4 +/− 6.5e3 |
| ChAdV68.5WTnt.GFP | 1.8e3 |
| ChAdV68.5WTnt.MAG25mer | 1.39e3 +/− 1.1e3 |

*SD is only reported where multiple Production runs have been performed

XV.B.4. Evaluation of Immunogenicity in Tumor Models

Figure 15:
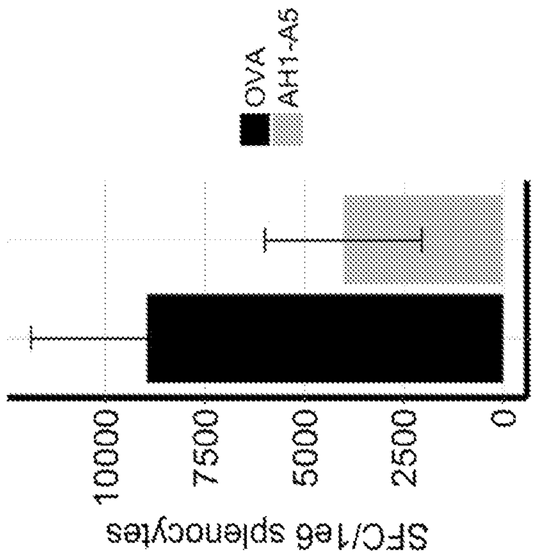
FIG. 15 illustrates ChAdV68 eliciting T-Cell responses to mouse tumor antigens in mice. Mice were immunized with ChAdV68.5WTnt.MAG25mer, and T-cell responses to the MHC class I epitope SIINFEKL (SEQ ID NO: 133) (OVA) were measured in C57BL/6J female mice and the MHC class I epitope AH1-A5 measured in Balb/c mice. Mean spot forming cells (SFCs) per $10^6$ splenocytes measured in ELISpot assays presented. Error bars represent standard deviation.

C68 vector expressing mouse tumor antigens were evaluated in mouse immunogenicity studies to demonstrate the C68 vector elicits T-cell responses. T-cell responses to the MHC class I epitope SIINFEKL (SEQ ID NO: 133) were measured in C57BL/6J female mice and the MHC class I epitope AH1-A5 (Slansky et al., 2000, Immunity 13:529-538) measured in Balb/c mice. As shown in FIG. 15, strong T-cell responses relative to control were measured after immunization of mice with ChAdV68.5WTnt.MAG25mer. Mean cellular immune responses of 8957 or 4019 spot forming cells (SFCs) per $10^6$ splenocytes were observed in ELISpot assays when C57BL/6J or Balb/c mice were immunized with ChAdV68.5WTnt.MAG25mer, respectively, 10 days after immunization.

Tumor infiltrating lymphocytes were also evaluated in CT26 tumor model evaluating ChAdV and co-administration of a an anti-CTLA4 antibody. Mice were implanted with CT26 tumors cells and 7 days after implantation, were immunized with ChAdV vaccine and treated with anti-CTLA4 antibody (clone 9D9) or IgG as a control. Tumor infiltrating lymphocytes were analyzed 12 days after immunization. Tumors from each mouse were dissociated using the gentleMACS Dissociator (Miltenyi Biotec) and mouse tumor dissociation kit (Miltenyi Biotec). Dissociated cells were filtered through a 30 micron filter and resuspended in complete RPMI. Cells were counted on the Attune NXT flow cytometer (Thermo Fisher) using propidium iodide staining to exclude dead and apoptotic cells. Cell were then adjusted to the appropriate concentration of live cells for subsequent analysis. Antigen specific cells were identified by MHC-tetramer complexes and co-stained with anti-CD8 and a viability marker. Tumors were harvested 12 days after prime immunization.

Figure 41:
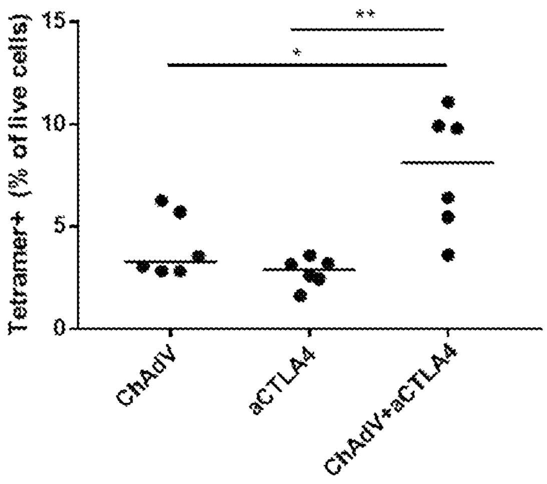
FIG. 41 shows frequency of CD8+ T cells recognizing the CT26 tumor antigen AH1 in CT26 tumor-bearing mice. P values determined using the one-way ANOVA with Tukey's multiple comparisons test; **$P<0.001$, *$P<0.05$. ChAdV=ChAdV68.5WTnt.MAG25mer; aCTLA4=anti-CTLA4 antibody, clone 9D9.

Antigen-specific CD8+ T cells within the tumor comprised a median of 3.3%, 2.2%, or 8.1% of the total live cell population in ChAdV, anti-CTLA4, and ChAdV+anti-CTLA4 treated groups, respectively (FIG. 41 and Table 36). Treatment with anti-CTLA in combination with active ChAdV immunization resulted in a statistically significant increase in the antigen-specific CD8+ T cell frequency over both ChAdV alone and anti-CTLA4 alone demonstrating anti-CTLA4, when co-administered with the chAd68 vaccine, increased the number of infiltrating T cells within a tumor.

TABLE 36

Tetramer+ infiltrating CD8 T cell frequencies in CT26 tumors

| Treatment | Median % tetramer+ |
|---|---|
| ChAdV68.5WTnt.MAG25mer (ChAdV) | 3.3 |
| Anti-CTLA4 | 2.2 |
| ChAdV68.5WTnt.MAG25mer (ChAdV) + anti-CTLA4 | 8.1 |

XVI. Alphavirus Antigen Cassette Delivery Vector

XVI.A. Alphavirus Delivery Vector Evaluation Materials and Methods

In Vitro Transcription to Generate RNA

For in vitro testing: plasmid DNA was linearized by restriction digest with PmeI, column purified following manufacturer's protocol (GeneJet DNA cleanup kit, Thermo) and used as template. In vitro transcription was performed using the RiboMAX Large Scale RNA production System (Promega) with the m7G cap analog (Promega) according to manufacturer's protocol. mRNA was purified using the RNeasy kit (Qiagen) according to manufacturer's protocol.

For in vivo studies: RNA was generated and purified by TriLInk Biotechnologies and capped with Enzymatic Cap1.

Transfection of RNA

HEK293A cells were seeded at 6e4 cells/well for 96 wells and 2e5 cells/well for 24 wells, ~16 hours prior to transfection. Cells were transfected with mRNA using MessengerMAX lipofectamine (Invitrogen) and following manufacturer's protocol. For 96-wells, 0.15 uL of lipofectamine and 10 ng of mRNA was used per well, and for 24-wells, 0.75 uL of lipofectamine and 150 ng of mRNA was used per well. A GFP expressing mRNA (TriLink Biotechnologies) was used as a transfection control.

Luciferase Assay

Luciferase reporter assay was performed in white-walled 96-well plates with each condition in triplicate using the ONE-Glo luciferase assay (Promega) following manufacturer's protocol. Luminescence was measured using the SpectraMax.

qRT-PCR

Transfected cells were rinsed and replaced with fresh media 2 hours post transfection to remove any untransfected mRNA. Cells were then harvested at various timepoints in RLT plus lysis buffer (Qiagen), homogenized using a QiaShredder (Qiagen) and RNA was extracted using the RNeasy kit (Qiagen), all according to manufacturer's protocol. Total RNA was quantified using a Nanodrop (Thermo Scientific). qRT-PCR was performed using the Quantitect Probe One-Step RT-PCR kit (Qiagen) on the qTower$^3$ (Analytik Jena) according to manufacturer's protocol, using 20 ng of total RNA per reaction. Each sample was run in triplicate for each probe. Actin or GusB were used as reference genes. Custom primer/probes were generated by IDT (Table 8).

TABLE 8 qPCR primers/probes

| Target | | SEQ ID NO: | |
|---|---|---|---|
| Luci | Primer1 | 58 | GTGGTGTGCAGCGAGAATAG |
| | Primer2 | 59 | CGCTCGTTGTAGATGTCGTTAG |
| | Probe | 60 | /56-FAM/TTGCAGTTC/ZEN/TTCATGCCCGTGTTG/3IABkFQ/ |
| GusB | Primer1 | 61 | GTTTTTGATCCAGACCCAGATG |
| | Primer2 | 62 | GCCCATTATTCAGAGCGAGTA |
| | Probe | 63 | /56-FAM/TGCAGGGTT/ZEN/TCACCAGGATCCAC/3IABkFQ/ |
| ActB | Primer1 | 64 | CCTTGCACATGCCGGAG |
| | Primer2 | 65 | ACAGAGCCTCGCCTTTG |
| | Probe | 66 | /56-FAM/TCATCCATG/ZEN/GTGAGCTGGCGG/3IABkFQ/ |
| MAG-25mer Set1 | Primer1 | 67 | CTGAAAGCTCGGTTTGCTAATG |
| | Primer2 | 68 | CCATGCTGGAAGAGACAATCT |
| | Probe | 69 | /56-FAM/CGTTTCTGA/ZEN/TGGCGCTGACCGATA/3IABkFQ/ |
| MAG-25mer Set2 | Primer1 | 70 | TATGCCTATCCTGTCTCCTCTG |
| | Primer2 | 71 | GCTAATGCAGCTAAGTCCTCTC |
| | Probe | 72 | /56-FAM/TGTTTACCC/ZEN/TGACCGTGCCTTCTG/3IABkFQ/ |

B16-OVA Tumor Model

C57BL/6J mice were injected in the lower left abdominal flank with $10^5$ B16-OVA cells/animal. Tumors were allowed to grow for 3 days prior to immunization.

CT26 Tumor Model

Balb/c mice were injected in the lower left abdominal flank with $10^6$ CT26 cells/animal. Tumors were allowed to grow for 7 days prior to immunization.

Immunizations

For srRNA vaccine, mice were injected with 10 ug of RNA in 100 uL volume, bilateral intramuscular injection (50 uL per leg). For Ad5 vaccine, mice were injected with $5\times10^{10}$ viral particles (VP) in 100 uL volume, bilateral intramuscular injection (50 uL per leg). Animals were injected with anti-CTLA-4 (clone 9D9, BioXcell), anti-PD-1 (clone RMP1-14, BioXcell) or anti-IgG (clone MPC-11, BioXcell), 250 ug dose, 2 times per week, via intraperitoneal injection.

In Vivo Bioluminescent Imaging

At each timepoint mice were injected with 150 mg/kg luciferin substrate via intraperitoneal injection and bioluminescence was measured using the IVIS In vivo imaging system (PerkinElmer) 10-15 minutes after injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count x % confluence/[100%-% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVI.B. Alphavirus Vector

XVI.B.1. Alphavirus Vector In Vitro Evaluation

Figure 10:
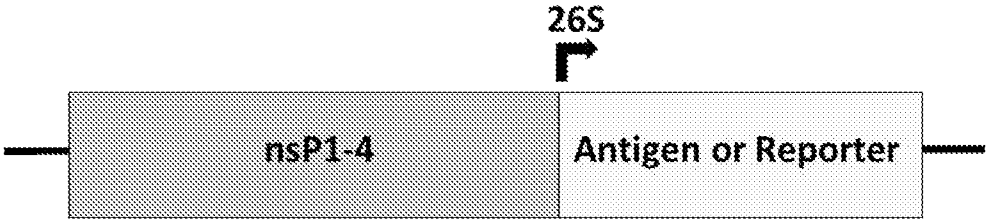
FIG. 10 illustrates the alphavirus derived VEE self-replicating RNA (srRNA) vector.

In one implementation of the present invention, a RNA alphavirus backbone for the antigen expression system was generated from a Venezuelan Equine Encephalitis (VEE) (Kinney, 1986, Virology 152:400-413) based self-replicating RNA (srRNA) vector. In one example, the sequences encoding the structural proteins of VEE located 3' of the 26S subgenomic promoter were deleted (VEE sequences 7544 to 11,175 deleted; numbering based on Kinney et al 1986; SEQ ID NO: 6) and replaced by antigen sequences (SEQ ID NO: 14 and SEQ ID NO: 4) or a luciferase reporter (e.g., VEE-Luciferase, SEQ ID NO: 15) (FIG. 10). RNA was transcribed from the srRNA DNA vector in vitro, transfected into HEK293A cells and luciferase reporter expression was measured. In addition, an (non-replicating) mRNA encoding luciferase was transfected for comparison. An ~30,000-fold increase in srRNA reporter signal was observed for VEE-Luciferase srRNA when comparing the 23 hour measurement vs the 2 hour measurement (Table 9). In contrast, the mRNA reporter exhibited a less than 10-fold increase in signal over the same time period (Table 9).

TABLE 9

Expression of luciferase from VEE self-replicating vector increases over time. HEK293A cells transfected with 10 ng of VEE-Luciferase srRNA or 10 ng of non-replicating luciferase mRNA (TriLink L-6307) per well in 96 wells. Luminescence was measured at various times post transfection. Luciferase expression is reported as relative luminescence units (RLU). Each data point is the mean +/− SD of 3 transfected wells.

| Construct | Timepoint (hr) | Mean RLU | Standard Dev (triplicate wells) |
|---|---|---|---|
| mRNA | 2 | 878.6666667 | 120.7904522 |
| mRNA | 5 | 1847.333333 | 978.515372 |
| mRNA | 9 | 4847 | 868.3271273 |
| mRNA | 23 | 8639.333333 | 751.6816702 |
| SRRNA | 2 | 27 | 15 |
| SRRNA | 5 | 4884.333333 | 2955.158935 |
| SRRNA | 9 | 182065.5 | 16030.81784 |
| SRRNA | 23 | 783658.3333 | 68985.05538 |

In another example, replication of the srRNA was confirmed directly by measuring RNA levels after transfection of either the luciferase encoding srRNA (VEE-Luciferase) or an srRNA encoding a multi-epitope cassette (VEE-MAG25mer) using quantitative reverse transcription polymerase chain reaction (qRT-PCR). An ~150-fold increase in RNA was observed for the VEE-luciferase srRNA (Table 10), while a 30-50-fold increase in RNA was observed for the VEE-MAG25mer srRNA (Table 11). These data confirm that the VEE srRNA vectors replicate when transfected into cells.

TABLE 10

Direct measurement of RNA replication in VEE-Luciferase srRNA transfected cells. HEK293A cells transfected with VEE-Luciferase srRNA (150 ng per well, 24-well) and RNA levels quantified by qRT-PCR at various times after transfection. Each measurement was normalized based on the Actin reference gene and fold-change relative to the 2 hour timepoint is presented.

| Timepoint (hr) | Luciferase Ct | Actin Ct | dCt | Ref dCt | ddCt | Relative Fold change |
|---|---|---|---|---|---|---|
| 2 | 20.51 | 18.14 | 2.38 | 2.38 | 0.00 | 1.00 |
| 4 | 20.09 | 18.39 | 1.70 | 2.38 | −0.67 | 1.59 |
| 6 | 15.50 | 18.19 | −2.69 | 2.38 | −5.07 | 33.51 |
| 8 | 13.51 | 18.36 | −4.85 | 2.38 | −7.22 | 149.43 |

TABLE 11

Direct measurement of RNA replication in VEE-MAG25mer srRNA transfected cells. HEK293 cells transfected with VEE-MAG25mer srRNA (150 ng per well, 24-well) and RNA levels quantified by qRT-PCR at various times after transfection. Each measurement was normalized based on the GusB reference gene and fold-change relative to the 2 hour timepoint is presented. Different lines on the graph represent 2 different qPCR primer/probe sets, both of which detect the epitope cassette region of the srRNA.

| Primer/ probe | Timepoint (hr) | Ct | GusB Ct | dCt | Ref dCt | ddCt | Relative Fold-Change |
|---|---|---|---|---|---|---|---|
| Set1 | 2 | 18.96 | 22.41 | −3.45 | −3.45 | 0.00 | 1.00 |
| Set1 | 4 | 17.46 | 22.27 | −4.81 | −3.45 | −1.37 | 2.58 |
| Set1 | 6 | 14.87 | 22.04 | −7.17 | −3.45 | −3.72 | 13.21 |
| Set1 | 8 | 14.16 | 22.19 | −8.02 | −3.45 | −4.58 | 23.86 |
| Set1 | 24 | 13.16 | 22.01 | −8.86 | −3.45 | −5.41 | 42.52 |
| Set1 | 36 | 13.53 | 22.63 | −9.10 | −3.45 | −5.66 | 50.45 |
| Set2 | 2 | 17.75 | 22.41 | −4.66 | −4.66 | 0.00 | 1.00 |
| Set2 | 4 | 16.66 | 22.27 | −5.61 | −4.66 | −0.94 | 1.92 |
| Set2 | 6 | 14.22 | 22.04 | −7.82 | −4.66 | −3.15 | 8.90 |
| Set2 | 8 | 13.18 | 22.19 | −9.01 | −4.66 | −4.35 | 20.35 |
| Set2 | 24 | 12.22 | 22.01 | −9.80 | −4.66 | −5.13 | 35.10 |
| Set2 | 36 | 13.08 | 22.63 | −9.55 | −4.66 | −4.89 | 29.58 |

XVI.B.2. Alphavirus Vector In Vivo Evaluation

Figure 11:
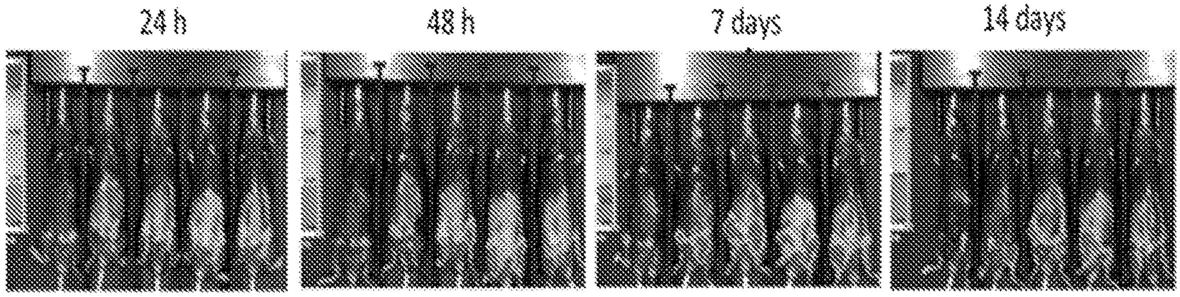
FIG. 11 illustrates in vivo reporter expression after inoculation of C57BL/6J mice with VEE-Luciferase srRNA. Shown are representative images of luciferase signal following immunization of C57BL/6J mice with VEE-Luciferase srRNA (10 ug per mouse, bilateral intramuscular injection, MC3 encapsulated) at various timepoints.

In another example, VEE-Luciferase reporter expression was evaluated in vivo. Mice were injected with 10 μg of VEE-Luciferase srRNA encapsulated in lipid nanoparticle (MC3) and imaged at 24 and 48 hours, and 7 and 14 days post injection to determine bioluminescent signal. Luciferase signal was detected at 24 hours post injection and increased over time and appeared to peak at 7 days after srRNA injection (FIG. 11).

XVI.B.3. Alphavirus Vector Tumor Model Evaluation

In one implementation, to determine if the VEE srRNA vector directs antigen-specific immune responses in vivo, a VEE srRNA vector was generated (VEE-UbAAY, SEQ ID NO: 14) that expresses 2 different MHC class I mouse tumor epitopes, SIINFEKL (SEQ ID NO: 133) and AH1-A5 (Slansky et al., 2000, Immunity 13:529-538). The SFL (SIINFEKL (SEQ ID NO: 133)) epitope is expressed by the B16-OVA melanoma cell line, and the AH1-A5 (SPSYAYHQF (SEQ ID NO: 137); Slansky et al., 2000, Immunity) epitope induces T cells targeting a related epitope (AH1/SPSYVYHQF (SEQ ID NO: 196); Huang et al., 1996, Proc Natl Acad Sci USA 93:9730-9735) that is expressed by the CT26 colon carcinoma cell line. In one example, for in vivo studies, VEE-UbAAY srRNA was generated by in vitro transcription using T7 polymerase (TriLink Biotechnologies) and encapsulated in a lipid nanoparticle (MC3).

Figure 12A:
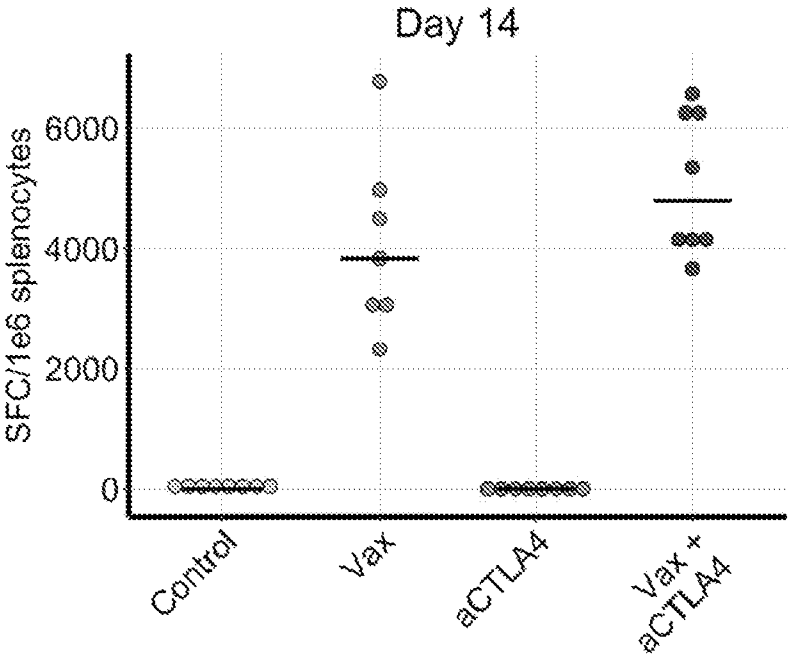
FIG. 12A illustrates T-cell responses measured 14 days after immunization with VEE srRNA formulated with MC3 LNP in B16-OVA tumor bearing mice. B16-OVA tumor bearing C57BL/6J mice were injected with 10 μg of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL (SEQ ID NO: 133)-specific T-cell responses were assessed by IFN-gamma ELISPOT and are reported as spot-forming cells (SFC) per 106 splenocytes. Lines represent medians.
Figure 12B:
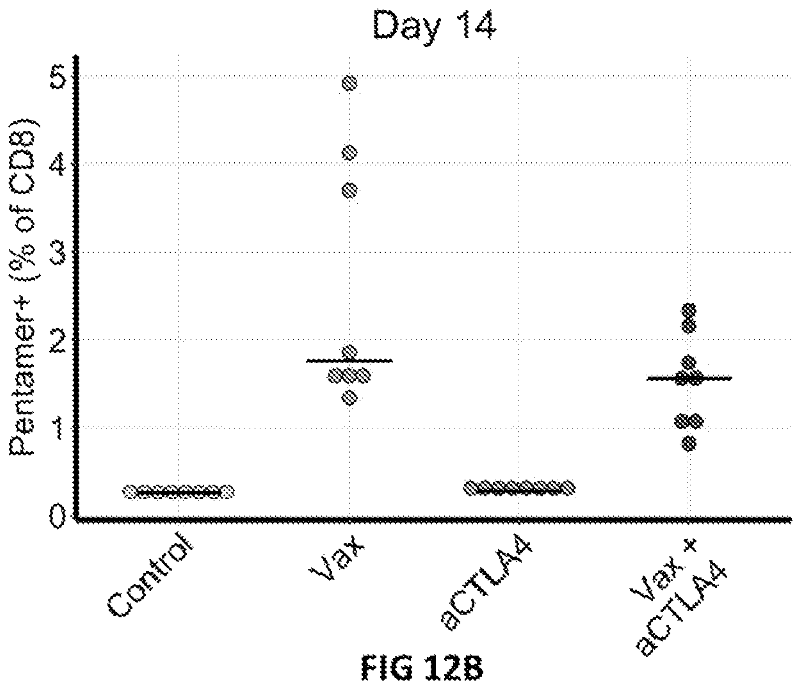
FIG. 12B illustrates T-cell responses measured 14 days after immunization with VEE srRNA formulated with MC3 LNP in B16-OVA tumor bearing mice. B16-OVA tumor bearing C57BL/6J mice were injected with 10 μg of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL (SEQ ID NO: 133)-specific T-cell responses were assessed by MHCI-pentamer staining, reported as pentamer positive cells as a percent of CD8 positive cells. Lines represent medians.

A strong antigen-specific T-cell response targeting SFL, relative to control, was observed two weeks after immunization of B16-OVA tumor bearing mice with MC3 formulated VEE-UbAAY srRNA. In one example, a median of 3835 spot forming cells (SFC) per $10^6$ splenocytes was measured after stimulation with the SFL peptide in ELISpot assays (FIG. 12A, Table 12) and 1.8% (median) of CD8 T-cells were SFL antigen-specific as measured by pentamer staining (FIG. 12B, Table 12). In another example, co-administration of an anti-CTLA-4 monoclonal antibody (mAb) with the VEE srRNA vaccine resulted in a moderate increase in overall T-cell responses with a median of 4794.5 SFCs per $10^6$ splenocytes measured in the ELISpot assay (FIG. 12A, Table 12).

TABLE 12

Results of ELISPOT and MHCI-pentamer staining assays 14 days post VEE srRNA immunization in B16-OVA tumor bearing C57BL/6J mice.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Control | 1 | 47 | 0.22 | Vax | 1 | 6774 | 4.92 |
| | 2 | 80 | 0.32 | | 2 | 2323 | 1.34 |
| | 3 | 0 | 0.27 | | 3 | 2997 | 1.52 |
| | 4 | 0 | 0.29 | | 4 | 4492 | 1.86 |
| | 5 | 0 | 0.27 | | 5 | 4970 | 3.7 |
| | 6 | 0 | 0.25 | | 6 | | 4.13 |
| | 7 | 0 | 0.23 | | 7 | 3835 | 1.66 |
| | 8 | 87 | 0.25 | | 8 | 3119 | 1.64 |
| aCTLA4 | 1 | 0 | 0.24 | Vax + | 1 | 6232 | 2.16 |
| | 2 | 0 | 0.26 | aCTLA4 | 2 | 4242 | 0.82 |
| | 3 | 0 | 0.39 | | 3 | 5347 | 1.57 |
| | 4 | 0 | 0.28 | | 4 | 6568 | 2.33 |
| | 5 | 0 | 0.28 | | 5 | 6269 | 1.55 |
| | 6 | 0 | 0.28 | | 6 | 4056 | 1.74 |
| | 7 | 0 | 0.31 | | 7 | 4163 | 1.14 |
| | 8 | 6 | 0.26 | | 8 | 3667 | 1.01 |

* Note that results from mouse #6 in the Vax group were excluded from analysis due to high variability between triplicate wells.

Figure 13A:
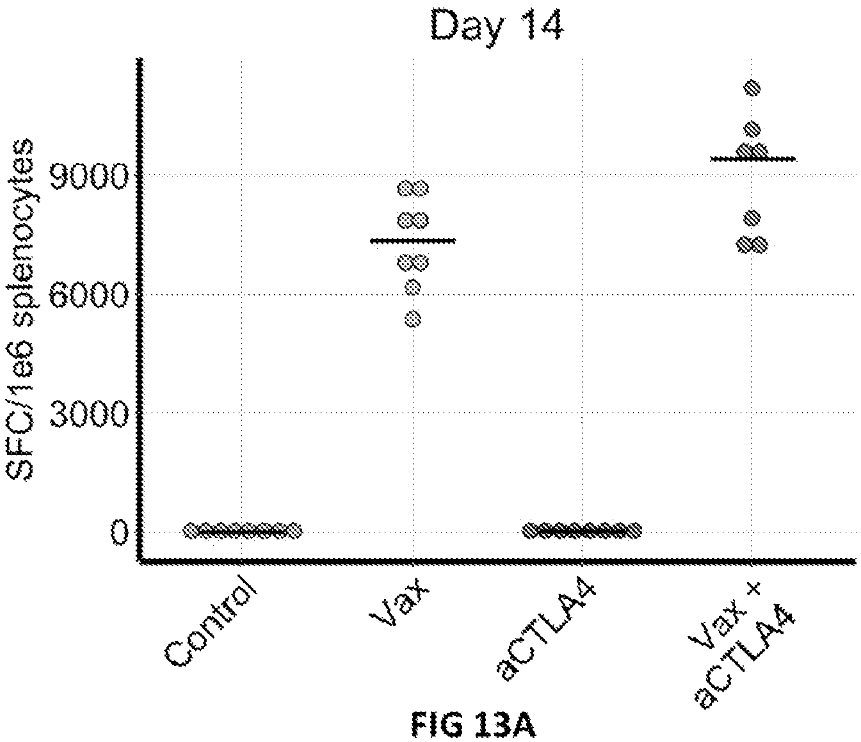
FIG. 13A illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus.
Figure 13B:
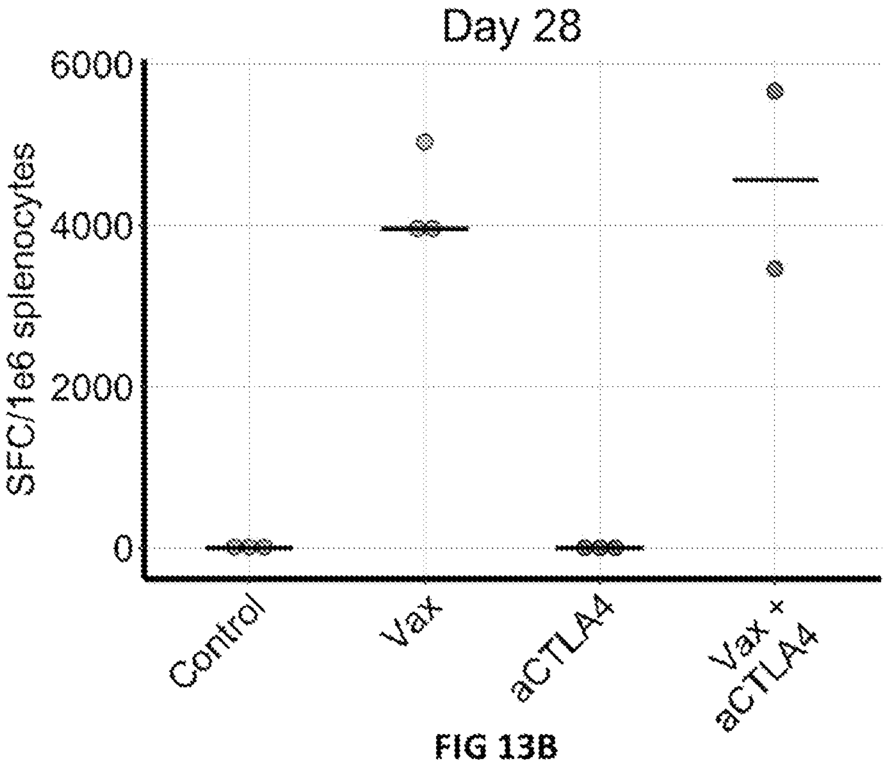
FIG. 13B illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus and 14 days post boost with srRNA (day 28 after prime).
Figure 13C:
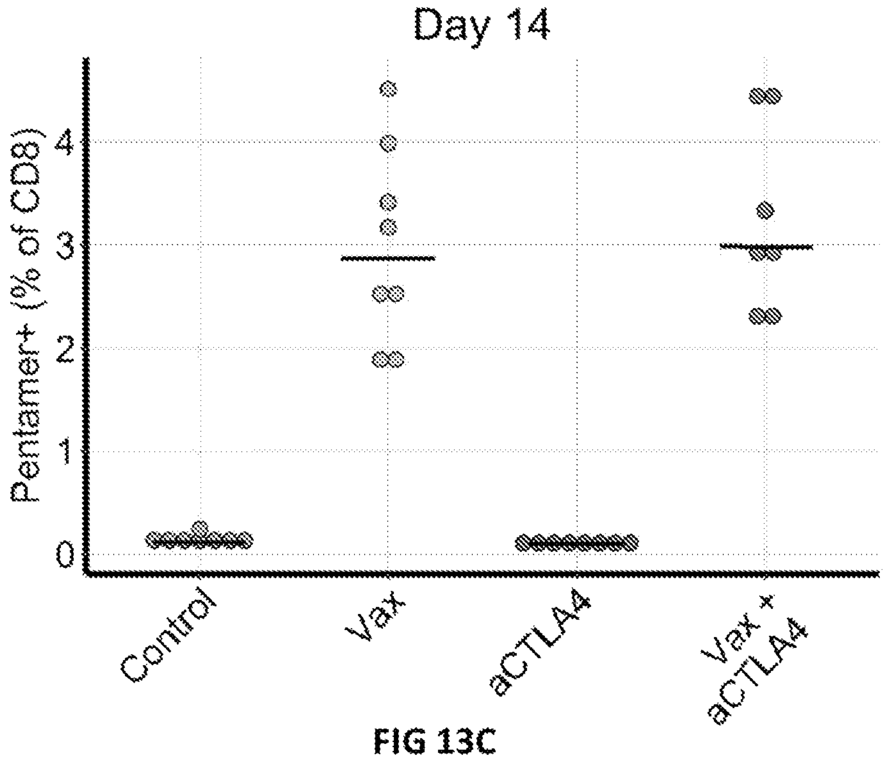
FIG. 13C illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus.
Figure 13D:
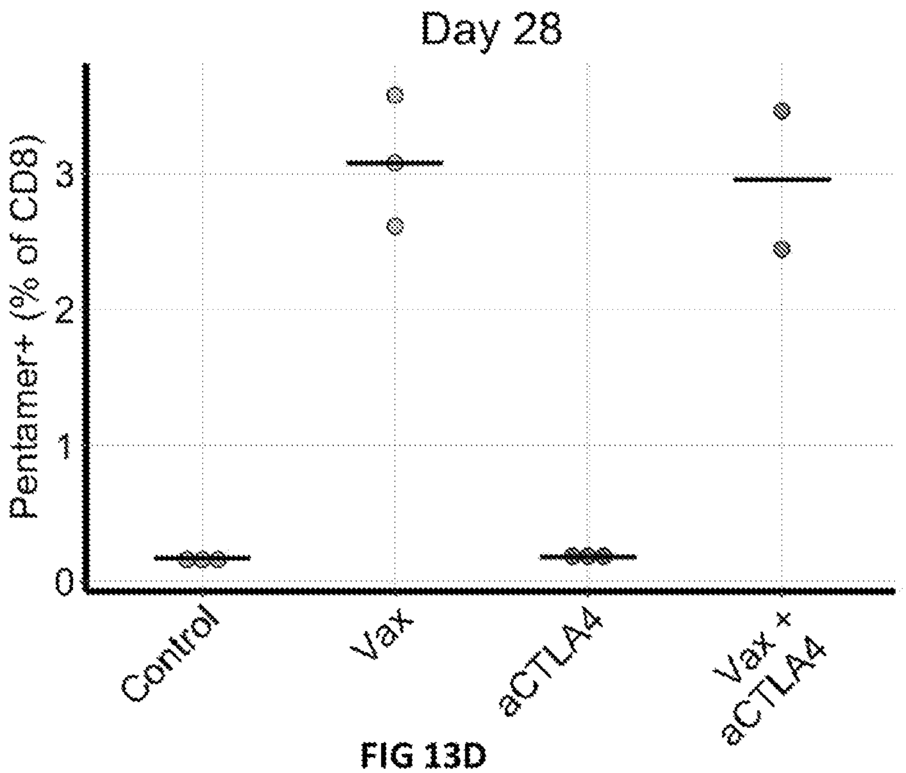
FIG. 13D illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus and 14 days post boost with srRNA (day 28 after prime).

In another implementation, to mirror a clinical approach, a heterologous prime/boost in the B16-OVA and CT26 mouse tumor models was performed, where tumor bearing mice were immunized first with adenoviral vector expressing the same antigen cassette (Ad5-UbAAY), followed by a boost immunization with the VEE-UbAAY srRNA vaccine 14 days after the Ad5-UbAAY prime. In one example, an antigen-specific immune response was induced by the Ad5-UbAAY vaccine resulting in 7330 (median) SFCs per $10^6$ splenocytes measured in the ELISpot assay (FIG. 13A, Table 13) and 2.9% (median) of CD8 T-cells targeting the SFL antigen as measured by pentamer staining (FIG. 13C, Table 13). In another example, the T-cell response was maintained 2 weeks after the VEE-UbAAY srRNA boost in the B16-OVA model with 3960 (median) SFL-specific SFCs per $10^6$ splenocytes measured in the ELISpot assay (FIG. 13B, Table 13) and 3.1% (median) of CD8 T-cells targeting the SFL antigen as measured by pentamer staining (FIG. 13D, Table 13).

TABLE 13

Immune monitoring of B16-OVA mice following heterologous prime/boost with Ad5 vaccine prime and srRNA boost.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Day 14 | | | | | | | |
| Control | 1 | 0 | 0.10 | Vax | 1 | 8514 | 1.87 |
| | 2 | 0 | 0.09 | | 2 | 7779 | 1.91 |
| | 3 | 0 | 0.11 | | 3 | 6177 | 3.17 |
| | 4 | 46 | 0.18 | | 4 | 7945 | 3.41 |
| | 5 | 0 | 0.11 | | 5 | 8821 | 4.51 |
| | 6 | 16 | 0.11 | | 6 | 6881 | 2.48 |
| | 7 | 0 | 0.24 | | 7 | 5365 | 2.57 |
| | 8 | 37 | 0.10 | | 8 | 6705 | 3.98 |
| aCTLA4 | 1 | 0 | 0.08 | Vax + | 1 | 9416 | 2.35 |
| | 2 | 29 | 0.10 | aCTLA4 | 2 | 7918 | 3.33 |
| | 3 | 0 | 0.09 | | 3 | 10153 | 4.50 |
| | 4 | 29 | 0.09 | | 4 | 7212 | 2.98 |
| | 5 | 0 | 0.10 | | 5 | 11203 | 4.38 |
| | 6 | 49 | 0.10 | | 6 | 9784 | 2.27 |
| | 7 | 0 | 0.10 | | 8 | 7267 | 2.87 |
| | 8 | 31 | 0.14 | | | | |
| Day 28 | | | | | | | |
| Control | 2 | 0 | 0.17 | Vax | 1 | 5033 | 2.61 |
| | 4 | 0 | 0.15 | | 2 | 3958 | 3.08 |
| | 6 | 20 | 0.17 | | 4 | 3960 | 3.58 |
| aCTLA4 | 1 | 7 | 0.23 | Vax + | 4 | 3460 | 2.44 |
| | 2 | 0 | 0.18 | aCTLA4 | 5 | 5670 | 3.46 |
| | 3 | 0 | 0.14 | | | | |

Figure 14A:
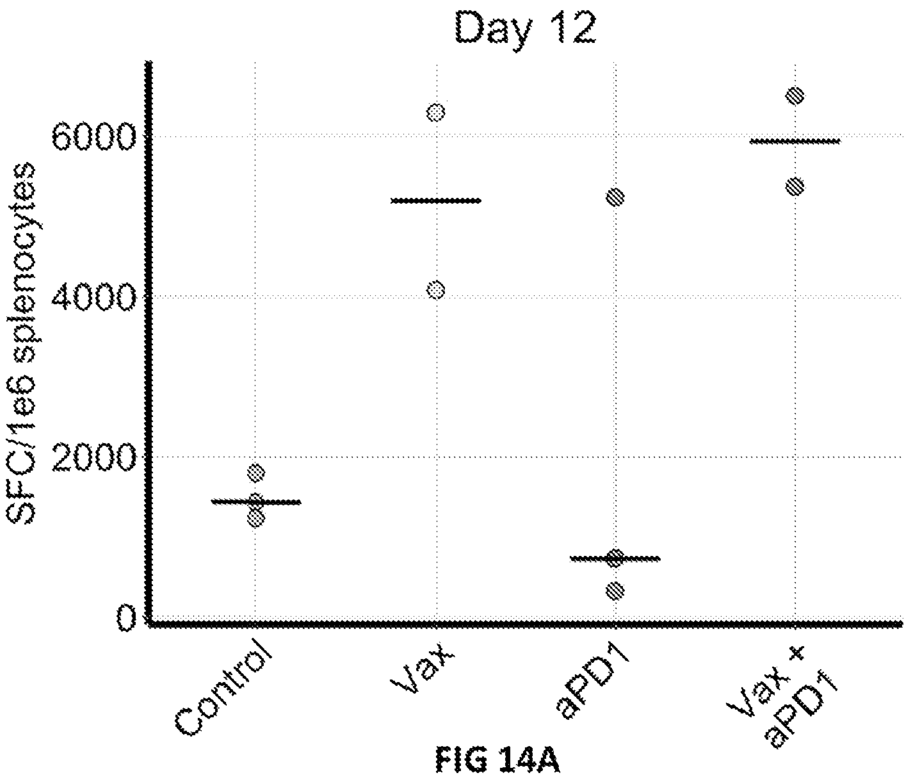
FIG. 14A illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus.
Figure 14B:
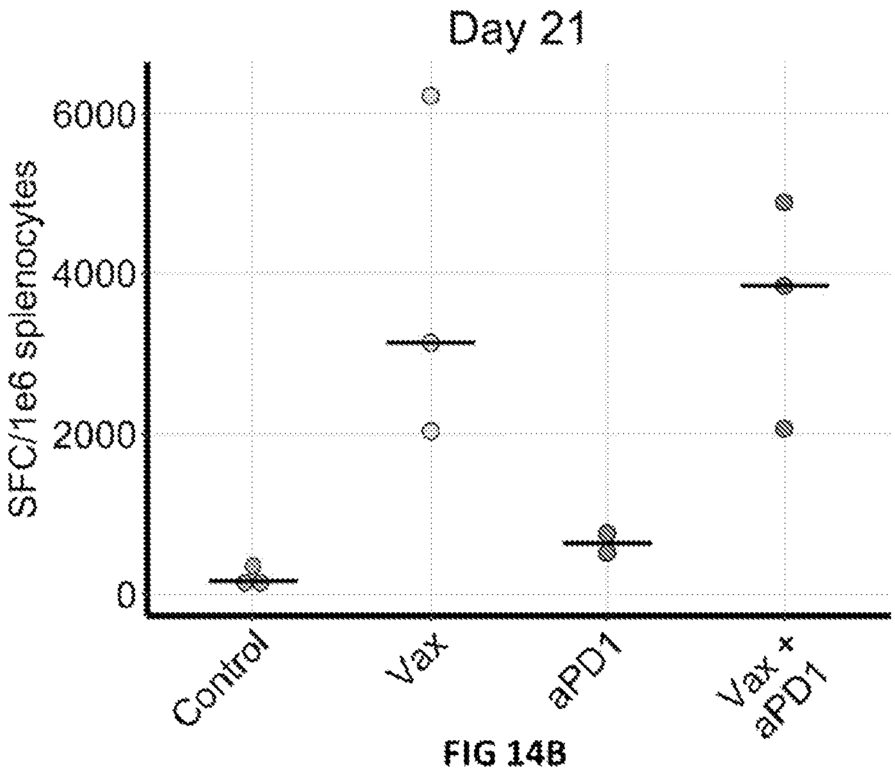
FIG. 14B illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus and 6 days post boost with srRNA (day 21 after prime).

In another implementation, similar results were observed after an Ad5-UbAAY prime and VEE-UbAAY srRNA boost in the CT26 mouse model. In one example, an AH1 antigen-specific response was observed after the Ad5-UbAAY prime (day 14) with a mean of 5187 SPCs per $10^6$ splenocytes measured in the ELISpot assay (FIG. 14A, Table 14) and 3799 SPCs per $10^6$ splenocytes measured in the ELISpot assay after the VEE-UbAAY srRNA boost (day 28) (FIG. 14B, Table 14).

TABLE 14

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| Control | 1 | 1799 | Control | 9 | 167 |
| | 2 | 1442 | | 10 | 115 |
| | 3 | 1235 | | 11 | 347 |
| aPD1 | 1 | 737 | aPD1 | 8 | 511 |
| | 2 | 5230 | | 11 | 758 |
| | 3 | 332 | Vax | 9 | 3133 |
| Vax | 1 | 6287 | | 10 | 2036 |
| | 2 | 4086 | | 11 | 6227 |
| Vax + aPD1 | 1 | 5363 | Vax + aPD1 | 8 | 3844 |
| | 2 | 6500 | | 9 | 2071 |
| | | | | 11 | 4888 |

XVII. ChAdV/srRNA Combination Tumor Model Evaluation

Various dosing protocols using ChAdV68 and self-replicating RNA (srRNA) were evaluated in murine CT26 tumor models.

XVII.A ChAdV/srRNA Combination Tumor Model Evaluation

Methods and Materials

Tumor Injection

Balb/c mice were injected with the CT26 tumor cell line. 7 days after tumor cell injection, mice were randomized to the different study arms (28-40 mice per group) and treatment initiated. Balb/c mice were injected in the lower left abdominal flank with $10^6$ CT26 cells/animal. Tumors were allowed to grow for 7 days prior to immunization. The study arms are described in detail in Table 15.

TABLE 15

ChAdV/srRNA Combination Tumor Model Evaluation Study Arms

| Group | N | Treatment | Dose | Volume | Schedule | Route |
|---|---|---|---|---|---|---|
| 1 | 40 | chAd68 control | 1e11 vp | 2x 50 uL | day 0 | IM |
| | | srRNA control | 10 ug | 50 uL | day 14, 28, 42 | IM |
| | | Anti-PD1 | 250 ug | 100 uL | 2x/week (start day 0) | IP |
| 2 | 40 | chAd68 control | 1e11 vp | 2x 50 uL | day 0 | IM |
| | | srRNA control | 10 ug | 50 uL | day 14, 28, 42 | IM |
| | | Anti-IgG | 250 ug | 100 uL | 2x/week (start day 0) | IP |
| 3 | 28 | chAd68 vaccine | 1e11 vp | 2x 50 uL | day 0 | IM |
| | | srRNA vaccine | 10 ug | 50 uL | day 14, 28, 42 | IM |
| | | Anti-PD1 | 250 ug | 100 uL | 2x/week (start day 0) | IP |

TABLE 15-continued

ChAdV/srRNA Combination Tumor Model Evaluation Study Arms

| Group | N | Treatment | Dose | Volume | Schedule | Route |
|---|---|---|---|---|---|---|
| 4 | 28 | chAd68 vaccine | 1e11 vp | 2x 50 uL | day 0 | IM |
| | | srRNA vaccine | 10 ug | 50 uL | day 14, 28, 42 | IM |
| | | Anti-IgG | 250 ug | 100 uL | 2x/week (start day 0) | IP |
| 5 | 28 | srRNA vaccine | 10 ug | 50 uL | day 0, 28, 42 | IM |
| | | chAd68 vaccine | 1e11 vp | 2x 50 uL | day 14 | IM |
| | | Anti-PD1 | 250 ug | 100 uL | 2x/week (start day 0) | IP |
| 6 | 28 | srRNA vaccine | 10 ug | 50 uL | day 0, 28, 42 | IM |
| | | chAd68 vaccine | 1e11 vp | 2x 50 uL | day 14 | IM |
| | | Anti-IgG | 250 ug | 100 uL | 2x/week (start day 0) | IP |
| 7 | 40 | srRNA vaccine | 10 ug | 50 uL | day 0, 14, 28, 42 | IM |
| | | Anti-PD1 | 250 ug | 100 uL | 2x/week (start day 0) | IP |
| 8 | 40 | srRNA vaccine | 10 ug | 50 uL | day 0, 14, 28, 42 | IM |
| | | Anti-IgG | 250 ug | 100 uL | 2x/week (start day 0) | IP |

Immunizations

For srRNA vaccine, mice were injected with 10 ug of VEE-MAG25mer srRNA in 100 uL volume, bilateral intramuscular injection (50 uL per leg). For C68 vaccine, mice were injected with $1\times10^{11}$ viral particles (VP) of ChAdV68.5WTnt.MAG25mer in 100 uL volume, bilateral intramuscular injection (50 uL per leg). Animals were injected with anti-PD-1 (clone RMP1-14, BioXcell) or anti-IgG (clone MPC-11, BioXcell), 250 ug dose, 2 times per week, via intraperitoneal injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count x % confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVII.B ChAdV/srRNA Combination Evaluation in a CT26 Tumor Model

The immunogenicity and efficacy of the ChAdV68.5WTnt.MAG25mer/VEE-MAG25mer srRNA heterologous prime/boost or VEE-MAG25mer srRNA homologous prime/boost vaccines were evaluated in the CT26 mouse tumor model. Balb/c mice were injected with the CT26 tumor cell line. 7 days after tumor cell injection, mice were randomized to the different study arms and treatment initiated. The study arms are described in detail in Table 15 and more generally in Table 16.

TABLE 16

Prime/Boost Study Arms

| Group | Prime | Boost |
|---|---|---|
| 1 | Control | Control |
| 2 | Control + anti-PD-1 | Control + anti-PD-1 |
| 3 | ChAdV68.5WTnt.MAG25mer | VEE-MAG25mer srRNA |
| 4 | ChAdV68.5WTnt.MAG25mer + anti-PD-1 | VEE-MAG25mer srRNA + anti-PD-1 |
| 5 | VEE-MAG25mer srRNA | ChAdV68.5WTnt.MAG25mer |
| 6 | VEE-MAG25mer srRNA + anti-PD-1 | ChAdV68.5WTnt.MAG25mer + anti-PD-1 |
| 7 | VEE-MAG25mer srRNA | VEE-MAG25mer srRNA |
| 8 | VEE-MAG25mer srRNA + anti-PD-1 | VEE-MAG25mer srRNA + anti-PD-1 |

Spleens were harvested 14 days after the prime vaccination for immune monitoring. Tumor and body weight measurements were taken twice a week and survival was monitored. Strong immune responses relative to control were observed in all active vaccine groups.

Figure 16:
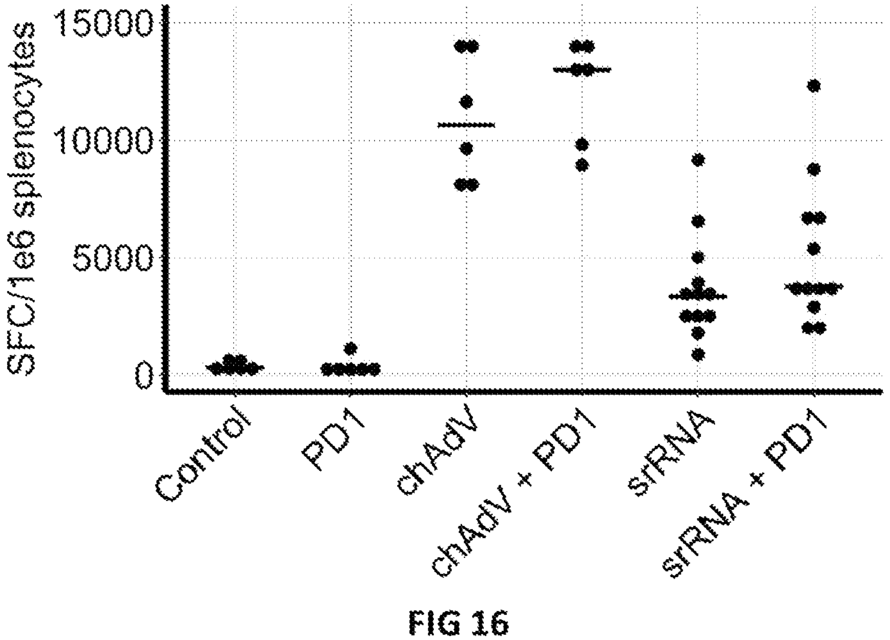
FIG. 16 illustrates cellular immune responses in a CT26 tumor model following a single immunization with either ChAdV6, ChAdV+anti-PD-1, srRNA, srRNA+anti-PD-1, or anti-PD-1 alone. Antigen-specific IFN-gamma production was measured in splenocytes for 6 mice from each group using ELISpot. Results are presented as spot forming cells (SFC) per $10^6$ splenocytes. Median for each group indicated by horizontal line. P values determined using the Dunnett's multiple comparison test; *P<0.0001, P<0.001, *P<0.05. ChAdV=ChAdV68.5WTnt.MAG25mer; srRNA=VEE-MAG25mer srRNA.

Median cellular immune responses of 10,630, 12,976, 3319, or 3745 spot forming cells (SFCs) per $10^6$ splenocytes were observed in ELISpot assays in mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 16 and Table 17). In contrast, the vaccine control (group 1) or vaccine control with anti-PD-1 (group 2) exhibited median cellular immune responses of 296 or 285 SFC per $10^6$ splenocytes, respectively.

TABLE 17

Cellular immune responses in a CT26 tumor model

| Treatment | Median SFC/$10^6$ Splenocytes |
|---|---|
| Control | 296 |
| PD1 | 285 |
| ChAdV68.5WTnt.MAG25mer (ChAdV) | 10630 |
| ChAdV68.5WTnt.MAG25mer + PD1 (ChAdV + PD-1) | 12976 |
| VEE-MAG25mer srRNA (srRNA) | 3319 |
| VEE-MAG25mer srRNA + PD-1 (srRNA + PD1) | 3745 |

Consistent with the ELISpot data, 5.6, 7.8, 1.8 or 1.9% of CD8 T cells (median) exhibited antigen-specific responses in intracellular cytokine staining (ICS) analyses for mice immunized with ChAdV68.5WTnt.MAG25mer (ChAdV/group 3), ChAdV68.5WTnt.MAG25mer+anti-PD-1

Figure 17:
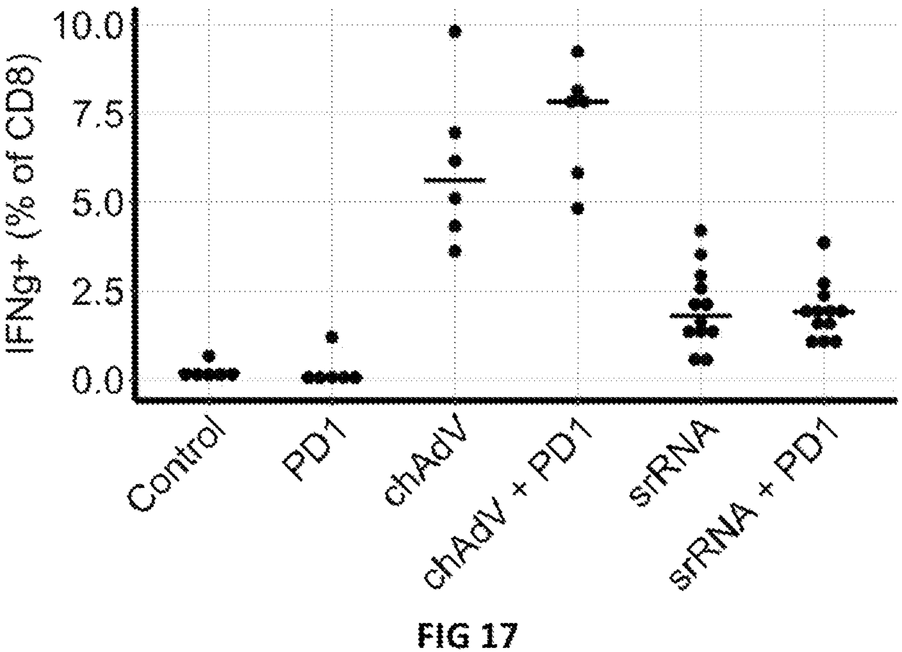
FIG. 17 illustrates CD8 T-Cell responses in a CT26 tumor model following a single immunization with either ChAdV6, ChAdV+anti-PD-1, srRNA, srRNA+anti-PD-1, or anti-PD-1 alone. Antigen-specific IFN-gamma production in CD8 T cells measured using ICS and results presented as antigen-specific CD8 T cells as a percentage of total CD8 T cells. Median for each group indicated by horizontal line. P values determined using the Dunnett's multiple comparison test; *P<0.0001, P<0.001, *P<0.05. ChAdV=ChAdV68.5WTnt.MAG25mer; srRNA=VEE-MAG25mer srRNA.

(ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 17 and Table 18). Mice immunized with the vaccine control or vaccine control combined with anti-PD-1 showed antigen-specific CD8 responses of 0.2 and 0.1%, respectively.

TABLE 18

CD8 T-Cell responses in a CT26 tumor model

| Treatment | Median % CD8 IFN-gamma Positive |
|---|---|
| Control | 0.21 |
| PD1 | 0.1 |
| ChAdV68.5WTnt.MAG25mer (ChAdV) | 5.6 |
| ChAdV68.5WTnt.MAG25mer + PD1 (ChAdV + PD-1) | 7.8 |
| VEE-MAG25mer srRNA (srRNA) | 1.8 |
| VEE-MAG25mer srRNA + PD-1 (srRNA + PD1) | 1.9 |

Figure 18:
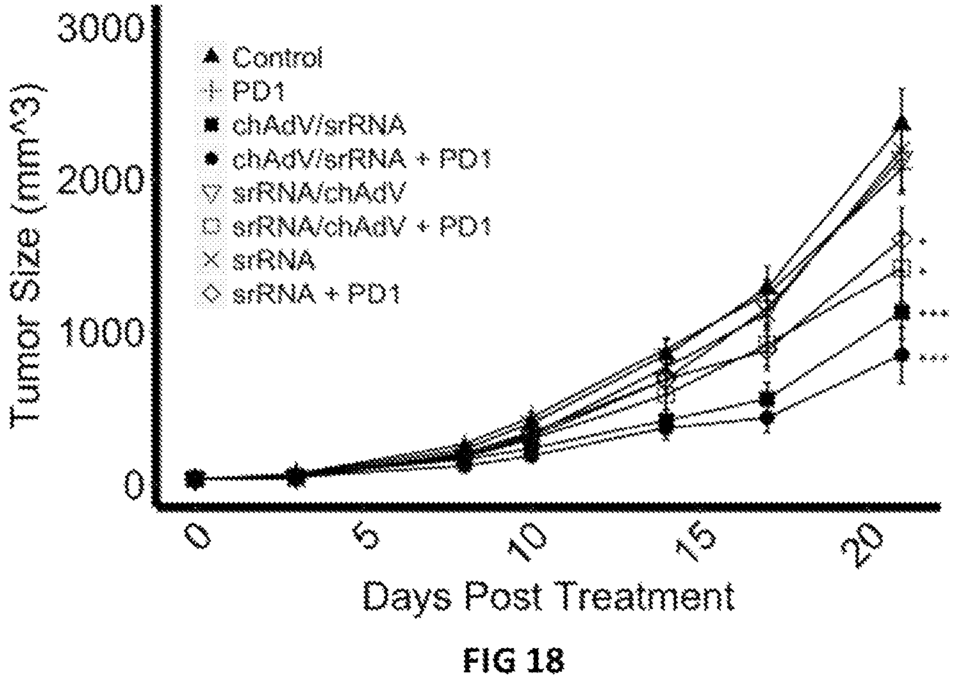
FIG. 18 illustrates tumor growth in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. Tumor volumes measured twice per week and mean tumor volumes presented for the first 21 days of the study. 22-28 mice per group at study initiation. Error bars represent standard error of the mean (SEM). P values determined using the Dunnett's test; *P<0.0001, P<0.001, *P<0.05. ChAdV=ChAdV68.5WTnt.MAG25mer; srRNA=VEE-MAG25mer srRNA.

Tumor growth was measured in the CT26 colon tumor model for all groups, and tumor growth up to 21 days after treatment initiation (28 days after injection of CT-26 tumor cells) is presented. Mice were sacrificed 21 days after treatment initiation based on large tumor sizes (>2500 $mm^3$); therefore, only the first 21 days are presented to avoid analytical bias. Mean tumor volumes at 21 days were 1129, 848, 2142, 1418, 2198 and 1606 $mm^3$ for ChAdV68.5WTnt.MAG25mer prime/VEE-MAG25mer srRNA boost (group 3), ChAdV68.5WTnt.MAG25mer prime/VEE-MAG25mer srRNA boost+anti-PD-1 (group 4), VEE-MAG25mer srRNA prime/ChAdV68.5WTnt.MAG25mer boost (group 5), VEE-MAG25mer srRNA prime/ChAdV68.5WTnt.MAG25mer boost+anti-PD-1 (group 6), VEE-MAG25mer srRNA prime/VEE-MAG25mer srRNA boost (group 7) and VEE-MAG25mer srRNA prime/VEE-MAG25mer srRNA boost+anti-PD-1 (group 8), respectively (FIG. 18 and Table 19). The mean tumor volumes in the vaccine control or vaccine control combined with anti-PD-1 were 2361 or 2067 $mm^3$, respectively. Based on these data, vaccine treatment with ChAdV68.5WTnt.MAG25mer/VEE-MAG25mer srRNA (group 3), ChAdV68.5WTnt.MAG25mer/VEE-MAG25mer srRNA+anti-PD-1 (group 4), VEE-MAG25mer srRNA/ChAdV68.5WTnt.MAG25mer+anti-PD-1 (group 6) and VEE-MAG25mer srRNA/VEE-MAG25mer srRNA+anti-PD-1 (group 8) resulted in a reduction of tumor growth at 21 days that was significantly different from the control (group 1).

TABLE 19

Tumor size at day 21 measured in the CT26 model

| Treatment | Tumor Size ($mm^3$) | SEM |
|---|---|---|
| Control | 2361 | 235 |
| PD1 | 2067 | 137 |
| chAdV/srRNA | 1129 | 181 |
| chAdV/srRNA + PD1 | 848 | 182 |
| srRNA/chAdV | 2142 | 233 |
| srRNA/chAdV + PD1 | 1418 | 220 |

TABLE 19-continued

| Tumor size at day 21 measured in the CT26 model | | |
|---|---|---|
| Treatment | Tumor Size ($mm^3$) | SEM |
| srRNA | 2198 | 134 |
| srRNA + PD1 | 1606 | 210 |

Figure 19:
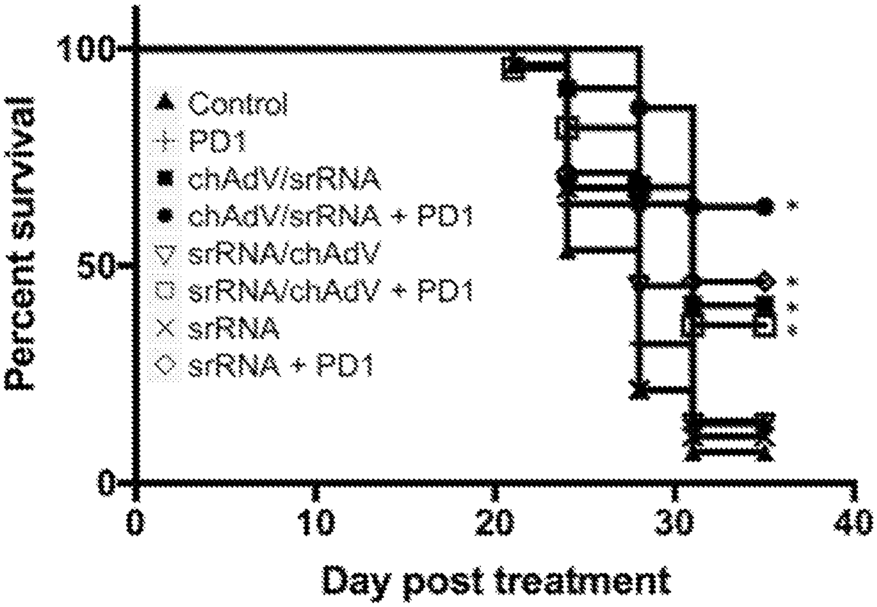
FIG. 19 illustrates survival in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. P values determined using the log-rank test; *P<0.0001, P<0.001, *P<0.01. ChAdV=ChAdV68.5WTnt.MAG25mer; srRNA=VEE-MAG25mer srRNA.

Survival was monitored for 35 days after treatment initiation in the CT-26 tumor model (42 days after injection of CT-26 tumor cells). Improved survival was observed after vaccination of mice with 4 of the combinations tested. After vaccination, 64%, 46%, 41% and 36% of mice survived with ChAdV68.5WTnt.MAG25mer prime/VEE-MAG25mer srRNA boost in combination with anti-PD-1 (group 4; P<0.0001 relative to control group 1), VEE-MAG25mer srRNA prime/VEE-MAG25mer srRNA boost in combination with anti-PD-1 (group 8; P=0.0006 relative to control group 1), ChAdV68.5WTnt.MAG25mer prime/VEE-MAG25mer srRNA boost (group 3; P=0.0003 relative to control group 1) and VEE-MAG25mer srRNA prime/ChAdV68.5WTnt.MAG25mer boost in combination with anti-PD-1 (group 6; P=0.0016 relative to control group 1), respectively (FIG. 19 and Table 20). Survival was not significantly different from the control group 1 (≤14%) for the remaining treatment groups [VEE-MAG25mer srRNA-prime/ChAdV68.5WTnt.MAG25mer boost (group 5), VEE-MAG25mer srRNA prime/VEE-MAG25mer srRNA boost (group 7) and anti-PD-1 alone (group 2)].

TABLE 20

| Survival in the CT26 model | | | | | | | | |
|---|---|---|---|---|---|---|---|---|
| Timepoint | Control | PD1 | chAdV/ srRNA | chAdV/ srRNA + PD1 | srRNA/ chAdV | srRNA/ chAdV + PD1 | srRNA | srRNA + PD1 |
| 0 | 100 | 100 | 100 | 100.00 | 100.00 | 100 | 100 | 100 |
| 21 | 96 | 100 | 100 | 100 | 100 | 95 | 100 | 100 |
| 24 | 54 | 64 | 91 | 100 | 68 | 82 | 68 | 71 |
| 28 | 21 | 32 | 68 | 86 | 45 | 68 | 21 | 64 |
| 31 | 7 | 14 | 41 | 64 | 14 | 36 | 11 | 46 |
| 35 | 7 | 14 | 41 | 64 | 14 | 36 | 11 | 46 |

In conclusion, ChAdV68.5WTnt.MAG25mer and VEE-MAG25mer srRNA elicited strong T-cell responses to mouse tumor antigens encoded by the vaccines, relative to control. Administration of a ChAdV68.5WTnt.MAG25mer prime and VEE-MAG25mer srRNA boost with or without co-administration of anti-PD-1, VEE-MAG25mer srRNA prime and ChAdV68.5WTnt.MAG25mer boost in combination with anti-PD-1 or administration of VEE-MAG25mer srRNA as a homologous prime boost immunization in combination with anti-PD-1 to tumor bearing mice resulted in improved survival.

XVIII. Non-Human Primate Studies

Various dosing protocols using ChAdV68 and self-replicating RNA (srRNA) were evaluated in non-human primates (NHP).

Materials and Methods

A priming vaccine was injected intramuscularly (IM) in each NHP to initiate the study (vaccine prime). One or more boosting vaccines (vaccine boost) were also injected intramuscularly in each NHP. Bilateral injections per dose were administered according to groups outlined in tables and summarized below.

Immunizations

Mamu-A*01 Indian rhesus macaques were immunized bilaterally with $1\times10^{12}$ viral particles ($5\times10^{11}$ viral particles per injection) of ChAdV68.5WTnt.MAG25mer, 30 μg of VEE-MAG25 MER srRNA, 100 μg of VEE-MAG25mer srRNA or 300 μg of VEE-MAG25mer srRNA formulated in LNP-1 or LNP-2. Vaccine boosts of 30 μg, 100 μg or 300 μg VEE-MAG25mer srRNA were administered intramuscularly at the indicated time after prime vaccination.

Immune Monitoring

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune NxT flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISPOT harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count x % confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Specific CD4 and CD8 T cell responses to 6 different rhesus macaque Mamu-A*01 class I epitopes encoded in the vaccines were monitored from PBMCs by measuring induction of intracellular cytokines, such as IFN-gamma, using flow cytometry. The results from both methods indicate that cytokines were induced in an antigen-specific manner to epitopes.

Immunogenicity in Rhesus Macaques

This study was designed to (a) evaluate the immunogenicity and preliminary safety of VEE-MAG25mer srRNA 30 μg and 100 μg doses as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2; (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5WTnt.MAG25mer or VEE-MAG25mer srRNA vector encoding model antigens that includes multiple Mamu-A*01 restricted epitopes. The study arms were as described below.

TABLE 21

Non-GLP immunogenicity study in Indian Rhesus Macaques

| Group | Prime | Boost 1 | Boost 2 |
|---|---|---|---|
| 1 | VEE-MAG25mer srRNA-LNP1 (30 μg) | VEE-MAG25mer srRNA-LNP1 (30 μg) | VEE-MAG25mer srRNA-LNP1 (30 μg) |
| 2 | VEE-MAG25mer srRNA-LNP1 (100 μg) | VEE-MAG25mer srRNA-LNP1 (100 μg) | VEE-MAG25mer srRNA-LNP1 (100 μg) |
| 3 | VEE-MAG25mer srRNA-LNP2 (100 μg) | VEE-MAG25mer srRNA-LNP2 (100 μg) | VEE-MAG25mer srRNA-LNP2 (100 μg) |
| 4 | ChAdV68.5WTnt. MAG25mer | VEE-MAG25mer srRNA-LNP1 (100 μg) | VEE-MAG25mer srRNA-LNP1 (100 μg) |

PBMCs were collected prior to immunization and on weeks 1, 2, 3, 4, 5, 6, 8, 9, and 10 after the initial immunization for immune monitoring.

Results

Antigen-specific cellular immune responses in peripheral blood mononuclear cells (PBMCs) were measured to six different Mamu-A*01 restricted epitopes prior to immunization and 1, 2, 3, 4, 5, 6, 8, 9, and 10 weeks after the initial immunization. Animals received a boost immunization with VEE-MAG25mer srRNA on weeks 4 and 8 with either 30 μg or 100 μg doses, and either formulated with LNP1 or LNP2, as described in Table 21. Combined immune responses to all six epitopes were plotted for each immune monitoring timepoint (FIG. 20A-D and Tables 22-25).

Figure 20A:
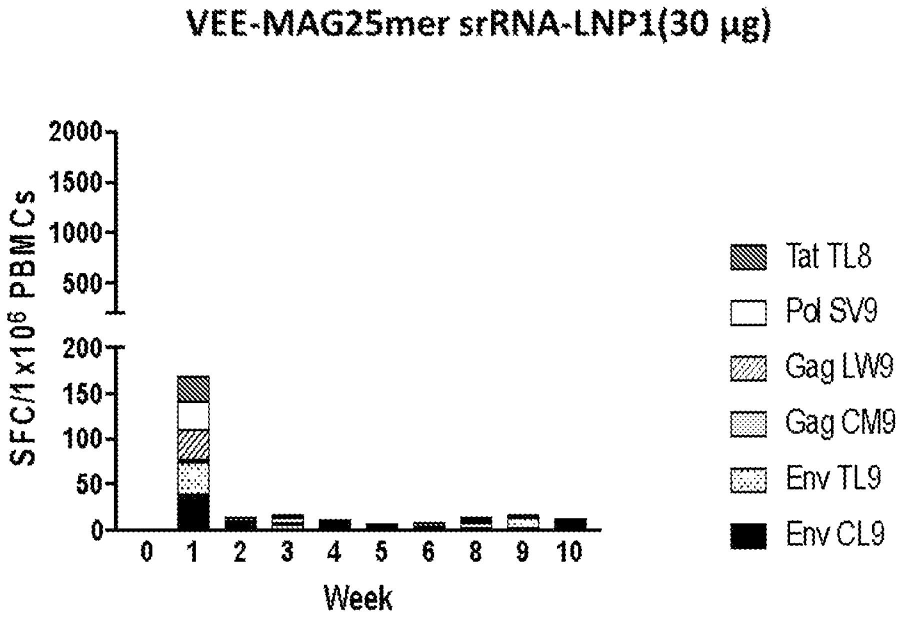
FIG. 20 illustrates antigen-specific cellular immune responses measured using ELISpot. Antigen-specific IFN-gamma production to six different mamu A01 restricted epitopes was measured in PBMCs for the VEE-MAG25mer srRNA-LNP1 (30 μg) (FIG. 20A), VEE-MAG25mer srRNA-LNP1 (100 μg) (FIG. 20B), or VEE-MAG25mer srRNA-LNP2 (100 μg) (FIG. 20C) homologous prime/boost or the ChAdV68.5WTnt.MAG25mer/VEE-MAG25mer srRNA heterologous prime/boost group (FIG. 20D) using ELISpot 1, 2, 3, 4, 5, 6, 8, 9, or 10 weeks after the first boost immunization (6 rhesus macaques per group). Results are presented as mean spot forming cells (SFC) per $10^6$ PBMCs for each epitope in a stacked bar graph format. Values for each animal were normalized to the levels at pre-bleed (week 0).
Figure 20B:
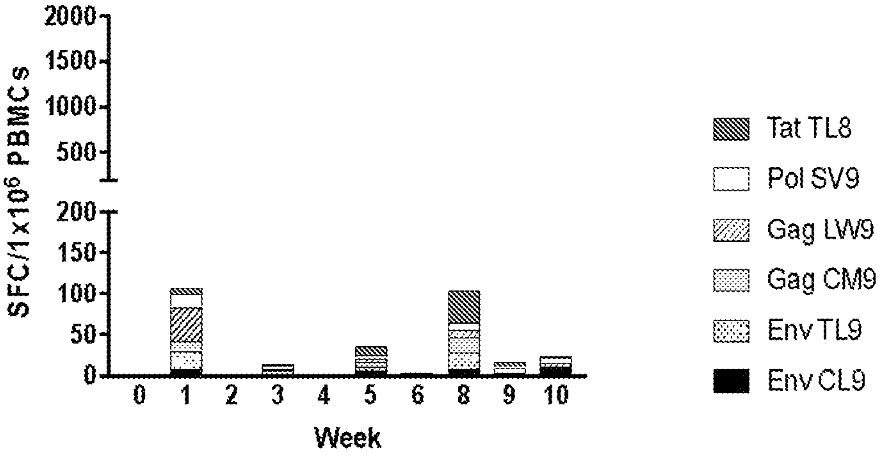
Figure 20C:
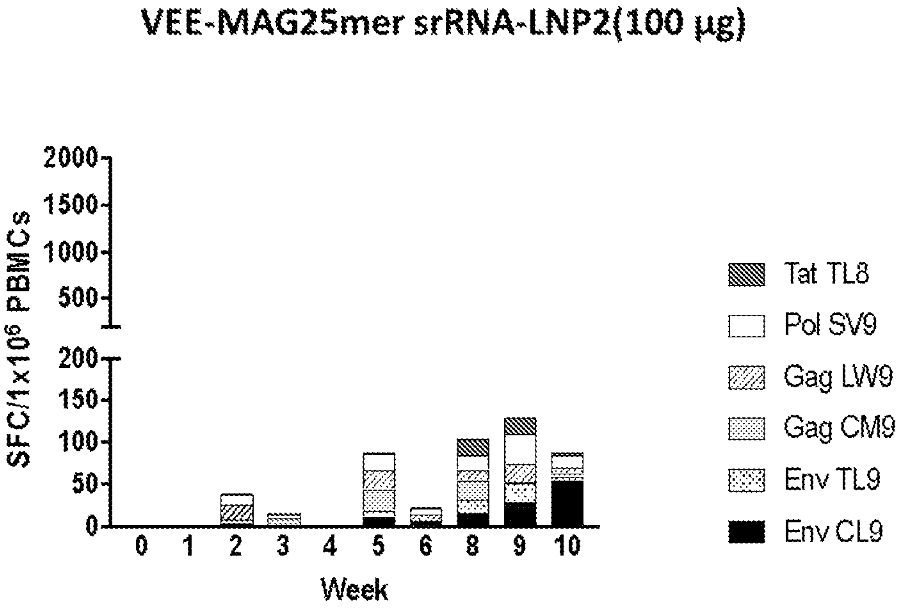

Combined antigen-specific immune responses were observed at all measurements with 170, 14, 15, 11, 7, 8, 14, 17, 12 SFCs per $10^6$ PBMCs (six epitopes combined) 1, 2, 3, 4, 5, 6, 8, 9, or 10 weeks after an initial VEE-MAG25mer srRNA-LNP1 (30 μg) prime immunization, respectively (FIG. 20A). Combined antigen-specific immune responses were observed at all measurements with 108, −3, 14, 1, 37, 4, 105, 17, 25 SFCs per $10^6$ PBMCs (six epitopes combined) 1, 2, 3, 4, 5, 6, 8, 9, or 10 weeks after an initial VEE-MAG25mer srRNA-LNP1 (100 μg) prime immunization, respectively (FIG. 20B). Combined antigen-specific immune responses were observed at all measurements with −17, 38, 14, −2, 87, 21, 104, 129, 89 SFCs per $10^6$ PBMCs (six epitopes combined) 1, 2, 3, 4, 5, 6, 8, 9, or 10 weeks after an initial VEE-MAG25mer srRNA-LNP2 (100 μg) prime immunization, respectively (FIG. 20C). Negative values are a result of normalization to pre-bleed values for each epitope/animal.

Figure 20D:
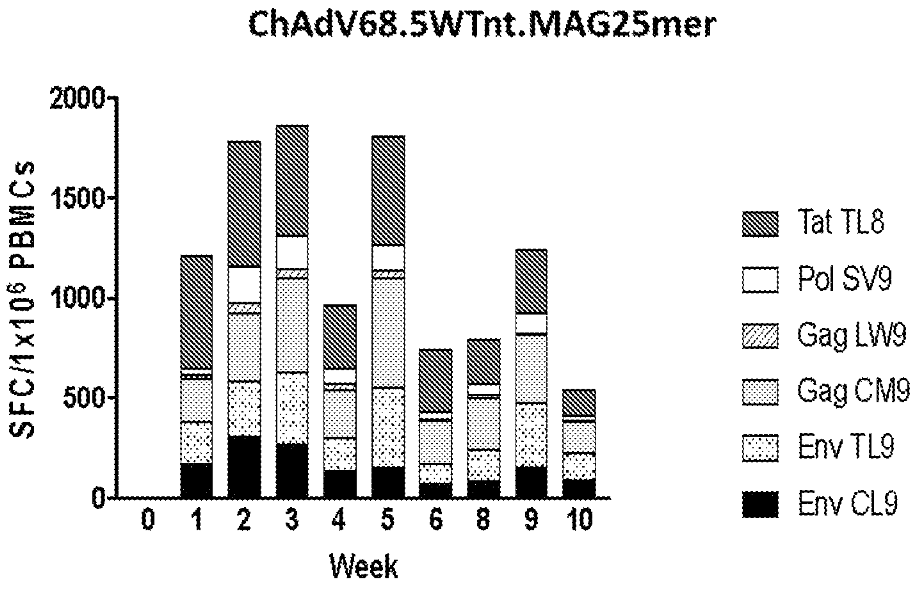

Combined antigen-specific immune responses were observed at all measurements with 1218, 1784, 1866, 973, 1813, 747, 797, 1249, and 547 SFCs per $10^6$ PBMCs (six epitopes combined) 1, 2, 3, 4, 5, 6, 8, 9, or 10 weeks after an initial ChAdV68.5WTnt.MAG25mer prime immunization, respectively (FIG. 20D). The immune response showed the expected profile with peak immune responses measured ~2-3 weeks after the prime immunization followed by a contraction in the immune response after 4 weeks. Combined antigen-specific cellular immune responses of 1813 SFCs per $10^6$ PBMCs (six epitopes combined) were measured 5 weeks after the initial immunization with ChAdV68.5WTnt.MAG25mer (i.e., 1 week after the first boost with VEE-MAG25mer srRNA). The immune response measured 1 week after the first boost with VEE-MAG25mer srRNA (week 5) was comparable to the peak immune response measured for the ChAdV68.5WTnt.MAG25mer prime immunization (week 3) (FIG. 20D). Combined antigen-specific cellular immune responses of 1249 SFCs per $10^6$ PBMCs (six epitopes combined) was measured 9 weeks after the initial immunization with ChAdV68.5WTnt.MAG25mer, respectively (i.e., 1 week after the second boost with VEE-MAG25mer srRNA). The immune responses measured 1 week after the second boost with VEE-MAG25mer srRNA (week 9) was ~2-fold higher than that measured just before the boost immunization (FIG. 20D).

TABLE 22

Mean spot forming cells (SFC) per $10^6$ PBMCs for each epitope ± SEM for VEE-MAG25mer srRNA-LNP1(30 μg) (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 39.7 ± 22.7 | 35.4 ± 25.1 | 3.2 ± 3.6 | 33 ± 28.1 | 30.9 ± 20.3 | 28.3 ± 17.5 |
| 3 | 2 ± 2.4 | 0.2 ± 1.8 | 1.8 ± 2.4 | 3.7 ± 1.9 | 1.7 ± 2.8 | 4.9 ± 2.3 |
| 4 | 1 ± 1.8 | 0.3 ± 1.2 | 5.5 ± 3.6 | 2.3 ± 2.2 | 5.7 ± 2.7 | 0.8 ± 0.8 |
| 5 | 0.5 ± 0.9 | 1.4 ± 3.8 | 3.1 ± 1.6 | 2.3 ± 2.7 | 1.9 ± 2 | 1.4 ± 1.2 |
| 6 | 1.9 ± 1.8 | −0.3 ± 3 | 1.7 ± 1.2 | 1.4 ± 1.4 | 0.8 ± 1.1 | 1.1 ± 1 |
| 8 | −0.4 ± 0.8 | −0.9 ± 2.9 | 0.5 ± 1.3 | 3 ± 1.1 | 2.2 ± 2.1 | 3.7 ± 2 |
| 9 | 1 ± 1.7 | 1.2 ± 4.2 | 7.2 ± 3.9 | 0.5 ± 0.7 | 1.6 ± 3 | 3 ± 1 |
| 10 | 3.8 ± 1.8 | 11 ± 5 | −1.1 ± 1.1 | 1.9 ± 0.9 | 1.3 ± 1.6 | 0.2 ± 0.5 |

TABLE 23

Mean spot forming cells (SFC) per $10^6$ PBMCs for each epitope ± SEM for VEE-MAG25mer srRNA-LNP1(100 μg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 7.9 ± 17.2 | 23.2 ± 17.4 | 11.4 ± 4.9 | 41.7 ± 16.5 | 15 ± 13.5 | 8.9 ± 6.2 |
| 3 | −3.1 ± 4.6 | −7.2 ± 6.5 | 2.3 ± 2.3 | −0.3 ± 2.7 | 2.7 ± 5.1 | 2.2 ± 1.4 |
| 4 | 1.9 ± 3.8 | −6.2 ± 7.6 | 10.5 ± 4.1 | 1.2 ± 2.9 | 5.6 ± 4.9 | 1.1 ± 0.8 |
| 5 | −2.6 ± 7 | −8 ± 5.9 | 1.5 ± 1.7 | 6.4 ± 2.3 | 0.7 ± 4.3 | 3.3 ± 1.3 |
| 6 | 6.3 ± 6.3 | 4.4 ± 8.3 | 6.6 ± 4.4 | 5.2 ± 5.2 | 3.9 ± 5 | 10.8 ± 6.9 |
| 8 | −3.6 ± 7.2 | −6.8 ± 7.3 | −0.8 ± 1.2 | 3.4 ± 4.2 | 6.4 ± 7.5 | 5.7 ± 2.7 |
| 9 | 8.1 ± 2.4 | 20.6 ± 23.4 | 18.9 ± 5.7 | 8.1 ± 8.9 | 9 ± 11.2 | 40 ± 17.6 |
| 10 | 3.1 ± 8 | −3.9 ± 8.5 | 3.3 ± 1.8 | 0.6 ± 2.9 | 7.4 ± 6.4 | 6.1 ± 2.5 |

TABLE 24

Mean spot forming cells (SFC) per $10^6$ PBMCs for each epitope ± SEM for VEE-MAG25mer srRNA-LNP2(100 μg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | −5.9 ± 3.8 | −0.3 ± 0.5 | −0.5 ± 1.5 | −5.7 ± 6.1 | −1 ± 1.3 | −3.2 ± 5.5 |
| 3 | 0.7 ± 5.2 | 3.4 ± 2.4 | 4.2 ± 4.6 | 18.3 ± 15.5 | 11.9 ± 5.1 | −0.4 ± 8.2 |
| 4 | −3.8 ± 5.5 | 2.3 ± 1.8 | 11.3 ± 6.1 | −3.1 ± 5.6 | 8.5 ± 4 | −1.5 ± 6.1 |
| 5 | −3.7 ± 5.7 | −0.1 ± 0.7 | −0.2 ± 1.6 | 3.4 ± 8.5 | 3 ± 3.1 | −4.6 ± 5 |
| 6 | 12.3 ± 15 | 7.8 ± 4.9 | 24.7 ± 19.8 | 23.2 ± 22.5 | 18.7 ± 15.8 | 0.5 ± 6.2 |
| 8 | 5.9 ± 12.3 | −0.1 ± 0.7 | −0.5 ± 1.3 | 8.8 ± 14.4 | 8.7 ± 8 | −1.3 ± 4 |
| 9 | 16.1 ± 13.4 | 16.5 ± 4 | 22.9 ± 4.2 | 13 ± 13.2 | 16.4 ± 7.8 | 19.6 ± 9.2 |
| 10 | 29.9 ± 21.8 | 22 ± 19.5 | 0.5 ± 2.6 | 22.2 ± 22.6 | 35.3 ± 15.8 | 19.4 ± 17.3 |

TABLE 25

Mean spot forming cells (SFC) per $10^6$ PBMCs for each epitope ± SEM for ChAdV68.5WTnt.MAG25mer prime

| | Antigen | | | | | |
|---|---|---|---|---|---|---|
| Wk | Env CL9 | Env TL9 | Gag CM9 | Gag LW9 | Pol SV9 | Tat TL8 |
| 1 | 178 ± 68.7 | 206.5 ± 94.8 | 221.2 ± 120 | 15.4 ± 16.7 | 33.3 ± 25.9 | 563.5 ± 174.4 |
| 2 | 311.2 ± 165.5 | 278.8 ± 100.9 | 344.6 ± 110.8 | 46.3 ± 13.5 | 181.6 ± 76.8 | 621.4 ± 220.9 |
| 3 | 277.3 ± 101.1 | 359.6 ± 90.5 | 468.2 ± 106.6 | 41.7 ± 11.1 | 169.8 ± 57.8 | 549.4 ± 115.7 |

TABLE 25-continued

| Mean spot forming cells (SFC) per $10^6$ PBMCs for each epitope ± SEM for ChAdV68.5WTnt.MAG25mer prime | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 4 | 140 ± 46.5 | 169.6 ± 46.8 | 239.4 ± 37 | 26.5 ± 11.4 | 75 ± 31.6 | 322.2 ± 50.7 |
| 5 | 155.6 ± 62.1 | 406.7 ± 96.4 | 542.7 ± 143.3 | 35.1 ± 16.6 | 134.2 ± 53.7 | 538.5 ± 91.9 |
| 6 | 78.9 ± 42.5 | 95.5 ± 29.4 | 220.9 ± 75.3 | −1.4 ± 5.3 | 43.4 ± 19.6 | 308.1 ± 42.6 |
| 8 | 88.4 ± 30.4 | 162.1 ± 30.3 | 253.4 ± 78.6 | 21.4 ± 11.2 | 53.7 ± 22.3 | 217.8 ± 45.2 |
| 9 | 158.5 ± 69 | 322.3 ± 87.2 | 338.2 ± 137.1 | 5.6 ± 12.4 | 109.2 ± 17.9 | 314.8 ± 43.4 |
| 10 | 97.3 ± 32.5 | 133.2 ± 27 | 154.9 ± 59.2 | 10 ± 6 | 26 ± 16.7 | 125.5 ± 27.7 |

Non-GLP RNA Dose Ranging Study (Higher Doses) in Indian Rhesus Macaques

This study was designed to (a) evaluate the immunogenicity of VEE-MAG25mer srRNA at a dose of 300 μg as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2 at the 300 μg dose; and (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Vaccine immunogenicity in nonhuman primate species, such as Rhesus, is the best predictor of vaccine potency in humans. Furthermore, select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5-WTnt.MAG25mer or VEE-MAG25mer srRNA encoding model antigens that includes multiple Mamu-A*01 restricted antigens. The study arms were as described below.

PBMCs were collected prior to immunization and 4, 5, 6, 7, 8, 10, 11, 12, 13, 14, 15, 16, 17, 18, 19, 20, 21, 22, 23 or 24 weeks after the initial immunization for immune monitoring for group 1 (heterologous prime/boost). PBMCs were collected prior to immunization and 4, 5, 7, 8, 10, 11, 12, 13, 14, or 15 weeks after the initial immunization for immune monitoring for groups 2 and 3 (homologous prime/boost).

TABLE 26

| Non-GLP immunogenicity study in Indian Rhesus Macaques | | | | |
|---|---|---|---|---|
| Group | Prime | Boost 1 | Boost 2 | Boost 3 |
| 1 | ChAdV68.5WTnt. MAG25mer | VEE-MAG25mer srRNA-LNP2 (300 μg) | VEE-MAG25mer srRNA-LNP2 (300 μg) | VEE-MAG25mer srRNA-LNP2 (300 μg) |
| 2 | VEE-MAG25mer srRNA-LNP2 (300 μg) | VEE-MAG25mer srRNA-LNP2 (300 μg) | VEE-MAG25mer srRNA-LNP2 (300 μg) | |
| 3 | VEE-MAG25mer srRNA-LNP1 (300 μg) | VEE-MAG25mer srRNA-LNP1 (300 μg) | VEE-MAG25mer srRNA-LNP1 (300 μg) | |

Results

Figure 21:
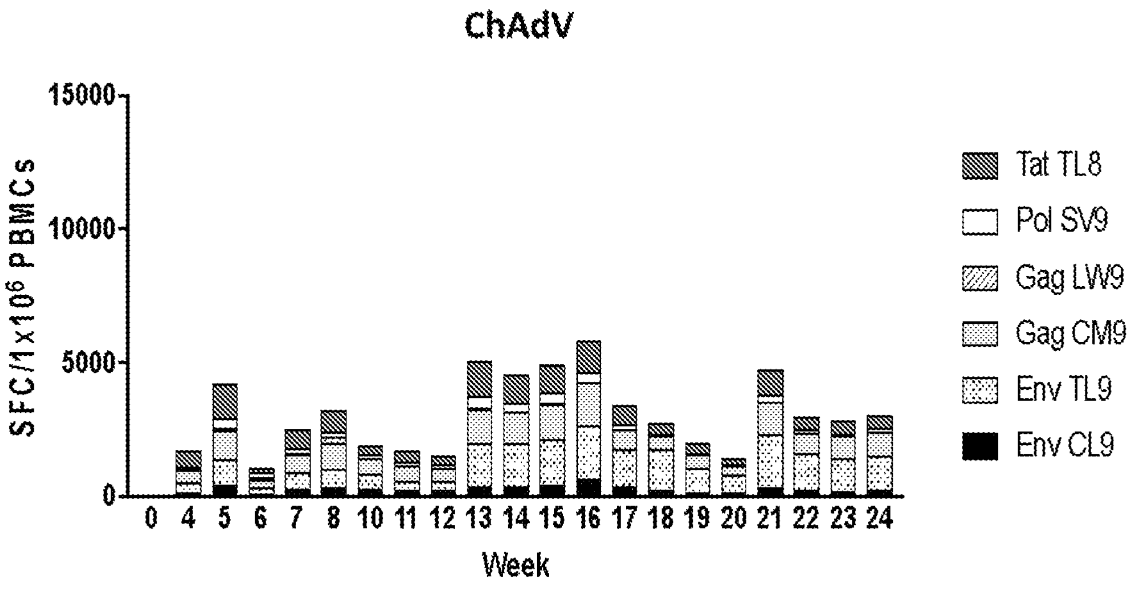
FIG. 21 shows antigen-specific cellular immune response measured using ELISpot. Antigen-specific IFN-gamma production to six different mamu A01 restricted epitopes was measured in PBMCs after immunization with the ChAdV68.5WTnt.MAG25mer/VEE-MAG25mer srRNA heterologous prime/boost regimen using ELISpot prior to immunization and 4, 5, 6, 7, 8, 10, 11, 12, 13, 14, 15, 16, 17, 18, 19, 20, 21, 22, 23 or 24 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were immunized with ChAdV68.5-WTnt.MAG25mer. Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, 15, 16, 17, 18, 19, 20, 21, 22, 23 or 24 weeks after the initial immunization (FIG. 21 and Table 27). Animals received boost immunizations with VEE-MAG25mer srRNA using the LNP2 formulation on weeks 4, 12, and 20. Combined antigen-specific immune responses of 1750, 4225, 1100, 2529, 3218, 1915, 1708, 1561, 5077, 4543, 4920, 5820, 3395, 2728, 1996, 1465, 4730, 2984, 2828, or 3043 SFCs per $10^6$ PBMCs (six epitopes combined) were measured 4, 5, 6, 7, 8, 10, 11, 12, 13, 14, 15, 16, 17, 18, 19, 20, 21, 22, 23 or 24 weeks after the initial immunization with ChAdV68.5WTnt.MAG25mer (FIG. 21). Immune responses measured 1 week after the second boost immunization (week 13) with VEE-MAG25mer srRNA were ~3-fold higher than that measured just before the boost immunization (week 12). Immune responses measured 1 week after the third boost immunization (week 21) with VEE-MAG25mer srRNA, were ~3-fold higher than that measured just before the boost immunization (week 20), similar to the response observed for the second boost.

Figure 22:
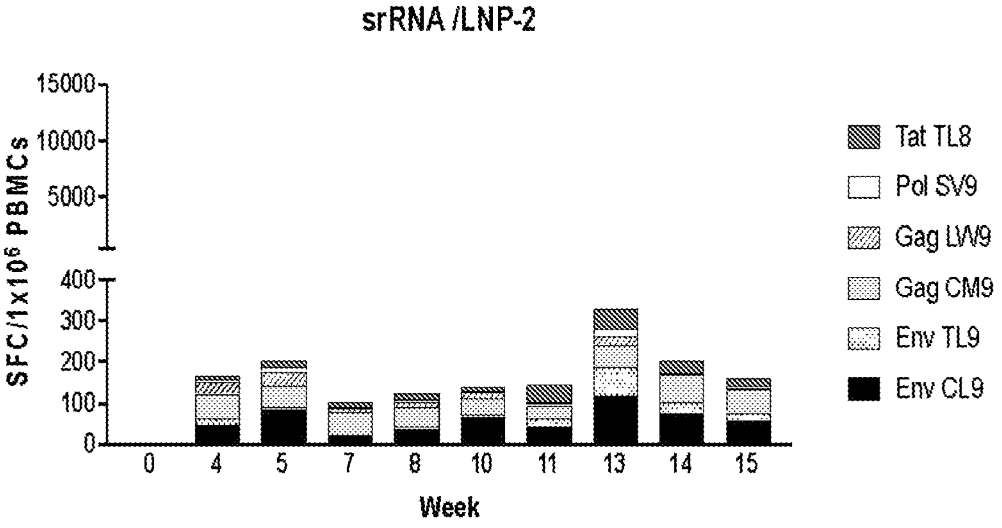
FIG. 22 shows antigen-specific cellular immune response measured using ELISpot. Antigen-specific IFN-gamma production to six different mamu A01 restricted epitopes was measured in PBMCs after immunization with the VEE-MAG25mer srRNA LNP2 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.
Figure 23:
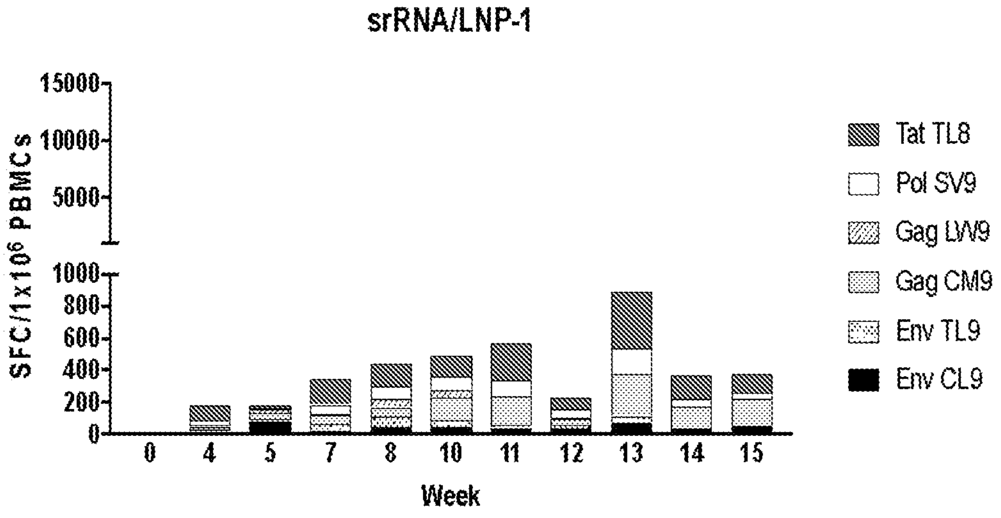
FIG. 23 shows antigen-specific cellular immune response measured using ELISpot. Antigen-specific IFN-gamma production to six different mamu A01 restricted epitopes was measured in PBMCs after immunization with the VEE-MAG25mer srRNA LNP1 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were also immunized with VEE-MAG25mer srRNA using two different LNP formulations (LNP1 and LNP2). Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, or 15 weeks after the initial immunization (FIGS. 22 and 23, Tables 28 and 29). Animals received boost immunizations with VEE-MAG25mer srRNA using the respective LNP1 or LNP2 formulation on weeks 4 and 12. Combined antigen-specific immune responses of 168, 204, 103, 126, 140, 145, 330, 203, and 162 SFCs per $10^6$ PBMCs (six epitopes combined) were measured 4, 5, 7, 8, 10, 11, 13, 14, 15 weeks after the immunization with VEE-MAG25mer srRNA-LNP2 (FIG. 22). Combined antigen-specific immune responses of 189, 185, 349, 437, 492, 570, 233, 886, 369, and 381 SFCs per $10^6$ PBMCs (six epitopes combined) were measured 4, 5, 7, 8, 10, 11, 12, 13, 14, 15 weeks after the immunization with VEE-MAG25mer srRNA-LNP1 (FIG. 23).

TABLE 27

Mean spot forming cells (SFC) per $10^6$ PBMCs for each epitope ± SEM for priming vaccination with ChAdV68.5WTnt.MAG25mer (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |

TABLE 28

Mean spot forming cells (SFC) per $10^6$ PBMCs for each epitope ± SEM for priming vaccination with VEE-MAG25mer srRNA-LNP2 (300 μg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 4 | 46 ± 27.1 | 18.4 ± 6.8 | 58.3 ± 45.8 | 29.9 ± 20.8 | 4.9 ± 2.3 | 10.7 ± 4 |
| 5 | 85.4 ± 54 | 5.2 ± 5.8 | 52.4 ± 51.2 | 34.5 ± 35 | 11.8 ± 12.2 | 14.4 ± 7.9 |
| 7 | 18.6 ± 32.5 | 1.9 ± 1.7 | 59.4 ± 55.7 | 9.3 ± 10.7 | 3.3 ± 3 | 10.7 ± 6.1 |
| 8 | 36.6 ± 39.4 | 6.3 ± 3.9 | 48.7 ± 39.9 | 13.5 ± 8.8 | 3.8 ± 3.6 | 17.2 ± 9.7 |
| 10 | 69.1 ± 59.1 | 4.4 ± 1.9 | 39.3 ± 38 | 14.7 ± 10.8 | 4.4 ± 5.3 | 8.5 ± 5.3 |
| 11 | 43 ± 38.8 | 22.6 ± 21.1 | 30.2 ± 26.2 | 3.3 ± 2.2 | 5.8 ± 3.5 | 40.3 ± 25.5 |
| 13 | 120.4 ± 78.3 | 68.2 ± 43.9 | 54.2 ± 36.8 | 21.8 ± 7.4 | 17.7 ± 6.1 | 47.4 ± 27.3 |
| 14 | 76 ± 44.8 | 28 ± 19.5 | 65.9 ± 64.3 | −0.3 ± 1.3 | 2.5 ± 2 | 31.1 ± 26.5 |
| 15 | 58.9 ± 41.4 | 19.5 ± 15.1 | 55.4 ± 51 | 2.5 ± 2 | 5.5 ± 3.6 | 20.1 ± 15.7 |

TABLE 29

Mean spot forming cells (SFC) per $10^6$ PBMCs for each epitope ± SEM for priming vaccination with VEE-MAG25mer srRNA-LNP1 (300 μg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 4 | 19.5 ± 8.7 | 13.3 ± 13.1 | 16.5 ± 15.3 | 10.5 ± 7.3 | 35.9 ± 24.8 | 92.9 ± 91.6 |
| 5 | 87.9 ± 43.9 | 12.7 ± 11.7 | 37.2 ± 31.9 | 21.1 ± 23.8 | 13.2 ± 13.7 | 12.6 ± 13.7 |
| 7 | 21.1 ± 13.3 | 48.8 ± 48.4 | 51.7 ± 39.5 | 9.1 ± 10.5 | 58.6 ± 55.8 | 159.4 ± 159 |
| 8 | 47.7 ± 21.7 | 66.4 ± 52.2 | 59.8 ± 57.4 | 49.4 ± 28 | 79.4 ± 63 | 133.8 ± 132.1 |
| 10 | 49 ± 30.2 | 42.2 ± 41.1 | 139.3 ± 139.3 | 51.6 ± 51.2 | 78.2 ± 75.8 | 131.7 ± 131.6 |
| 11 | 42 ± 26.8 | 20.9 ± 21.4 | 177.1 ± 162 | −6.3 ± 4.3 | 104.3 ± 104.1 | 231.5 ± 230.1 |
| 12 | 40.2 ± 19 | 20.3 ± 11.9 | 42.2 ± 46.7 | 3.7 ± 6.7 | 57 ± 44.7 | 70 ± 69.2 |
| 13 | 81.2 ± 48.9 | 38.2 ± 37.6 | 259.4 ± 222.2 | −4 ± 4.1 | 164.1 ± 159.3 | 347.3 ± 343.5 |
| 14 | 34.5 ± 31.8 | 5.3 ± 11.6 | 138.6 ± 137.3 | −4.7 ± 5.2 | 52.3 ± 52.9 | 142.6 ± 142.6 |
| 15 | 49 ± 24 | 6.7 ± 9.8 | 167.1 ± 163.8 | −6.4 ± 4.2 | 47.8 ± 42.3 | 116.6 ± 114.5 |

srRNA Dose Ranging Study

In one implementation of the present invention, an srRNA dose ranging study can be conducted in mamu A01 Indian rhesus macaques to identify which srRNA dose to progress to NHP immunogenicity studies. In one example, Mamu A01 Indian rhesus macaques can be administered with an srRNA vector encoding model antigens that includes multiple mamu A01 restricted epitopes by IM injection. In another example, an anti-CTLA-4 monoclonal antibody can be administered SC proximal to the site of IM vaccine injection to target the vaccine draining lymph node in one group of animals. PBMCs can be collected every 2 weeks after the initial vaccination for immune monitoring. The study arms are described in below (Table 30).

TABLE 30

Non-GLP RNA dose ranging study in Indian Rhesus Macaques

| Group | Prime | Boost 1 | Boost 2 |
|---|---|---|---|
| 1 | srRNA-LNP (Low Dose) | srRNA-LNP (Low Dose) | srRNA-LNP (Low Dose) |
| 2 | srRNA-LNP (Mid Dose) | srRNA-LNP (Mid Dose) | srRNA-LNP (Mid Dose) |
| 3 | srRNA-LNP (High Dose) | srRNA-LNP (High Dose) | srRNA-LNP (High Dose) |
| 4 | srRNA-LNP (High Dose) + anti-CTLA-4 | srRNA-LNP (High Dose) + anti-CTLA-4 | srRNA-LNP (High Dose) + anti-CTLA-4 |

* Dose range of srRNA to be determined with the high dose ≤300 μg.

Immunogenicity Study in Indian Rhesus Macaques

Figure 34:
FIG. 34 illustrates the vaccination strategy used to evaluate immunogenicity of the antigen-cassette containing vectors in rhesus macaques. Triangles indicate chAd68 vaccination (1e12 vp/animal) at weeks 0 & 32. Circles represent alphavirus vaccination at weeks 0, 4, 12,20, 28 & 32. Squares represent administration of an anti-CTLA4 antibody.

Vaccine studies were conducted in mamu A01 Indian rhesus macaques (NHPs) to demonstrate immunogenicity using the antigen vectors. FIG. 34 illustrates the vaccination strategy. Three groups of NHPs were immunized with ChAdV68.5-WTnt.MAG25mer and either with the checkpoint inhibitor anti-CTLA-4 antibody Ipilimumab (Groups 5 & 6) or without the checkpoint inhibitor (Group 4). The antibody was administered either intra-venously (group 5) or subcutaneously (group 6). Triangles indicate chAd68 vaccination (1e12 vp/animal) at weeks 0 & 32. Circles represent alphavirus vaccination at weeks 0, 4, 12, 20, 28 and 32.

Figure 35:
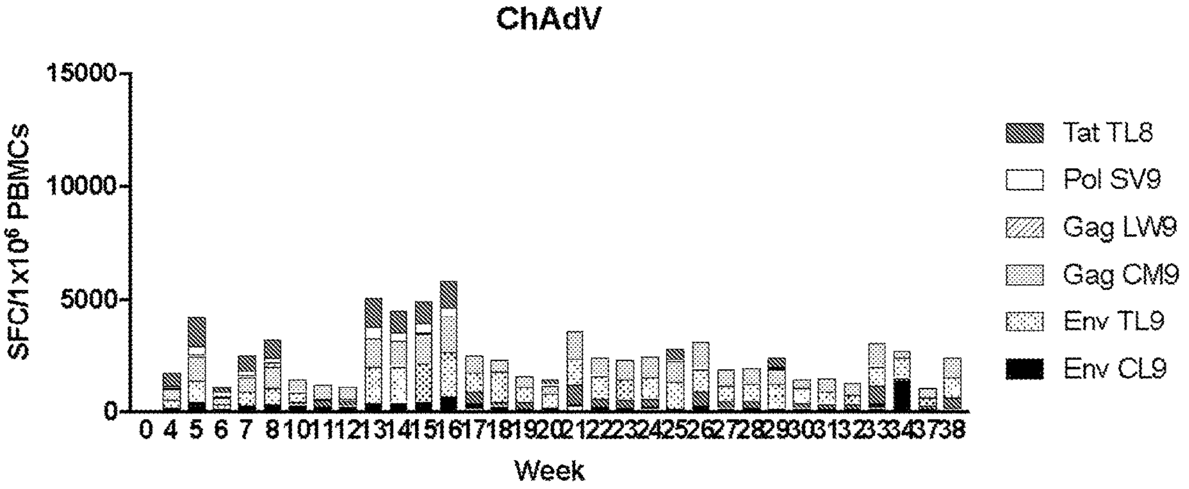
FIG. 35 shows a time course of CD8+ anti-epitope responses in Rhesus Macaques dosed with chAd-MAG alone (Group 4). Mean SFC/1e6 splenocytes is shown.
Figure 36:
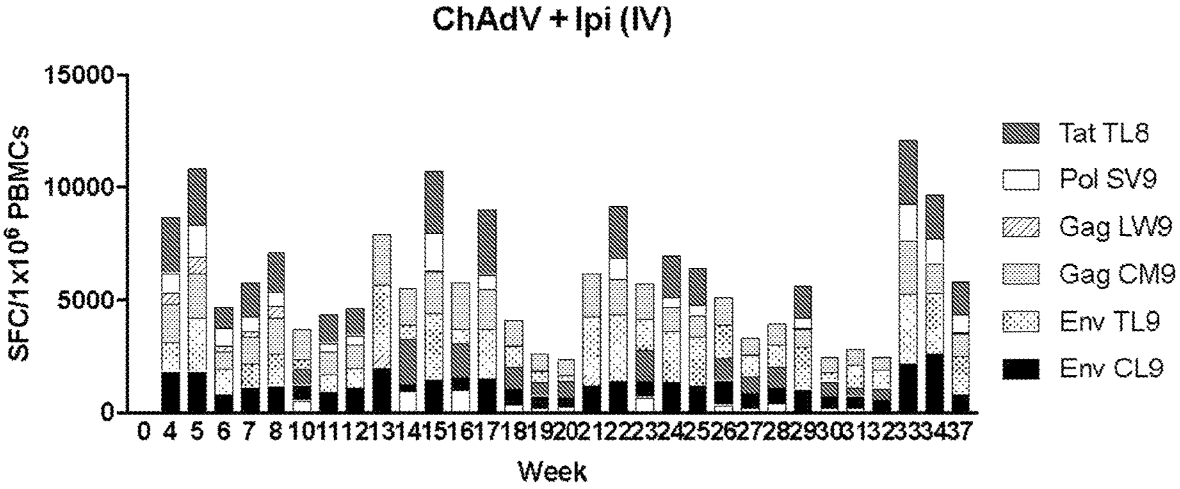
FIG. 36 shows a time course of CD8+ anti-epitope responses in Rhesus Macaques dosed with chAd-MAG plus anti-CTLA4 antibody (Ipilimumab) delivered IV. (Group 5). Mean SFC/1e6 splenocytes is shown.
Figure 37:
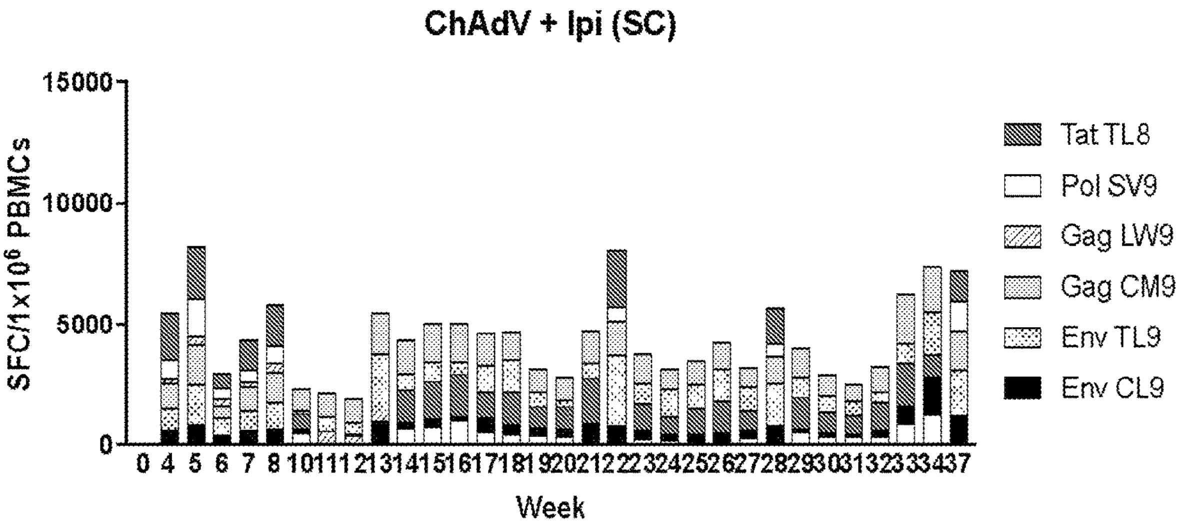
FIG. 37 shows a time course of CD8+ anti-epitope responses in Rhesus Macaques dosed with chAd-MAG plus anti-CTLA4 antibody (Ipilimumab) delivered SC (Group 6). Mean SFC/1e6 splenocytes is shown.

The time course of CD8+ anti-epitope responses in the immunized NHPs are presented for chAd-MAG immunization alone (FIG. 35 and Table 31A), chAd-MAG immunization with the checkpoint inhibitor delivered IV (FIG. 36 and Table 31B), and chAd-MAG immunization with the checkpoint inhibitor delivered SC (FIG. 37 and Table 31C). The results demonstrate chAd68 vectors efficiently primed CD8+ responses in primates, alphavirus vectors efficiently boosted the chAD68 vaccine priming response, checkpoint inhibitor whether delivered IV or SC amplified both priming and boosting responses, and chAd vectors readministered post vaccination to effectively boosted the immune responses.

TABLE 31A

CD8+ anti-epitope responses in Rhesus Macaques dosed with chAd-MAG (Group 4). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |
| 25 | 136.4 ± 52.6 | 1207.1 ± 501.6 | 924 ± 358.5 | 6.2 ± 10.5 | 74.1 ± 34.4 | 484.6 ± 116.7 |
| 26 | 278.2 ± 114.4 | 1645 ± 661.7 | 1170.2 ± 469.9 | −2.9 ± 5.7 | 80.6 ± 55.8 | 784.4 ± 214.1 |
| 27 | 159 ± 56.8 | 961.7 ± 547.1 | 783.6 ± 366.4 | −5 ± 4.3 | 63.6 ± 27.5 | 402.9 ± 123.4 |
| 28 | 189.6 ± 75.7 | 1073.1 ± 508.8 | 668.3 ± 312.5 | −5.7 ± 4.1 | 80.3 ± 38.3 | 386.4 ± 122 |
| 29 | 155.3 ± 69.1 | 1102.9 ± 606.1 | 632.9 ± 235 | 34.5 ± 24.2 | 80 ± 35.5 | 422.5 ± 122.9 |
| 30 | 160.2 ± 59.9 | 859 ± 440.9 | 455 ± 209.1 | −3 ± 5.3 | 60.5 ± 28.4 | 302.7 ± 123.2 |
| 31 | 122.2 ± 49.7 | 771.1 ± 392.7 | 582.2 ± 233.5 | −5.7 ± 4.1 | 55.1 ± 27.3 | 295.2 ± 68.3 |
| 32 | 119.3 ± 28.3 | 619.4 ± 189.7 | 566 ± 222.1 | −3.7 ± 5.1 | 21.9 ± 4.5 | 320.5 ± 76.4 |
| 33 | 380.5 ± 122 | 1636.1 ± 391.4 | 1056.2 ± 205.7 | −5.7 ± 4.1 | 154.5 ± 38.5 | 988.4 ± 287.7 |
| 34 | 1410.8 ± 505.4 | 972.4 ± 301.5 | 319.6 ± 89.6 | −4.8 ± 4.2 | 141.1 ± 49.8 | 1375.5 ± 296.7 |
| 37 | 130.8 ± 29.2 | 500 ± 156.9 | 424.9 ± 148.9 | −3.5 ± 4.7 | 77.7 ± 24.6 | 207.1 ± 42.4 |
| 38 | 167.7 ± 54.8 | 1390.8 ± 504.7 | 830.4 ± 329.1 | −5.5 ± 4.1 | 111.8 ± 43.2 | 516 ± 121.7 |

TABLE 31B

CD8+ anti-epitope responses in Rhesus Macaques dosed with chAd-MAG plus anti-CTLA4 antibody (Ipilimumab) delivered IV. (Group 5). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 1848.1 ± 432.2 | 1295.7 ± 479.7 | 1709.8 ± 416.9 | 513.7 ± 219.8 | 838.5 ± 221.1 | 2514.6 ± 246.5 |
| 5 | 1844.1 ± 410.2 | 2367.5 ± 334.4 | 1983.1 ± 370.7 | 732.1 ± 249.4 | 1429.7 ± 275.3 | 2517.7 ± 286.5 |
| 6 | 822.4 ± 216.7 | 1131.2 ± 194.7 | 796.8 ± 185.8 | 226.8 ± 70 | 802.2 ± 101.4 | 913.5 ± 222.7 |
| 7 | 1147.2 ± 332.9 | 1066 ± 311.2 | 1149.8 ± 467.3 | 267.4 ± 162.6 | 621.5 ± 283.2 | 1552.2 ± 395.1 |
| 8 | 1192.7 ± 188.8 | 1461.5 ± 237.7 | 1566.9 ± 310.5 | 522.5 ± 118.6 | 662.3 ± 142.4 | 1706 ± 216.7 |
| 10 | 1249 ± 220.3 | 1170.6 ± 227.7 | 1297.3 ± 264.7 | −0.3 ± 4.4 | 551.8 ± 90.5 | 1425.3 ± 142.6 |
| 11 | 934.2 ± 221.7 | 808 ± 191.3 | 1003.1 ± 293.4 | 1.9 ± 4.3 | 364.2 ± 76.6 | 1270.8 ± 191.6 |
| 12 | 1106.2 ± 216.6 | 896.7 ± 190.7 | 1020.1 ± 243.3 | 1.3 ± 3.9 | 436.6 ± 90 | 1222 ± 155.4 |
| 13 | 2023.8 ± 556.3 | 3696.7 ± 1.7 | 2248.5 ± 436.4 | −4.5 ± 3.5 | 2614 ± 406.1 | 3700 ± 0 |
| 14 | 1278.7 ± 240 | 2639.5 ± 387 | 1654.6 ± 381.1 | −6 ± 2.1 | 988.8 ± 197.9 | 2288.3 ± 298.7 |
| 15 | 1458.9 ± 281.8 | 2932.5 ± 488.7 | 1893.4 ± 499 | 74.6 ± 15.6 | 1657.8 ± 508.9 | 2709.1 ± 428.7 |
| 16 | 1556.8 ± 243 | 2143.8 ± 295.2 | 2082.8 ± 234.2 | −5.8 ± 2.5 | 1014.6 ± 161.4 | 2063.7 ± 86.7 |
| 17 | 1527 ± 495.1 | 2213 ± 677.1 | 1767.7 ± 391.8 | 15.1 ± 5.9 | 633.8 ± 133.9 | 2890.8 ± 433.9 |
| 18 | 1068.2 ± 279.9 | 1940.9 ± 204.1 | 1114.1 ± 216.1 | −5.8 ± 2.5 | 396.6 ± 77.6 | 1659.4 ± 171.7 |
| 19 | 760.7 ± 362.2 | 1099.5 ± 438.4 | 802.7 ± 192.5 | −2.4 ± 3.3 | 262.2 ± 62.2 | 1118.6 ± 224.2 |
| 20 | 696.3 ± 138.2 | 954.9 ± 198 | 765.1 ± 248.4 | −1.4 ± 4.4 | 279.6 ± 89.3 | 1139 ± 204.5 |
| 21 | 1201.4 ± 327.9 | 3096 ± 1.9 | 1901 ± 412.1 | −5.8 ± 2.5 | 1676.3 ± 311.5 | 2809.3 ± 195.8 |
| 22 | 1442.5 ± 508.3 | 2944.7 ± 438.6 | 1528.4 ± 349.6 | 2.8 ± 5.1 | 940.7 ± 160.5 | 2306.3 ± 218.6 |
| 23 | 1400.4 ± 502.2 | 2757.1 ± 452.9 | 1604.2 ± 450.1 | −5.1 ± 2.3 | 708.1 ± 162.6 | 2100.4 ± 362.9 |
| 24 | 1351 ± 585.1 | 2264.5 ± 496 | 1080.6 ± 253.8 | 0.3 ± 6.5 | 444.2 ± 126.4 | 1823.7 ± 306.5 |
| 25 | 1211.5 ± 505.2 | 2160.4 ± 581.8 | 970.8 ± 235.9 | 2.5 ± 3.8 | 450.4 ± 126.9 | 1626.2 ± 261.3 |
| 26 | 1443 ± 492.5 | 2485 ± 588 | 1252.5 ± 326.4 | −0.2 ± 6 | 360.2 ± 92.3 | 2081.9 ± 331.1 |
| 27 | 896.2 ± 413.3 | 1686 ± 559.5 | 751 ± 192.1 | −3.7 ± 2.5 | 247.4 ± 82.8 | 1364.1 ± 232 |
| 28 | 1147.8 ± 456.9 | 1912.1 ± 417.1 | 930.3 ± 211.4 | −5.8 ± 2.5 | 423.9 ± 79.6 | 1649.3 ± 315 |
| 29 | 1038.5 ± 431.9 | 1915.2 ± 626.1 | 786.8 ± 205.9 | 23.5 ± 8.3 | 462.8 ± 64 | 1441.5 ± 249.7 |
| 30 | 730.5 ± 259.3 | 1078.6 ± 211.5 | 699.1 ± 156.2 | −4.4 ± 2.7 | 234.4 ± 43.9 | 1160.6 ± 112.6 |
| 31 | 750.4 ± 328.3 | 1431 ± 549.9 | 650.6 ± 141.1 | −5.2 ± 3 | 243.4 ± 56.4 | 868.9 ± 142.8 |
| 32 | 581.4 ± 227.7 | 1326.6 ± 505.2 | 573.3 ± 138 | −3.2 ± 4.2 | 160.8 ± 49.2 | 936.4 ± 110.4 |
| 33 | 2198.4 ± 403.8 | 3093.4 ± 123.3 | 2391.8 ± 378.4 | 7.1 ± 8.5 | 1598.1 ± 343.1 | 2827.5 ± 289.5 |
| 34 | 2654.3 ± 337 | 2709.9 ± 204.3 | 1297.5 ± 291.4 | 0.4 ± 4.2 | 1091.8 ± 242.9 | 1924 ± 245.7 |
| 37 | 846.8 ± 301.7 | 1706.9 ± 196 | 973.6 ± 149.3 | 50.5 ± 45.2 | 777.3 ± 140.2 | 1478.8 ± 94.3 |

TABLE 31C

CD8+ anti-epitope responses in Rhesus Macaques dosed with chAd-MAG plus anti-CTLA4 antibody (Ipilimumab) delivered SC (Group 6). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 4 | 598.3 ± 157.4 | 923.7 ± 306.8 | 1075.6 ± 171.8 | 180.5 ± 74.1 | 752.3 ± 245.8 | 1955.3 ± 444.4 |
| 5 | 842.2 ± 188.5 | 1703.7 ± 514.2 | 1595.8 ± 348.4 | 352.7 ± 92.3 | 1598.9 ± 416.8 | 2163.7 ± 522.1 |
| 6 | 396.4 ± 45.3 | 728.3 ± 232.7 | 503.8 ± 151.9 | 282 ± 69 | 463.1 ± 135.7 | 555.2 ± 191.5 |
| 7 | 584.2 ± 177 | 838.3 ± 254.9 | 1013.9 ± 349.4 | 173.6 ± 64.3 | 507.4 ± 165.7 | 1222.8 ± 368 |
| 8 | 642.9 ± 134 | 1128.6 ± 240.6 | 1259.1 ± 163.8 | 366.1 ± 72.8 | 726.7 ± 220.9 | 1695.6 ± 359.4 |
| 10 | 660.4 ± 211.4 | 746.9 ± 222.7 | 944.8 ± 210.2 | −12 ± 1.9 | 523.4 ± 230.7 | 787.3 ± 308.3 |
| 11 | 5712 ± 162 | 609.4 ± 194.3 | 937.9 ± 186.5 | −8.9 ± 2.3 | 511.6 ± 229.6 | 1033.3 ± 315.7 |
| 12 | 485.3 ± 123.7 | 489.4 ± 142.7 | 919.3 ± 214.1 | −8.9 ± 2.3 | 341.6 ± 139.4 | 1394.7 ± 432.1 |
| 13 | 986.9 ± 154.5 | 2811.9 ± 411.3 | 1687.7 ± 344.3 | −4.1 ± 5.1 | 1368.5 ± 294.2 | 2751 ± 501.9 |
| 14 | 945.9 ± 251.4 | 2027.7 ± 492.8 | 1386.7 ± 326.7 | −5.7 ± 2.8 | 708.9 ± 277.1 | 1588.2 ± 440.1 |
| 15 | 1075.2 ± 322.4 | 2386 ± 580.7 | 1606.3 ± 368.1 | −5.4 ± 3.2 | 763.3 ± 248.8 | 1896.5 ± 507.8 |
| 16 | 1171.8 ± 341.6 | 2255.1 ± 439.6 | 1672.2 ± 342.3 | −7.8 ± 2.4 | 1031.6 ± 228.8 | 1896.4 ± 419.9 |
| 17 | 1118.2 ± 415.4 | 2156.3 ± 476 | 1345.3 ± 377.7 | −1.1 ± 6.7 | 573.7 ± 118.8 | 1614.4 ± 382.3 |
| 18 | 861.3 ± 313.8 | 2668.2 ± 366.8 | 1157.2 ± 259.6 | −8.9 ± 2.3 | 4812 ± 164 | 1725.8 ± 511.4 |
| 19 | 719.2 ± 294.2 | 1447.2 ± 285 | 968 ± 294.5 | −2.2 ± 4.6 | 395.6 ± 106.1 | 1199.6 ± 289.2 |
| 20 | 651.6 ± 184 | 1189.8 ± 242.8 | 947.4 ± 249.8 | −8.9 ± 2.3 | 355 ± 106.3 | 1234.7 ± 361.7 |
| 21 | 810.3 ± 301.9 | 2576.2 ± 283.7 | 1334 ± 363.1 | −8.9 ± 2.3 | 892.2 ± 305 | 1904.4 ± 448.1 |
| 22 | 775 ± 196.4 | 2949 ± 409.7 | 1421.8 ± 309.7 | 38 ± 27.8 | 577 ± 144.2 | 2330.6 ± 572.3 |
| 23 | 584.9 ± 240.2 | 1977.9 ± 361.4 | 1209.8 ± 405.1 | −7.3 ± 3.2 | 273.7 ± 93.3 | 1430.6 ± 363.9 |
| 24 | 485.4 ± 194.4 | 1819.8 ± 325.5 | 837.2 ± 261.4 | −3.4 ± 4.1 | 234.4 ± 71.1 | 943.9 ± 243.3 |
| 25 | 452.3 ± 175 | 2072 ± 405.7 | 957.1 ± 293.1 | −8.9 ± 2.3 | 163 ± 43.2 | 13412 ± 394.7 |
| 26 | 517.9 ± 179.1 | 2616 ± 567.5 | 1126.6 ± 289 | −8.3 ± 2.3 | 199.9 ± 89.2 | 1615.7 ± 385.6 |
| 27 | 592.8 ± 171.7 | 1838.3 ± 372.4 | 749.3 ± 170.4 | −7.3 ± 2.5 | 325.5 ± 98.7 | 1110.7 ± 308.8 |
| 28 | 793 ± 228.5 | 1795.4 ± 332.3 | 1068.7 ± 210.3 | 2.5 ± 4.1 | 553.1 ± 144.3 | 1480.8 ± 357.1 |

TABLE 31C-continued

CD8+ anti-epitope responses in Rhesus Macaques dosed with chAd-MAG plus anti-CTLA4 antibody (Ipilimumab) delivered SC (Group 6). Mean SFC/1e6 splenocytes +/− the standard error is shown

| | Antigen | | | | | |
|---|---|---|---|---|---|---|
| Wk | Env CL9 | Env TL9 | Gag CM9 | Gag LW9 | Pol SV9 | Tat TL8 |
| 29 | 661.8 ± 199.9 | 2140.6 ± 599.3 | 1202.7 ± 292.2 | −8.7 ± 2.8 | 558.9 ± 279.2 | 1424.2 ± 408.6 |
| 30 | 529.1 ± 163.3 | 1528.2 ± 249.8 | 840.5 ± 218.3 | −8.9 ± 2.3 | 357.7 ± 149.4 | 1029.3 ± 335 |
| 31 | 464.8 ± 152.9 | 1332.2 ± 322.7 | 726.3 ± 194.3 | −8.9 ± 2.3 | 354.3 ± 158.6 | 884.4 ± 282 |
| 32 | 612.9 ± 175.3 | 1584.2 ± 390.2 | 1058.3 ± 219.8 | −8.7 ± 2.8 | 364.6 ± 149.8 | 1388.8 ± 467.3 |
| 33 | 1600.2 ± 416.7 | 2597.4 ± 367.9 | 2086.4 ± 414.8 | −6.3 ± 3.3 | 893.8 ± 266 | 2490.6 ± 416.4 |
| 34 | 2814.6 ± 376.2 | 2713.6 ± 380.8 | 1888.8 ± 499.4 | −7.5 ± 3.1 | 1288.9 ± 438.9 | 2428.1 ± 458.9 |
| 37 | 1245.9 ± 471.7 | 1877.7 ± 291.2 | 1606.6 ± 441.9 | 14.2 ± 13 | 1227.5 ± 348.1 | 1260.7 ± 342 |

Memory Phenotyping in Indian Rhesus Macaques

Figure 38:
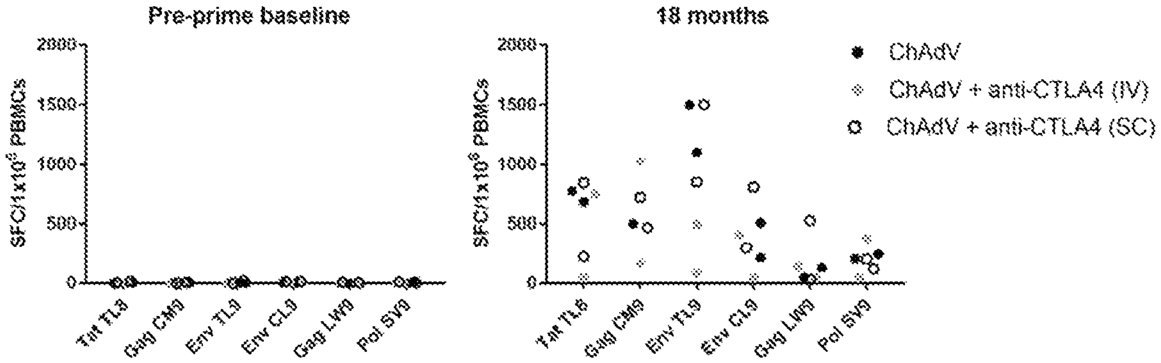
FIG. 38 shows antigen-specific memory responses generated by ChAdV68/samRNA vaccine protocol measured by ELISpot. Results are presented as individual dot plots, with each dot representing a single animal. Pre-immunization baseline (left panel) and memory response at 18 months post-prime (right panel) are shown.

Rhesus macaque were immunized with ChAdV68.5WTnt.MAG25mer/VEE-MAG25mer srRNA heterologous prime/boost regimen with or without anti-CTLA4, and boosted again with ChAdV68.5WTnt.MAG25mer. Groups were assessed 11 months after the final ChAdV68 administration (study month 18). by ELISpot was performed as described. FIG. 38 and Table 43 shows cellular responses to six different Mamu-A*01 restricted epitopes as measured by ELISpot both pre-immunization (left panel) and after 18 months (right panel). The detection of responses to the restricted epitopes demonstrates antigen-specific memory responses were generated by ChAdV68/samRNA vaccine protocol.

Figure 39:
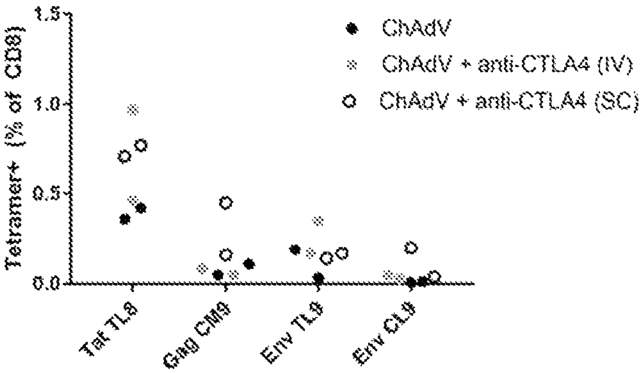
FIG. 39 shows memory cell phenotyping of antigen-specific CD8+ T-cells by flow cytometry using combinatorial tetramer staining and CD45RA/CCR7 co-staining.
Figure 40:
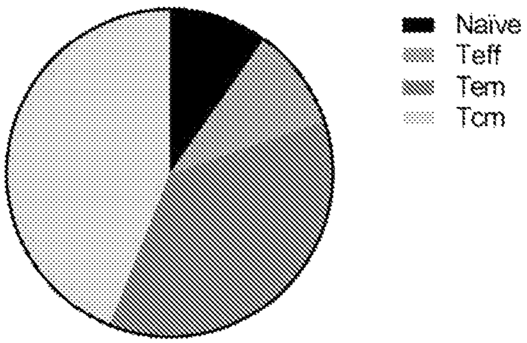
FIG. 40 shows the distribution of memory cell types within the sum of the four Mamu-A*01 tetramer+CD8+ T-cell populations at study month 18. Memory cells were characterized as follows: CD45RA+CCR7+=naïve, CD45RA+CCR7−=effector (Teff), CD45RA-CCR7+=central memory (Tcm), CD45RA-CCR7−=effector memory (Tem).

To assess memory, CD8+ T-cells recognizing 4 different rhesus macaque Mamu-A*01 class I epitopes encoded in the vaccines were monitored using dual-color Mamu-A*01 tetramer labeling, with each antigen being represented by a unique double positive combination, and allowed the identification of all 4 antigen-specific populations within a single sample. Memory cell phenotyping was performed by co-staining with the cell surface markers CD45RA and CCR7. FIG. 39 and Table 44 shows the results of the combinatorial tetramer staining and CD45RA/CCR7 co-staining for memory T-cells recognizing four different Mamu-A*01 restricted epitopes. The T cell phenotypes were also assessed by flow cytometry. FIG. 40 shows the distribution of memory cell types within the sum of the four Mamu-A*01 tetramer+CD8+ T-cell populations at study month 18. Memory cells were characterized as follows: CD45RA+CCR7+=naïve, CD45RA+CCR7-=effector (Teff), CD45RA-CCR7+=central memory (Tcm), CD45RA-CCR7-= effector memory (Tem). Collectively, the results demonstrate that memory responses were detected at least one year following the last boost indicating long lasting immunity, including effector, central memory, and effector memory populations.

TABLE 43

Mean spot forming cells (SFC) per $10^6$ PBMCs for each animal at both pre-prime and memory assessment time points (18 months).

| | Pre-prime baseline | | | | | | 18 months | | | | | |
|---|---|---|---|---|---|---|---|---|---|---|---|---|
| Animal | Tat TL8 | Gag CM9 | Env TL9 | Env CL9 | Gag LW9 | Pol SV9 | Tat TL8 | Gag CM9 | Env TL9 | Env CL9 | Gag LW9 | Pol SV9 |
| 1 | 1.7 | 0.0 | 0.0 | 5.0 | 0.0 | 13.7 | 683.0 | 499.2 | 1100.3 | 217.5 | 47.7 | 205.3 |
| 2 | 0.0 | 0.0 | 0.0 | 0.2 | 0.1 | 0.0 | 773.4 | ND | 1500.0 | 509.3 | 134.5 | 242.5 |
| 3 | 0.0 | 0.0 | 6.7 | 6.8 | 10.2 | 3.3 | 746.3 | 167.5 | 494.1 | 402.8 | 140.6 | 376.0 |
| 4 | 0.0 | 0.0 | 0.0 | 0.0 | 0.0 | 0.0 | 47.6 | 1023.9 | 85.1 | 44.2 | 44.2 | 47.6 |
| 5 | 15.3 | 6.7 | 18.6 | 15.6 | 5.2 | 12.1 | 842.4 | 467.7 | 1500.0 | 805.9 | 527.8 | 201.8 |
| 6 | 3.1 | 0.0 | 0.0 | 15.5 | 6.9 | 5.3 | 224.3 | 720.3 | 849.0 | 296.9 | 32.4 | 121.9 |

ND = not determined due to technical exclusion

TABLE 44

| Percent Mamu-A*01 tetramer positive out of live CD8+ cells | | | | |
|---|---|---|---|---|
| Animal | Tat TL8 | Gag CM9 | Env TL9 | Env CL9 |
| 1 | 0.42 | 0.11 | 0.19 | 0.013 |
| 2 | 0.36 | 0.048 | 0.033 | 0.00834 |
| 3 | 0.97 | 0.051 | 0.35 | 0.048 |
| 4 | 0.46 | 0.083 | 0.17 | 0.028 |
| 5 | 0.77 | 0.45 | 0.14 | 0.2 |
| 6 | 0.71 | 0.16 | 0.17 | 0.04 |

XIX. Vaccination in Combination with Interferon Signalling Suppression

To increase the expression and potency of the alphavirus-based samRNA vaccine, the impact of type I IFN mediated suppression on antigen expression and immunogenicity of the vaccine was evaluated. See, e.g., Pepini et al. *J Immunol.* 2017 May 15; 198(10):4012-4024.

Materials and Methods

C57BL/6J mice were immunized with an LNP formulated VEE-Luciferase samRNA (SEQ ID NO: 15) (10 μg per mouse, delivered intramuscularly, bilateral) and either anti-IFNAR MAb or Tofacitinib. Anti-IFNAR MAb (clone MAR1-5A3, BioXcell) was delivered intraperitoneally as a single dose 24 hours prior to immunization (2 mg). Tofacitinib was delivered orally, 2 mg, 2×/day starting 24 hours prior to immunization and continuing for 6 days. Relative luminescence (RLU) was quantified for each mouse at days 1, 2 and 5 following immunization with VEE-Luciferase.

Balb/c mice were immunized with VEE-MAG25mer samRNA (SEQ ID NO: 4; 10 μg per mouse, delivered intramuscularly, bilateral) and either anti-IFNAR MAb or Tofacitinib. Anti-IFNAR MAb (clone MAR1-5A3, BioXcell) was delivered intraperitoneally as a single dose 24 hours prior to immunization (2 mg). Tofacitinib was delivered orally, 2 mg, 2×/day starting 24 hours prior to immunization and continuing for 8 days. Mice were sacrificed, and spleens collected at 12 days post immunization with VEE-MAG. T-cell responses to the AH1-A5 peptide (SPSYAYHQF (SEQ ID NO: 137)) were measured using intracellular cytokine staining.

Results

Figure 26A:
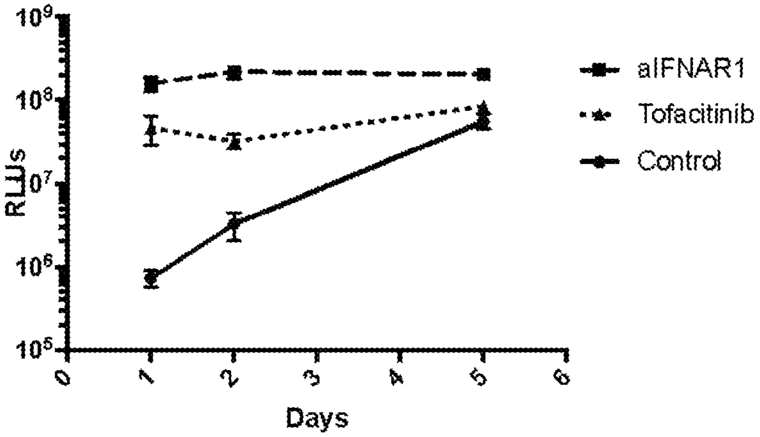
FIG. 26A shows in vivo reporter expression after immunization of C57BL/6J mice with VEE-Luciferase samRNA combined with either anti-IFNAR MAb or Tofacitinib. Relative luminescence (RLU) was quantified for each mouse at days 1, 2 and 5 following immunization with VEE-Luciferase (10 μg per mouse, delivered intramuscularly, bilateral). Anti-IFNAR MAb (clone MAR1-5A3, BioXcell) was delivered intraperitoneally as a single dose 24 hours prior to immunization (2 mg). Tofacitinib was delivered orally, 2 mg, 2×/day starting 24 hours prior to immunization and continuing for 6 days. Mean+/−SEM, 5 mice group.

To inhibit type I IFN, either a monoclonal antibody (MAR1-5A3) that blocks the IFNαβ receptor (IFNAR), or a small molecule inhibitor of JAK1 and JAK3, Tofacitinib, was injected into mice 24-hours prior to vaccination with either VEE-Luciferase expressing the luciferase reporter gene, or VEE-MAG, expressing a model antigen cassette. Luciferase expression was evaluated at various timepoints post-immunization by in vivo imaging. Pretreatment with aIFNAR MAb led to a ~200-fold increase and with Tofacitinib a ~60-fold increase in luciferase expression at 24 hours post immunization (FIG. 26A; Table 32).

TABLE 32

| Mean RLU values after immunization of C57BL/6J mice with VEE-Luciferase SAM combined with either anti-IFNAR MAb or Tofacitinib. | | | |
|---|---|---|---|
| | Day 1 | Day 2 | Day 5 |
| Control | 7.34E+05 | 3.25E+06 | 5.56E+07 |
| aIFNAR | 1.59E+08 | 2.24E+08 | 2.06E+08 |
| Tofacitinib | 4.71E+07 | 3.25E+07 | 8.49E+07 |

Figure 26B:
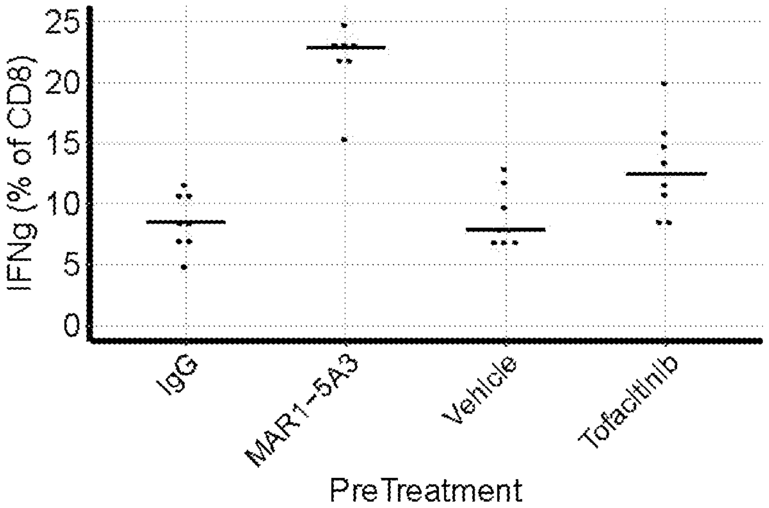
FIG. 26B shows in vivo vivo antigen-specific T-cell response after immunization of Balb/c mice with VEE-MAG samRNA combined with either anti-IFNAR MAb or Tofacitinib or control. T-cell responses to the AH1-A5 peptide (SPSYAYHQF (SEQ ID NO: 137)) were measured using intracellular cytokine staining. Mice were sacrificed, and spleens collected at 12 days post immunization with VEE-MAG (10 μg, IM). Anti-IFNAR MAb (clone MAR1-5A3, BioXcell) was delivered intraperitoneally as a single dose 24 hours prior to immunization (2 mg). Tofacitinib was delivered orally, 2 mg, 2×/day starting 24 hours prior to immunization and continuing for 8 days. 8 mice per group, bar represents median.

Antigen-specific T-cell response was measured by intracellular cytokine staining, 12 days post immunization. Consistent with the increased expression, pretreatment with either aIFNAR MAb or Tofacitinib led to a significant increase in antigen-specific T-cells (aIFNAR: mean 22% IFNg+(% of CD8+) compared to 9% in IgG treated controls, $p<0.001$; Tofacitinib: mean 13% IFNg+(% of CD8+) compared to 9% in vehicle treated controls, $p<0.05$). See FIG. 26B and Table 33.

TABLE 33

| Mean antigen-specific T-cells (% of CD8) 12 days post immunization with VEE-MAG SAM combined with either anti-IFNAR MAb or Tofacitinib or control. | |
|---|---|
| Pretreatment | IFNg+ (% of CD8) |
| IgG | 8.6 |
| MAR1-5A3 | 22.2 |
| Vehicle | 8.9 |
| Tofacitinib | 12.9 |

XX. Evaluation of Interferon Signalling Suppression Timing

The impact of timing and/or continuation of type I IFN mediated suppression on antigen expression and immunogenicity of the vaccine was evaluated.

Materials and Methods

Balb/c mice were immunized with VEE-MAG25mer samRNA (SEQ ID NO: 4; 1 μg per mouse, delivered intramuscularly, bilateral) and either anti-IFNAR MAb or anti-IgG antibody control. Anti-IFNAR MAb (clone MAR1-5A3, BioXcell) was delivered intraperitoneally (2 mg) at the specified time pre or post-immunization with samRNA, as indicated below. Mice were sacrificed, and spleens collected at 12 days post immunization with VEE-MAG. Antigen-specific (AH1-A5) IFN-gamma production in CD8 T cells was measured using intracellular cytokine staining and percentage of AH1-A5 specific CD8 T cells was measured using MHC Class I tetramer staining.

Results

Figure 27A:
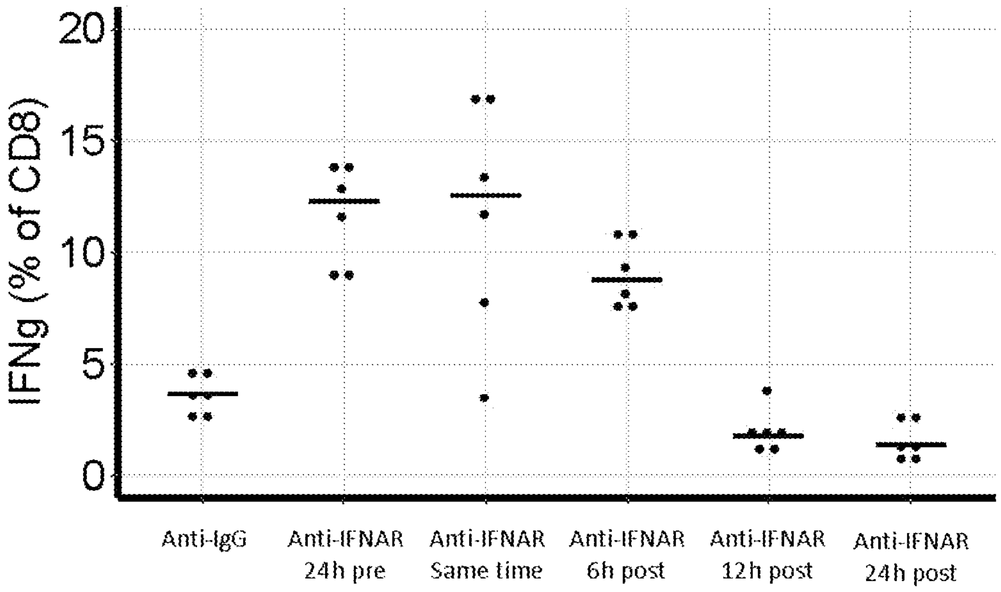
FIG. 27A shows early suppression of IFNα is required for increased samRNA expression and immune response. CD8 T-Cell responses in Balb/c mice at 12 days following a single immunization with 1 μg samRNA. Mice were also treated with either anti-IgG antibody control or a monoclonal blocking antibody targeting IFNAR at the specified time pre or post-immunization with samRNA. Antibody treatments were all at a 2 mg dose, delivered intraperitoneally. Antigen-specific (AH1-A5) IFN-gamma production in CD8 T cells measured using intracellular cytokine staining and results presented as antigen-specific CD8 T cells as a percentage of total CD8 T cells. Median for each group indicated by horizontal line.

To further evaluate inhibition of type I IFN in improving immune responses in samRNA vaccinations, the timing of administering the anti-IFNAR Mab relative to administering the samRNA vaccine was evaluated. Specifically, an anti-IFNAR MAb was administered 24 hours before, at the same time, 6 hours after, 12 hours after, or 24 hours after administering the samRNA vaccine. The immune response was assessed assaying antigen-specific (AH1-A5) IFN-gamma production in CD8 T cells and quantified as a percentage of total CD8 T cells. As shown in FIG. 27A and Table 34A, administration of the anti-IFNAR MAb 24 hours before, at the same time, or 6 hours after administering the samRNA vaccine resulted in a significantly improved antigen-specific immune response relative to administering a control antibody. In contrast, administration of the anti-IFNAR Mab 12 hours after or 24 hours after administering the samRNA vaccine did not result in an improved immune response relative to administering a control antibody. Accordingly, the results demonstrated that early suppression of IFNα led to an improved antigen-specific immune response.

TABLE 34A

| AH1-A5 specific IFN-gamma production (percentage of total CD8 T cells) | | | | | |
|---|---|---|---|---|---|
| Group | Ab Treatment | Median | Mean | SD | P-value* |
| 1 | aIgG | 3.6 | 3.6 | 0.9 | |
| 2 | 24 h pre | 12.3 | 11.7 | 2.3 | 1.8E−05 |
| 3 | Same time | 12.5 | 11.7 | 5.3 | 2.1E−05 |
| 4 | 6 h post | 8.8 | 9.1 | 1.5 | 3.5E−03 |
| 5 | 12 h post | 1.8 | 2.0 | 1.0 | 0.68 |
| 6 | 24 h post | 1.4 | 1.6 | 0.8 | 0.49 |

*Dunnett's test

Figure 27B:
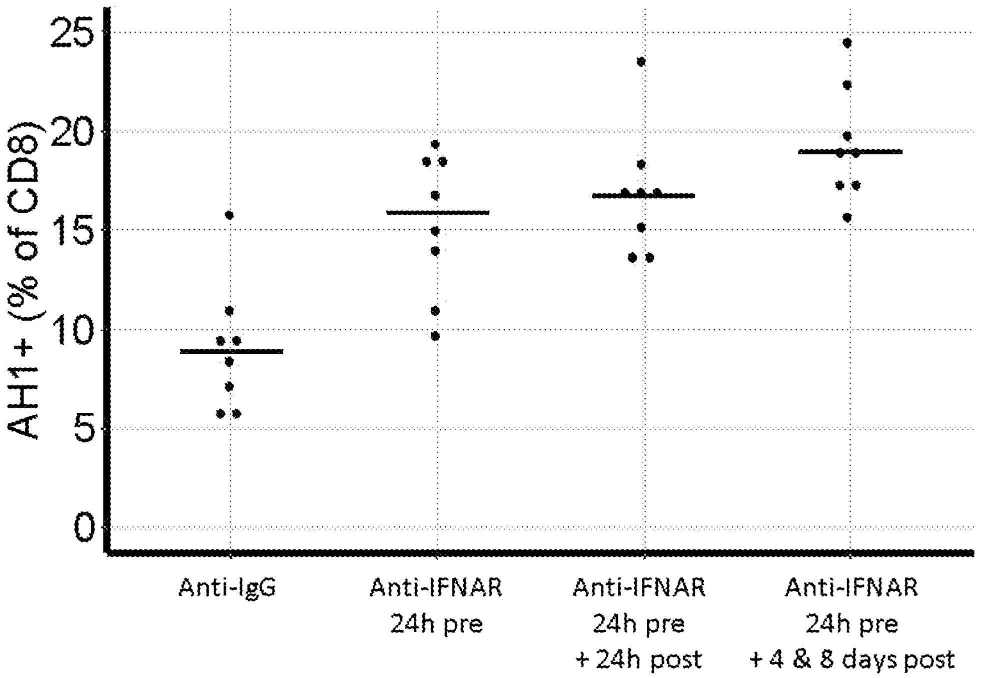
FIG. 27B shows continued IFNα suppression does not decrease immune response. CD8 T-Cell responses in Balb/c mice at 12 days following a single immunization with 1 μg samRNA. Mice were treated with either anti-IgG antibody control or a monoclonal blocking antibody targeting IFNAR at the specified time pre and post-immunization with samRNA. Antibody treatments were all at a 2 mg dose, delivered intraperitoneally. Antigen-specific (AH1-A5) CD8 T cells measured using MHC Class I tetramer staining and results presented as antigen-specific CD8 T cells as a percentage of total CD8 T cells. Median for each group indicated by horizontal line.
Figure 27C:
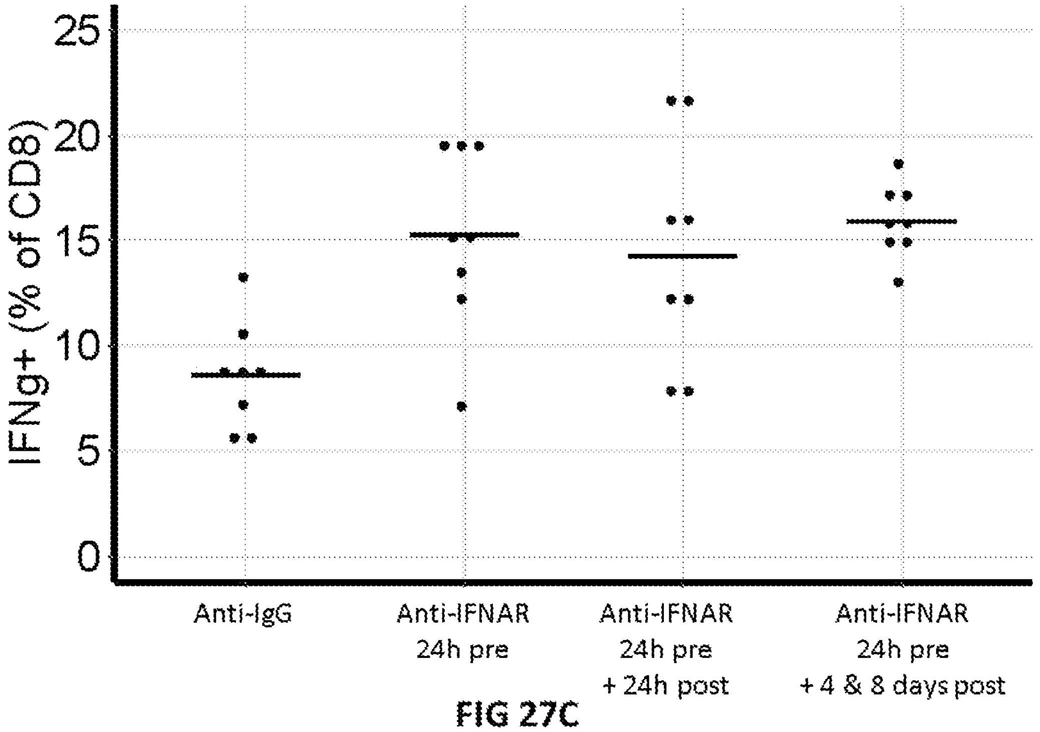
FIG. 27C shows continued IFNα suppression does not decrease immune response. CD8 T-Cell responses in Balb/c mice at 12 days following a single immunization with 1 μg samRNA. Mice were treated with either anti-IgG antibody control or a monoclonal blocking antibody targeting IFNAR at the specified time pre and post-immunization with samRNA. Antibody treatments were all at a 2 mg dose, delivered intraperitoneally. Antigen-specific (AH1-A5) IFN-gamma production in CD8 T cells measured using intracellular cytokine staining and results presented as antigen-specific CD8 T cells as a percentage of total CD8 T cells. Median for each group indicated by horizontal line.

To further evaluate inhibition of type I IFN in improving immune responses in samRNA vaccinations, continued administration of the anti-IFNAR Mab was evaluated, such as whether continued inhibition of type I IFN signaling would negatively impact the overall immune response (e.g., T cell activation), despite the increased expression of SAM. To assess the above, an anti-IFNAR MAb was administered 24 hours before, both 24 hours before and 24 hours after, or 24 hours before and days 4 and 8 after administering the samRNA vaccine. The immune response was assessed assaying antigen-specific (AH1-A5) MHC tetramer staining and IFN-gamma production in CD8 T cells and quantified as a percentage of total CD8 T cells. As shown in FIG. 27B and Table 34B (MHC-tetramer staining) and FIG. 27C and Table 34C (IFN-gamma production), additional subsequent administration of the anti-IFNAR MAb after administering the samRNA vaccine did not alter the immune response relative to administering a single treatment of the anti-IFNAR MAb 24 hours before samRNA vaccination, though all anti-IFNAR MAb treatment protocols did result in an improved antigen-specific immune response relative to administering the control antibody. Accordingly, the results demonstrated that continued IFNα suppression does not noticeably alter (e.g., blunt) the increased epitope-specific immune response resulting from inhibition of type I IFN signaling.

TABLE 34B

| AH1-A5 specific MHC-tetramer staining (percentage of total CD8 T cells) | | | | |
|---|---|---|---|---|
| Group | aIFNAR.regimen | Median | Mean | SD |
| 1 | control | 8.9 | 9.1 | 3.3 |
| 2 | 2 mg IP 24 h pre | 15.9 | 15.4 | 3.6 |
| 3 | 2 mg IP 24 h pre + 24 h post | 16.8 | 16.9 | 3.2 |
| 4 | 2 mg IP 24 h pre + d4 and d8 post | 19.0 | 19.4 | 2.9 |

TABLE 34C

| AH1-A5 specific IFN-gamma production (percentage of total CD8 T cells) | | | | |
|---|---|---|---|---|
| Group | aIFNAR.regimen | Median | Mean | SD |
| 1 | control | 8.6 | 8.6 | 2.6 |
| 2 | 2 mg IP 24 h pre | 15.2 | 15.3 | 4.4 |

TABLE 34C-continued

| AH1-A5 specific IFN-gamma production (percentage of total CD8 T cells) | | | | |
|---|---|---|---|---|
| Group | aIFNAR.regimen | Median | Mean | SD |
| 3 | 2 mg IP 24 h pre + 24 h post | 14.3 | 14.5 | 5.4 |
| 4 | 2 mg IP 24 h pre + d4 and d8 post | 15.9 | 16.0 | 1.8 |

XXI. Evaluation of Interferon Signalling Suppression Administration Route

The impact of the administration route of type I IFN mediated suppression on antigen expression and immunogenicity of the vaccine was evaluated.

Materials and Methods

Balb/c mice were immunized with VEE-MAG25mer samRNA (SEQ ID NO: 4; 1 μg per mouse, delivered intramuscularly bilateral) and either anti-IFNAR MAb or anti-IgG antibody control. Anti-IFNAR MAb (clone MAR1-5A3, BioXcell) was delivered either IP or intramuscularly (0.5 mg) at 24 hours prior to immunization with samRNA. The anti-IgG antibody control was delivered IP (0.5 mg) at 24 hours prior to immunization with samRNA. Mice were sacrificed, and spleens collected at 12 days post immunization with VEE-MAG. Antigen-specific (AH1-A5) IFN-gamma production in CD8 T cells was measured using intracellular cytokine staining and percentage of AH1-A5 specific CD8 T cells was measured using MHC Class I tetramer staining.

Results

Figure 28A:
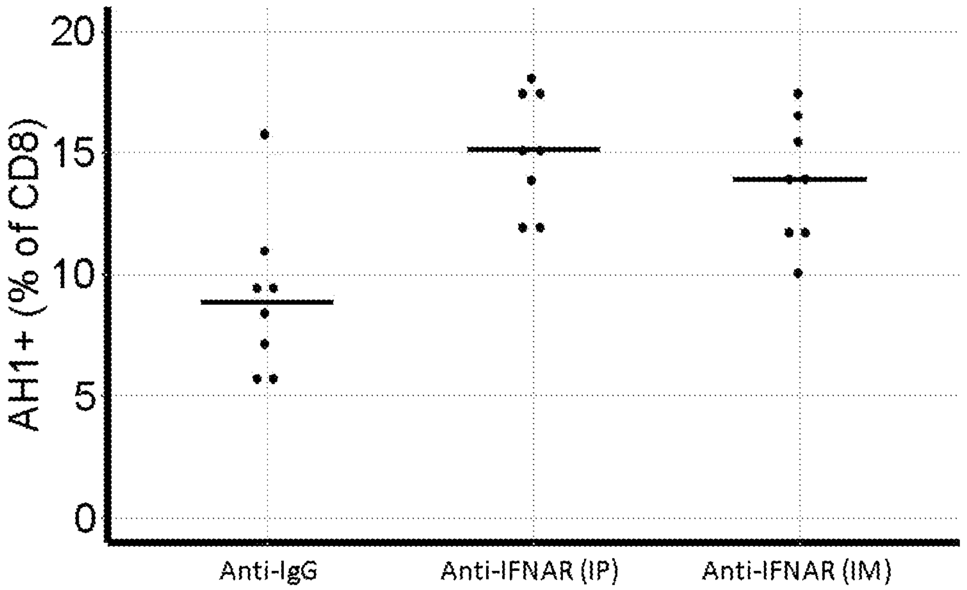
FIG. 28A shows local suppression of IFNα is as effective in increasing samRNA immune response as systemic delivery. CD8 T-Cell responses in Balb/c mice at 12 days following a single immunization with 1 μg samRNA. Mice were treated with either anti-IgG antibody control, delivered intraperitoneally (IP), or a monoclonal blocking antibody targeting IFNAR, delivered either IP or intramuscularly, 24 hours prior to immunization with samRNA. Antibody treatments were all at a 0.5 mg dose. All intramuscular injections were delivered bilaterally to the anterior tibialis. Antigen-specific (AH1-A5) CD8 T cells measured using MHC Class I tetramer staining and results presented as antigen-specific CD8 T cells as a percentage of total CD8 T cells. Median for each group indicated by horizontal line.
Figure 28B:
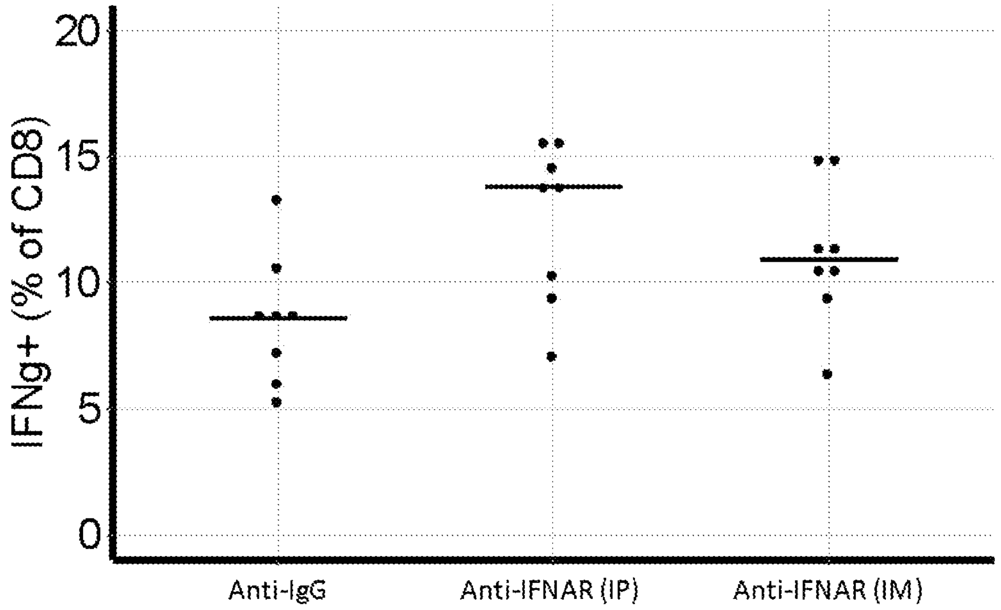
FIG. 28B shows local suppression of IFNα is as effective in increasing samRNA immune response as systemic delivery. CD8 T-Cell responses in Balb/c mice at 12 days following a single immunization with 1 μg samRNA. Mice were treated with either anti-IgG antibody control, delivered intraperitoneally (IP), or a monoclonal blocking antibody targeting IFNAR, delivered either IP or intramuscularly, 24 hours prior to immunization with samRNA. Antibody treatments were all at a 0.5 mg dose. All intramuscular injections were delivered bilaterally to the anterior tibialis. Antigen-specific (AH1-A5) IFN-gamma production in CD8 T cells measured using intracellular cytokine staining and results presented as antigen-specific CD8 T cells as a percentage of total CD8 T cells. Median for each group indicated by horizontal line.

To further evaluate inhibition of type I IFN in improving immune responses in samRNA vaccinations, the route of administration of the anti-IFNAR Mab was evaluated. Specifically, an anti-IFNAR MAb was administered was delivered either IP or intramuscularly (IM) (0.5 mg) at 24 hours prior to immunization with samRNA. The immune response was assessed assaying antigen-specific (AH1-A5) MHC tetramer staining and IFN-gamma production in CD8 T cells and quantified as a percentage of total CD8 T cells. As shown in FIG. 28A and Table 35A (MHC-tetramer staining) and FIG. 28B and Table 35B (IFN-gamma production), administering the anti-IFNAR MAb either IM (locally) or IP (systemically) result in an significantly improved immune response relative to administering the control antibody. Accordingly, the results demonstrate local suppression of type I IFN signaling is as effective as systemic delivery in increasing immune responses to a samRNA vaccine.

TABLE 35A

| AH1-A5 specific MHC-tetramer staining (percentage of total CD8 T cells) | | | | | |
|---|---|---|---|---|---|
| Group | aIFNAR.regimen | Median | Mean | SD | P-value* |
| 1 | control | 8.9 | 9.1 | 3.3 | — |
| 5 | 0.5 mg IP | 15.2 | 15.2 | 2.4 | 5.7E−04 |
| 6 | 0.5 mg IM | 14.0 | 13.9 | 2.6 | 4.8E−03 |

*Dunnett's test

TABLE 35B

| AH1-A5 specific IFN-gamma production (percentage of total CD8 T cells) | | | | | |
|---|---|---|---|---|---|
| Group | aIFNAR.regimen | Median | Mean | SD | P-value* |
| 1 | control | 8.6 | 8.6 | 2.6 | — |
| 5 | 0.5 mg IP | 13.8 | 12.5 | 3.2 | 0.02 |
| 6 | 0.5 mg IM | 10.9 | 11.2 | 2.8 | 0.14 |

*Dunnett's test

Certain Sequences

Vectors, cassettes, and antibodies referred to herein are described below and referred to by SEQ ID NO.

Tremelimumab VL (SEQ ID NO:16)
Tremelimumab VH (SEQ ID NO:17)
Tremelimumab VH CDR1 (SEQ ID NO:18)
Tremelimumab VH CDR2 (SEQ. ID NO:19)
Tremelimumab VH CDR3 (SEQ ID NO:20)
Tremelimumab V1 CDR1 (SEQ ID NO:21)
Tremelimumab VL CDR2 (SEQ ID NO:22)
Tremelimumab VL CDR3 (SEQ ID NO:23)
Durvalumab (MEDI4736) VL (SEQ ID NO:24)
MEDI4736 VH (SEQ ID NO:25)
MEDI4736 VH CDR1 (SEQ ID NO:26)
MEDI4736 VH CDR2 (SEQ ID NO:27)
MEDI4736 VH CDR3 (SEQ ID NO:28)
MEDI4736 VL CPR1 (SEQ ID NO:29)
MEDI4736 VL CDR2 (SEQ ID NO:30)
MEDI4736 VL CDR3 (SEQ ID NO:31)
UbA76-25merPDTT nucleotide (SEQ ID NO:32)
UbA76-25merPDTT polypeptide (SEQ ID NO:33)
MAG-25merPDTT nucleotide (SEQ ID NO:34)
MAG-25merPDTT polypeptide (SEQ ID NO:35)
Ub7625merPDTT_NoSFL nucleotide (SEQ ID NO:36)
Ub7625merPDTT_NoSFL polypeptide (SEQ ID NO:37)
ChAd768.5WTnt.MAG25mer (SEQ ID NO:2); AC_000011.1 with E1 (nt 577 to 3403) and E3 (nt 27,125-31,825) sequences deleted; corresponding ATCC VR-594 nucleotides substituted at five positions; model neoantigen cassette under the control of the CMV promoter/enhancer inserted in place of deleted E1; SV40 polyA 3' of cassette
Venezuelan equine encephalitis virus [VEE] (SEQ ID NO:3) GenBank: L01442.2
VEE-MAG25mer (SEQ ID NO:4); contains MAG-25merPDTT nucleotide (bases 30-1755)
Venezuelan equine encephalitis virus strain TC-83 [TC-83] (SEQ ID NO:5) GenBank: L01443.1
VEE Delivery Vector (SEQ ID NO:6); VEE genome with nucleotides 7544-11175 deleted [alphavirus structural proteins removed]
TC-83 Delivery Vector (SEQ ID NO:7); TC-83 genome with nucleotides 7544-11175 deleted [alphavirus structural proteins removed]
VEE Production Vector (SEQ ID NO:8); VEE genome with nucleotides 7544-11175 deleted, plus 5' T7-promoter, plus 3' restriction sites
TC-83 Production Vector (SEQ ID NO:9); TC-83 genome with nucleotides 7544-11175 deleted, plus 5' T7-promoter, plus 3' restriction sites
VEE-UbAAY (SEQ ID NO:14); VEE delivery vector with MHC class I mouse tumor epitopes SIINFEKL and AH1-A5 inserted
VEE-Luciferase (SEQ ID NO:15); VEE delivery vector with luciferase gene inserted at 7545
ubiquitin (SEQ ID NO:38) >UbG76 0-228
Ubiquitin A76 (SEQ ID NO:39) >UbA76 0-228
HLA-A2 (MHC class I) signal peptide (SEQ ID NO:40) >MHC SignalPep 0-78
HLA-A2 (MHC class I) Trans Membrane domain (SEQ ID NO:41) >HLA A2 TM Domain 0-201
IgK Leader Seq (SEQ ID NO:42) >IgKLeader Seq 0-60
Human DC-Lamp (SEQ ID NO:43) >HumanDCLAMP 0-3178
Mouse LAMP1 (SEQ ID NO:44) >MouseLamp1 0-1858
Human Lamp1 cDNA (SEQ ID NO:45) >Human Lamp1 0-2339
Tetanus toxoid nulceic acid sequence (SEQ ID NO:46)
Tetanus toxoid amino acid sequence (SEQ ID NO:47)
PADRE nulceotide sequence (SEQ ID NO:48)
PADRE amino acid sequence (SEQ ID NO:49)
WPRE (SEQ ID NO:50) >WPRE 0-593
IRES (SEQ ID NO:51) >eGFP_IRES_SEAP_Insert 1746-2335
GFP (SEQ ID NO:52)
SEAP (SEQ ID NO:53)
Firefly Luciferase (SEQ ID NO:54)
FMDV 2A (SEQ TD NO:55)

REFERENCES

1. Desrichard, A., Snyder, A. & Chan, T. A. Cancer Neoantigens and Applications for Immunotherapy. *Clin. Cancer Res. Off. J. Am. Assoc. Cancer Res*. (2015). doi: 10.1158/1078-0432.CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest*. 125, 3413-3421 (2015).
4. Rizvi, N. A. et al. Cancer immunology. Mutational landscape determines sensitivity to PD-1 blockade in non-small cell lung cancer. *Science* 348, 124-128 (2015).
5. Snyder, A. et al. Genetic basis for clinical response to CTLA-4 blockade in melanoma. *N. Engl. J. Med.* 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J. Y. United States Patent Application: 20110293637-COMPOSITIONS AND METHODS OF IDENTIFYING TUMOR SPECIFIC NEOANTIGENS. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&1=50&s1=20110293637.PGNR.>
9. Lundegaard, C., Hoof, I., Lund, O. & Nielsen, M. State of the art and challenges in sequence based T-cell epitope prediction. *Immunome Res.* 6 Suppl 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).
12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. U.S. patent application Ser. No. 01/202,08706-OPTIMIZATION OF MULTIGENE ANALYSIS OF TUMOR SAMPLES. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&1=50&s1=20120208706.PGNR.>
17. Target Capture for NextGen Sequencing-IDT. at <http://www.idtdna.com/pages/products/nextgen/target-capture>
18. Shukla, S. A. et al. Comprehensive analysis of cancer-associated somatic mutations in class I HLA genes. *Nat. Biotechnol.* 33, 1152-1158 (2015).
19. Cieslik, M. et al. The use of exome capture RNA-seq for highly degraded RNA with application to clinical cancer sequencing. *Genome Res.* 25, 1372-1381 (2015).
20. Bodini, M. et al. The hidden genomic landscape of acute myeloid leukemia:
subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf. Engl.* 28, 1811-1817 (2012).
22. Cibulskis, K. et al. Sensitive detection of somatic point mutations in impure and heterogeneous cancer samples. *Nat. Biotechnol.* 31, 213-219 (2013).
23. Wilkerson, M. D. et al. Integrated RNA and DNA sequencing improves mutation detection in low purity tumors. *Nucleic Acids Res.* 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf. Engl.* 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf. Engl.* 25, 2865-2871 (2009).
26. Lam, H. Y. K. et al. Nucleotide-resolution analysis of structural variants using BreakSeq and a breakpoint library. *Nat. Biotechnol.* 28, 47-55 (2010).
27. Frampton, G. M. et al. Development and validation of a clinical cancer genomic profiling test based on massively parallel DNA sequencing. *Nat. Biotechnol.* 31, 1023-1031 (2013).
28. Boegel, S. et al. HLA typing from RNA-Seq sequence reads. *Genome Med.* 4, 102 (2012).
29. Liu, C. et al. ATHLATES: accurate typing of human leukocyte antigen through exome sequencing. *Nucleic Acids Res.* 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).
32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf. Engl.* (2011). doi: 10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).

39. Anders, S., Pyl, P. T. & Huber, W. HTSeq—a Python framework to work with high-throughput sequencing data. *Bioinforma. Oxf. Engl.* 31, 166-169 (2015).

40. Furney, S. J. et al. SF3B1 mutations are associated with alternative splicing in uveal melanoma. *Cancer Discov.* (2013). doi: 10.1158/2159-8290.CD-13-0330

41. Zhou, Q. et al. A chemical genetics approach for the functional assessment of novel cancer genes. *Cancer Res.* (2015). doi: 10.1158/0008-5472.CAN-14-2930

42. Maguire, S. L. et al. SF3B1 mutations constitute a novel therapeutic target in breast cancer. *J. Pathol.* 235, 571-580 (2015).

43. Carithers, L. J. et al. A Novel Approach to High-Quality Postmortem Tissue Procurement: The GTEx Project. *Biopreservation Biobanking* 13, 311-319 (2015).

44. Xu, G. et al. RNA COMPASS: a dual approach for pathogen and host transcriptome analysis of RNA-seq datasets. *PloS One* 9, e89445 (2014).

45. Andreatta, M. & Nielsen, M. Gapped sequence alignment using artificial neural networks: application to the MHC class I system. *Bioinforma. Oxf. Engl.* (2015). doi: 10.1093/bioinformatics/btv639

46. Jørgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).

47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).

48. Nielsen, M., Lundegaard, C., Lund, O. & Keşmir, C. The role of the proteasome in generating cytotoxic T-cell epitopes: insights obtained from improved predictions of proteasomal cleavage. *Immunogenetics* 57, 33-41 (2005).

49. Boisvert, F. M. et al. A Quantitative Spatial Proteomics Analysis of Proteome Turnover in Human Cells. *Mol. Cell. Proteomics* 11, M111.011429-M111.011429 (2012).

50. Duan, F. et al. Genomic and bioinformatic profiling of mutational neoepitopes reveals new rules to predict anticancer immunogenicity. *J. Exp. Med.* 211, 2231-2248 (2014).

51. Janeway's Immunobiology: 9780815345312: Medicine & Health Science Books @ Amazon.com. at <http://www.amazon.com/Janeways-Immunobiology-Kenneth-Murphy/dp/0815345313>

52. Calis, J. J. A. et al. Properties of MHC Class I Presented Peptides That Enhance Immunogenicity. *PLoS Comput. Biol.* 9, e1003266 (2013).

53. Zhang, J. et al. Intratumor heterogeneity in localized lung adenocarcinomas delineated by multiregion sequencing. *Science* 346, 256-259 (2014)

54. Walter, M. J. et al. Clonal architecture of secondary acute myeloid leukemia. *N. Engl. J. Med.* 366, 1090-1098 (2012).

55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255:1261-1263.

56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.

57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.

58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6

59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.

60. Goldman J M, Hibbin J, Kearney L, Orchard K, Th'ng K H. HLA-D R monoclonal antibodies inhibit the proliferation of normal and chronic granulocytic leukaemia myeloid progenitor cells. Br J Haematol. 1982 November; 52 (3): 411-20.

61. Eng J K, Jahan T A, Hoopmann M R. Comet: an open-source M S/M S sequence database search tool. Proteomics. 2013 January; 13(1):22-4. doi: 10.1002/pmic.201200439. Epub 2012 Dec. 4.

62. Eng J K, Hoopmann M R, Jahan T A, Egertson J D, Noble W S, MacCoss M J. A deeper look into Comet—implementation and features. J Am Soc Mass Spectrom. 2015 November; 26(11):1865-74. doi: 10.1007/s13361-015-1179-x. Epub 2015 Jun. 27.

63. Lukas Käll, Jesse Canterbury, Jason Weston, William Stafford Noble and Michael J. MacCoss. Semi-supervised learning for peptide identification from shotgun proteomics datasets. Nature Methods 4:923-925, November 2007

64. Lukas Käll, John D. Storey, Michael J. MacCoss and William Stafford Noble. Assigning confidence measures to peptides identified by tandem mass spectrometry. Journal of Proteome Research, 7(1):29-34, January 2008

65. Lukas Käll, John D. Storey and William Stafford Noble. Nonparametric estimation of posterior error probabilities associated with peptides identified by tandem mass spectrometry. Bioinformatics, 24(16):142-148, August 2008

66. Kinney R M, B J Johnson, V L Brown, D W Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.

67. Jill E Slansky, Frederique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity, Volume 13, Issue 4, 1 Oct. 2000, *Pages* 529-538.

68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA; 93 (18): 9730-9735, 1996 Sep. 3.

69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. *J Gen Virol* 67:1951-1960, 1986.

70. Aarnoudse, C. A., Kruse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99, 7-13.
71. Alexander, J., Sidney, J., Southwood, S., Ruppert, J., Oseroff, C., Maewal, A., Snoke, K., Serra, H. M., Kubo, R. T., and Sette, A. (1994). Development of high potency universal DR-restricted helper epitopes by modification of high affinity DR-blocking peptides. Immunity 1, 751-761.
72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4, 4166.
73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24, 2102-2109.
74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450.
75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.
76. Janetzki, S., Price, L., Schroeder, H., Britten, C. M., Welters, M. J. P., and Hoos, A. (2015). Guidelines for the automated evaluation of Elispot assays. *Nat Protoc* 10, 1098-1115.
77. Lyons, G. E., Moore, T., Brasic, N., Li, M., Roszkowski, J. J., and Nishimura, M. I. (2006). Influence of human CD8 on antigen recognition by T-cell receptor-transduced cells. *Cancer Res* 66, 11455-11461.
78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. *Blood* 119, 368-376.
79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.
80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.
81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.
82. Pushko P, Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.
83. Strauss, J H and E G Strauss. The alphaviruses: gene expression, replication, and evolution. Microbiol Rev. 1994 September; 58 (3): 491-562.
84. Rhême C, Ehrengruber M U, Grandgirard D. Alphaviral cytotoxicity and its implication in vector development. Exp Physiol. 2005 January; 90 (1): 45-52. Epub 2004 Nov. 12.
85. Riley, Michael K. II, and Wilfred Vermerris. Recent Advances in Nanomaterials for Gene Delivery-A Review. Nanomaterials 2017, 7 (5), 94.
86. Frolov I, Hardy R, Rice C M. Cis-acting RNA elements at the 5' end of Sindbis virus genome RNA regulate minus- and plus-strand RNA synthesis. RNA. 2001 November; 7 (11): 1638-51.
87. Jose J, Snyder J E, Kuhn R J. A structural and functional perspective of alphavirus replication and assembly. Future Microbiol. 2009 September; 4 (7): 837-56.
88. Bo Li and C. olin N. Dewey. RSEM: accurate transcript quantification from RNA-Seq data with or without a reference genome. BMC Bioinformatics, 12:323, August 2011
89. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sébastien Lemieux, Pierre Thibault, and Claude Perreault. MHC class I-associated peptides derive from selective regions of the human genome. The Journal of Clinical Investigation, 2016,
90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.
91. Mommen G P., Marino, F., Meiring H D., Poelen, M C., van Gaans-van den Brink, J A., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423 April 2016.
92. Sebastian Kreiter, Mathias Vormehr, Niels van de Roemer, Mustafa Diken, Martin Lower, Jan Diekmann, Sebastian Boegel, Barbara Schrörs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to caner. Nature 520, 692-696, April 2015.
93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.
94. Andreatta M., Karosiene E., Rasmussen M., Stryhn A., Buus S., Nielsen M. Accurate pan-specific prediction of peptide-MHC class II binding affinity with improved binding core identification. Immunogenetics 67 (11-12) 641-650, November 2015.
95. Nielsen, M., Lund, O. NN-align. An artificial neural network-based alignment algorithm for MHC class II peptide binding prediction. BMC Bioinformatics 10:296, September 2009.
96. Nielsen, M., Lundegaard, C., Lund, O. Prediction of MHC class II binding affinity using SMM-align, a novel stabilization matrix alignment method. BMC Bioinformatics 8:238, July 2007.

97. Zhang, J., et al. PEAKS D B: de novo sequencing assisted database search for sensitive and accurate peptide identification. Molecular & *Cellular Proteomics.* 11 (4): 1-8. Jan. 2, 2012.

98. Jensen, Kamilla Kjaergaard, et al. "Improved Methods for Predicting Peptide Binding Affinity to MHC Class II Molecules." Immunology, 2018, doi: 10.1111/imm.12889.

99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. Nat. Biotechnol. 30, 413-421

100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271.e11.

101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nat. Biotechnol. 33, 1152-1158.

102. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

103. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

What is claimed is:

1. A method for stimulating an immune response in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising:

(a) an RNA alphavirus backbone, wherein the RNA alphavirus backbone comprises the nucleic acid sequence set forth in SEQ ID NO: 6, comprising:

(i) at least one promoter nucleotide sequence, and (ii) at least one polyadenylation (poly(A)) sequence; and (b) a cassette, wherein the cassette comprises:

(i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising:

a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence;

(ii) optionally, a second promoter nucleotide sequence operably linked to the at least one nucleic acid sequence; and (iii) optionally, at least one second poly(A) sequence, wherein the second poly(A) sequence is a native poly(A) sequence or an exogenous poly(A) sequence to the alphavirus.

2. A method for stimulating a tumor specific immune response in a subject, the method comprising administering to the subject a composition for delivery of an expression system and administering to the subject an inhibitor of Type I interferon signaling, wherein the composition for delivery of the expression system comprises the expression system, wherein the expression system comprises one or more vectors, the one or more vectors comprising:

(a) an RNA alphavirus backbone, wherein the RNA alphavirus backbone comprises the nucleic acid sequence set forth in SEQ ID NO: 6, comprising:

(i) at least one promoter nucleotide sequence, and (ii) at least one polyadenylation (poly(A)) sequence; and (b) a cassette, wherein the cassette comprises:

(i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising:

a. an epitope-encoding nucleic acid sequence, optionally comprising at least one alteration that makes the encoded epitope sequence distinct from the corresponding peptide sequence encoded by a wild-type nucleic acid sequence, b. optionally a 5' linker sequence, and c. optionally a 3' linker sequence;

(ii) optionally, a second promoter nucleotide sequence operably linked to the at least one nucleic acid sequence; and (iii) optionally, at least one second poly(A) sequence, wherein the second poly(A) sequence is a native poly(A) sequence or an exogenous poly(A) sequence to the alphavirus.

3. A method of enhancing delivery of an alphavirus-based expression system, the method comprising administering to the subject a composition for delivery of an expression system and administering to the subject an inhibitor of Type I interferon signaling,
  wherein the composition for delivery of the expression system comprises the expression system,
  wherein the expression system comprises one or more vectors,
  the one or more vectors comprising:
  (a) an RNA alphavirus backbone, wherein the RNA alphavirus backbone comprises the nucleic acid sequence set forth in SEQ ID NO: 6, comprising:
    (i) at least one promoter nucleotide sequence, and
    (ii) at least one polyadenylation (poly(A)) sequence; and
  (b) a cassette, wherein the cassette comprises:
    (i) at least one nucleic acid sequence, optionally wherein the at least one nucleic acid sequence comprises a polypeptide-encoding nucleic acid sequence, optionally wherein the polypeptide-encoding nucleic acid sequence is an antigen-encoding nucleic acid sequence comprising:
      a. an epitope-encoding nucleic acid sequence, optionally comprising at least one alteration that makes the encoded epitope sequence distinct from the corresponding peptide sequence encoded by a wild-type nucleic acid sequence,
      b. optionally a 5' linker sequence, and
      c. optionally a 3' linker sequence;
    (ii) optionally, a second promoter nucleotide sequence operably linked to the at least one nucleic acid sequence; and
    (iii) optionally, at least one second poly(A) sequence, wherein the second poly(A) sequence is a native poly(A) sequence or an exogenous poly(A) sequence to the alphavirus.

4. The method of claim 1, wherein:
  (a) the RNA alphavirus backbone sequence comprises a 26S promoter nucleotide sequence and a poly(A) sequence, wherein the 26S promoter sequence is endogenous to the RNA alphavirus backbone, and wherein the poly(A) sequence is endogenous to the RNA alphavirus backbone; and
  (b) the cassette is integrated between the 26S promoter nucleotide sequence and the poly(A) sequence, wherein the cassette is operably linked to the 26S promoter nucleotide sequence; and
  wherein the inhibitor of Type I interferon signaling comprises an anti-IFNαβ receptor (IFNAR) blocking antibody.

5. The method of claim 1, wherein:
  the antigen-encoding nucleic acid sequence encodes a polypeptide sequence capable of undergoing antigen processing into the encoded epitope, and/or the epitope-encoding nucleic acid sequence encodes an epitope known or suspected to be presented by MHC class I on a surface of a cell, optionally wherein the surface of the cell is a tumor cell surface or an infected cell surface, and optionally wherein the cell is the subject's cell, optionally wherein the cell is a tumor cell selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T cell lymphocytic leukemia, non-small cell lung cancer, and small cell lung cancer, or
  optionally wherein the cell is an infected cell selected from the group consisting of: a pathogen infected cell, a virally infected cell optionally an HIV infected cell, a bacterially infected cell, a fungally infected cell, and a parasitically infected cell; or
  the polypeptide-encoding nucleic acid sequence encodes a full-length protein or functional portion thereof, optionally wherein the full-length protein or functional portion thereof is selected from the group consisting of: an antibody, a cytokine, a chimeric antigen receptor (CAR), a T-cell receptor, and a genome-editing system nuclease; or
  the at least one nucleic acid sequence comprises a non-coding nucleic acid sequence, optionally wherein the non-coding nucleic acid sequence is an RNA interference (RNAi) polynucleotide or genome-editing system polynucleotide.

6. The method of claim 1, wherein the cassette comprises:
  i) the at least one nucleic acid sequence comprising the polypeptide-encoding nucleic acid sequence, wherein the polypeptide-encoding nucleic acid sequence is an antigen-encoding nucleic acid sequence comprising:
    a. an epitope-encoding nucleic acid sequence, optionally comprising at least one alteration that makes the encoded epitope sequence distinct from the corresponding peptide sequence encoded by a wild-type nucleic acid sequence
    b. optionally a 5' linker sequence, and
    c. optionally a 3' linker sequence;
  (ii) optionally, a second promoter nucleotide sequence operably linked to the antigen-encoding nucleic acid sequence;
  (iii) optionally, at least one MHC class II epitope-encoding nucleic acid sequence;
  (iv) optionally, at least one nucleic acid sequence encoding a GPGPG amino acid linker sequence (SEQ ID NO: 56); and
  (v) optionally, at least one second poly(A) sequence, wherein the second poly(A) sequence is a native poly (A) sequence or an exogenous poly(A) sequence to the alphavirus;
  optionally wherein an ordered sequence of each element of the cassette is described in the formula, from 5' to 3', comprising $$Pa\text{-}(L5b\text{-}Nc\text{-}L3d)X\text{-}(G5e\text{-}Uf)Y\text{-}G3g$$

wherein P comprises the second promoter nucleotide sequence, where a=0 or 1,
  N comprises one of the epitope-encoding nucleic acid sequences, wherein the epitope-encoding nucleic acid sequence comprises an MHC class I epitope-encoding nucleic acid sequence, where c=1,
  L5 comprises the 5' linker sequence, where b=0 or 1,
  L3 comprises the 3' linker sequence, where d=0 or 1,
  G5 comprises one of the at least one nucleic acid sequences encoding a GPGPG amino acid linker, where e=0 or 1,
  G3 comprises one of the at least one nucleic acid sequences encoding a GPGPG amino acid linker, where g=0 or 1,
  U comprises one of the at least one MHC class II epitope-encoding nucleic acid sequence, where f=1,
  X=1 to 400, where for each X the corresponding Nc is an epitope-encoding nucleic acid sequence, optionally wherein for each X the corresponding Nc is a distinct MHC class I epitope-encoding nucleic acid sequence, and Y=0, 1, or 2, where for each Y the corresponding $U_f$ is an epitope-encoding nucleic acid sequence, optionally wherein for each Y the corresponding $U_f$ is a distinct MHC class II epitope-encoding nucleic acid sequence.

7. The method of claim 6, wherein a=0, b=1, d=1, e=1, g=1, X=20, Y=2, the at least one promoter nucleotide sequence is a single 26S promoter nucleotide sequence provided by the RNA alphavirus backbone, the at least one polyadenylation poly(A) sequence is a poly(A) sequence of at least 100 consecutive A nucleotides provided by the RNA alphavirus backbone, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 2 amino acids in length, L3 is a native 3' linker sequence that encodes a native C-terminal amino acid sequence of the MHC I epitope, and wherein the 3' linker sequence encodes a peptide that is at least 2 amino acids in length, U is each of a PADRE class II sequence and a Tetanus toxoid MHC class II sequence, each of the MHC class I epitope-encoding nucleic acid sequences encodes a polypeptide that is between 13 and 25 amino acids in length.

8. The method of claim 1, wherein:

the composition for delivery of the expression system further comprises a nanoparticulate delivery vehicle that optionally encapsulates the expression system and optionally has a diameter of about 100 nm, optionally wherein the nanoparticulate delivery vehicle is a lipid nanoparticle (LNP), optionally wherein the LNP comprises ionizable amino lipids, optionally wherein the ionizable amino lipids comprise MC3-like (dilinoleylmethyl-4-dimethylaminobutyrate) molecules; and/or the inhibitor of Type I interferon signaling is selected from the group consisting of: an IFNα inhibitor, an IFNβ inhibitor, an IFNAR inhibitor, and a Type I interferon signaling pathway inhibitor, optionally wherein the inhibitor of Type I interferon signaling is selected from the group consisting of:

an antibody or an antigen-binding fragment thereof, a small molecule inhibitor, a RNAi polynucleotide, a genome-editing system, and an Fc-fusion protein, optionally wherein the antibody is selected from the group consisting of: an anti-IFNα antibody, an anti-IFNβ antibody, an anti-IFNαβ receptor (IFNAR) blocking antibody, optionally wherein the anti-IFNα antibody is selected from the group consisting of: Sifalimumab, Rontalizumab, and ASG-009, or optionally wherein the anti-IFNAR blocking antibody is selected from the group consisting of: MAR1-5A3, Anifrolumab, AmS3A5-1, 64G12, H2K6, H2K1, H3K6, H3K1 3F11, 4G5, 11E2, and 9D4, or wherein the Type I interferon signaling pathway inhibitor comprises a JAK kinase inhibitor optionally a JAK1/2 inhibitor or a JAK1/3 inhibitor, optionally wherein the JAK kinase inhibitor comprises a small molecule, optionally wherein the JAK1/3 inhibitor is Tofacitinib; and/or the inhibitor of Type I interferon signaling is administered before, concurrently with, or after administration of the composition for delivery of the expression system, optionally wherein:

the inhibitor of Type I interferon signaling is administered 24 hours or less before administration of the composition for delivery of the expression system, or the inhibitor of Type I interferon signaling is administered less than 12 hours after administration of the composition for delivery of the expression system, or the inhibitor of Type I interferon signaling is administered 6 hours or less after administration of the composition for delivery of the expression system, or the inhibitor of Type I interferon signaling is administered between 24 hours before and 6 hours or less after administration of the composition for delivery of the expression system;

and/or optionally wherein:

the composition for delivery of the expression system is administered intramuscularly (IM), intradermally (ID), subcutaneously (SC), or intravenously (IV); and/or the inhibitor of Type I interferon signaling is administered intramuscularly (IM), intradermally (ID), subcutaneously (SC), or intravenously (IV); and/or a single administration of the inhibitor of Type I interferon signaling is administered.

9. The method of claim 1, wherein:

the cassette is integrated between the at least one promoter nucleotide sequence and the at least one poly(A) sequence; and/or the at least one promoter nucleotide sequence is operably linked to the cassette; and/or the one or more vectors are self-replicating within a mammalian cell; and/or the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Venezuelan equine encephalitis virus, or the RNA alphavirus backbone comprises at least sequences for nonstructural protein-mediated amplification, a 26S promoter sequence, and a poly(A) sequence encoded by the nucleotide sequence of the Venezuelan equine encephalitis virus, optionally wherein sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof, and/or wherein the RNA alphavirus backbone does not encode structural virion proteins capsid, E2 and E1 optionally wherein the cassette is inserted in place of structural virion proteins within the nucleotide sequence of the Venezuelan equine encephalitis virus, optionally wherein the insertion of the cassette provides for transcription of a polycistronic RNA comprising the nsP1-4 genes and the at least one nucleic acid sequence, wherein the nsP1-4 genes and the at least one nucleic acid sequence are in separate open reading frames; and/or the at least one promoter nucleotide sequence is the native 26S promoter nucleotide sequence encoded by the RNA alphavirus backbone or is an exogenous RNA promoter; and/or wherein the second promoter nucleotide sequence is a 26S promoter nucleotide sequence or the second promoter nucleotide sequence comprises multiple 26S promoter nucleotide sequences, wherein each 26S promoter nucleotide sequence provides for transcription of one or more of the separate open reading frames.

10. The method of claim 1, wherein:

the one or more vectors are each at least 300 nt in size, each at least 1 kb in size, each 2 kb in size and/or each less than 5 kb in size; and/or at least one of the epitope-encoding nucleic acid sequences encodes an epitope that, when expressed and translated, is capable of being presented by MHC class I on a cell of the subject; and/or at least one of the epitope-encoding nucleic acid sequences encodes an epitope that, when expressed and translated, is capable of being presented by MHC class II on a cell of the subject.

11. The method of claim 1, wherein:

the at least one nucleic acid sequence comprises two or more nucleic acid sequences, or the at least one nucleic acid sequence comprises two or more polypeptide-encoding nucleic acid sequences optionally wherein each polypeptide-encoding nucleic acid sequence is linked directly to one another; and/or each polypeptide-encoding nucleic acid sequence is linked to a distinct polypeptide-encoding nucleic acid sequence with a nucleic acid sequence encoding a linker, optionally wherein the polypeptide-encoding nucleic acid sequence is an antigen-encoding nucleic acid sequence, and wherein the linker links two MHC class I epitope-encoding nucleic acid sequences or an MHC class I epitope-encoding nucleic acid sequence to an MHC class II epitope-encoding nucleic acid sequence, optionally wherein the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length, or wherein the polypeptide-encoding nucleic acid sequence is an antigen-encoding nucleic acid sequence, and wherein the linker links two MHC class II epitope-encoding nucleic acid sequences or an MHC class II sequence to an MHC class I epitope-encoding nucleic acid sequence, optionally wherein the linker comprises the sequence GPGPG (SEQ ID NO: 56); and/or the polypeptide-encoding nucleic acid sequence is an antigen-encoding nucleic acid sequence, and wherein the antigen-encoding nucleic acid sequences is linked, operably or directly, to a separate or contiguous sequence that enhances the expression, stability, cell trafficking, processing and presentation, and/or immunogenicity of the antigen-encoding nucleic acid sequence, optionally wherein the separate or contiguous sequence comprises at least one of: a ubiquitin sequence, a ubiquitin sequence modified to increase proteasome targeting, an immunoglobulin signal sequence, a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

12. The method of claim 1, wherein:

the epitope-encoding nucleic acid sequence comprises at least one alteration that makes the encoded epitope have increased binding affinity to its corresponding MHC allele relative to the translated, corresponding wild-type nucleic acid sequence; and/or the epitope-encoding nucleic acid sequence comprises at least one alteration that makes the encoded epitope have increased binding stability to its corresponding MHC allele relative to the translated, corresponding wild-type nucleic acid sequence; and/or the epitope-encoding nucleic acid sequence comprises at least one alteration that makes the encoded epitope have an increased likelihood of presentation on its corresponding MHC allele relative to the translated, corresponding wild-type nucleic acid sequence;

and/or the at least one alteration comprises a point mutation, a frameshift mutation, a non-frameshift mutation, a deletion mutation, an insertion mutation, a splice variant, a genomic rearrangement, or a proteasome-generated spliced antigen; and/or the subject is known or suspected to have cancer, optionally wherein stimulating the immune response treats the cancer and/or wherein the cancer is selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer; and/or wherein the subject has one or more tumors, optionally wherein stimulating the immune response reduces tumor volume of the one or more tumors.

13. The method of claim 1, wherein:

the at least one nucleic acid sequence comprises at least 2-10, 2, 3, 4, 5, 6, 7, 8, 9, or 10 nucleic acid sequences, optionally wherein each nucleic acid sequence encodes a distinct non-coding nucleic acid sequence, a distinct polypeptide-encoding nucleic acid sequence, or a combination thereof; or the at least one nucleic acid sequence comprises at least 11-20, 15-20, 11-100, 11-200, 11-300, 11-400, 11, 12, 13, 14, 15, 16, 17, 18, 19, 20 or up to 400 nucleic acid sequences, optionally wherein each nucleic acid sequence encodes a distinct non-coding nucleic acid sequence, a distinct polypeptide-encoding nucleic acid sequence, or a combination thereof; or the at least one nucleic acid sequence comprises at least 2-10, 2, 3, 4, 5, 6, 7, 8, 9, or 10 polypeptide-encoding nucleic acid sequences; or the at least one nucleic acid sequence comprises at least 11-20, 15-20, 11-100, 11-200, 11-300, 11-400, 11, 12, 13, 14, 15, 16, 17, 18, 19, 20 or up to 400 polypeptide-encoding nucleic acid sequences; or the at least one nucleic acid sequence comprises at least 2-10, 2, 3, 4, 5, 6, 7, 8, 9, or 10 antigen-encoding nucleic acid sequences; or the at least one nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences; or the at least one nucleic acid sequence comprises at least 2-400 antigen-encoding nucleic acid sequences and wherein at least two of the antigen-encoding nucleic acid sequences encode polypeptide sequences or portions thereof that are presented by MHC class I on a cell surface.

14. The method of claim 1, wherein:

when administered to the subject and translated, at least one of the epitopes encoded by the epitope-encoding nucleic acid sequence are presented on antigen presenting cells resulting in an immune response targeting a cell presenting at least one of the epitopes on the cell surface; and/or the epitope-encoding nucleic acid sequences comprises at least one MHC class I epitope-encoding nucleic acid sequence or MHC class II epitope-encoding nucleic acid sequence, and, when administered to the subject and translated, at least one of the MHC class I or class II epitopes are presented on antigen presenting cells resulting in an immune response targeting a cell presenting at least one of the epitopes on the cell surface, and optionally wherein the expression of each of the MHC class I and/or class II epitope-encoding nucleic acid sequences is driven by the at least one promoter nucleotide sequence.

15. The method of claim 1, wherein the epitope-encoding nucleic acid sequences comprises at least one MHC class I epitope-encoding nucleic acid sequence, and wherein each antigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length; and/or the at least one MHC class II epitope-encoding nucleic acid sequence is present, optionally wherein the at least one MHC class II epitope-encoding nucleic acid sequence is present and comprises at least one MHC class II epitope-encoding nucleic acid sequence that comprises at least one alteration that makes the encoded epitope sequence distinct from the corresponding peptide sequence encoded by a wild-type nucleic acid sequence; and/or the epitope-encoding nucleic acid sequence comprises an MHC class II epitope-encoding nucleic acid sequence and wherein each antigen-encoding nucleic acid sequence encodes a polypeptide sequence that is 12-20, 12, 13, 14, 15, 16, 17, 18, 19, 20, or 20-40 amino acids in length; and/or the epitope-encoding nucleic acid sequences comprises an MHC class II epitope-encoding nucleic acid sequence, wherein the at least one MHC class II epitope-encoding nucleic acid sequence is present, and wherein the at least one MHC class II epitope-encoding nucleic acid sequence comprises at least one universal MHC class II epitope-encoding nucleic acid sequence, optionally wherein the at least one universal sequence comprises at least one of Tetanus toxoid and PADRE; and/or the at least one promoter nucleotide sequence or the second promoter nucleotide sequence is inducible or non-inducible; and/or the at least one poly(A) sequence comprises a poly(A) sequence native to the alphavirus or exogenous to the alphavirus; and/or the at least one poly(A) sequence is operably linked to at least one of the at least one nucleic acid sequences; and/or wherein the at least one poly(A) sequence is at least 20, at least 30, at least 40, at least 50, at least 60, at least 70, at least 80, or at least 90 consecutive A nucleotides, or is at least 100 consecutive A nucleotides.

16. The method of claim 1, wherein:

the cassette further comprises at least one of: an intron sequence, a woodchuck hepatitis virus posttranscriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one nucleic acid sequences; and/or the cassette further comprises a reporter gene, optionally, green fluorescent protein (GFP), a GFP variant, secreted alkaline phosphatase, luciferase, a luciferase variant, or a detectable peptide or epitope, optionally wherein the detectable peptide or epitope is selected from the group consisting of an HA tag, a Flag tag, a His-tag, or a V5 tag; and/or the one or more vectors further comprises one or more nucleic acid sequences encoding at least one immune modulator, optionally wherein the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof, optionally wherein the antibody or antigen-binding fragment thereof is a Fab fragment, a Fab' fragment, a single chain Fv (scFv), a single domain antibody (sdAb) either as single specific or multiple specificities linked together, or full-length single-chain antibody, and/or wherein the heavy and light chain sequences of the antibody are a contiguous sequence separated by either a self-cleaving sequence optionally 2A or IRES; or the heavy and light chain sequences of the antibody are linked by a flexible linker optionally consecutive glycine residues, or wherein the immune modulator is a cytokine, optionally wherein the cytokine is at least one of IL-2, IL-7, IL-12, IL-15, or IL-21 or variants thereof of each.

17. The method of claim 1, wherein the epitope-encoding nucleic acid sequence comprises a MHC class I epitope-encoding nucleic acid sequence, and wherein the MHC class I epitope-encoding nucleic acid sequence is selected by performing the steps of:

(a) obtaining at least one of exome, transcriptome, or whole genome tumor nucleotide sequencing data from the tumor, wherein the tumor nucleotide sequencing data is used to obtain data representing peptide sequences of each of a set of epitopes;

(b) inputting the peptide sequence of each epitope into a presentation model to generate a set of numerical likelihoods that each of the epitopes is presented by one or more of the MHC alleles on the tumor cell surface of the tumor, the set of numerical likelihoods having been identified at least based on received mass spectrometry data; and (c) selecting a subset of the set of epitopes based on the set of numerical likelihoods to generate a set of selected epitopes which are used to generate the MHC class I epitope-encoding nucleic acid sequence, optionally wherein a number of the set of selected epitopes is 2-20; and/or the presentation model represents dependence between:

(1) presence of a pair of a particular one of the MHC alleles and a particular amino acid at a particular position of a peptide sequence, and (2) likelihood of presentation on the tumor cell surface, by the particular one of the MHC alleles of the pair, of such a peptide sequence comprising the particular amino acid at the particular position; and/or selecting the set of selected epitopes comprises selecting epitopes that have an increased likelihood of being presented on the tumor cell surface relative to unselected epitopes based on the presentation model; and/or selecting the set of selected epitopes comprises selecting epitopes that have an increased likelihood of being capable of inducing a tumor-specific immune response in the subject relative to unselected epitopes based on the presentation model; and/or selecting the set of selected epitopes comprises selecting epitopes that have an increased likelihood of being capable of being presented to naïve T cells by professional antigen presenting cells (APCs) relative to unselected epitopes based on the presentation model, optionally wherein the APC is a dendritic cell (DC); and/or selecting the set of selected epitopes comprises selecting epitopes that have a decreased likelihood of being subject to inhibition via central or peripheral tolerance relative to unselected epitopes based on the presentation model; and/or the set of selected epitopes comprises selecting epitopes that have a decreased likelihood of being capable of inducing an autoimmune response to normal tissue in the subject relative to unselected epitopes based on the presentation model; and/or exome or transcriptome nucleotide sequencing data is obtained by performing sequencing on the tumor tissue, optionally wherein the sequencing is next generation sequencing (NGS) or any massively parallel sequencing approach.

18. The method of claim 1, wherein:

the cassette comprises junctional epitope sequences formed by adjacent sequences in the cassette, optionally wherein at least one or each junctional epitope sequence has an affinity of greater than 500 nM for MHC and/or wherein each junctional epitope sequence is non-self; and/or the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject, optionally wherein the non-therapeutic predicted MHC class I or class II epitope sequence is a junctional epitope sequence formed by adjacent sequences in the cassette; and/or the prediction is based on presentation likelihoods generated by inputting sequences of the non-therapeutic epitopes into a presentation model; and/or an order of the antigen-encoding nucleic acid sequences in the cassette is determined by a series of steps comprising:

(a) generating a set of candidate cassette sequences corresponding to different orders of the antigen-encoding nucleic acid sequences;

(b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for a vaccine; and/or the composition for delivery of the expression system and/or the inhibitor of Type I interferon signaling are formulated in a pharmaceutical composition comprising a pharmaceutically acceptable carrier; and/or the method further comprises administering an adjuvant.

* * * * *